(12) United States Patent
Maillard et al.

(10) Patent No.: US 12,428,413 B2
(45) Date of Patent: Sep. 30, 2025

(54) RHO KINASE INHIBITORS AND COMPOSITIONS AND METHODS OF USE THEREOF

(71) Applicant: CHDI Foundation, Inc., New York, NY (US)

(72) Inventors: Michel C. Maillard, Playa Vista, CA (US); Matthew R. Lee, San Diego, CA (US); Celia Dominguez, Los Angeles, CA (US); Michael Barnes, Saffron Walden (GB); Alan F. Haughan, Saffron Walden (GB); Tammy Ladduwahetty, Saffron Walden (GB); Christopher A. Luckhurst, Saffron Walden (GB); Andrew J. Stott, Saffron Walden (GB); Jason Tierney, Saffron Walden (GB)

(73) Assignee: CHDI Foundation, Inc., New York, NY (US)

( * ) Notice: Subject to any disclaimer, the term of this patent is extended or adjusted under 35 U.S.C. 154(b) by 910 days.

(21) Appl. No.: 17/621,567

(22) PCT Filed: Jun. 26, 2020

(86) PCT No.: PCT/US2020/039964

§ 371 (c)(1),
(2) Date: Dec. 21, 2021

(87) PCT Pub. No.: WO2020/264405

PCT Pub. Date: Dec. 30, 2020

(65) Prior Publication Data

US 2022/0388998 A1 Dec. 8, 2022

Related U.S. Application Data

(60) Provisional application No. 62/868,793, filed on Jun. 28, 2019.

(51) Int. Cl.
*C07D 413/14* (2006.01)
*C07D 213/75* (2006.01)
*C07D 401/04* (2006.01)
*C07D 405/14* (2006.01)
*C07D 471/04* (2006.01)
*C07D 487/04* (2006.01)
*C07D 487/08* (2006.01)

(52) U.S. Cl.
CPC ......... *C07D 413/14* (2013.01); *C07D 213/75* (2013.01); *C07D 401/04* (2013.01); *C07D 405/14* (2013.01); *C07D 471/04* (2013.01); *C07D 487/04* (2013.01); *C07D 487/08* (2013.01); *C07B 2200/05* (2013.01)

(58) Field of Classification Search
None
See application file for complete search history.

(56) References Cited

FOREIGN PATENT DOCUMENTS

EP 0718287 A2 6/1996
WO WO 2005/068468 A2 7/2005

OTHER PUBLICATIONS

International Search Report and Written Opinion in International Application No. PCT/US2020/039964, mailed on May 11, 2020. 10 pages.

*Primary Examiner* — Bong-Sook Baek
(74) *Attorney, Agent, or Firm* — Sheppard Mullin Richter & Hampton LLP

(57) ABSTRACT

Provided herein are certain inhibitors of ROCK (rho-kinases or rho-associated kinases), which are useful as medicament, for the treatment Huntington's disease in particular.

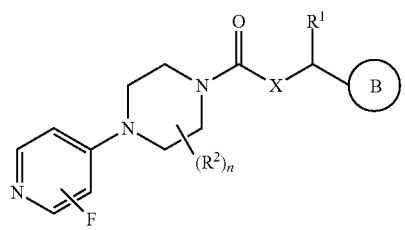

19 Claims, No Drawings

RHO KINASE INHIBITORS AND COMPOSITIONS AND METHODS OF USE THEREOF

CROSS-REFERENCE TO RELATED PATENT APPLICATIONS

This application is a U.S. National Stage Application under 35 U.S.C. § 371 of International Patent Application No. PCT/US2020/039964, filed Jun. 26, 2020, which application claims the benefit of priority under 35 U.S.C. § 119(e) of U.S. Provisional Application 62/868,793, filed Jun. 28, 2019, each of which is hereby incorporated by reference in its entirety.

FIELD

Provided herein are certain inhibitors of ROCK (rho-kinases or rho-associated kinases), compositions thereof, and methods of their use.

BACKGROUND

Rho-kinases ("ROCK") are proteins that are potent, widespread biochemical modulators involved in multiple biological processes. In humans, ROCK has two distinct isoforms, ROCK1 and ROCK2, which are members of the AGC family of serine/threonine kinases and are ubiquitously expressed across tissues. ROCK1 and ROCK2 have central roles in numerous cell functions including smooth muscle cell contraction, cytokinesis, cell proliferation, cell adhesion, and cell migration, indicating they have potentially far reaching therapeutic applications. Among others, these include cardiovascular diseases, pulmonary diseases, ocular diseases, erectile dysfunction, cancer, gastrointestinal diseases, fibrotic diseases, neurodegenerative diseases, neurological injuries, chronic and neuropathic pain, and diabetes.

ROCK signaling components are reported to be elevated in brain and blood cellular components from Huntington's Disease (HD) patients. Correspondingly, identification of primary and secondary sets of proteins that interact with huntingtin (HTT) led to identification of Rho GTPase signaling components that act as modifiers of mutant HTT (mHTT) toxicity. Additionally, sequential network interaction filtering applied over known and novel HTT interactors identify ROCK1 as HTT interactor, suggesting that altered levels of ROCK in HD might play a role in the pathogenesis of the disease. Treatment of cell cultures expressing polyglutamine fragments (as in mutated HTT) with increased expression of the ROCK-downstream protein profilin or ROCK inhibitors leads to decreased mHTT aggregation.

ROCK plays a role in other neurological diseases and injuries. ROCK protein levels and activation of its signaling pathway is enhanced in brain of patients with mild cognitive impairment and Alzheimer's disease. Correspondingly, decreasing ROCK1 expression through RNAi treatment in primary cortical neurons reduced amyloid R levels.

There remains an unmet need for new drugs to treat neurodegenerative diseases such as HD, Parkinson's disease, and Alzheimer's, among others.

SUMMARY

The present disclosure relates to compounds useful for inhibiting ROCK. Some embodiments provide for a compound of Formula I:

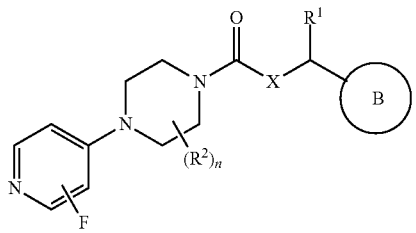

or a deuterated analog, pharmaceutically acceptable salt, solvate, prodrug, stereoisomer, or mixture of stereoisomers thereof, wherein:
  ring B is a 6-10 membered aryl or 6-10 membered heteroaryl ring, wherein ring B is optionally substituted with 1-5 $R^4$;
  X is —O— or —N($R^3$)—;
  $R^1$ is H or optionally substituted $C_{1-3}$ alkyl;
  $R^2$ is oxo, halo, $C_{1-3}$ alkyl, $C_{1-3}$ haloalkyl, $C_{1-3}$ hydroxyalkyl, or $C_{1-3}$ alkoxy; or
  two $R^2$, together with the carbon atoms to which they are attached, join together to form a cycloalkyl or heterocycloalkyl ring;
  $R^3$ is H or $C_{1-3}$ alkyl; or
  $R^2$ and $R^3$, together with the atoms to which they are attached, join together to form a cycloalkyl or heterocycloalkyl ring;
  each $R^4$ is independently halo, $C_{1-3}$ alkyl, $C_{1-3}$ alkoxy, or $C_{1-3}$ haloalkoxy; or
  two $R^4$, together with the atoms to which they are attached, join together to form a heterocycloalkyl ring, wherein the heterocycloalkyl ring is optionally substituted with 1-3 halo or $C_{1-3}$ alkyl; and
  n is 0, 1, or 2.

Also provided are additional compounds as described herein. In some embodiments, provided is a compound selected from Table 1, or a pharmaceutically acceptable salt thereof.

Also provided is a pharmaceutical composition comprising a compound, or a deuterated analog, pharmaceutically acceptable salt, solvate, prodrug, stereoisomer, or mixture of stereoisomers thereof, described herein and a pharmaceutically acceptable carrier.

Also provided is a process for preparing a pharmaceutical composition comprising admixing a compound, or a deuterated analog, pharmaceutically acceptable salt, solvate, prodrug, stereoisomer, or mixture of stereoisomers thereof, described herein and a pharmaceutically acceptable carrier.

Also provided is a method for treating or preventing a condition or disorder mediated by at least one isoform of ROCK in a patient in need thereof comprising administering to the patient a therapeutically effective amount of a compound, or a deuterated analog, pharmaceutically acceptable salt, solvate, prodrug, stereoisomer, or mixture of stereoisomers thereof, described herein.

Also provided is a method for treating or preventing a condition or disorder in a patient in need thereof comprising administering to the patient a therapeutically effective amount of a compound, or a deuterated analog, pharmaceutically acceptable salt, solvate, prodrug, stereoisomer, or mixture of stereoisomers thereof, described herein, wherein the condition or disorder is selected from Huntington's disease (HD), spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

In some embodiments, provided is a compound selected from those in Table 1, or a deuterated analog, pharmaceutically acceptable salt, solvate, prodrug, stereoisomer, or mixture of stereoisomers thereof.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom.

By "optional" or "optionally" is meant that the subsequently described event or circumstance may or may not occur, and that the description includes instances where the event or circumstance occurs and instances in which it does not. An "optionally substituted" group is one that may be unsubstituted or may be substituted with the indicated or defined groups. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses a straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_1$ alkylene is a methylene group. The term "alkylene" encompasses straight chain and branched chain di-radical having the indicated number of carbon atoms, usually from 1 to 20 carbon atoms, for example 1 to 8 carbon atoms, such as 1 to 6 carbon atoms, or 1 to 4 carbon atoms. Examples of $C_1$-$C_4$ alkylene include methylene, 1,1-ethylene, 1,2-ethylene, 1,1-propylene, 1,2-propylene, 1,3-propylene, 1,1-butylene, 1,2-butylene, 1,3-butylene, 1,4-butylene, 2-methyl-1,2-propylene, and 2-methyl-1,3-propylene.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a partially unsaturated non-aromatic, or fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged, spirocyclic, and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group, i.e., it is considered an aryl group. A cycloalkyl may be a "cycloalkenyl," which is a cycloalkyl that includes at least one unit of unsaturation.

The term "halo" includes fluoro, chloro, bromo, and iodo, and the term "halogen" includes fluorine, chlorine, bromine, and iodine.

The term "haloalkyl" denotes an $C_{1-6}$ alkyl group wherein the alkyl is substituted with one halogen up to fully substituted and a fully substituted $C_{1-6}$ haloalkyl can be represented by the formula $C_nL_{2n+1}$ wherein L is a halogen and "n" is 1, 2, 3 or 4; when more than one halogen is present then they may be the same or different and selected from the group consisting of F, Cl, Br and I, such as F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "hydroxyalkyl" denotes an alkyl group as defined herein wherein the alkyl is substituted with one, two, three, or four hydroxy groups, with one hydroxy group on each carbon atom. Examples of hydroxyalkyl groups include, but are not limited to, hydroxymethyl, 3-hydroxypropyl, 2-hydroxy-sec-butyl, 3,4-dihydroxybutyl and the like.

The term "haloalkoxy" denotes a haloalkyl which is directly attached to an oxygen atom. Examples include, but not limited to, difluoromethoxy, trifluoromethoxy, 2,2,2-trifluoroethoxy, pentafluoroethoxy and the like.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, saturated or partially unsaturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. The term "heterocycloalkyl" includes heterocycloalkenyl groups (i.e. the heterocycloalkyl group having at least one double bond) and may comprise one or more oxo (=O) or N-oxide (—$O^-$) moieties. Heterocycloalkyl groups may be monocyclic (i.e., heteromonocyclic) or polycyclic (e.g., bicyclic (i.e., heterobicyclic), including spirocyclic and bridged ring systems). That is, the definition of heterobicyclic encompasses a heteromonocyclic ring 1,1-disubstituted with a cycloalkyl or heteromonocyclic group, as well as a ring system wherein a heteromonocyclic ring is 1,2- or 1,3-fused to another cycloalkyl or heteromonocyclic ring (where a carbon or nitrogen atom can form the ring junction (where the structure is chemically feasible)), as well as a ring system wherein a heteromonocyclic ring has a $C_1$-$C_2$ alkyl bridge, as well as a ring system wherein a heteromonocyclic ring is 1,2-fused to an aromatic or heteroaromatic ring, provided that the moiety is bound to the parent structure via a non-aromatic carbon or nitrogen atom.

Examples of monocyclic heterocycloalkyl (i.e., heteromonocyclic) groups include oxiranyl, aziridinyl, azetidinyl, oxetanyl, pyrrolidinyl, imidazolidinyl, pyrazolidinyl, piperidinyl, piperazinyl, morpholinyl and thiomorpholinyl.

Examples of a $C_6$ heterobicyclyl group include 3-azabicyclo[3.1.0]hexan-3-yl.

Examples of a $C_5$-$C_{10}$ heterobicyclyl group having an aromatic ring include indolin-1-yl, isoindolin-2-yl, 1,2,3,4-tetrahydroquinolin-2-yl, 3,4-dihydroquinolin-1(2H)-yl, and 7,8-dihydro-1,6-naphthyridin-6(5H)-yl.

Examples of heterobicyclyl ring systems including a spirocycle include: 1-oxa-5-azaspiro[3.3]heptan-5-yl, 1-oxa-6-azaspiro[3.3]heptan-6-yl, 6-oxa-1-azaspiro[3.3]heptan-1-yl, 2-oxa-6-azaspiro[3.3]heptan-6-yl, 1,5-diazaspiro[3.3]heptan-1-yl, 1,6-diazaspiro[3.3]heptan-6-yl, 1,6-diazaspiro[3.3]heptan-1-yl, 2,6-diazaspiro[3.3]heptan-2-yl, 1-oxa-5-azaspiro[3.4]octan-5-yl, 1-oxa-6-azaspiro[3.4]octan-6-yl, 2-oxa-5-azaspiro[3.4]octan-5-yl, 2-oxa-6-azaspiro[3.4]octan-6-yl, 1,5-diazaspiro[3.4]octan-5-yl, 1,6-diazaspiro[3.4]octan-6-yl, 2,5-diazaspiro[3.4]octan-5-yl, 2,6-diazaspiro[3.4]octan-6-yl, 1-oxa-5-azaspiro[3.5]nonan-5-yl, 1-oxa-6-azaspiro[3.5]nonan-6-yl, 1-oxa-7-azaspiro[3.5]nonan-7-yl, 2-oxa-5-azaspiro[3.5]nonan-5-yl, 2-oxa-6-azaspiro[3.5]nonan-6-yl, 2-oxa-7-azaspiro[3.5]nonan-7-yl, 1,5-diazaspiro[3.5]nonan-5-yl, 1,6-diazaspiro[3.5]nonan-6-yl, 1,7-diazaspiro[3.5]nonan-7-yl, 2,5-diazaspiro[3.5]nonan-5-yl, 2,6-diazaspiro[3.5]nonan-6-yl, 2,7-diazaspiro[3.5]nonan-7-yl, 1-oxa-5-azaspiro[3.6]decan-5-yl, 1-oxa-6-azaspiro[3.6]decan-6-yl, 1-oxa-7-azaspiro[3.6]decan-7-yl, 2-oxa-5-azaspiro[3.6]decan-5-yl, 2-oxa-6-azaspiro[3.6]decan-6-yl, 2-oxa-7-azaspiro[3.6]decan-7-yl, 1,5-diazaspiro[3.6]decan-5-yl, 1,6-diazaspiro[3.6]decan-6-yl, 1,7-diazaspiro[3.6]decan-7-yl 2,5-diazaspiro[3.6]decan-5-yl, 2,6-diazaspiro[3.6]decan-6-yl, 2,7-diazaspiro[3.6]decan-7-yl.

Examples of heterobicyclyl ring systems including a $C_1$-$C_4$ bridged-alkylene include 2-azabicyclo[2.2.1]heptan-2-yl, 2-azabicyclo[3.2.1]octan-2-yl, 3-azabicyclo[3.2.1]octan-3-yl, and 6-azabicyclo[3.2.1]octan-6-yl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

A "solvate" refers to an association or complex of one or more solvent molecules and a compound described herein. Examples of solvents that form solvates include, but are not limited to, water, isopropanol, ethanol, methanol, dimethylsulfoxide, ethyl acetate, acetic acid and ethanolamine.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives at a hydroxy group), amides (e.g., at an amino group), guanidines (e.g., at an amino group), carbamates (e.g., N,N-dimethylaminocarbonyl at a hydroxy group) derived from functional groups in compounds described herein, and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term "substituted," as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, —$O(C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$ alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

A "stereoisomer" refers to one of a set of compounds made up of the same atoms bonded by the same bonds but having different three-dimensional structures, which are not interchangeable. The term "enantiomer" refers to one of a pair of stereoisomers that are nonsuperimposable mirror images of one another. It is intended that a compound drawn as a single stereoisomer encompasses a mixture of stereoisomers. In particular, an asymmetric ("chiral") carbon center, with respect to each such center in a compound, may be an enriched mixture or may be a racemic mixture.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) or supercritical fluid chromatograph (SFC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_q-COOH$ where q is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein the terms "group," "moiety," "radical," or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or a deuterated analog, pharmaceutically acceptable salt, solvate, prodrug, stereoisomer, or mixture of stereoisomers thereof, having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of ROCK activity.

The terms "ROCK inhibitor" and "inhibitor of ROCK" are intended to mean a compound, or a deuterated analog, pharmaceutically acceptable salt, solvate, prodrug, stereoisomer, or mixture of stereoisomers thereof, described herein which is capable of interacting with ROCK and inhibiting its enzymatic activity.

The term "a condition or disorder mediated by ROCK" as used herein refers to a condition or disorder in which ROCK and/or the action of ROCK is important or necessary, e.g., for the onset, progress, expression, etc. of that condition, or a condition which is known to be treated by ROCK inhibitors.

The term "effect" describes a change or an absence of a change in cell phenotype or cell proliferation. "Effect" can also describe a change or an absence of a change in the catalytic activity of ROCK. "Effect" can also describe a change or an absence of a change in an interaction between ROCK and a natural binding partner.

The term "inhibiting ROCK activity" is intended to mean reducing the enzymatic activity of ROCK. The concentration of inhibitor which reduces the activity of a ROCK enzyme to 50% of that of the uninhibited enzyme is determined as the $IC_{50}$ value. In some embodiments, such reduction of a ROCK enzymatic activity is at least 50%, such as at least about 75%, for example, at least about 90%. In some embodiments, a ROCK enzymatic activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

"Treatment" or "treating" means any treatment of a disease state in a patient, including
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I, are specifically embraced by herein just as if each and every combination was individually and explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, such as those conditions or disorders mediated by ROCK, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

| List of Abbreviations and Acronyms | |
|---|---|
| BINAP | (2,2'-Bis(diphenylphosphino)-1,1'-binaphthyl) |
| Boc | tert-butyloxycarbonyl |
| BuLi | Butyl lithium |
| Cbz | Benzloxycarbonyl |
| $Cs_2CO_3$ | Cesium carbonate |
| DAST | Diethylaminosulfur trifluoride |
| DBU | 1,8-Diazabicyclo[5.4.0]undec-7-ene |
| DCM | Dichloromethane |
| DIAD | Diisopropyl azodiformate |
| DIPEA | Diisopropylethylamine |
| DMAP | Dimethylaminopyridine |
| DME | Dimethoxyethane |
| DMF | Dimethylformamide |
| DMSO | Dimethylsulfoxide |
| EDC | N-Ethyl-N'-(3-dimethylaminopropyl) carbodiimide |
| ES+ | Electrospray Positive Ionisation |
| $Et_2O$ | Diethyl ether |
| EtOAc | ethyl acetate |
| EtOH | Ethanol |
| h | Hour |
| HCl | Hydrochloric acid |
| HOBt | 1-Hydroxybenzotriazole |
| HPLC | High Performance Liquid Chromatography |
| $K_2CO_3$ | Potassium carbonate |
| KOtBu | Potassium tert-butoxide |
| LCMS | Liquid Chromatography Mass Spectrometry |
| M | Molarity |
| MeCN | Acetonitrile |
| MeOH | Methanol |
| $MgSO_4$ | Magnesium sulfate |
| MS | Mass Spectrometry |
| $N_2$ | nitrogen |
| $Na_2CO_3$ | Sodium carbonate |
| $Na_2SO_4$ | Sodium sulfate |
| NaH | Sodium hydride |
| $NaHCO_3$ | Sodium hydrogen carbonate |
| NaOH | Sodium hydroxide |
| NaOtBu | Sodium tert-butoxide |
| $NH_4Cl$ | Ammonium chloride |
| NMR | Nuclear Magnetic Resonance |
| Pd/C | Palladium on carbon |
| $Pd_2(dba)_3$ | Tris(dibenzylideneacetone)dipalladium(0) |
| $PdCl_2(tBu_2Pferrocene)_2$ | [1,1'-Bis(di-tert-butylphosphino)ferrocene] dichloropalladium(II) |
| PMB | Para-methoxy benzyl |
| $PPh_3$ | Triphenyl phosphine |
| RT | Room temperature |
| RT | Retention time |
| RuPhos | 2-Dicyclohexylphosphino-2',6'-di-iso-propoxy-1,1'-biphenyl |
| RuPhos Pd G1 | Chloro-(2-Dicyclohexylphosphino-2',6'-diisopropoxy-1,1'-biphenyl)[2-(2-aminoethyl)phenyl]palladium(II) |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| SCX | Strong Cation Exchange |
| SFC | Supercritical Fluid |
| TFA | Trifluoroacetic acid |
| TFAA | Trifluoroacetic anhydride |
| THF | Tetrahydrofuran |
| XPhos PdG2 | Chloro(2-dicyclohexylphosphino-2',4',6'-triisopropyl-1,1'-biphenyl)[2-(2'-amino-1,1'-biphenyl)]palladium(II) |

Compounds

Provided herein is a compound of formula I:

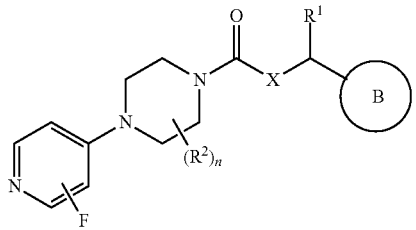

or a deuterated analog, pharmaceutically acceptable salt, solvate, prodrug, stereoisomer, or mixture of stereoisomers thereof, wherein:
  ring B is a 6-10 membered aryl or 6-10 membered heteroaryl ring, wherein ring B is optionally substituted with 1-5 $R^4$;
  X is —O— or —N($R^3$)—;
  $R^1$ is H or optionally substituted $C_{1-3}$ alkyl;
  $R^2$ is oxo, halo, $C_{1-3}$ alkyl, $C_{1-3}$ haloalkyl, $C_{1-3}$ hydroxyalkyl, or $C_{1-3}$ alkoxy; or
  two $R^2$, together with the carbon atoms to which they are attached, join together to form a cycloalkyl or heterocycloalkyl ring;
  $R^3$ is H or $C_{1-3}$ alkyl; or
  $R^2$ and $R^3$, together with the atoms to which they are attached, join together to form a cycloalkyl or heterocycloalkyl ring;
  each $R^4$ is independently halo, $C_{1-3}$ alkyl, $C_{1-3}$ alkoxy, or $C_{1-3}$ haloalkoxy; or
  two $R^4$, together with the atoms to which they are attached, join together to form a heterocycloalkyl ring, wherein the heterocycloalkyl ring is optionally substituted with 1-3 halo or $C_{1-3}$ alkyl; and
  n is 0, 1, or 2.

In some embodiments, provided herein is a compound of formula Ia:

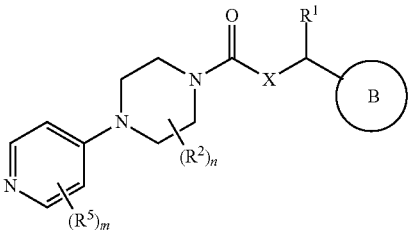

or a deuterated analog, pharmaceutically acceptable salt, solvate, prodrug, stereoisomer, or mixture of stereoisomers thereof, wherein:
  ring B is a 6-10 membered aryl or 6-10 membered heteroaryl ring, wherein ring B is optionally substituted with 1-5 $R^4$;
  X is —O— or —N($R^3$)—;
  $R^1$ is H or optionally substituted $C_{1-3}$ alkyl;
  $R^2$ is oxo, halo, $C_{1-3}$ alkyl, $C_{1-3}$ haloalkyl, $C_{1-3}$ hydroxyalkyl, or $C_{1-3}$ alkoxy; or
  two $R^2$, together with the carbon atoms to which they are attached, join together to form a cycloalkyl or heterocycloalkyl ring;

$R^3$ is H or $C_{1-3}$ alkyl; or $R^2$ and $R^3$, together with the atoms to which they are attached, join together to form a cycloalkyl or heterocycloalkyl ring;

each $R^4$ is independently halo, $C_{1-3}$ alkyl, $C_{1-3}$ alkoxy, or $C_{1-3}$ haloalkoxy; or two $R^4$, together with the atoms to which they are attached, join together to form a heterocycloalkyl ring, wherein the heterocycloalkyl ring is optionally substituted with 1-3 halo or $C_{1-3}$ alkyl;

each $R^5$ is independently halo;

m is 1 or 2; and n is 0, 1, or 2.

In some embodiments, the compound of formula I is a compound of formula II:

II

In some embodiments, the compound of formula I is a compound of formula II(a):

II(a)

where p is 0, 1, or 2.

In some embodiments, n is 0.

In some embodiments, n is 1, and $R^2$ is methyl.

In some embodiments, n is 2, and each $R^2$ is methyl.

In some embodiments, the compound of formula I is a compound of formula III:

III

In some embodiments, the compound of formula I is a compound of formula III(a):

III(a)

In some embodiments, the compound of formula I is a compound of formula III(b):

III(b)

In some embodiments, the compound of formula I is a compound of formula IV(a):

IV(a)

and $R^1$ is optionally substituted $C_{1-3}$ alkyl.

In some embodiments, the compound of formula I is a compound of formula IV(b):

IV(b)

and $R^1$ is optionally substituted $C_{1-3}$ alkyl.

In some embodiments, the compound of formula I is a compound of formula IV(c):

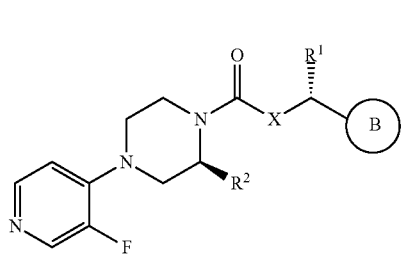

IV(c)

and R¹ is optionally substituted $C_{1-3}$ alkyl.

In some embodiments, the compound of formula I is a compound of formula IV(d):

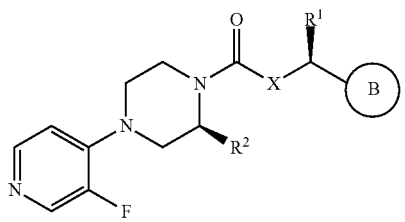

IV(d)

and R¹ is optionally substituted $C_{1-3}$ alkyl.

In some embodiments, the compound of formula I is a compound of formula V:

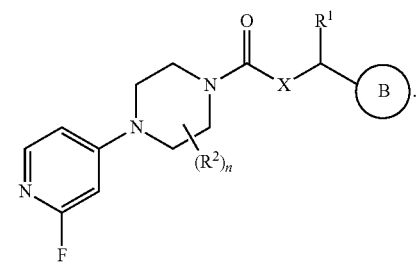

V

In some embodiments, the compound of formula I is a compound of formula V(a):

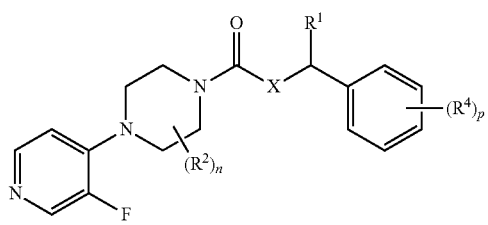

V(a)

where p is 0, 1, or 2.

In some embodiments, the compound of formula I is a compound of formula V(b):

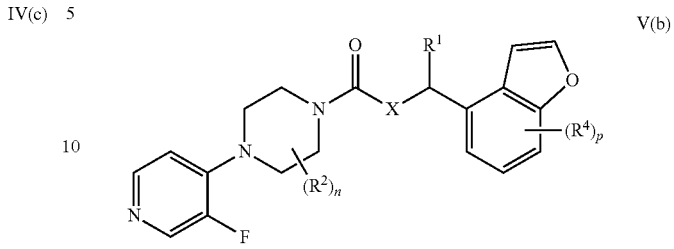

V(b)

where p is 0, 1, or 2.

In some embodiments, the compound of formula I is a compound of formula V(c):

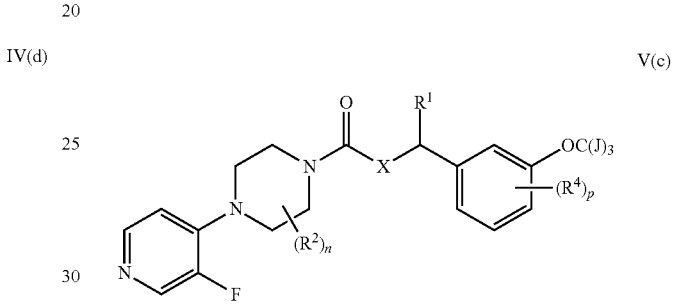

V(c)

where each J is independently H, D, or F, and p is 0, 1, or 2. In some embodiments of formula V(c), each J is H.

In some embodiments, the compound of formula I is a compound of formula V(d):

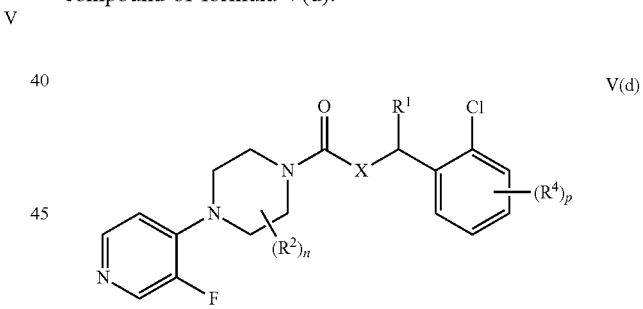

V(d)

where p is 0, 1, or 2.

In some embodiments, the compound of formula I is a compound of formula

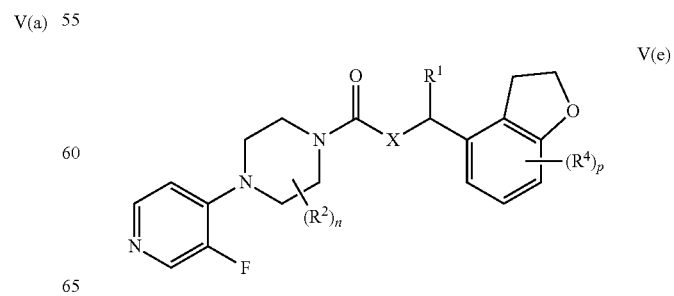

V(e)

where p is 0, 1, or 2.

In some embodiments, the compound of formula I is a compound of formula V(f):

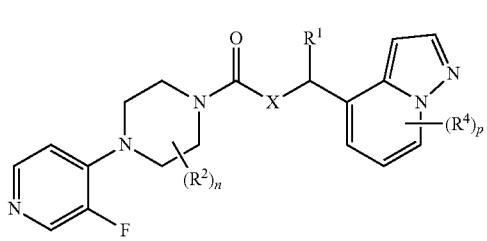

V(f)

where p is 0, 1, or 2.

In some embodiments, X is —N(R$^3$)—.

In some embodiments, R$^3$ is H.

In some embodiments, R$^1$ is H. In some embodiments, R$^1$ is optionally substituted C$_{1-3}$ alkyl. In some embodiments, R$^1$ is H, methyl or CD$_3$. In some embodiments, R$^1$ is methyl.

In some embodiments, R$^2$ is halo, C$_{1-3}$ alkyl, C$_{1-3}$ haloalkyl, C$_{1-3}$ hydroxyalkyl, or C$_{1-3}$ alkoxy. In some embodiments, R$^2$ is C$_{1-3}$ alkyl, C$_{1-3}$ haloalkyl, or C$_{1-3}$ alkoxy. In some embodiments, R$^2$ is C$_{1-3}$ alkyl. In some embodiments, R$^2$ is methyl.

In some embodiments, two R$^2$, together with the carbon atoms to which they are attached, join together to form a cyclopropyl. In some embodiments, two R$^2$ join together to form a bridging methylene.

In some embodiments, R$^1$ is methyl and R$^2$ is methyl.

In some embodiments, X is —N(R$^3$)— and R$^2$ and R$^3$, together with the atoms to which they are attached, join together to form a 5- or 6-membered unsubstituted cycloalkyl ring.

In some embodiments, ring B is a 6-10 membered aryl optionally substituted with 1 to 3 substituents selected from halo, C$_{1-3}$ alkyl, C$_{1-3}$ alkoxy, and C$_{1-3}$ haloalkoxy; or two R$^4$, together with the atoms to which they are attached, join together to form a heterocycloalkyl ring. In some embodiments, ring B is phenyl optionally substituted with 1 to 3 substituents selected from halo, C$_{1-3}$ alkyl, C$_{1-6}$ alkoxy, and C$_{1-3}$ haloalkoxy. In some embodiments, ring B is phenyl substituted with 1 substituent selected from halo, C$_{1-6}$ alkyl, C$_{1-6}$ alkoxy, and C$_{1-3}$ haloalkoxy.

In some embodiments, ring B is phenyl and two R$^4$, together with the atoms to which they are attached, join together to form a heterocycloalkyl ring.

In some embodiments, ring B is a 6-10 membered heteroaryl optionally substituted with 1 to 3 substituents selected from halo, C$_{1-3}$ alkyl, C$_{1-6}$ alkoxy, and C$_{1-3}$ haloalkoxy.

In some embodiments, X is —N(H)—. In some embodiments, X is O.

In some embodiments, R$^4$ is selected from F, Cl, Br, methyl, CD$_3$, methoxy, OCD$_3$, and OCHF$_2$.

In some embodiments, each R$^5$ is independently selected from Cl and F. In some embodiments, each R$^5$ is F.

In some embodiments, m is 1 and R$^5$ is F.

In some embodiments, provided is a compound selected from those in described in the Examples section provided herein.

In some embodiments, provided is a pharmaceutical composition comprising a compound provided herein and a pharmaceutically acceptable carrier.

Treatment Methods and Uses

The compounds disclosed herein are useful for treating or preventing conditions or disorders mediated, at least in part, by ROCK. Treatments for such conditions may be in the form of oral preparations, intravenous injections, topical agents, suppositories, direct injection into tissue of interest, and other delivery methods. Treatments may include coadministration of compounds described herein and other therapeutic agents and/or pharmaceutically acceptable vehicles.

In some embodiments, provided is a method of treating or preventing a condition or disorder mediated, at least in part, by ROCK in a patient in need thereof, comprising administering to the patient a therapeutically effective amount of a compound or a pharmaceutical composition provided herein.

Exemplary conditions or disorders mediated, at least in part, by ROCK are as follows.

Huntington's Disease (HD)

ROCK signaling components are reported to be elevated in brain and blood cellular components from HD patients. Correspondingly, identification of primary and secondary sets of proteins that interact with huntingtin (HTT) led to identification of Rho GTPase signaling components that act as modifiers of mutant HTT (mHTT) toxicity. Additionally, sequential network interaction filtering applied over known and novel HTT interactors identify ROCK1 as HTT interactor, suggesting that altered levels of ROCK in HD might play a role in the pathogenesis of the disease.

Treatment of cell cultures expressing poly-glutamine fragments (as in mutated HTT) with increased expression of the ROCK-downstream protein profilin or ROCK inhibitors leads to decreased mHTT aggregation.

Oral administration of the ROCK inhibitor Y27632 to the R6/2 mouse model of HD reduces levels of mutant huntingtin and improves motor performance. Intravitreal administration of the ROCK inhibitor HA-1077 (Fasudil) improves electroretinogram responses and decreases retinal neuropathology in the R6/2 mouse model of HD.

Spinal Cord and Brain Injury

Intrathecal administration of the ROCK inhibitor Y27632 after cervical-level dorsal column transection in rats evoked more numerous axonal sprouting and improved motor performance than vehicle.

Chronic Pulmonary Hypertension

Subcutaneous injection of the ROCK inhibitor Y27632 in hypoxia-exposed rats attenuated right ventricular hypertrophy and normalized right ventricular systolic function.

Parkinson's Disease

Administration of the ROCK inhibitor Fasudil decreases molecular, neuropathological (dopamine cell loss, α-synuclein accumulation), and behavioral defects in the lipopolysaccharide (LPS)-induced model of Parkinson's disease (PD).

Cultured neurons exposed to the MPTP metabolite MPP+ under treatment with Fasudil exhibited higher survival and neurite length. Correspondingly, in MPTP treated animals, treatment with Fasudil increased the number of TH neurons, improved striatal innervation by dopaminergic fibers, and increased motor performance.

Amyotrophic Lateral Sclerosis

In vitro exposure of cultured primary motorneurons to the ROCK inhibitor Y27632 improved survival and increased neurite length. In vivo oral administration of Y27632 to the SOD1$^{G93A}$ mouse model of ALS improved motor function in male mice. In vitro application of the ROCK inhibitor Fasudil to kainic acid-lesioned cultured motorneurons increased survival. In vivo treatment of the SOD1$^{G93A}$ mouse model of ALS with the ROCK inhibitor Fasudil increased their survival and improved motor function. Additionally, treated animals exhibited increased survival of motorneurons and modulated spinal cord glial infiltration.

Cerebral Cavernous Malformation

Brain tissue from cerebral cavernous malformation (CCM) patients exhibited increased ROCK signaling. The Ccm1+/− and Ccm2+/− models of CCM exhibit increased ROCK signaling, and interaction of CCMs with ROCK is critical to modulate vascular leak. The ROCK inhibitor Fasudil reverses vascular leak in these animal models.

ROCK inhibition seems to have a disease-modifying effect, as Ccm1+/−Msh2−/− mouse model of CCM treated since weaning to 5 months of age with Fasudil exhibited decreased prevalence of lesions. This indicates that ROCK activation plays a role in the pathogenesis of CCM.

Fasudil treatment decreases iron deposition in the late stages, and increased survival in the Ccm+/−Msh2−/− mouse model of CCM.

Cardiovascular Disease

ROCK pathway activation is elevated in coronary artery disease (CAD) patients, as demonstrated by increased levels of phosphorylation of myosin light chain (MLC). Oral administration of the ROCK inhibitor Fasudil exerted beneficial effects by increasing flow-mediated vasodilation in CAD patients although not in healthy volunteers.

In a Phase 2 clinical trial with a ROCK inhibitor for stable angina, Fasudil increased ischemic threshold for angina by increasing exercise duration, as compared to the ones taking placebo.

Utilizing the deoxycorticosterone acetate (DOCA)-salt hypertensive rat model of high blood pressure (HBP), it was demonstrated that ROCK activation (as well as IP3 signaling) are involved in parallel in the arterial tone development in the DOCA model. Also, ROCK2 polymorphism has been identified as influencer of the increase in systemic vascular resistance and altered responsiveness to the renin/angiotensin system, leading to high blood pressure.

Rats with cardiac hypertrophy induced by suprarenal abdominal aortic constriction underwent treatment with the ROCK inhibitor GSK-576371, which decreased left ventricle thickness and collagen deposition.

Alzheimer's Disease (AD)

Altered ROCK signaling pathway has been reported in different cellular and animal models of the disease, although several times exhibiting changes in a biphasic manner, dependent on age, brain region or subcellular compartment.

ROCK protein levels and activation of its signaling pathway is enhanced in brain of patients with mild cognitive impairment and Alzheimer's disease. Correspondingly, decreasing ROCK1 expression through RNAi treatment in primary cortical neurons reduced amyloid β levels.

Intracranial injection of ROCK-II siRNA in the senescence-accelerated mouse model of AD resulted in an increase in the number of hippocampal cholinergic (ChAT+) neurons, as well as in shorter escape latencies and reduced mean swimming distance in the Morris water maze (MWW) test. Altogether, these suggest that ROCK inhibition might play a beneficial role at the histopathological as well as behavioral levels of recovery in AD.

Glaucoma

The ROCK inhibitor Y27632 inhibits carbachol-induced contraction of ciliary muscle strips, as well as rounding of cell bodies and disruption of actin bundles and focal adhesion formation in cultured human trabecular mesh cells. In vivo topical, intracameral or intravitreal administration of the same inhibitor to rabbit eyes resulted in decreased intraocular pressure, increased outflow, and pupil dilation.

Topical administration of the dual ROCK and LIMK inhibitor LX7101 to dexamethasone induced ocular hypertensive mice reduced intraocular pressure to even lower levels than current therapeutic options timolol and latanoprost.

The effect of the ROCK inhibitor Ripasudil on open-angle glaucoma and ocular hypertension was tested through a multicenter, randomized, open label, crossover study. Significant intraocular pressure reduction was detected from 1 through 7 hours after instillation.

Multiple Sclerosis (MS)

Increased ROCK signaling activity was detected in serum from MS patients, as compared to healthy volunteer controls. Similarly, enhanced ROCK activity was detected in the autoimmune encephalomyelitis (EAE) mouse model of MS. MS serum-induced damage of synaptic formation in cultured primary neurons was rescued by treatment with the ROCK inhibitor Fasudil, which recovered cell viability as well as neurite length.

Behavioral rescue of EAE induced in mice was obtained by in vivo intraperitoneal treatment with either Fasudil or the Y27632 derivative WAR-5. WAR-5 treatment also decreased ROCK activity in brain, spinal cord, spleen; ameliorated spinal cord demyelination, and reduced inflammatory response and infiltration.

Intranasal delivery of the Fasudil derivative FSD-C10 to the EAE mouse model of MS decreased ROCK activation in spinal cord and spleen (although not significantly in brain). Treatment also decreased spinal cord inflammatory response and infiltration, as well as behavioral impairment, while increasing the expression of neurotrophic markers BDNF and NGF.

Corneal Lesions

Six times a day, seven day long topical application of the ROCK inhibitor Y27632 to wounded primate retinas by freezing, demonstrated a beneficial effect consistent in recovery of the corneal endothelium with more zonula occludens 1 and Na/K ATPase expression, as well as a higher density of corneal endothelium cells. A similar treatment scheme was followed in four patients with central corneal edema and four patients with diffuse corneal edema. Beneficial reduction in corneal thickness and ongoing remodeling was confirmed, although no significant increase in visual acuity was detected.

Treatment of organ culture human cornea with Y27632 demonstrated that cell viability was not compromised and cell proliferation was not evoked by treatment. Importantly, no toxicity was detected, and treatment promoted enhanced adhesion and wound healing.

Diabetes

ROCK activity is enhanced in kidney cortices of the db/db mouse model of diabetes. The effect of ROCK inhibition on diabetic profile and nephropathy was assessed by a 16-long intraperitoneal administration of Fasudil which led to a range of beneficial changes, some of them comparable to the effect of simvastatin, including decreased urinary albumin and collagen IV excretion, reduction in mesangial matrix and in glomerular basement membrane thickness.

The streptozotocin-induced diabetes rat model was used to assess ROCK inhibition as potential modulator of diabetic microvascular retinopathy. Both activated Rho-GTP and phosphorylated MYPT1 were elevated in retinas from diabetic rats. Intravitreal injections of Fasudil every three days for two weeks ameliorated the impact of neutrophils on retinal endothelial cells, reducing the number of dead or injured cells.

A borderline significant increase in ROCK-I and ROCK-II is present in the myocardial tissue of the streptozocin-induced rat model of diabetes. Coronary vasculature responded to Fasudil (IV administration) with greater vasodilation than controls, and additionally reduced the incidence of segmental constrictions. These results altogether show that ROCK inhibition promotes enhanced perfusion in the early diabetic heart.

Chronic and Neuropathic Pain

The effect of the ROCK inhibitor AS1892802 was tested on the monoiodoacetate-induced arthritis and streptozotocin-induced neuropathy rat models. While single oral doses did exhibit only slight and short duration effects, repeated dosing induced enhanced long-lasting analgesic effects in both models.

Intrathecal administration of the ROCK inhibitor H-1152 had a beneficial effect by decreasing neuropathic pain induced by L5 spinal nerve transection, and by decreasing the magnitude of the second phase of pain in the formalin-induced model of inflammatory pain.

Stroke & Ischemia

Partial hepatic ischemia for 2 hours was performed in rats, followed by reperfusion. Pretreatment with the ROCK inhibitor Y27632 by oral administration led to increase in survival of 75% at one week after ischemia, compared to 25% in the vehicle-treated animals. Correspondingly, treated animals also exhibited higher hepatic tissue blood flow post-ischemia, reduction in sinusoidal derangement and in necrosis, as well as improved liver function compared to controls. Thus, ROCK inhibition pretreatment plays a protective role in hepatic ischemia/reperfusion.

Ischemia reperfusion modeled by middle cerebral artery occlusion in rats was utilized to test the effect of pretreatment with ROCK inhibitors 2 days before induced ischemia. Pretreatment with either Fasudil or Y27632 resulted in reduction of infarct volume, restoration of eNOS levels, and improved neurological score, indicating that ROCK inhibition might be beneficial for the management of cerebral ischemic events.

Animal models of stroke suggest that ROCK activation constitutes a pathogenic factor in stroke. Blood samples collected from patients who suffered acute ischemic stroke within 24 hours of the event showed that ROCK signaling is enhanced in leukocytes, peaking at 48 hours from the event. In vitro treatment of leukocytes with the ROCK inhibitor Fasudil led to decreased ROCK signaling, indicating that enhanced ROCK signaling is common to stroke in humans and to animal models.

Retinopathy

In vivo intravitreal administration of the ROCK inhibitor AMA0428 to the laser-induced choroidal neovascularization (CNV) mouse model of macular degeneration showed several beneficial effects preventing inflammatory response, reducing angiogenesis, vessel leakage, fibrosis and choroidal neovascularization area.

Spinal Muscular Atrophy (SMA)

Mutations or deletions of the gene survival motor neuron 1 (SMN1) gene cause SMA. Smn depletion in mice evokes increased activation of RhoA, which prompted the use of ROCK inhibition as a potential therapeutic strategy. Lifespan, neuromuscular junction (NMJ) size, NMJ with mature terminals, and muscle histopathology were modified beneficially in the Smn2B/+ mouse model of SMA in response to in vivo administration of the ROCK inhibitor Y27632.

Oral dosing of Fasudil resulted in improved survival, increase in muscle fiber size and in postsynaptic endplate size in the Smn2B/+ mouse model of SMA.

Erectile Dysfunction

The effect of chronic exposure to Fasudil in a vasculogenic erectile dysfunction rat model was tested. 6-week long treatment with Fasudil led to beneficial effects consisting of decreased pelvic atherosclerosis, lower plasma level of von Willebrand factor (indicator of endothelial injury), normalized ROCK activation, rescued eNOS expression and erectile function.

Nephropathy (Non-Hypertensive)

In the puromycin-induced mouse model of nephrosis, treatment with the ROCK inhibitor Y-27632 improved renal function and histopathology, demonstrating that the beneficial effect of ROCK inhibition on nephropathy is not exclusively related to its effect on systemic blood pressure.

Hypertensive Nephropathy

In subtotally nephrectomized spontaneously hypertensive rats, treatment with the ROCK inhibitor Fasudil did not have an effect on systolic blood pressure but improved the profile of urinary protein excretion, and ameliorated the histologic profile of nephropathy.

Hypertension (High Blood Pressure)

Administration of the ROCK inhibitor Y-27632 to three different models of hypertension in rats (spontaneous hypertensive, renal hypertensive, and DOCA-salt hypertensive) reduced blood pressure at a higher rate than in control rats.

Optic Nerve Lesion

The ROCK inhibitor Y-27632 dose-dependently increased retinal ganglion cell regeneration in the rat optic nerve crush model. Another RICK inhibitor, dimethylfasudil, showed a trend towards a similar effect in an intermediate concentration. Similar positive results were reported after applying the ROCK inhibitor Y-39983 in the vitreous and crushed cat optic nerve.

Hepatic Fibrosis

Utilizing the rat model of hepatic fibrosis induced by dimethylnitrosamine, it was demonstrated that oral administration of the ROCK inhibitor Y-27632 reduced not only the levels of molecular markers of hepatic damage, but also the occurrence of hepatic fibrosis.

Lupus

Peripheral blood mononuclear cells from systemic lupus erythematosus exhibited higher levels of ROCK activity, which were also correlated with disease severity indicators. Treatment with the ROCK inhibitor Fasudil improved survival, renal function and immune profile in the NZB/W F1 female mouse model of lupus, in a similar way to what had been reported in the MRL/lpr mouse model of lupus.

Liver Failure after Transplant

Treatment of both donor and recipient rats with the ROCK inhibitor Y-27632 evoked improved survival of recipients, as well as lower levels of AST and ALT aminotransferases and reduced necrosis.

Encephalomyelitis

The ROCK inhibitor and Fasudil derivative FaD-1 ameliorated neurological impairment, reduced demyelination and neuroinflammation in the myelin oligodendrocyte glycoprotein (MOG 35-55) immunization-induced mouse model of encephalomyelitis.

Epilepsy

ROCK inhibitors Y-27632 and Fasudil decreased myoclonus, clonic and tonic convulsions in kindling models of epilepsy.

Glioblastoma

Intravenous Fasudil restricted dispersion of inoculated eGFP-T98G glioblastoma cells into mice striatum, and increased animal survival.

In some embodiments, the condition or disorder is selected from Huntington's disease (HD), spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

In some embodiments, the condition or disorder is Huntington's disease.

Pharmaceutical Compositions and Modes of Administration

In some embodiments, a compound, or a deuterated analog, pharmaceutically acceptable salt, solvate, prodrug, stereoisomer, or mixture of stereoisomers thereof, described herein is administered as a pharmaceutical composition. Accordingly, provided are pharmaceutical compositions comprising at least one compound, or a deuterated analog, pharmaceutically acceptable salt, solvate, prodrug, stereoisomer, or mixture of stereoisomers thereof, described herein, together with at least one pharmaceutically acceptable vehicle chosen from carriers, adjuvants, and excipients. A compound of the present disclosure can be formulated into pharmaceutical compositions using techniques well known to those in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or a deuterated analog, pharmaceutically acceptable salt, solvate, prodrug, stereoisomer, or mixture of stereoisomers thereof, is sufficient to provide a practical quantity of material for administration per unit dose of the compound, or a deuterated analog, pharmaceutically acceptable salt, solvate, prodrug, stereoisomer, or mixture of stereoisomers thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or a deuterated analog, pharmaceutically acceptable salt, solvate, prodrug, stereoisomer, or mixture of stereoisomers thereof, described herein.

Effective concentrations of at least one compound, or a deuterated analog, pharmaceutically acceptable salt, solvate, prodrug, stereoisomer, or mixture of stereoisomers thereof, described herein are mixed with a suitable pharmaceutically acceptable vehicle. In instances in which the compound, or a deuterated analog, pharmaceutically acceptable salt, solvate, prodrug, stereoisomer, or mixture of stereoisomers thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of a compound, or a deuterated analog, pharmaceutically acceptable salt, solvate, prodrug, stereoisomer, or mixture of stereoisomers thereof, described herein, the resulting mixture may be a solution, suspension, emulsion or the like. The form of the resulting mixture depends upon a number of factors, including the intended mode of administration and the solubility of the compound, or a deuterated analog, pharmaceutically acceptable salt, solvate, prodrug, stereoisomer, or mixture of stereoisomers thereof, in the chosen vehicle. The effective concentration sufficient for ameliorating the symptoms of the disease treated may be empirically determined.

A compound, or a deuterated analog, pharmaceutically acceptable salt, solvate, prodrug, stereoisomer, or mixture of stereoisomers thereof, described herein may be administered orally, topically, parenterally, intravenously, by intramuscular injection, by inhalation or spray, sublingually, transdermally, via buccal administration, rectally, as an ophthalmic solution, intravitreally, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, a deuterated analog, pharmaceutically acceptable salt, solvate, prodrug, stereoisomer, or mixture of stereoisomers thereof, described herein. In some embodiments, oral pharmaceutical compositions contain at least 5% (weight %) of at least one compound, or a deuterated analog, pharmaceutically acceptable salt, solvate, prodrug, stereoisomer, or mixture of stereoisomers thereof, described herein. Some embodiments contain from 25% to 50% or from 5% to 75% of at least one compound, or a deuterated analog, pharmaceutically acceptable salt, solvate, prodrug, stereoisomer, or mixture of stereoisomers thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or a deuterated analog, pharmaceutically acceptable salt, solvate, prodrug, stereoisomer, or mixture of stereoisomers thereof, described herein can be incorporated into oral liquid preparations such as aqueous or oily suspensions, solutions, emulsions, syrups, or elixirs, for example. Furthermore, pharmaceutical compositions containing the compound, or a deuterated analog, pharmaceutically acceptable salt, solvate, prodrug, stereoisomer, or mixture of stereoisomers thereof, described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or a deuterated analog, pharmaceutically acceptable salt, solvate, prodrug, stereoisomer, or mixture of stereoisomers thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or a deuterated analog, pharmaceutically acceptable salt, solvate, prodrug, stereoisomer, or mixture of stereoisomers thereof, described herein may be administered parenterally in a sterile medium. Parenteral administration includes subcutaneous injections, intravenous, intramuscular, intrathecal injection or infusion techniques. The compound, or a deuterated analog, pharmaceutically acceptable salt, solvate, prodrug, stereoisomer, or mixture of stereoisomers thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or a deuterated analog, pharmaceutically acceptable salt, solvate, prodrug, stereoisomer, or mixture of stereoisomers thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or a deuterated analog, pharmaceutically acceptable salt, solvate, prodrug, stereoisomer, or mixture of stereoisomers thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or a deuterated analog, pharmaceutically acceptable salt, solvate, prodrug, stereoisomer, or mixture of stereoisomers thereof, described herein may also be formulated for transdermal administration as a transdermal patch.

Topical pharmaceutical compositions comprising at least one compound, or a deuterated analog, pharmaceutically acceptable salt, solvate, prodrug, stereoisomer, or mixture of stereoisomers thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

The compound, or a deuterated analog, pharmaceutically acceptable salt, solvate, prodrug, stereoisomer, or mixture of stereoisomers thereof, described herein may also be administered in a liposome delivery system. Liposomes may be classified as small unilamellar vesicles, large unilamellar vesicles, and multilamellar vesicles. Liposomes can be formed from a variety of amphipathic molecules, in particular phospholipids. Constituents of liposomes may include cholesterol, stearylamine and/or phosphatidylcholines. Liposomes are suitable for various routes of administration including topical and injection into various tissues. Thus, intravitreal (e.g., in treatment of glaucoma), intraperitoneal, intravenous, intravascular, intraarticular, and intramuscular administration of liposomes is contemplated.

Other pharmaceutical compositions useful for attaining systemic delivery of the compound, or a deuterated analog, pharmaceutically acceptable salt, solvate, prodrug, stereoisomer, or mixture of stereoisomers thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or a deuterated analog, pharmaceutically acceptable salt, solvate, prodrug, stereoisomer, or mixture of stereoisomers thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or a deuterated analog, pharmaceutically acceptable salt, solvate, prodrug, stereoisomer, or mixture of stereoisomers thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Packages

Also provided are packaged pharmaceutical compositions. Such packaged compositions include a pharmaceutical composition comprising at least one compound, or a deuterated analog, pharmaceutically acceptable salt, solvate, prodrug, stereoisomer, or mixture of stereoisomers thereof, described herein, and instructions for using the composition to treat a subject (typically a human patient). In some embodiments, the instructions are for using the pharmaceutical composition to treat a subject suffering a condition or disorder mediated by ROCK. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or a deuterated analog, pharmaceutically acceptable salt, solvate, prodrug, stereoisomer, or mixture of stereoisomers thereof, can be administered alone, as mixtures, or in combination with other active agents.

Combination Therapy

The methods described herein include methods for treating or preventing Huntington's disease, including treating loss of motor control, psychiatric symptoms, memory and/or cognitive impairment associated with Huntington's disease, comprising administering to a subject, simultaneously or sequentially, at least one compound, or a deuterated analog, pharmaceutically acceptable salt, solvate, prodrug, stereoisomer, or mixture of stereoisomers thereof, described herein and one or more additional agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In methods using simultaneous administration, the agents can be present in a combined composition or can be administered separately. As a result, also provided are pharmaceutical compositions comprising at least one compound, or a deuterated analog, pharmaceutically acceptable salt, solvate, prodrug, stereoisomer, or mixture of stereoisomers thereof, described herein and one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided are packaged pharmaceutical compositions containing a pharmaceutical composition comprising at least one compound, or a deuterated analog, pharmaceutically acceptable salt, solvate, prodrug, stereoisomer, or mixture of stereoisomers thereof, described herein, and another composition comprising one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone.

Also provided are methods for treating or preventing Alzheimer's disease, including treating memory and/or cognitive impairment associated with Alzheimer's disease, comprising administering to a subject, simultaneously or sequentially, at least one compound, or a deuterated analog, pharmaceutically acceptable salt, solvate, prodrug, stereoisomer, or mixture of stereoisomers thereof, described herein and one or more additional agents used in the treatment of Alzheimer's disease such as, but not limited to, Reminyl®, Cognex®, Aricept®, Exelon®, Akatinol®, Neotropin™, Eldepryl®, Estrogen and Clioquinol. In methods using simultaneous administration, the agents can be present in a combined composition or can be administered separately. Also provided are pharmaceutical compositions comprising at least one compound, or a deuterated analog, pharmaceutically acceptable salt, solvate, prodrug, stereoisomer, or mixture of stereoisomers thereof, described herein, and one or more additional pharmaceutical agents used in the treatment of Alzheimer's disease such as, but not limited to, Reminyl®, Cognex®, Aricept®, Exelon®, Akatinol®, Neotropin™, Eldepryl®, Estrogen and Clioquinol. Similarly, also provided are packaged pharmaceutical compositions containing a pharmaceutical composition comprising at least one compound, or a deuterated analog, pharmaceutically acceptable salt, solvate, prodrug, stereoisomer, or mixture of stereoisomers thereof, described herein, and another composition comprising one or more additional pharmaceutical agents used in the treatment of Alzheimer's disease such as, but not limited to Reminyl®, Cognex®, Aricept®, Exelon®, Akatinol®, Neotropin™, Eldepryl®, Estrogen and Clioquinol.

In methods using simultaneous administration, the agents can be present in a combined composition or can be administered separately. Also provided are pharmaceutical compositions comprising at least one compound, or a deuterated analog, pharmaceutically acceptable salt, solvate, prodrug, stereoisomer, or mixture of stereoisomers thereof, described herein, and one or more anti-tumor agent as described herein. Similarly, also provided are packaged pharmaceutical compositions containing a pharmaceutical composition comprising at least one compound, or a deuterated analog, pharmaceutically acceptable salt, solvate, prodrug, stereoisomer, or mixture of stereoisomers thereof, described herein, and another composition comprising one or more one or more anti-tumor agent as described herein. When used in combination with one or more additional pharmaceutical agent or agents, the compounds described herein may be administered prior to, concurrently with, or following administration of the additional pharmaceutical agent or agents.

Dosing

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or a deuterated analog, pharmaceutically acceptable salt, solvate, prodrug, stereoisomer, or mixture of stereoisomers thereof, described herein is typically administered at dosage levels and in a manner customary for ROCK inhibitors. For example, the compound, or a deuterated analog, pharmaceutically acceptable salt, solvate, prodrug, stereoisomer, or mixture of stereoisomers thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or a deuterated analog, pharmaceutically acceptable salt, solvate, prodrug, stereoisomer, or mixture of stereoisomers thereof, described herein, for example, 0.1-50 mg of at least one compound, or a deuterated analog, pharmaceutically acceptable salt, solvate, prodrug, stereoisomer, or mixture of stereoisomers thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or a deuterated analog, pharmaceutically acceptable salt, solvate, prodrug, stereoisomer, or mixture of stereoisomers thereof, described herein.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Compounds were named with the aid of the Cambridgesoft Chemistry Cartridge (v. 16.0.0.82) software.

Analytical Methods

Analytical Method 1:

| | |
|---|---|
| Instrumentation | UPLC + Waters DAD + Waters SQD2, single quadrapole UPLC-MS |
| MassLynx Files | |
| Column | Acquity UPLC HSS C18 1.8 µm 100 × 2.1 mm. (Plus guard cartridge), maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.5 mL/min |

| Gradient Program | Time (mins) | % A | % B |
|---|---|---|---|
| | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

| | |
|---|---|
| Sample | 0.5-2 µL (concentration ~0.2-1 mg/mL). |
| Detectors | UV, diode array 210 nm-400 nm Resolution 1.2 nm Other wavelength traces are extracted from the DAD data MS, mass 100-700 (or ~1500 for HM method) in ES+ & ES− (300 µL/min split to MS) |

Analytical Method 2:

| Instrumentation | UPLC + Waters DAD + Waters SQD2, single quadrapole UPLC-MS |
|---|---|
| MassLynx Files | |
| Column | Acquity UPLC BEH Shield RP18 1.7 µm 100 × 2.1 mm. (Plus guard cartridge), maintained at temp |
| Mobile Phase A | Water (High purity via PureLab Option unit) with 10 mM ammonium bicarbonate (ammonium hydrogen carbonate) |
| Mobile Phase B | Acetonitrile (Far UV grade) |
| Flow | 0.5 mL/min |

| Gradient Program | Time (mins) | % A | % B |
|---|---|---|---|
| | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |
| Sample | 0.5-2 µL (concentration ~0.2-1 mg/mL). | | |
| Detectors | UV, diode array 210 nm-400 nm Resolution 1.2 nm Other wavelength traces are extracted from the DAD data MS, mass 100-700 (or ~1500 for HM method) in ES+ & ES− (300 µL/min split to MS) | | |

Analytical Method 3:

| Instrumentation | UPLC + Waters DAD + Waters SQD2, single quadrapole UPLC-MS |
|---|---|
| MassLynx Files | |
| Column | Acquity UPLC HSS C18 1.8 µm 100 × 2.1 mm. (Plus guard cartridge), maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |
| Sample | 0.5-2 µL (concentration ~0.2-1 mg/mL). | | |
| Detectors | UV, diode array 210 nm-400 nm Resolution 1.2 nm Other wavelength traces are extracted from the DAD data MS, mass 100-700 (or ~1500 for HM method) in ES+ & ES− (300 µL/min split to MS) | | |

Analytical Method 4:

| Instrumentation | UPLC + Waters DAD + Waters SQD2, single quadrapole UPLC-MS |
|---|---|
| MassLynx Files | |
| Column | Acquity UPLC BEH Shield RP18 1.7 µm 100 × 2.1 mm. (Plus guard cartridge), maintained at temp |
| Mobile Phase A | Water (High purity via PureLab Option unit) with 10 mM ammonium bicarbonate (ammonium hydrogen carbonate) |
| Mobile Phase B | Acetonitrile (Far UV grade) |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |
| Sample | 0.5-2 µL (concentration ~0.2-1 mg/mL). | | |
| Detectors | UV, diode array 210 nm-400 nm Resolution 1.2 nm Other wavelength traces are extracted from the DAD data MS, mass 100-700 (or ~1500 for HM method) in ES+ & ES− (300 µL/min split to MS) | | |

SFC Method:

Analytical Method SFC1:

| Column | See Specific Method |
|---|---|
| Column Dimensions | 250 × 4.6 mm id 5 µm |
| Mobile Phase | A - $CO_2$ |
| | B - Primary Solvents |
| | B - Secondary Solvents |

| Gradient | Time (min) | % B |
|---|---|---|
| | 0 | 5 |
| | 0.5 | 5 |
| | 3 | 55 |
| | 4.5 | 55 |
| | 4.6 | 5 |
| | 5 | 5 |
| Temperature | 40° C. | |
| Flow Rate | 5.0 mL/min | |
| System Back Pressure | 120 bar | |
| Detector | DAD 210-400 nm | |
| Injection Volume | 5 µL, variable | |
| MS | Electrospray +/− ve ionization | |
| Cone voltage | 25 V | |
| Source Temperature | 150° C. | |
| Mass Range | 100-1000 amu | |
| | Solvents and reagents used are TPLC gradient grade or equivalent | |
| $CO_2$ Grade | 99.995% | |
| B - Primary Solvents | Methanol/Ethanol/Isopropanol | |
| B - Secondary Solvents | Methanol (+0.1% Diethylamine)/ Ethanol (+0.1% Diethylamine)/ Isopropanol (+0.1% Diethylamine) or as specified | |

Analytical Method SFC4:

| Column | See Specific Method |
|---|---|
| Column Dimensions | 150 × 2.1 mm id 5 µm |
| | 100 × 3.0 mm id 1.7 µm |
| Mobile Phase | A - $CO_2$ |
| | B - Primary Solvents |
| | B - Secondary Solvents |

| Gradient | Time (min) | % B |
|---|---|---|
| | 0 | 5 |
| | 0.5 | 5 |
| | 3 | 55 |
| | 4.5 | 55 |
| | 4.6 | 5 |
| | 5 | 5 |
| Temperature | 40° C. | |
| Flow Rate | 0.95 mL/min | |
| System Back Pressure | 120 bar | |
| Detector | DAD 210-400 nm | |
| Injection Volume | 2 µL, variable | |
| MS | Electrospray +/− ve ionization | |
| Cone voltage | 25 V | |
| Source Temperature | 150° C. | |
| Mass Range | 100-1000 amu | |

| Solvents and reagents used are TPLC gradient grade or equivalent |  |
| --- | --- |
| CO$_2$ Grade | 99.995% |
| B - Primary Solvents | Methanol/Ethanol/Isopropanol |
| B - Secondary Solvents | Methanol (+0.1% Diethylamine)/ |
|  | Ethanol (+0.1% Diethylamine)/ |
|  | Isopropanol (+0.1% Diethylamine) |
|  | or as specified |

General Synthetic Methods

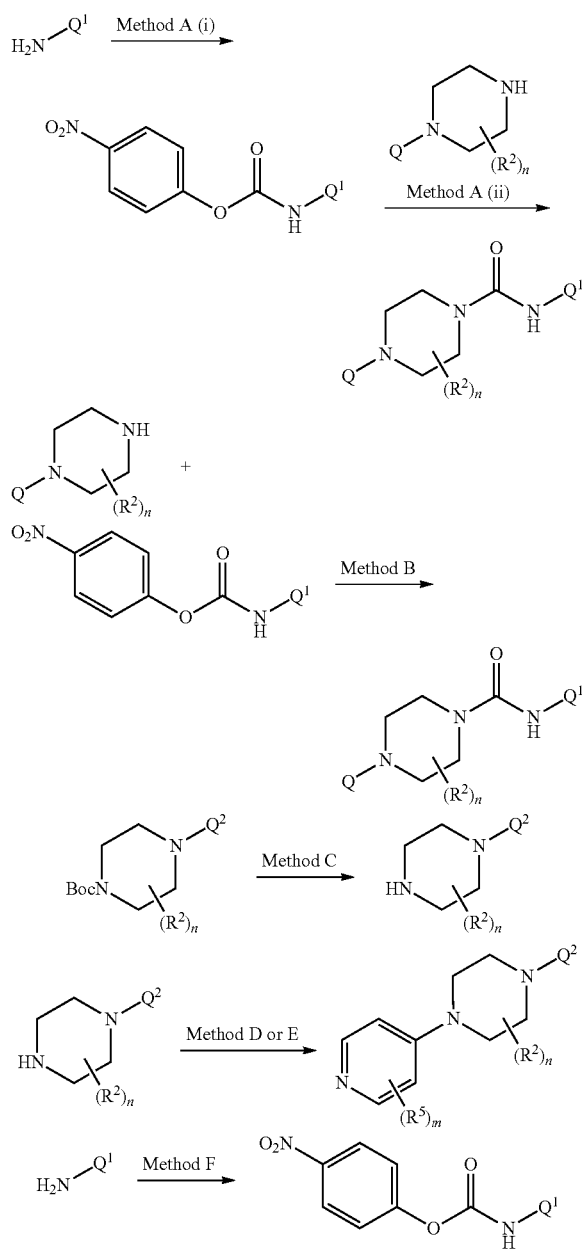

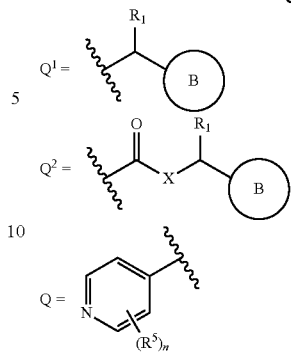

where $R^1$, $R^2$, $R^5$, m, n, X, and ring B are as defined herein.

Method A—Urea Formation (In-Situ Carbamate Generation)

To a stirred solution of 4-nitrophenyl chloroformate (0.5 mmol, 1 eq.) in DCM (2 mL) at r.t. was added a solution of amine (0.5 mmol, 1 eq.) in DCM (1 mL) dropwise and TEA (1-3 eq.). The mixture was stirred at r.t. for 30 min and then a solution of piperazine (0.5 mmol, 1 eq.) in DCM (1 mL) added (additional TEA was added if salt used). The reaction mixture was concentrated.

Method B—Urea Formation

To a stirred solution of activated carbamate (1 eq) in DCM (0.1 M) at r.t. was added piperazine (1.1 eq) and TEA (1-3 eq.). The mixture was stirred at r.t. for 2-17 h. The reaction mixture was washed with H$_2$O and the biphasic mixture passed through a phase separator. The organics were concentrated to dryness.

Method C—Boc-Deprotection

Boc-Piperazine (1 eq) and 4N HCl in dioxane (10 eq.) were combined and stirred for 35 mins-24 h. Reaction mixture was then evaporated to dryness and used directly in next step.

Method D—S$_N$Ar Coupling

A solution of piperazine (1 eq.), fluorinated heterocycle (1 eq.) and Cs$_2$CO$_3$ (1 eq.) in anhydrous DMF (0.1 M) was stirred at 80° C. for 2-17 h. The reaction was then diluted with EtOAc, washed with water (2×), dried (MgSO$_4$) and evaporated to dryness.

Method E—Buchwald Coupling

A mixture of brominated pyridine (1 eq), Boc-protected piperazine (1.1 eq.), RuPhos Pd G1 (0.05 eq.), RuPhos (0.05 eq.), sodium tert-butoxide (1.1 eq.) in dry dioxane (~0.1 M) was degassed with nitrogen for 10 min before heating to 100° C. in a sealed tube under nitrogen for 18 h. The mixture was partitioned between EtOAc and saturated NaHCO$_3$ solution. The organics were separated, washed with water and brine, passed through a phase separator and concentrated to dryness.

Method F—Activated Carbamate Formation

4-Nitrophenyl chloroformate (1.2 eq.) and dichloromethane (0.25 M) were combined under a nitrogen atmosphere. The amine (1 eq.) was added followed by pyridine (2.4 eq.). After 2 h-18 h the reaction mixture was the evaporated to dryness onto silica and purified by flash chromatography gave the activated carbamate.

When the amine was not commercially available, it was prepared from the corresponding aldehyde or carboxylic acid according to the following route:

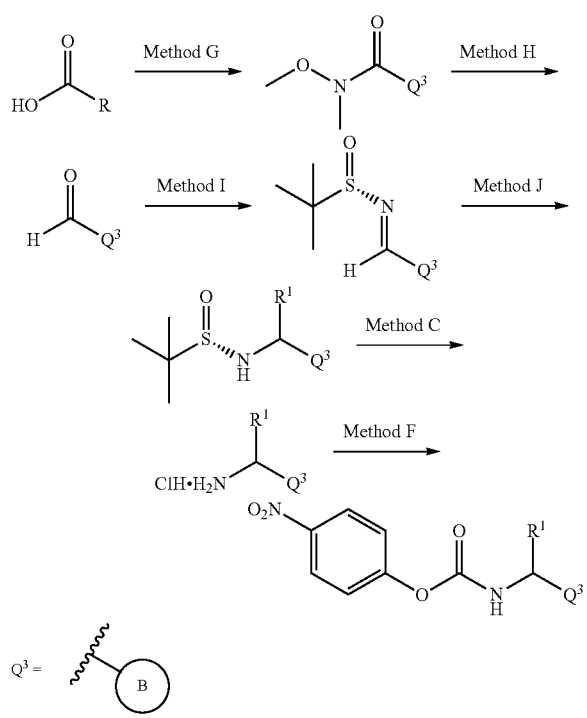

where R¹ and ring B are as defined herein.

Method G—Weinreb Amide Formation

A solution of 2-methylbenzofuran-4-carboxylic acid (1 eq.) in DCM (0.25 M) was treated with DIPEA (3.0 mL, 17.0 mmol), 1-hydroxybenzotriazole (1 eq.) 5.68 mmol) and then N-(3-dimethylaminopropyl)-N'-ethylcarbodiimide hydrochloride (1.2 eq.). The reaction was stirred for 10 min, treated with N,O-dimethylhydroxylamine hydrochloride (1.5 eq.) and then stirred for 18 h. The mixture was washed with water, sat. NaHCO₃ soln. and brine before being passed through a hydrophobic frit and concentrated to near dryness. The residue was purified by column chromatography.

Method H—Reduction to Aldehyde

A solution of Weinreb amide (1.18 g, 5.38 mmol) in anhydrous THF (0.1 M) was cooled to −78° C., under N₂, and treated dropwise with lithium aluminum hydride (1 M in THF, 1.25 eq.). The reaction was allowed to warm to room temperature and stirred for 3 h. The mixture was cooled to 0° C., quenched by addition of EtOAc and poured into a rapidly stirred mixture of 10% citric acid solution and EtOAc. The organics were separated, washed with saturated NaHCO₃ solution and brine before being passed through a hydrophobic frit and concentrated to dryness, giving the aldehyde, which was used without further purification.

Method I—Sulfinamide Formation

The aldehyde (1 eq.) and THF (0.5 M) were combined under a nitrogen atmosphere. Ti(OiPr)₄ (2 eq.) was added followed by (S)-(−)-2-methyl-propanesulfinamide (1 eq.). the reaction was stirred for 18 hr then quenched with water. The mixture was filtered through Celite and the filter cake rinsed with DCM. The filtrate was extracted with DCM (4×), the organics combined and passed through a hydrophobic frit. The organics were evaporated to near dryness and the residue purified by column chromatography.

Method J—Grignard Addition

A solution of sulfinamide (1 eq., 366 mg, 1.39 mmol) in DCM (0.1 M) was cooled to −78° C., under N₂, and treated dropwise with methyl magnesium bromide (3 M in diethyl ether, 2 to 4 eq.). The reaction was allowed to warm to room temperature and after 18 h the reaction was quenched with saturated aqueous NH₄Cl solution and extracted with dichloromethane (2×), the organics were passed through a hydrophobic frit, evaporated to near dryness and the residue purified by column chromatography.

4-Nitrophenyl (R)-(1-(3-methoxyphenyl)ethyl)carbamate (Intermediate 1)

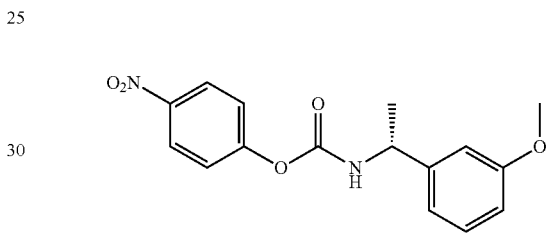

A stirred solution of p-nitrophenylchloroformate (3.27 g, 16.3 mmol) in DCM (40 mL), at 0° C., under nitrogen, was treated dropwise with a solution of (R)-1-(3-methoxyphenyl)ethylamine (2.00 mL, 13.5 mmol) and pyridine (1.3 mL, 16.3 mmol) in DCM (20 mL). The reaction was allowed to warm to rt and then stirred for 17 h. The mixture was diluted with DCM and washed with water, saturated NaHCO₃ solution, 10% (w/v) citric acid solution and brine before being dried (phase separator) and concentrated to dryness. The crude material was purified by gradient column chromatography 0-25% EtOAc in i-hexane gave the title compound. ¹H NMR (400 MHz, CDCl₃) 8.23 (2H, d, J=9.2 Hz), 7.33-7.28 (3H, m), 6.95 (1H, d, J=7.7 Hz), 6.91-6.89 (1H, m), 6.87-6.83 (1H, m), 5.38 (1H, d, J=7.3 Hz), 4.93-4.85 (1H, m), 3.83 (3H, s), 1.58 (3H, d, J=6.3 Hz).

The following intermediates were prepared from the commercially available starting materials stated below using the indicated methods described above:

| Intermediate no. | Intermediate name | Structure | Commercial Starting Material and Methods Used |
|---|---|---|---|
| 2 | 4-nitrophenyl (2-chlorobenzyl)carbamate | ![structure] | (2-chlorophenyl)methanamine (Method F) |

| Intermediate no. | Intermediate name | Structure | Commercial Starting Material and Methods Used |
|---|---|---|---|
| 3 | 4-nitrophenyl (R)-(1-(2-chlorophenyl)ethyl)carbamate | 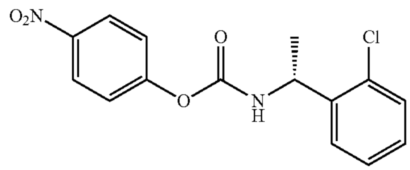 [SMILES: C[C@@H](NC(=O)Oc1ccc([N+](=O)[O-])cc1)c1ccccc1Cl] | (R)-1-(2-chlorophenyl)ethan-1-amine hydrochloride (Method F) |
| 4 | 4-nitrophenyl (R)-(1-(2-chloro-5-methoxyphenyl)ethyl)carbamate | 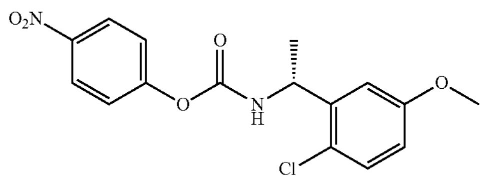 [SMILES: COc1ccc(Cl)c([C@@H](C)NC(=O)Oc2ccc([N+](=O)[O-])cc2)c1] | 2-Chloro-5-methoxybenzaldehyde (Methods I, J, C, F) |
| 5 | 4-nitrophenyl (R)-(1-(2-methylbenzofuran-4-yl)ethyl)carbamate | 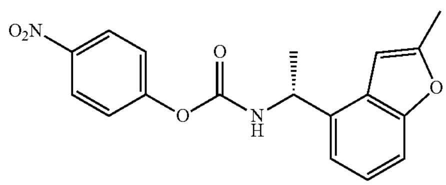 [SMILES: Cc1cc2c([C@@H](C)NC(=O)Oc3ccc([N+](=O)[O-])cc3)cccc2o1] | 2-methylbenzofuran-4-carboxylic acid (Methods G, H, I, J, C, F) |
| 6 | 4-nitrophenyl ((2,2-difluorobenzo[d][1,3]dioxol-4-yl)methyl)carbamate | 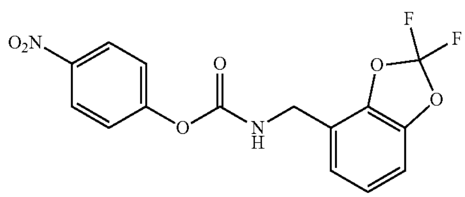 [SMILES: O=C(NCc1cccc2c1OC(F)(F)O2)Oc1ccc([N+](=O)[O-])cc1] | 4-aminomethyl-2,2-difluoro-1,3-benzodioxole (Method F) |
| 7 | 4-nitrophenyl (benzo[d][1,3]dioxol-4-ylmethyl)carbamate | 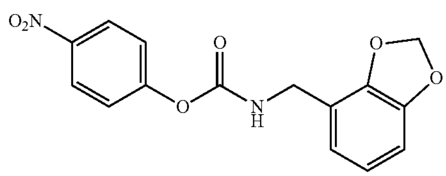 [SMILES: O=C(NCc1cccc2c1OCO2)Oc1ccc([N+](=O)[O-])cc1] | 2H-1,3-benzodioxol-4-ylmethanamine (Method F) |
| 8 | 4-nitrophenyl ((2,3-dihydrobenzo[b][1,4]dioxin-5-yl)methyl)carbamate | 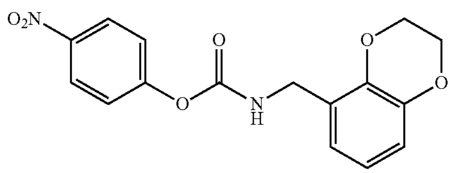 [SMILES: O=C(NCc1cccc2c1OCCO2)Oc1ccc([N+](=O)[O-])cc1] | (2,3-dihydro-1,4-benzodioxin-5-yl)methanamine hydrochloride (Method F) |
| 9 | 4-nitrophenyl (benzofuran-4-ylmethyl)carbamate | 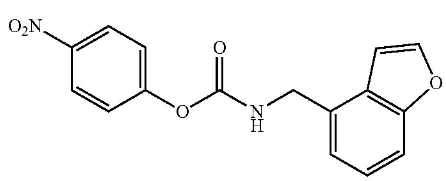 [SMILES: O=C(NCc1cccc2occc12)Oc1ccc([N+](=O)[O-])cc1] | [(Benzofuran-4-yl)methyl]amine (Method F) |
| 10 | 4-nitrophenyl-(1-(3-methylimidazo[1,2-a]pyridin-5-yl)ethyl)carbamate | 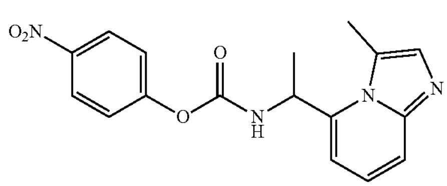 [SMILES: Cc1cnc2cccc(C(C)NC(=O)Oc3ccc([N+](=O)[O-])cc3)n12] | 3-Methylimidazo[1,2-a]pyridine-5-carbaldehyde (Methods I, J, C, F) |

-continued

| Intermediate no. | Intermediate name | Structure | Commercial Starting Material and Methods Used |
|---|---|---|---|
| 11 | 4-nitrophenyl (1-(2-chloro-4-fluorophenyl)ethyl) carbamate | 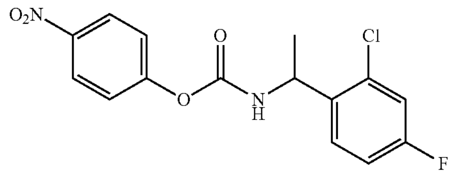 [SMILES: CC(NC(=O)Oc1ccc([N+](=O)[O-])cc1)c1ccc(F)cc1Cl] | 2-Chloro-4-fluorobenzaldehyde (Methods I, J, C, F) |
| 12 | 4-nitrophenyl (1-(2-chloro-3-fluorophenyl)ethyl) carbamate | 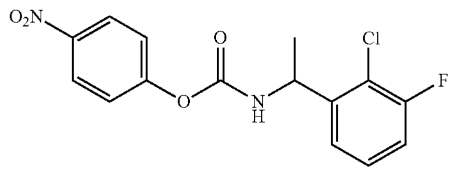 [SMILES: CC(NC(=O)Oc1ccc([N+](=O)[O-])cc1)c1cccc(F)c1Cl] | 2-Chloro-3-fluorobenzaldehyde (Methods I, J, C, F) |
| 13 | 4-nitrophenyl (1-(2-chloro-6-fluorophenyl)ethyl) carbamate | 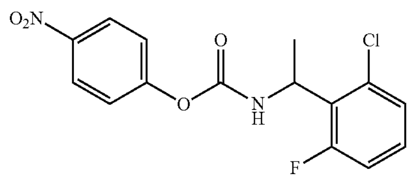 [SMILES: CC(NC(=O)Oc1ccc([N+](=O)[O-])cc1)c1c(F)cccc1Cl] | 2-Chloro-6-fluorobenzaldehyde (Methods I, J, C, F) |
| 14 | 4-nitrophenyl-(1-(1-methyl-1H-indol-7-yl)ethyl)carbamate | 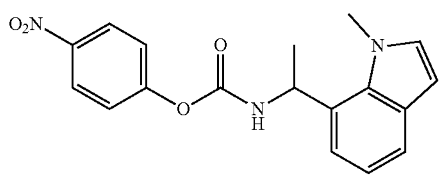 [SMILES: CC(NC(=O)Oc1ccc([N+](=O)[O-])cc1)c1cccc2ccn(C)c12] | 1-methyl-1H-indole-7-carbaldehyde (Methods I, J, C, F) |
| 15 | 4-nitrophenyl-(1-(2,2-difluorobenzo[d][1,3]dioxol-4-yl)ethyl)carbamate | 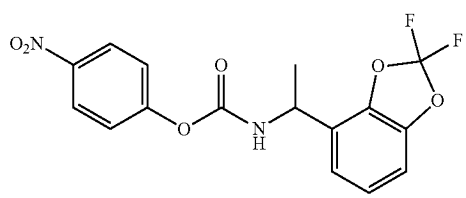 [SMILES: CC(NC(=O)Oc1ccc([N+](=O)[O-])cc1)c1cccc2c1OC(F)(F)O2] | 2,2-Difluoro-1,3-benzodioxazole-4-carboxaldehyde (Methods I, J, C, F) |
| 16 | 4-nitrophenyl (1-(3-fluoro-5-methoxyphenyl)ethyl) carbamate | 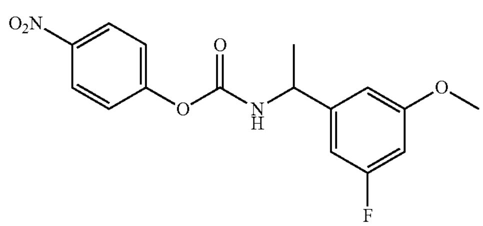 [SMILES: COc1cc(F)cc(C(C)NC(=O)Oc2ccc([N+](=O)[O-])cc2)c1] | 3-Fluoro-5-methoxybenzaldehyde (Methods I, J, C, F) |
| 17 | 4-nitrophenyl-(1-(4-fluoro-3-methoxyphenyl)ethyl) carbamate | 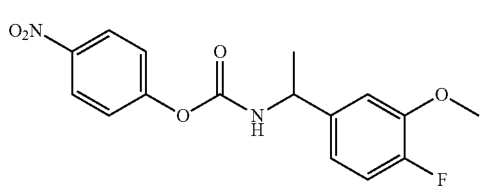 [SMILES: COc1cc(C(C)NC(=O)Oc2ccc([N+](=O)[O-])cc2)ccc1F] | 4-Fluoro-3-methoxybenzaldehyde (Methods I, J, C, F) |
| 18 | 4-nitrophenyl (2-fluoro-5-methoxybenzyl)carbamate | 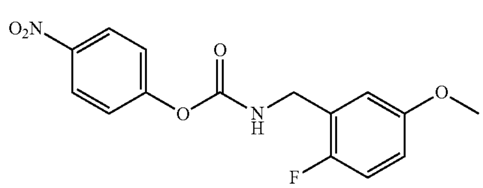 [SMILES: COc1ccc(F)c(CNC(=O)Oc2ccc([N+](=O)[O-])cc2)c1] | 2-Fluoro-5-methoxybenzaldehyde (Method F) |

| Intermediate no. | Intermediate name | Structure | Commercial Starting Material and Methods Used |
|---|---|---|---|
| 19 | 4-nitrophenyl-(1-(imidazo[1,2-a]pyridin-5-yl)ethyl)carbamate | 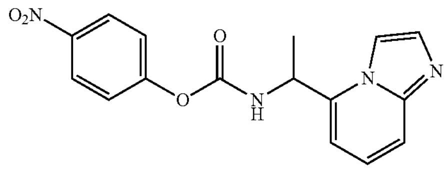 [SMILES: CC(NC(=O)Oc1ccc([N+](=O)[O-])cc1)c1cccc2nccn12] | Imidazo[1,2-a]pyridine-5-carbaldehyde (Methods I, J, C, F) |
| 20 | (1-(pyrazolo[1,5-a]pyridin-4-yl)ethyl)carbamate | 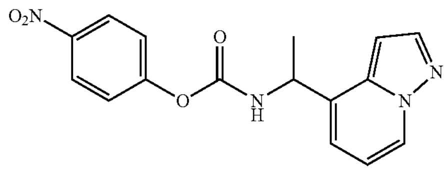 [SMILES: CC(NC(=O)Oc1ccc([N+](=O)[O-])cc1)c1cccn2nccc12] | Pyrazolo[1,5-a]pyridine-4-carbaldehyde (Methods I, J, C, F) |
| 21 | 4-nitrophenyl-(1-(2-methylbenzo[d]oxazol-4-yl)ethyl)carbamate | 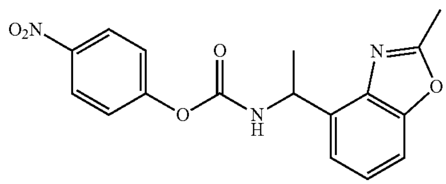 [SMILES: Cc1nc2c(C(C)NC(=O)Oc3ccc([N+](=O)[O-])cc3)cccc2o1] | 2-methylbenzo[d]oxazole-4-carboxylic acid (Methods G, H, I, J, C, F) |
| 22 | 4-nitrophenyl (1-(2-chlorophenyl)ethyl)carbamate | 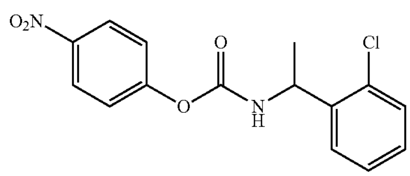 [SMILES: CC(NC(=O)Oc1ccc([N+](=O)[O-])cc1)c1ccccc1Cl] | 1-(2-chlorophenyl)ethan-1-amine hydrochloride (Method F) |
| 23 | 4-nitrophenyl (R)-(1-(2-chloro-3-methoxyphenyl)ethyl)carbamate | 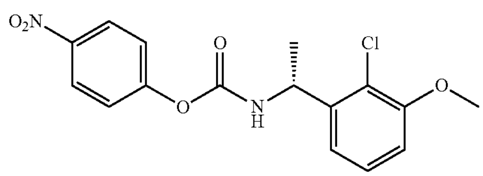 [SMILES: COc1cccc([C@@H](C)NC(=O)Oc2ccc([N+](=O)[O-])cc2)c1Cl] | 2-Chloro-3-methoxybenzaldehyde (Methods I, J, C, F) |
| 26 | 4-nitrophenyl (3-methoxybenzyl)carbamate | 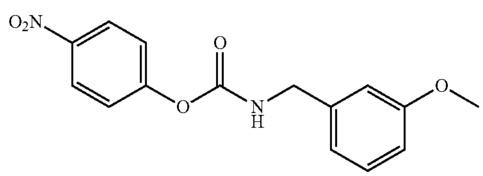 [SMILES: COc1cccc(CNC(=O)Oc2ccc([N+](=O)[O-])cc2)c1] | (3-methoxyphenyl)methanamine (Method F) |
| 27 | 4-nitrophenyl (1-(4-methyl-3,4-dihydro-2H-benzo[b][1,4]oxazin-5-yl)ethyl)carbamate | 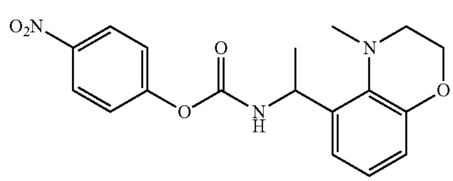 [SMILES: CC(NC(=O)Oc1ccc([N+](=O)[O-])cc1)c1cccc2c1N(C)CCO2] | 4-methyl-3,4-dihydro-2H-benzo[b][1,4]oxazine-5-carbaldehyde (Methods I, J, C, F) |
| 28 | 4-nitrophenyl (R)-(1-(2-fluoro-5-methoxyphenyl)ethyl)carbamate | 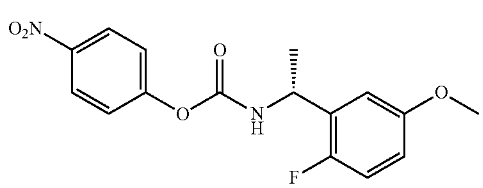 | 2-fluoro-5-methoxybenzaldehyde (Methods I, J, C, F) |

4-Nitrophenyl (R)-(1-(3-(methoxy-d₃)phenyl)ethyl-2,2,2-d₃)carbamate (Intermediate 29)

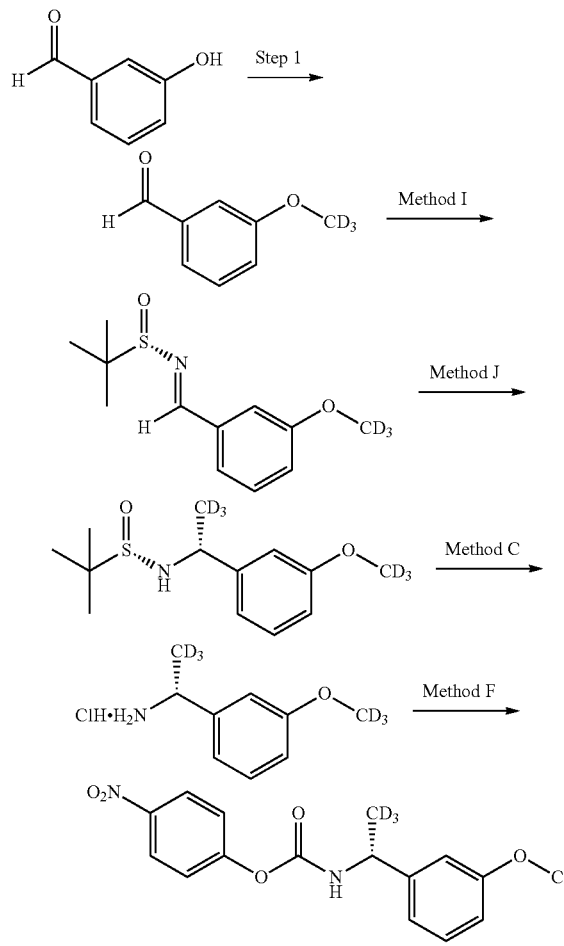

Step 1: 3-(Methoxy-d₃)benzaldehyde

3-Hydroxybenzaldehyde (2 g, 16.3 mmol), potassium carbonate (2.3 g, 16.6 mmol), DMF (20 mL) and CD₃-I (1 mL, 16.3 mmol) were combined and stirred at room temperature for 23 h. Reaction mixture was diluted with EtOAc, washed with water (3×), brine (1×), dried (MgSO₄) and organics evaporated to dryness gave 3-(methoxy-d₃)benzaldehyde.

Step 2: Following Method I 3-(Methoxy-d₃)benzaldehyde (2.27 g, 16.3 mmol) gave (S,E)-N-(3-(methoxy-d₃)benzylidene)-2-methylpropane-2-sulfinamide.

Step 3: Following Method J 3-(Methoxy-d₃)benzaldehyde (2.27 g, 16.3 mmol) gave (S,E)-N-(3-(methoxy-d₃)benzylidene)-2-methylpropane-2-sulfinamide.

Step 4: Following Method C (S)—N—((R)-1-(3-(Methoxy-d₃)phenyl)ethyl-2,2,2-d₃)-2-methylpropane-2-sulfinamide (2.18 g, 8.38 mmol) gave (R)-1-(3-(methoxy-d₃)phenyl)ethan-2,2,2-d₃-1-amine hydrochloride.

Step 5: Following Method F (R)-1-(3-(Methoxy-d₃)phenyl)ethan-2,2,2-d₃-1-amine hydrochloride (598 mg, 3.09 mmol) gave 4-nitrophenyl (R)-(1-(3-(methoxy-d₃)phenyl)ethyl-2,2,2-d₃)carbamate.

4-Nitrophenyl (R)-(1-(3-(methoxy-d₃)phenyl)ethyl)carbamate (Intermediate 30)

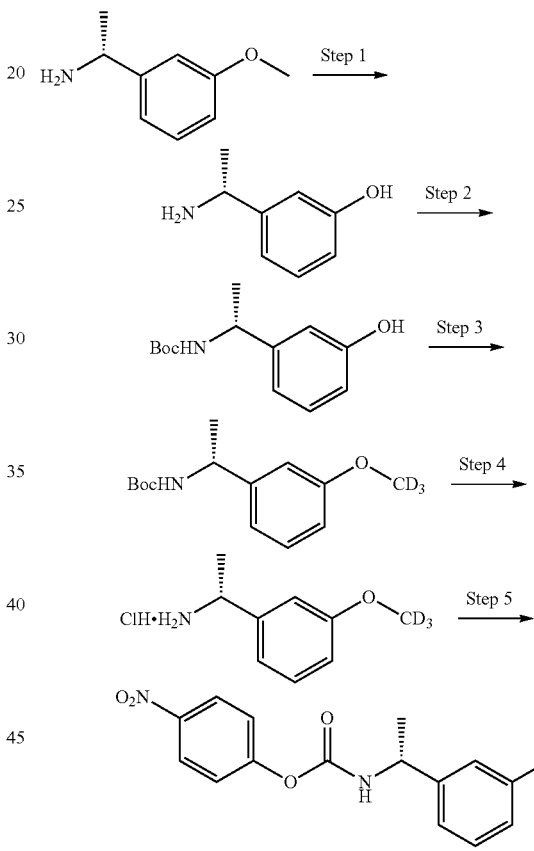

Step 1: (R)-3-(1-Aminoethyl)phenol (R)-1-(3-Methoxyphenyl)ethan-1-amine (1 g, 6.62 mmol) and dichloromethane (50 mL) were combined under a nitrogen atmosphere. Reaction was cooled with and ice bath and BBr₃ (1.3 mL, 13.25 mmol) added. Ice bath was removed and reaction stirred for 2 days. Reaction was cooled with ice bath, quenched with MeOH and evaporated to dryness gave (R)-3-(1-aminoethyl)phenol which was used directly in next step.

Step 2: Tert-butyl (R)-(1-(3-hydroxyphenyl)ethyl)carbamate (R)-3-(1-Aminoethyl)phenol (crude from previous step), triethylamine (4 mL), dichloromethane (5 mL) and di-t- butyl dicarbonate (1.6 g, 7.33 mol) were combined and stirred for 1 h. Reaction mixture was then evaporated to dryness onto silica and purified by flash chromatography gave tert-butyl (R)-(1-(3-hydroxyphenyl)ethyl)carbamate.

Step 3: (R)-(1-(3-(Methoxy-d₃)phenyl)ethyl)carbamate

Tert-butyl (R)-(1-(3-hydroxyphenyl)ethyl)carbamate (1.69 g), potassium carbonate (967 mg, 7 mmol), DMF (10 mL) and D₃-iodomethane (0.41 mL, 6.62 mmol) were combined and stirred for 22 h. Reaction mixture was diluted with EtOAc, washed with water (2×) and brine (1×). Evaporated to dryness onto silica and purified by flash chromatography gave tert-butyl (R)-(1-(3-(methoxy-d₃)phenyl)ethyl)carbamate.

Step 4: (R)-1-(3-(Methoxy-d₃)phenyl)ethan-1-amine hydrochloride

Tert-butyl (R)-(1-(3-(methoxy-d₃)phenyl)ethyl)carbamate (1.19 g, 4.68 mmol) and 4N HCl in dioxane (10 mL) were combined and stirred for 20 h. Reaction mixture was then evaporated to dryness gave (R)-1-(3-(methoxy-d₃)phenyl)ethan-1-amine hydrochloride.

Step 5: (R)-(1-(3-(Methoxy-d₃)phenyl)ethyl)carbamate

4-Nitrophenyl chloroformate (1.09 g, 5.4 mmol) and dichloromethane (20 mL) were combined under a nitrogen atmosphere. (R)-1-(3-(methoxy-d₃)phenyl)ethan-1-amine hydrochloride (857 mg, 4.5 mmol) was added followed by pyridine (0.87 mL, 10.8 mmol). After 3 h reaction mixture was the evaporated to dryness onto silica and purified by flash chromatography gave 4-nitrophenyl (R)-(1-(3-(methoxy-d₃)phenyl)ethyl)carbamate.

4-Nitrophenyl (benzofuran-4-ylmethyl)carbamate (Intermediate 31)

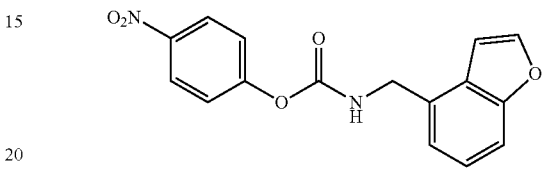

The intermediate was synthesized from benzofuran-4-carbonitrile according to the literature procedure reported in the Journal of Medicinal Chemistry, 59(7), 3215-3230; 2016.

The following intermediates were commercially acquired or made via the subsequently described methods.

| Intermediate | Structure | Name |
| --- | --- | --- |
| Intermediate 32 | 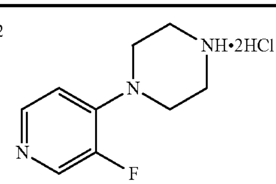 | 1-(3-fluoropyridin-4-yl) piperazine dihydrochloride |
| Intermediate 33 | 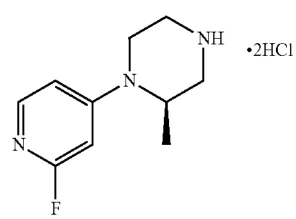 | (R)-1-(2-fluoropyridin-4-yl)-2-methylpiperazine dihydrochloride |
| Intermediate 34 | 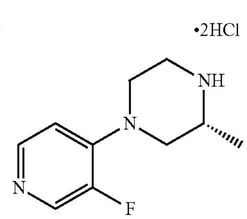 | (R)-1-(3-fluoropyridin-4-yl)-3-methylpiperazine dihydrochloride |
| Intermediate 35 | 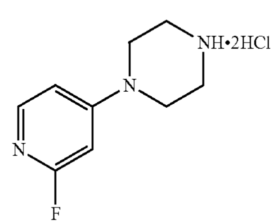 | 1-(2-fluoropyridin-4-yl)piperazine dihydrochloride |

-continued

| Intermediate | Structure | Name |
|---|---|---|
| Intermediate 36 | 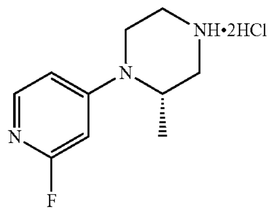 | (S)-1-(2-fluoropyridin-4-yl)-2-methylpiperazine dihydrochloride |
| Intermediate 37 | 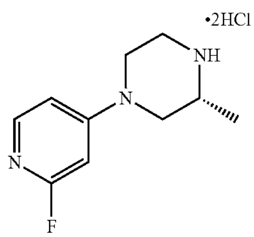 | (R)-1-(2-fluoropyridin-4-yl)-3-methylpiperazine dihydrochloride |
| Intermediate 38 | 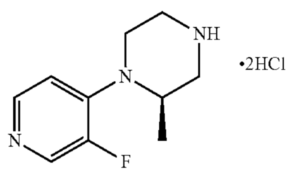 | (R)-1-(3-fluoropyridin-4-yl)-2-methylpiperazine dihydrochloride |
| Intermediate 39 | 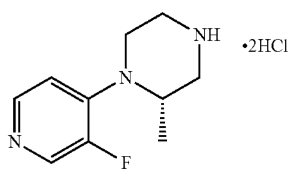 | (S)-1-(3-fluoropyridin-4-yl)-2-methylpiperazine dihydrochloride |
| Intermediate 40 | 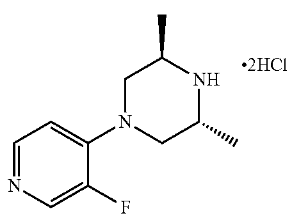 | (3R,5R)-1-(3-Fluoropyridin-4-yl)-3,5-dimethylpiperazine dihydrochloride |
| Intermediate 41 | 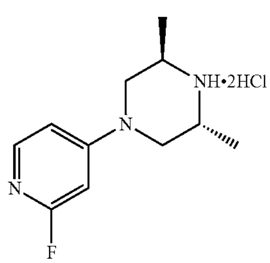 | (3R,5R)-1-(2-Fluoropyridin-4-yl)-3,5-dimethylpiperazine dihydrochloride |
| Intermediate 42 | 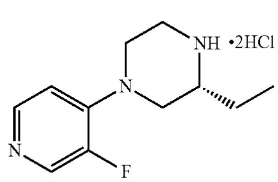 | (R)-3-Ethyl-1-(3-fluoropyridin-4-yl)piperazine dihydrochloride |

| Intermediate | Structure | Name |
|---|---|---|
| Intermediate 43 | 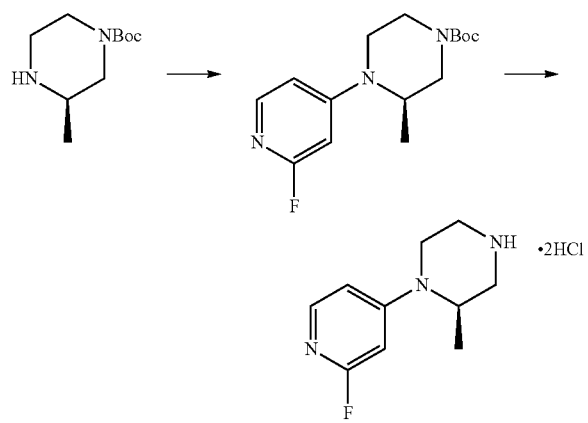 | (2R,5R)-1-(3-fluoropyridin-4-yl)-2,5-dimethylpiperazine dihydrochloride |

(R)-1-(2-Fluoropyridin-4-yl)-2-methylpiperazine dihydrochloride (Intermediate 33)

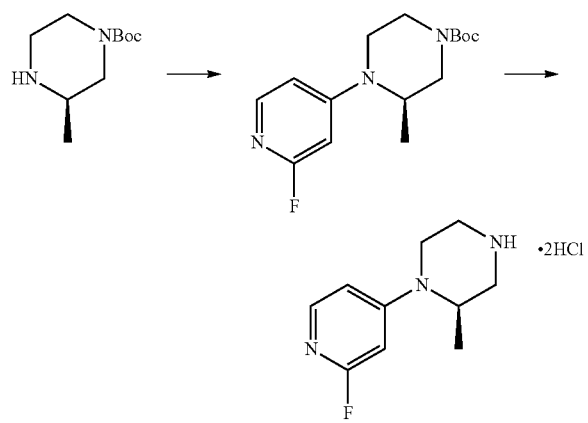

Step 1: Tert-butyl (R)-4-(2-fluoropyridin-4-yl)-3-methylpiperazine-1-carboxylate Following Method E from tert-butyl (R)-3-methylpiperazine-1-carboxylate (1.5 g, 7.49 mmol) and 4-bromo-2-fluoropyridine (1.20 g, 6.81 mmol). Purification by flash silica chromatography (gradient elution i-hex/EtOAc) gave the title compound.

(R)-1-(3-Fluoropyridin-4-yl)-3-methylpiperazine dihydrochloride (Intermediate 34)

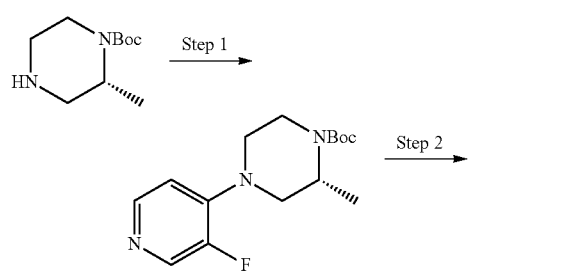

Step 1: Tert-butyl (R)-4-(3-fluoropyridin-4-yl)-2-methylpiperazine-1-carboxylate Following Method D from tert-butyl (R)-2-methylpiperazine-1-carboxylate (1.0 g, 4.99 mmol) and 3,4-difluoropyridine (0.57 g, 4.99 mmol). Purification by flash silica chromatography (gradient elution i-hex to 50% EtOAc in i-hex) gave the title compound.

Step 2: (R)-1-(3-Fluoropyridin-4-yl)-3-methylpiperazine Dihydrochloride

Following method C from tert-butyl (R)-4-(3-fluoropyridin-4-yl)-2-methylpiperazine-1-carboxylate (527 mg, 1.78 mmol) gave the title compound (1.78 mmol).

(S)-1-(2-Fluoropyridin-4-yl)-2-methylpiperazine dihydrochloride (Intermediate 36)

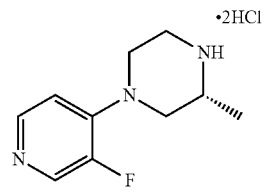

Step 1: Tert-butyl (S)-4-(2-fluoropyridin-4-yl)-3-methylpiperazine-1-carboxylate Following Method D from tert-butyl (S)-3-methylpiperazine-1-carboxylate (1.0 g, 4.99 mmol) and 3,4-difluoropyridine (0.57 g, 4.99 mmol). Purification by flash silica chromatography gave the title compound.

Step 2: (S)-1-(2-Fluoropyridin-4-yl)-2-methylpiperazine Dihydrochloride

Following method C from tert-butyl (S)-4-(2-fluoropyridin-4-yl)-3-methylpiperazine-1-carboxylate (239 mg, 0.81 mmol) gave the title compound.

(R)-1-(2-Fluoropyridin-4-yl)-3-methylpiperazine dihydrochloride (Intermediate 37)

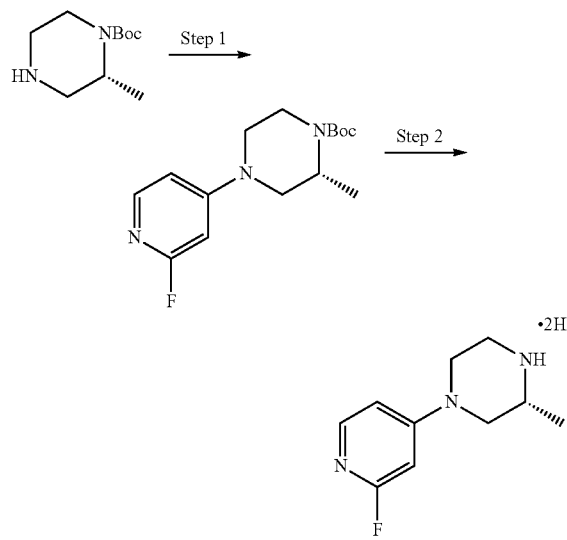

Step 1: Following Method E

Tert-butyl (R)-2-methylpiperazine-1-carboxylate (1.5 g, 7.49 mmol) and 3-fluoro-4-bromopyridine (1.2 g, 6.81 mmol). Purification by flash silica chromatography (gradient elution i-hex to 50% EtOAc in i-hex) gave the title compound.

Step 2: (R)-1-(2-Fluoropyridin-4-yl)-3-methylpiperazine.HCl

Following method C from tert-butyl (R)-4-(2-fluoropyridin-4-yl)-2-methylpiperazine-1-carboxylate (1.47 g, 4.98 mmol) gave the title compound.

(R)-1-(3-Fluoropyridin-4-yl)-2-methylpiperazine dihydrochloride (Intermediate 38)

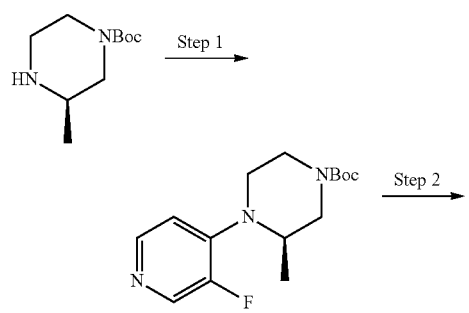

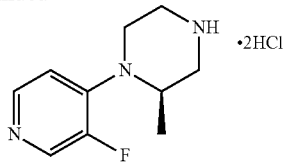

Step 1: Tert-butyl (R)-4-(3-fluoropyridin-4-yl)-3-methylpiperazine-1-carboxylate Following Method E from 4-bromo-3-fluoropyridine (250 mg, 1.42 mmol) and tert-butyl (R)-3-methylpiperazine-1-carboxylate (313 mg, 1.56 mmol). Purification by flash silica chromatography (5-100% EtOAc in i-hex) to give the title compound, which was used in the next step.

Step 2: (R)-1-(3-Fluoropyridin-4-yl)-2-methylpiperazine

Tert-butyl (R)-4-(3-fluoropyridin-4-yl)-3-methylpiperazine-1-carboxylate (166 mg, 0.56 mmol), acetonitrile (10 mL) and 4N HCl in dioxane (1 mL) were combined and stirred at room temperature for 18 h. The reaction mixture was then evaporated to dryness and azeotroped with toluene to give crude 2 HCl salt of title compound which was used crude in the next step.

(S)-1-(3-Fluoropyridin-4-yl)-2-methylpiperazine Dihydrochloride (Intermediate 39)

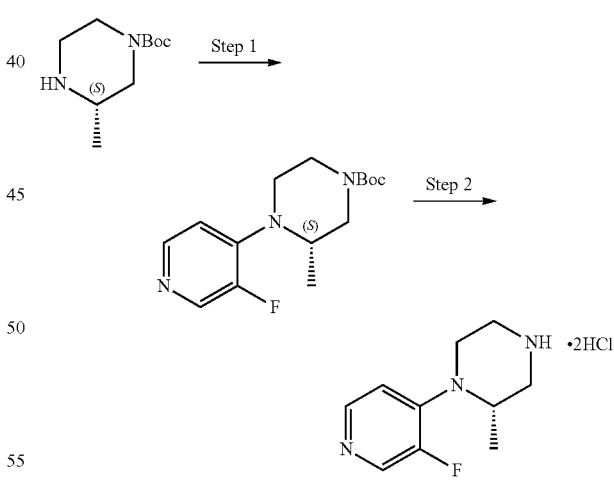

Step 1: Tert-butyl (S)-4-(3-fluoropyridin-4-yl)-3-methylpiperazine-1-carboxylate Following Method E from 4-bromo-3-fluoropyridine (250 mg, 1.42 mmol) and tert-butyl (S)-3-methylpiperazine-1-carboxylate (313 mg, 1.56 mmol). The crude material was purified by Interchim reverse phase C18 column in acetonitrile and water with 1% formic acid to give title compound.

Step 2: (S)-1-(3-Fluoropyridin-4-yl)-2-methylpiperazine

Following Method C from tert-butyl (S)-4-(3-fluoropyridin-4-yl)-3-methylpiperazine-1-carboxylate (172 mg, 0.56 mmol) gave the title compound which was used crude in the next step.

(3R,5R)-1-(3-Fluoropyridin-4-yl)-3,5-dimethylpiperazine Dihydrochloride (Intermediate 40)

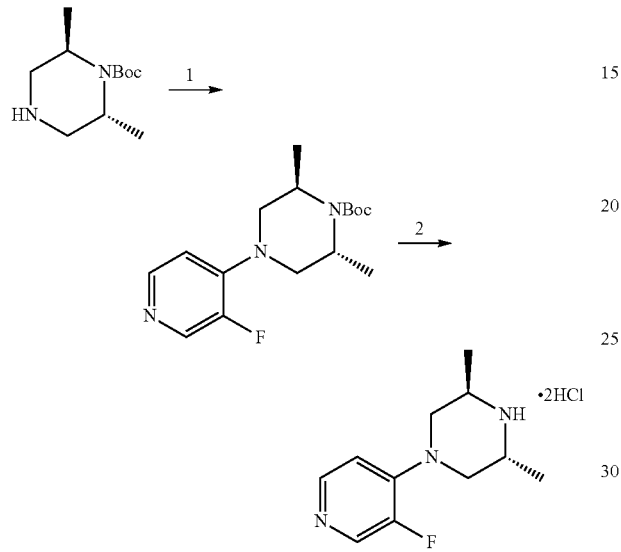

Step 1: Tert-butyl (2R,6R)-4-(3-Fluoropyridin-4-yl)-2,6-dimethylpiperazine-1-carboxylate A suspension of 3,4-difluoropyridine (268 mg, 2.33 mmol), tert-butyl (2R,6R)-2,6-dimethylpiperazine-1-carboxylate (500 mg, 2.33 mmol) and TEA (1.0 mL, 7.0 mmol) in 1,4-dioxane was heated at 100° C. for 5 days. The reaction was filtered, concentrated and the residue partitioned between EtOAc and saturated NaHCO₃ solution. The organics were separated and washed with water and brine before being passed through a phase separator and concentrated to dryness. The crude material was partially purified by gradient column chromatography 0-60% EtOAc in i-hex to give the title compound. Used crude in next step.

Step 2: (3R,5R)-1-(3-Fluoropyridin-4-yl)-3,5-dimethylpiperazine Dihydrochloride Following Method C from tert-butyl (2R,6R)-4-(3-fluoropyridin-4-yl)-2,6-dimethylpiperazine-1-carboxylate (191 mg, 0.61 mmol) gave the title compound. Used crude in the next step.

(3R,5R)-1-(2-Fluoropyridin-4-yl)-3,5-dimethylpiperazine Dihydrochloride (Intermediate

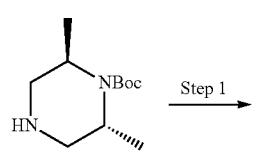

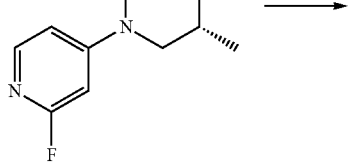

Step 1: Tert-Butyl (2R,6R)-4-(2-Fluoropyridin-4-yl)-2,6-dimethylpiperazine-1-carboxylate Following Method E from 4-bromo-2-fluoropyridine (373 mg, 2.12 mmol) and tert-butyl (2R,6R)-2,6-dimethylpiperazine-1-carboxylate (500 mg, 2.33 mmol). Purification by gradient column chromatography 0-100% EtOAc in isohexanes to give the title compound. ¹H NMR (400 MHz, CDCl₃) 7.89 (1H, d, J=6.1 Hz), 6.39 (1H, d, J=5.8 Hz), 6.03 (1H, s), 4.25-4.24 (2H, m), 3.71 (2H, dd, J=3.8, 12.1 Hz), 3.36 (2H, d, J=11.9 Hz), 1.50 (9H, s), 1.25 (6H, d, J=6.6 Hz).

Step 2: (3R,5R)-1-(2-Fluoropyridin-4-yl)-3,5-dimethylpiperazine Dihydrochloride Following Method C from tert-butyl (2R,6R)-4-(2-fluoropyridin-4-yl)-2,6-dimethylpiperazine-1-carboxylate (0.56 g, 1.81 mmol) gave the title compound. Used crude in the next step.

(R)-3-Ethyl-1-(3-fluoropyridin-4-yl)piperazine Dihydrochloride (Intermediate 42)

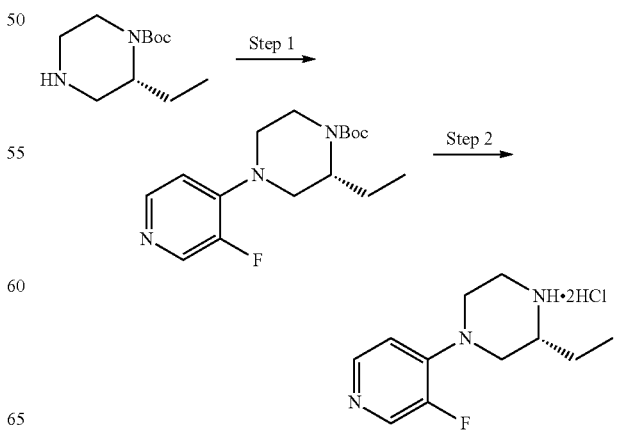

Step 1: Tert-butyl (R)-2-ethyl-4-(3-fluoropyridin-4-yl)piperazine-1-carboxylate Following method E from tert-butyl (R)-2-ethylpiperazine-1-carboxylate (0.50 g, 2.33 mmol) and 3,4-difluoropyridine (0.27 g, 2.33 mmol). Purification by flash silica chromatography (gradient elution i-hex to 100% EtOAc in i-hex) gave the title compound.

Step 2: (R)-3-Ethyl-1-(3-fluoropyridin-4-yl)piperazine Dihydrochloride

Following method C from tert-butyl (R)-2-ethyl-4-(3-fluoropyridin-4-yl)piperazine-1-carboxylate (493 mg, 1.59 mmol) gave the title compound. Used crude in the next step.

Final compounds were synthesized from the intermediates described above via the syntheses described below.

Example 1

(R)-4-(2-Fluoropyridin-4-yl)-N—((R)-1-(3-methoxyphenyl)ethyl)-2-methylpiperazine-1-carboxamide

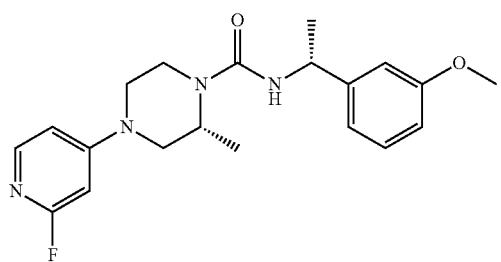

Following Method B from Intermediate 37 (250 mg, 1.08 mmol) and 4-nitrophenyl (R)-(1-(3-methoxyphenyl)ethyl) carbamate (Intermediate 1, 341 mg, 1.08 mmol). Purification by preparative-HPLC gave the title compound. LCMS (ES+) 373 (M+H)$^+$, RT 3.06 min (Analytical Method 1) $^1$H NMR (400 MHz, DMSO) 7.80 (1H, d, J=6.1 Hz), 7.22 (1H, dd, J=8.1, 8.1 Hz), 6.91-6.89 (2H, m), 6.82-6.76 (3H, m), 6.50-6.48 (1H, m), 4.89-4.80 (1H, m), 4.33-4.29 (1H, m), 3.86-3.77 (3H, m), 3.74 (3H, s), 3.20-3.09 (2H, m), 2.99-2.90 (1H, m), 1.37 (3H, d, J=7.2 Hz), 1.06 (3H, d, J=6.5 Hz), 6.83-6.75 (2H, m), 6.71 (1H, d, J=6.4 Hz), 4.89-4.81 (1H, m), 4.36-4.32 (1H, m), 3.87 (1H, d, J=13.2 Hz), 3.75 (3H, s), 3.66 (2H, dd, J=12.5, 19.8 Hz), 3.19-3.09 (2H, m), 2.98-2.90 (1H, m), 1.37 (3H, d, J=7.1 Hz), 1.14 (3H, d, J=6.6 Hz).

Example 2

(R)-1-(3-Methoxyphenyl)ethyl (R)-4-(2-fluoropyridin-4-yl)-2-methylpiperazine-1-carboxylate

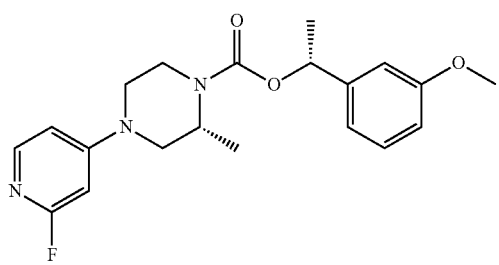

Following Method A from 4-nitrophenyl chloroformate (100 mg, 0.497 mmol) in DCM (2 mL), (R)-1-(3-methoxyphenyl)ethan-1-ol (75 mg, 0.493 mmol) in DCM (2 mL) and (R)-1-(2-fluoropyridin-4-yl)-3-methylpiperazine dihydrochloride (Intermediate 37, 134 mg, 0.493 mmol) and TEA (0.21 mL, 1.48 mmol) in DCM (5 mL). After 3 d the reaction mixture was washed with sat. NaHCO$_3$ soln. and brine, passed through a hydrophobic frit and concentrated to dryness. Purification by prep HPLC gave the title compound. LCMS (ES+) 374 (M+H)$^+$, RT 3.37 min (Analytical Method 2) $^1$H NMR (400 MHz, CDCl$_3$) 7.89 (1H, d, J=6.1 Hz), 7.30-7.26 (1H, m), 6.93 (1H, d, J=7.7 Hz), 6.88 (1H, s), 6.83 (1H, dd, J=2.4, 8.1 Hz), 6.49 (1H, d, J=6.0 Hz), 6.14 (1H, s), 5.83 (1H, q, J=6.6 Hz), 4.46-4.39 (1H, m), 4.05-3.98 (1H, m), 3.81 (3H, s), 3.70-3.64 (1H, m), 3.54 (1H, d, J=12.6 Hz), 3.42-3.25 (2H, m), 3.12-3.04 (1H, m), 1.56 (3H, d, J=6.5 Hz), 1.24 (3H, d, J=6.6 Hz).

Example 3

(R)—N—((R)-1-(2-Chloro-5-methoxyphenyl)ethyl)-4-(2-fluoropyridin-4-yl)-2-methylpiperazine-1-carboxamide

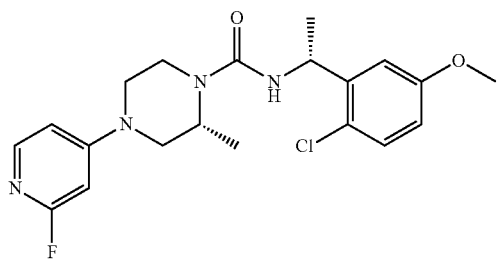

Following Method B from 4-nitrophenyl (R)-(1-(2-chloro-5-methoxyphenyl)ethyl)carbamate (Intermediate 4, 0.222 mmol) and (R)-1-(2-fluoropyridin-4-yl)-3-methylpiperazine dihydrochloride (Intermediate 37, 0.222 mmol). Purification by prep HPLC gave the title compound (48 mg). LCMS (ES+) 407 (M+H)$^+$, RT 3.24 min (Analytical Method 2), $^1$H NMR (400 MHz, MeOD) 7.81 (1H, d, J=6.2 Hz), 7.27 (1H, d, J=8.7 Hz), 6.98 (1H, d, J=2.9 Hz), 6.83-6.76 (2H, m), 6.44 (1H, dd, J=2.3, 2.3 Hz), 5.29-5.23 (1H, m), 4.42-4.36

(1H, m), 3.96-3.79 (3H, m), 3.79 (3H, s), 3.42-3.34 (2H, m, obsc), 3.19-3.10 (1H, m), 1.46 (3H, d, J=7.1 Hz), 1.23 (3H, d, J=6.6 Hz).

Example 4

(R)-4-(2-Fluoropyridin-4-yl)-2-methyl-N—((R)-1-(2-methylbenzofuran-4-yl)ethyl)piperazine-1-carboxamide

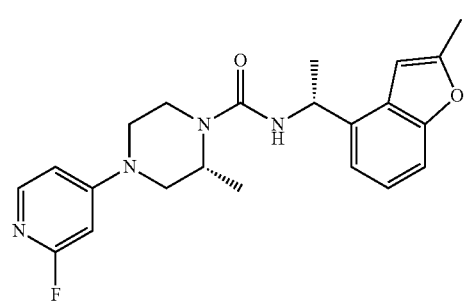

Following Method B from 4-nitrophenyl (R)-(1-(2-methylbenzofuran-4-yl)ethyl)carbamate (Intermediate 5, 0.138 mmol) and (R)-1-(2-fluoropyridin-4-yl)-3-methylpiperazine dihydrochloride (Intermediate 37, 0.138 mmol). Purification by prep HPLC gave the title compound. LCMS (ES+) 397 (M+H)+, RT 3.26 min (Analytical Method 2), ¹H NMR (400 MHz, MeOD) 7.80 (1H, d, J=6.2 Hz), 7.28 (1H, dd, J=3.1, 6.0 Hz), 7.18-7.15 (2H, m), 6.76 (1H, d, J=6.9 Hz), 6.62 (1H, s), 6.42 (1H, dd, J=2.3, 2.3 Hz), 5.31-5.23 (1H, m), 4.39-4.34 (1H, m), 3.95-3.77 (3H, m), 3.39-3.29 (2H, m, obsc), 3.34 (2H, s), 3.17-3.08 (1H, m), 2.46 (3H, s), 1.57 (3H, d, J=7.1 Hz), 1.22 (3H, d, J=6.7 Hz).

Example 5

(R)—N-((2,2-Difluorobenzo[d][1,3]dioxol-4-yl)methyl)-4-(2-fluoropyridin-4-yl)-2-methylpiperazine-1-carboxamide

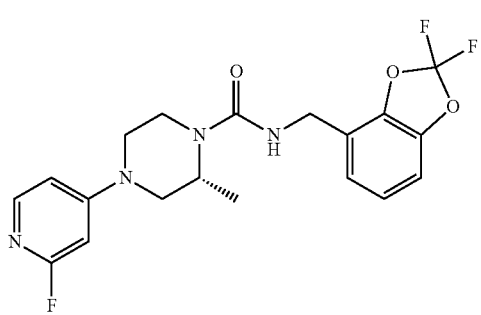

Following Method B from 4-nitrophenyl ((2,2-difluorobenzo[d][1,3]dioxol-4-yl)methyl)carbamate (Intermediate 6, 0.213 mmol) and (R)-1-(2-fluoropyridin-4-yl)-3-methylpiperazine dihydrochloride (Intermediate 37, 0.213 mmol). Purification by prep HPLC gave the title compound. LCMS (ES+) 409 (M+H)+, RT 3.19 min (Analytical Method 2), ¹H NMR (400 MHz, MeOD) 7.81 (1H, d, J=6.2 Hz), 7.14-7.10 (3H, m), 6.77 (1H, dd, J=2.0, 4.3 Hz), 6.43 (1H, dd, J=2.1, 2.1 Hz), 4.49 (2H, dd, J=15.5, 18.6 Hz), 4.33 (1H, ddd, J=3.3, 6.6, 13.3 Hz), 3.94-3.78 (3H, m), 3.44-3.36 (2H, m), 3.20-3.12 (1H, m), 1.25 (3H, d, J=6.6 Hz).

Example 6

(R)—N-(Benzo[d][1,3]dioxol-4-ylmethyl)-4-(2-fluoropyridin-4-yl)-2-methylpiperazine-1-carboxamide

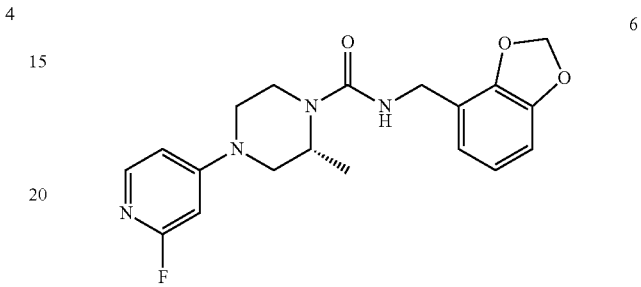

Following Method B from 4-nitrophenyl (benzo[d][1,3]dioxol-4-ylmethyl)carbamate (Intermediate 7, 0.237 mmol) and (R)-1-(2-fluoropyridin-4-yl)-3-methylpiperazine dihydrochloride (Intermediate 37, 0.237 mmol). Purification by prep HPLC gave the title compound. LCMS (ES+) 373 (M+H)+, RT 2.95 min (Analytical Method 1), ¹H NMR (400 MHz, MeOD) 7.81 (1H, d, J=6.2 Hz), 6.81 (2H, d, J=4.9 Hz), 6.78-6.73 (2H, m), 6.43 (1H, dd, J=2.1, 2.1 Hz), 5.96 (2H, s), 4.41-4.30 (3H, m), 3.93-3.77 (3H, m), 3.42-3.35 (2H, m), 3.20-3.12 (1H, m), 1.24 (3H, d, J=6.7 Hz).

Example 7

(R)—N-((2,3-Dihydrobenzo[b][1,4]dioxin-5-yl)methyl)-4-(2-fluoropyridin-4-yl)-2-methylpiperazine-1-carboxamide

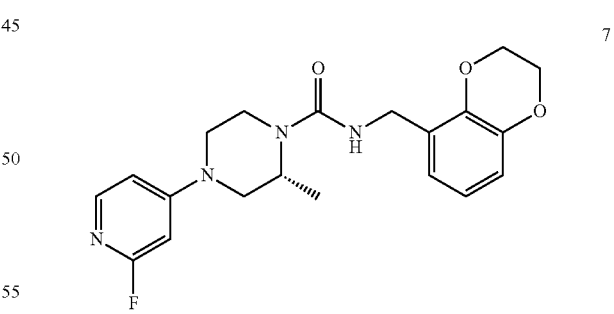

Following Method B from 4-nitrophenyl ((2,3-dihydrobenzo[b][1,4]dioxin-5-yl)methyl)carbamate (Intermediate 8, 0.227 mmol) and (R)-1-(2-fluoropyridin-4-yl)-3-methylpiperazine dihydrochloride (Intermediate 37, 0.227 mmol). Purification by prep HPLC gave the title compound. LCMS (ES+) 387 (M+H)+, RT 2.98 min (Analytical Method 2), ¹H NMR (400 MHz, MeOD) 7.81 (1H, d, J=6.2 Hz), 6.80-6.74 (4H, m), 6.43 (1H, dd, J=2.3, 2.3 Hz), 4.40-4.25 (7H, m), 3.93-3.77 (3H, m), 3.43-3.35 (2H, m), 3.21-3.13 (1H, m), 1.24 (3H, d, J=6.6 Hz).

Example 8

(R)—N-(Benzofuran-4-ylmethyl)-4-(2-fluoropyridin-4-yl)-2-methylpiperazine-1-carboxamide

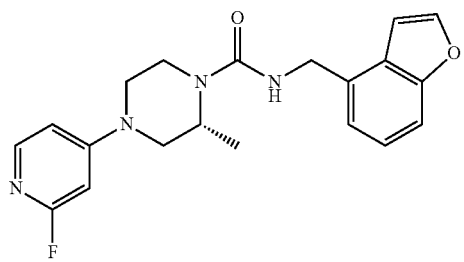

Following Method B from (R)-1-(2-fluoropyridin-4-yl)-3-methylpiperazine dihydrochloride (Intermediate 37, 145 mg, 0.63 mmol) and 4-nitrophenyl (benzofuran-4-ylmethyl)carbamate (Intermediate 9, 200 mg, 0.63 mmol). Purification by SCX gave the title compound. LCMS (ES+) 373 (M+H)$^+$, RT 2.82 min (Analytical Method 1), $^1$H NMR (400 MHz, MeOD) 7.82-7.76 (2H, m), 7.43-7.40 (1H, m), 7.29-7.17 (2H, m), 7.01 (1H, dd, J=1.0, 2.3 Hz), 6.78-6.75 (1H, m), 6.42 (1H, t, J=2.2 Hz), 4.67 (2H, d, J=8.9 Hz), 4.39-4.32 (1H, m), 3.95-3.78 (3H, m), 3.39 (2H, d, J=19.5 Hz), 3.20-3.12 (1H, m), 1.23 (3H, d, J=6.7 Hz).

Examples 9 and 10 (R)-4-(2-Fluoropyridin-4-yl)-2-methyl-N—((R)-1-(3-methylimidazo[1,2-a]pyridin-5-yl)ethyl)piperazine-1-carboxamide and (R)-4-(2-Fluoropyridin-4-yl)-2-methyl-N—((S)-1-(3-methylimidazo[1,2-a]pyridin-5-yl)ethyl)piperazine-1-carboxamide

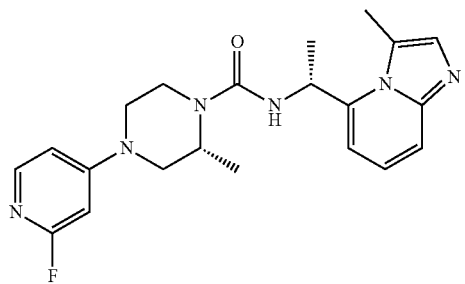

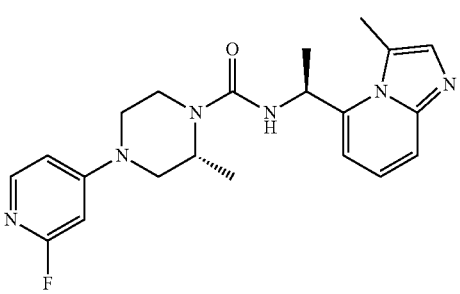

Following Method B from 4-nitrophenyl-(1-(3-methylimidazo[1,2-a]pyridin-5-yl)ethyl)carbamate (Intermediate 10, 0.70 mmol) and (R)-1-(2-fluoropyridin-4-yl)-3-methylpiperazine dihydrochloride (Intermediate 37, 0.56 mmol). Purification by prep HPLC and SFC to separate the isomers gave the title compounds.

Example 9: LCMS (ES+) 397 (M+H)$^+$, RT 2.34 min (Analytical Method 1), $^1$H NMR (400 MHz, MeOD) 7.81 (1H, d, J=6.3 Hz), 7.42 (1H, d, J=7.9 Hz), 7.35 (1H, s), 7.24 (1H, dd, J=7.1, 9.0 Hz), 6.96 (1H, d, J=6.9 Hz), 6.78 (1H, dd, J=1.8, 4.1 Hz), 6.44 (1H, dd, J=2.1, 2.1 Hz), 5.87 (1H, q, J=6.8 Hz), 4.44-4.38 (1H, m), 3.95-3.80 (3H, m), 3.45-3.36 (2H, m), 3.19-3.11 (1H, m), 2.85 (3H, s), 1.59 (3H, d, J=6.9 Hz), 1.24 (3H, d, J=6.7 Hz); SFC RT 1.3 min (SFC4, LUX CELLULOSE-4+0.1% DEAISO 55% IPA).

Example 10: LCMS (ES+) 397 (M+H)$^+$, RT 2.78 min (Analytical Method 2), $^1$H NMR (400 MHz, MeOD) 7.81 (1H, d, J=6.3 Hz), 7.44-7.42 (1H, m), 7.37 (1H, s), 7.26 (1H, dd, J=7.0, 8.9 Hz), 6.98 (1H, d, J=6.5 Hz), 6.78 (1H, dd, J=1.9, 4.3 Hz), 6.44 (1H, dd, J=2.1, 2.1 Hz), 5.88 (1H, q, J=6.9 Hz), 4.41-4.36 (1H, m), 3.98-3.89 (2H, m), 3.81 (1H, dd, J=1.2, 13.2 Hz), 3.44-3.38 (2H, m), 3.44-3.37 (2H, m), 3.20-3.12 (1H, m), 2.86 (3H, s), 1.59 (3H, d, J=6.9 Hz), 1.25 (3H, d, J=6.5 Hz); SFC RT 2.13 min (SFC4, LUX CELLULOSE-4+0.1% DEAISO 55% IPA).

Example 11

(R)-4-(2-Fluoropyridin-4-yl)-2-methyl-N-((2-methyl-2H-indazol-4-yl)methyl)piperazine-1-carboxamide

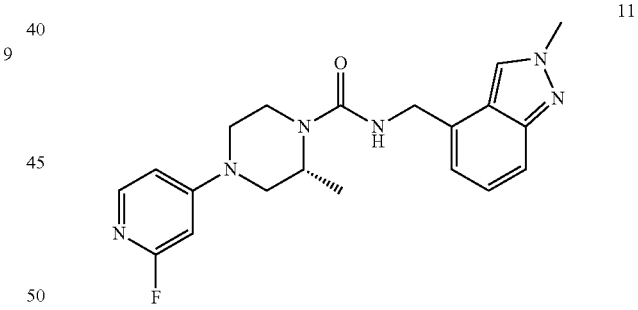

Following Method A from 4-aminomethyl-2-methyl-indazole dihydrochloride (65 mg, 0.331 mmol) and (R)-1-(2-fluoropyridin-4-yl)-3-methylpiperazine dihydrochloride (Intermediate 37, 90 mg, 0.331 mmol). Purification by prep HPLC gave the title compound. LCMS (ES+) 383 (M+H)$^+$, RT 2.79 min (Analytical Method 2), $^1$H NMR (400 MHz, MeOD) 8.29 (1H, s), 7.81 (1H, d, J=6.2 Hz), 7.50 (1H, d, J=8.7 Hz), 7.27 (1H, dd, J=6.8, 8.7 Hz), 7.01 (1H, d, J=6.8 Hz), 6.77 (1H, d, J=6.2 Hz), 6.42 (1H, dd, J=2.3, 2.3 Hz), 4.67 (2H, d, J=4.2 Hz), 4.39-4.34 (1H, m), 4.23 (3H, s), 3.96-3.77 (3H, m), 3.44-3.37 (2H, m), 3.20-3.12 (1H, m), 1.24 (3H, d, J=6.7 Hz).

Example 12

(R)—N—((R)-1-(Benzo[d][1,3]dioxol-4-yl)ethyl)-4-(2-fluoropyridin-4-yl)-2-methylpiperazine-1-carboxamide

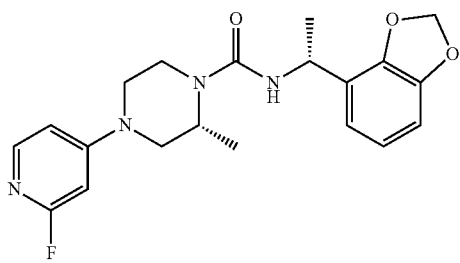

Following Method A from (R)-1-(benzo[d][1,3]dioxol-4-yl)ethan-1-amine dihydrochloride (45 mg, 0.224 mmol) and (R)-1-(2-fluoropyridin-4-yl)-3-methylpiperazine dihydrochloride (Intermediate 37, 60 mg, 0.224 mmol). Purification by prep HPLC gave the title compound. LCMS (ES+) 387 (M+H)$^+$, RT 3.09 min (Analytical Method 2), $^1$H NMR (400 MHz, MeOD) 8.19 (1H, d, J=6.0 Hz), 8.12 (1H, d, J=5.7 Hz), 7.01 (1H, dd, J=5.7, 8.3 Hz), 6.81 (2H, d, J=4.5 Hz), 6.73 (1H, dd, J=4.5, 4.5 Hz), 5.97 (2H, d, J=7.2 Hz), 5.13-5.05 (1H, m), 4.39-4.36 (1H, m), 3.95 (1H, d, J=13.3 Hz), 3.77-3.69 (2H, m), 3.34 (1H, m), 3.18 (1H, dd, J=3.5, 12.5 Hz), 3.05-2.97 (1H, m), 1.50 (3H, d, J=7.1 Hz), 1.32 (3H, d, J=6.6 Hz).

Example 13

(R)—N—((R)-1-(2-Chlorophenyl)ethyl)-4-(2-fluoropyridin-4-yl)-3-methylpiperazine-1-carboxamide

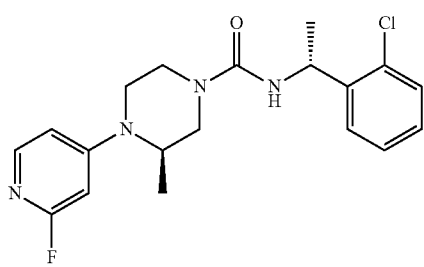

Following Method B from (R)-1-(2-fluoropyridin-4-yl)-2-methylpiperazine dihydrochloride (Intermediate 33, 54 mg, 0.23 mmol) and Intermediate 3 (75 mg, 0.23 mmol). Purification by preparative-HPLC gave the title compound. LCMS (ES+) 377 (M+H)$^+$, RT 3.27 min (Analytical Method 2), $^1$H NMR (400 MHz, DMSO) 7.82 (1H, d, J=6.1 Hz), 7.48 (1H, dd, J=1.5, 7.7 Hz), 7.38 (1H, d, J=7.7 Hz), 7.32 (1H, dd, J=7.1, 7.1 Hz), 7.26-7.21 (1H, m), 7.03 (1H, d, J=7.5 Hz), 6.78 (1H, d, J=6.2 Hz), 6.46 (1H, s), 5.22-5.17 (1H, m), 4.19-4.17 (1H, m), 4.04 (1H, d, J=13.3 Hz), 3.94 (1H, d, J=13.3 Hz), 3.69-3.64 (1H, m), 3.17-2.94 (3H, m), 1.35 (3H, d, J=7.1 Hz), 1.06 (3H, d, J=6.5 Hz).

Example 14

(R)—N—((R)-1-(2-Chloro-4-fluorophenyl)ethyl)-4-(2-fluoropyridin-4-yl)-3-methylpiperazine-1-carboxamide

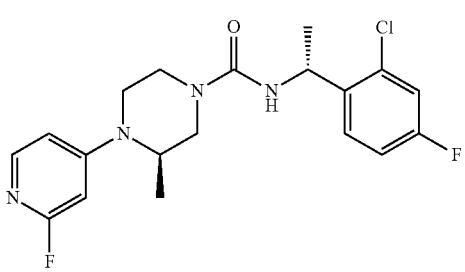

Following Method B from (R)-1-(2-fluoropyridin-4-yl)-2-methylpiperazine dihydrochloride (Intermediate 33, 63 mg, 0.19 mmol) and 4-nitrophenyl (1-(2-chloro-4-fluorophenyl)ethyl)carbamate (Intermediate 11, 43 mg, 0.19 mmol). Purification by preparative-HPLC and chiral SFC gave the title compound. Percentage ee: 100%. LCMS (ES+) 395 (M+H)$^+$, RT 3.24 min (Analytical Method 1), $^1$H NMR (400 MHz, DMSO) 7.82 (1H, d, J=6.1 Hz), 7.53-7.48 (1H, m), 7.38-7.35 (1H, m), 7.25-7.19 (1H, m), 7.03 (1H, d, J=7.4 Hz), 6.77 (1H, d, J=6.1 Hz), 6.45 (1H, s), 5.20-5.12 (1H, m), 4.20-4.16 (1H, m), 4.03 (1H, dd, J=1.1, 12.4 Hz), 3.92 (1H, d, J=13.3 Hz), 3.69-3.64 (1H, m), 3.16-2.94 (3H, m), 1.36-1.33 (3H, m), 1.05 (3H, d, J=6.5 Hz); SFC RT 3.36 min (SFC4, YMC AMYLOSE-C+0.1% DEAISO 20% IPA).

Example 15

(2R,6R)-4-(2-Fluoropyridin-4-yl)-N—((R)-1-(3-methoxyphenyl)ethyl)-2,6-dimethylpiperazine-1-carboxamide

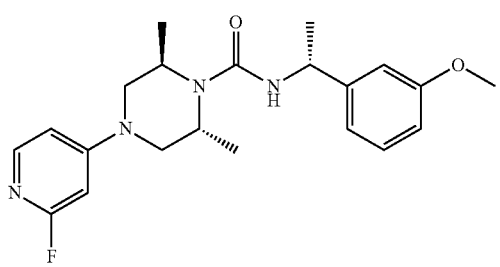

Following Method B from (3R,5R)-1-(2-fluoropyridin-4-yl)-3,5-dimethylpiperazine dihydrochloride (Intermediate 41, 85 mg, 0.316 mmol) and 4-nitrophenyl (R)-(1-(3-methoxyphenyl)ethyl)carbamate (Intermediate 1, 100 mg, 0.316 mmol). Purification by prep HPLC gave the title compound. LCMS (ES+) 387 (M+H)$^+$, RT 4.08 min (Analytical Method 4), $^1$H NMR (400 MHz, MeOD) 7.82 (1H, d, J=6.2 Hz), 7.25 (1H, dd, J=7.8, 7.8 Hz), 6.95 (2H, d, J=7.3 Hz), 6.82-6.79 (1H, m), 6.66 (1H, d, J=6.2 Hz), 6.45 (1H, d, J=7.7 Hz), 6.30 (1H, dd, J=2.2, 2.2 Hz), 5.05-4.96 (1H, m), 4.36 (2H, dd, J=2.4, 2.4 Hz), 3.83-3.77 (5H, m), 3.57 (2H, d, J=11.6 Hz), 1.52 (3H, d, J=7.1 Hz), 1.28 (6H, d, J=6.7 Hz).

Example 16

(R)-4-(3-fluoropyridin-4-yl)-N-(1-(3-methoxyphenyl)ethyl)piperazine-1-carboxamide

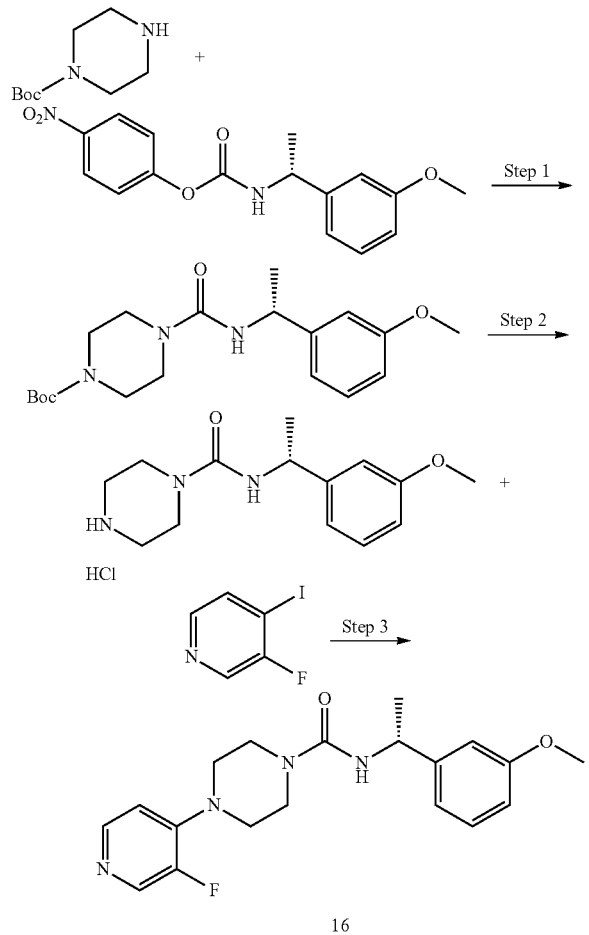

Step 1: (R)-4-((1-(3-Methoxyphenyl)ethyl)carbamoyl)piperazine-carboxylate

Following method B from tert-butyl piperazine-N-carboxylate (162 mg, 087 mmol) and 4-Nitrophenyl (R)-(1-(3-methoxyphenyl)ethyl)carbamate (Intermediate 1, 250 mg, 079 mmol). gave the title compound.

Step 2: (R)—N-(1-(3-Methoxyphenyl)ethyl)piperazine-1-carboxamide Hydrogen Chloride Following method C from tert-butyl (R)-4-((1-(3-methoxyphenyl)ethyl)carbamoyl)piperazine-1-carboxylate (90 mg, 0.248 mmol) gave the title compound. Used crude in the next step.

Step 3: (R)-4-(3-Fluoropyridin-4-yl)-N-(1-(3-methoxyphenyl)ethyl)piperazine-1-carboxamide (R)—N-(1-(3-Methoxyphenyl)ethyl)piperazine-1-carboxamide hydrogen chloride (65 mg, 0.247 mmol), 3-Fluoro-4-iodopyridine (110 mg, 0.494 mmol), Sodium tert-butoxide (95 mg, 0.988 mol), [1,1'-Bis(di-tert-butylphosphino)ferrocene]dichloropalladium(II) (16 mg, 0.025 mmol) in toluene (1 mL) were mixed and degassed with $N_2$ for 10 min before heating in a CEM microwave for 1 h at 115° C. To the reaction was added EtOAc, washed with brine dried by passing through a SPE cartridge and evaporating to give the crude product. The crude product was purified by prep HPLC to give the title compound. LCMS (ES+) 359 (M+H)$^+$, RT 2.93 min (Analytical Method 2), $^1$H NMR (400 MHz, DMSO), 8.29 (1H, d, J=5.6 Hz), 8.17 (1H, d, J=5.5 Hz), 7.22 (1H, dd, J=8.1, 8.1 Hz), 7.01 (1H, dd, J=5.5, 8.3 Hz), 6.92-6.87 (3H, m), 6.78 (1H, dd, J=2.1, 8.1 Hz), 4.87-4.79 (1H, m), 3.75 (3H, s), 3.50 (4H, dd, J=5.0, 5.0 Hz), 3.23 (4H, dd, J=5.0, 5.0 Hz), 1.37 (3H, d, J=7.2 Hz).

Example 17

(R)-1-(3-Methoxyphenyl)ethyl 4-(3-fluoropyridin-4-yl)piperazine-1-carboxylate

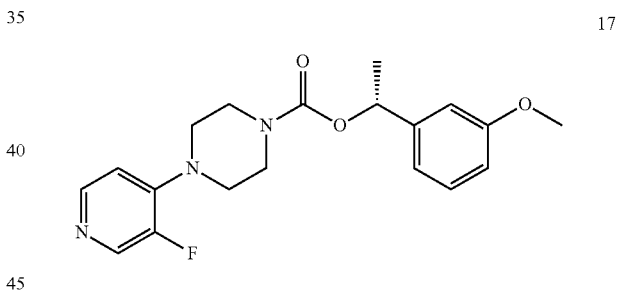

17

To a stirred solution of 4-nitrophenyl chloroformate (132 mg, 0.657 mmol) in DCM (5 mL) at r.t. was added a solution of (R)-1-(3-methoxyphenyl)ethan-1-ol (100 mg, 0.657 mmol) and TEA (0.27 mL, 1.97 mmol) in DCM (5 mL) dropwise. The mixture was stirred at r.t. for 30 min and then treated with 1-(3-fluoropyridin-4-yl) piperazine dihydrochloride (Intermediate 32, 167 mg, 0.657 mmol). After 2 d the reaction mixture was washed with sat. NaHCO$_3$ soln. and brine, passed through a hydrophobic frit and concentrated to dryness. Purification by prep HPLC gave the title compound. LCMS (ES+) 360 (M+H)$^+$, RT 2.30 min (Analytical Method 2), $^1$H NMR (400 MHz, CDCl$_3$) 8.25 (1H, d, J=5.4 Hz), 8.19 (1H, d, J=5.4 Hz), 7.30-7.25 (1H, m), 6.94 (1H, d, J=7.7 Hz), 6.89 (1H, s), 6.83 (1H, dd, J=2.4, 8.2 Hz), 6.73 (1H, dd, J=5.5, 7.8 Hz), 5.81 (1H, q, J=6.6 Hz), 3.82 (3H, s), 3.72-3.64 (4H, m), 3.26 (4H, dd, J=5.1, 5.1 Hz), 1.56 (3H, d, J=6.5 Hz).

Example 18

(R)—N-(1-(2-Fluoro-3-methoxyphenyl)ethyl)-4-(3-fluoropyridin-4-yl)piperazine-1-carboxamide

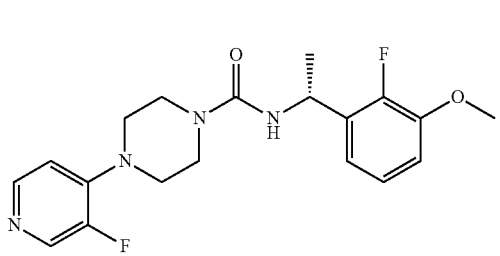

Following Method A from (R)-1-(2-fluoro-3-methoxyphenyl)ethan-1-amine hydrochloride (0.414 mmol) and 1-(3-fluoropyridin-4-yl) piperazine dihydrochloride (Intermediate 32, 0.414 mmol). Purification by prep HPLC gave the title compound. LCMS (ES+) 377 (M+H)$^+$, RT 2.96 min (Analytical Method 2), $^1$H NMR (400 MHz, DMSO) 8.29 (1H, d, J=5.6 Hz), 8.17 (1H, d, J=5.4 Hz), 7.09 (1H, dd, J=8.1, 8.1 Hz), 7.03-6.94 (4H, m), 5.13-5.08 (1H, m), 3.83 (3H, s), 3.50 (4H, dd, J=5.0, 5.0 Hz), 3.23 (4H, dd, J=5.0, 5.0 Hz), 1.36 (3H, d, J=7.1 Hz).

Example 19

(R)—N-(1-(2-Bromophenyl)ethyl)-4-(3-fluoropyridin-4-yl)piperazine-1-carboxamide

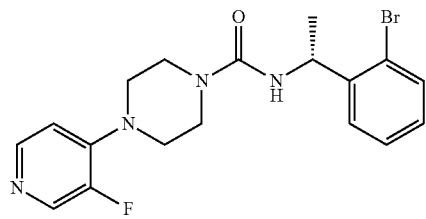

Following Method A from (R)-1-(2-bromophenyl)ethan-1-amine hydrochloride (0.414 mmol) and 1-(3-fluoropyridin-4-yl) piperazine dihydrochloride (Intermediate 32, 0.414 mmol). Purification by prep HPLC gave the title compound. LCMS (ES+) 407 (M+H)$^+$, RT 3.11 min (Analytical Method 2), $^1$H NMR (400 MHz, DMSO) 8.29 (1H, d, J=5.6 Hz), 8.17 (1H, d, J=5.5 Hz), 7.55 (1H, d, J=7.8 Hz), 7.50-7.47 (1H, m), 7.38 (1H, dd, J=7.3, 7.3 Hz), 7.18-7.13 (1H, m), 7.10 (1H, d, J=7.3 Hz), 7.02 (1H, dd, J=5.6, 8.3 Hz), 5.14-5.09 (1H, m), 3.51 (4H, dd, J=5.0, 5.0 Hz), 3.24 (4H, dd, J=5.0, 5.0 Hz), 1.34 (3H, d, J=7.0 Hz).

Example 20

(R)—N—((R)-1-(2-Chlorophenyl)ethyl)-4-(2-fluoropyridin-4-yl)-2-methylpiperazine-1-carboxamide

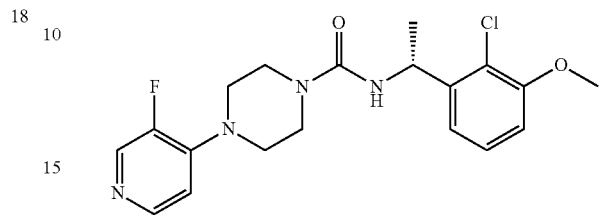

Following Method B from 4-nitrophenyl (R)-(1-(2-chloro-3-methoxyphenyl)ethyl)carbamate (Intermediate 23, 0.60 mmol) and 1-(3-fluoropyridin-4-yl) piperazine dihydrochloride (Intermediate 32, 0.60 mmol). Purification by prep HPLC and chiral prep HPLC to separate the trace of (S) isomer gave the title compound. LCMS (ES+) 393 (M+H)$^+$, RT 3.05 min (Analytical Method 2), $^1$H NMR (400 MHz, DMSO) 8.29 (1H, d, J=5.6 Hz), 8.17 (1H, d, J=5.5 Hz), 7.29 (1H, dd, J=8.0, 8.0 Hz), 7.09-6.98 (4H, m), 5.24-5.15 (1H, m), 3.85 (3H, s), 3.51 (4H, dd, J=5.1, 5.1 Hz), 3.23 (4H, dd, J=5.0, 5.0 Hz), 1.33 (3H, d, J=7.0 Hz); SFC RT 4.28 min (SFC1, YMC AMYLOSE-C+0.1% DEAISO 25% IPA).

Example 21

(R)—N-(1-(2-Chloro-4-fluorophenyl)ethyl)-4-(3-fluoropyridin-4-yl)piperazine-1-carboxamide

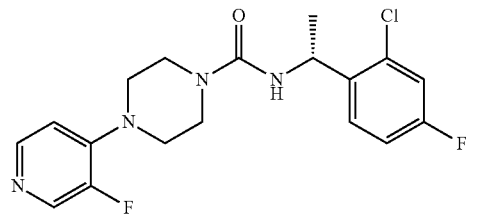

Following Method B from 1-(3-fluoropyridin-4-yl) piperazine dihydrochloride (Intermediate 32, 40 mg, 0.19 mmol) and 4-nitrophenyl (1-(2-chloro-4-fluorophenyl)ethyl)carbamate (Intermediate 11, 63 mg, 0.19 mmol). Purification by preparative-HPLC gave the title compound. Percentage ee: 84.1%. LCMS (ES+) 381 (M+H)$^+$, RT 2.62 min (Analytical Method 1), $^1$H NMR (400 MHz, DMSO) 8.29 (1H, d, J=5.6 Hz), 8.17 (1H, d, J=5.4 Hz), 7.52 (1H, dd, J=6.3, 8.7 Hz), 7.37 (1H, dd, J=2.6, 8.9 Hz), 7.26-7.21 (1H, m), 7.09-6.99 (2H, m), 5.18-5.09 (1H, m), 3.51 (4H, t, J=5.1 Hz), 3.24 (4H, t, J=5.0 Hz), 1.34 (3H, d, J=7.0 Hz); SFC RT 1.7 min (SFC1, YMC AMYLOSE-C+0.1% DEAISO 25% EtOH).

Examples 22 and 23 N-(1-(2-Chloro-3-fluorophenyl)ethyl)-4-(3-fluoropyridin-4-yl)piperazine-1-carboxamide (enantiomer 1) and N-(1-(2-Chloro-3-fluorophenyl)ethyl)-4-(3-fluoropyridin-4-yl)piperazine-1-carboxamide (enantiomer 2)

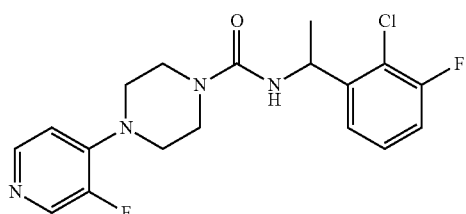

Enantiomer 1

22

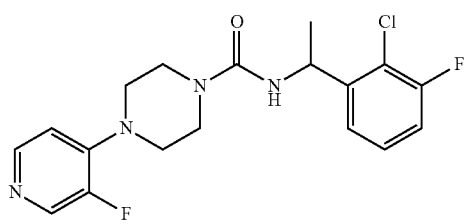

Enantiomer 2

23

Following Method B from 1-(3-fluoropyridin-4-yl) piperazine dihydrochloride (Intermediate 32, 74 mg, 0.34 mmol) and 4-nitrophenyl (1-(2-chloro-3-fluorophenyl)ethyl)carbamate (Intermediate 12, 115 mg, 0.34 mmol). Purification by preparative-HPLC and chiral SFC gave the title compounds.

Example 22: Percentage ee: 98.2%. LCMS (ES+) 381 (M+H)$^+$, RT 3.13 min (Analytical Method 2), $^1$H NMR (400 MHz, MeOD) 8.08-7.99 (2H, m), 7.22-7.13 (2H, m), 7.03-6.97 (1H, m), 6.91-6.86 (1H, m), 5.23-5.16 (1H, m), 3.52-3.48 (4H, m), 3.28-3.24 (4H, m), 1.36-1.33 (3H, m); SFC RT 1.76 min (SFC4, YMC AMYLOSE-C+0.1% DEAISO 20% EtOH).

Example 23: Percentage ee: 100%. LCMS (ES+) 381 (M+H)$^+$, RT 3.13 min (Analytical Method 2), $^1$H NMR (400 MHz, MeOD) 8.17 (2H, dd, J=5.8, 26.2 Hz), 7.36-7.26 (2H, m), 7.16-7.10 (1H, m), 7.02 (1H, dd, J=5.7, 8.2 Hz), 5.32 (1H, q, J=7.0 Hz), 3.65-3.62 (4H, m), 3.42-3.36 (4H, m), 1.48 (3H, d, J=7.0 Hz); SFC RT 2.73 min (SFC4, YMC AMYLOSE-C+0.1% DEAISO 20% EtOH).

Example 24

(R)—N-(1-(2-Chloro-5-methoxyphenyl)ethyl)-4-(3-fluoropyridin-4-yl)piperazine-1-carboxamide

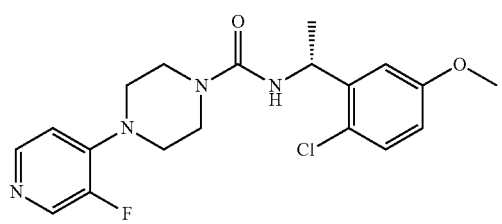

24

Following Method B from 4-nitrophenyl (R)-(1-(2-chloro-5-methoxyphenyl)ethyl)carbamate (Intermediate 4, 0.222 mmol) and 1-(3-fluoropyridin-4-yl) piperazine dihydrochloride (Intermediate 32, 0.222 mmol). Purification by prep HPLC gave the title compound. LCMS (ES+) 393 (M+H)$^+$, RT 3.15 min (Analytical Method 2), $^1$H NMR (400 MHz, MeOD) 8.20 (1H, d, J=6.0 Hz), 8.13 (1H, d, J=5.6 Hz), 7.27 (1H, d, J=8.8 Hz), 7.04-6.99 (2H, m), 6.81 (1H, dd, J=3.1, 8.8 Hz), 5.27 (1H, q, J=7.0 Hz), 3.81 (3H, s), 3.66-3.62 (4H, m), 3.42-3.37 (4H, m), 1.46 (3H, d, J=7.0 Hz); SFC RT 2.59 min (SFC1, LUX CELLULOSE-4+0.1% DEAISO 40% MeOH).

Example 25

4-(3-Fluoropyridin-4-yl)-N-(3-methoxybenzyl)piperazine-1-carboxamide

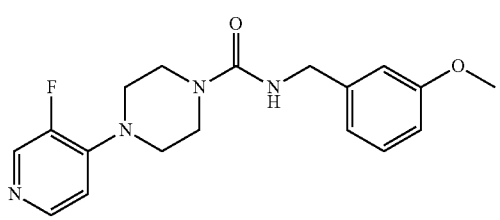

25

Following Method A from (3-methoxyphenyl)methanamine (0.31 mmol) and 1-(3-fluoropyridin-4-yl) piperazine dihydrochloride (Intermediate 32, 0.31 mmol). Purification by preparative-HPLC gave the title compound. LCMS (ES+) 354 (M+H)$^+$, RT 2.97 min (Analytical Method 2). $^1$H NMR (400 MHz, DMSO) 8.29 (1H, d, J=5.6 Hz), 8.17 (1H, d, J=5.5 Hz), 7.26-7.16 (2H, m), 7.01 (1H, dd, J=5.5, 8.3 Hz), 6.86 (2H, d, J=7.0 Hz), 6.80 (1H, dd, J=1.8, 7.2 Hz), 4.25 (2H, d, J=5.8 Hz), 3.74 (3H, s), 3.51 (4H, dd, J=5.1, 5.1 Hz), 3.24 (4H, dd, J=5.0, 5.0 Hz).

Example 26

N-(1-(2-Chloro-6-fluorophenyl)ethyl)-4-(3-fluoropyridin-4-yl)piperazine-1-carboxamide

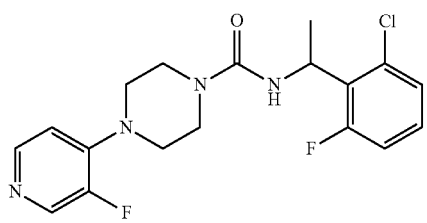

26

Following Method B from 1-(3-fluoropyridin-4-yl) piperazine dihydrochloride (Intermediate 32, 40 mg, 0.19 mmol) and 4-nitrophenyl (1-(2-chloro-6-fluorophenyl)ethyl)carbamate (Intermediate 13, 170 mg, 0.50 mmol). Purification by preparative-HPLC gave the title compound. ee: 49.1%. LCMS (ES+) 381 (M+H)$^+$, RT 2.74 min (Analytical Method 2), $^1$H NMR (400 MHz, DMSO) 8.28 (1H, d, J=5.6 Hz), 8.16 (1H, d, J=5.4 Hz), 7.30-7.15 (2H, m), 7.00 (1H, dd, J=5.6, 8.2 Hz), 6.90 (1H, d, J=6.5 Hz), 5.36-5.28

(1H, m), 3.50-3.44 (4H, m), 3.23-3.18 (4H, m), 1.48-1.45 (3H, m); SFC RT 4.06 min (SFC1, LUX CELLULOSE-4+ 0.1% DEAISO 30% MeOH).

Example 27

(R)—N-(1-(Benzo[d][1,3]dioxol-4-yl)ethyl)-4-(3-fluoropyridin-4-yl)piperazine-1-carboxamide

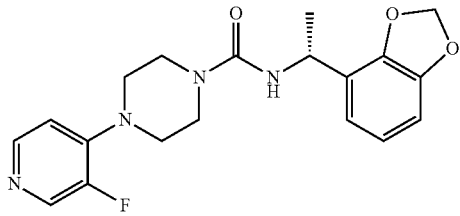

27

Following Method A from (R)-1-(benzo[d][1,3]dioxol-4-yl)ethan-1-amine hydrochloride (45 mg, 0.224 mmol) and 1-(3-fluoropyridin-4-yl) piperazine dihydrochloride (Intermediate 32, 57 mg, 0.224 mmol). Purification by prep HPLC gave the title compound after freeze drying. LCMS (ES+) 373 (M+H)$^+$, RT 3.00 min (Analytical Method 2), $^1$H NMR (400 MHz, MeOD) 8.19 (1H, d, J=6.0 Hz), 8.13 (1H, d, J=5.6 Hz), 7.01 (1H, dd, J=5.7, 8.1 Hz), 6.83-6.81 (2H, m), 6.73 (1H, dd, J=3.2, 5.7 Hz), 5.97 (2H, d, J=8.4 Hz), 5.07 (1H, q, J=7.1 Hz), 3.63 (4H, dd, J=3.9, 6.3 Hz), 3.42-3.38 (4H, m), 1.49 (3H, d, J=7.1 Hz).

Example 28

(R)—N-(1-(2,3-Dihydrobenzofuran-4-yl)ethyl)-4-(3-fluoropyridin-4-yl)piperazine-1-carboxamide

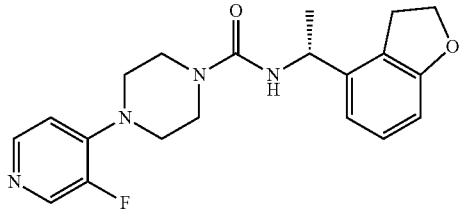

28

Following Method A from (R)-1-(2,3-dihydrobenzofuran-4-yl)ethan-1-amine hydrochloride (0.56 mmol) and 1-(3-fluoropyridin-4-yl)piperazine dihydrochloride (Intermediate 32, 0.56 mmol). Purification by prep HPLC gave the title compound. LCMS (ES+) 371 (M+H)$^+$, RT 3.13 min (Analytical Method 2). $^1$H NMR (400 MHz, DMSO) 8.26 (1H, d, J=5.6 Hz), 8.14 (1H, d, J=5.5 Hz), 7.04 (1H, dd, J=7.8, 7.8 Hz), 6.98 (1H, dd, J=5.3, 8.2 Hz), 6.87 (1H, d, J=7.8 Hz), 6.83 (1H, d, J=7.8 Hz), 6.58 (1H, d, J=7.8 Hz), 4.84-4.75 (1H, m), 4.53-4.47 (2H, m), 3.47 (4H, dd, J=5.0, 5.0 Hz), 3.23-3.15 (6H, m), 1.33 (3H, d, J=7.1 Hz).

Example 29

(R)—N-(1-(Benzofuran-4-yl)ethyl)-4-(3-fluoropyridin-4-yl)piperazine-1-carboxamide

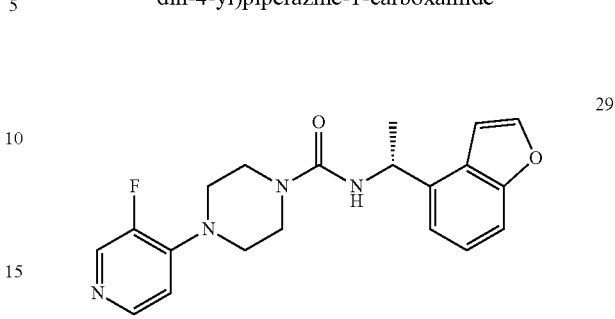

29

Following Method A from (R)-1-(benzofuran-4-yl)ethan-1-amine (0.5 mmol) and 1-(3-fluoropyridin-4-yl)piperazine dihydrochloride (Intermediate 32, 0.5 mmol). Purification by preparative-HPLC gave the title compound. LCMS (ES+) 395 (M+H)$^+$, RT 3.39 min (Analytical Method 2), $^1$H NMR (400 MHz, DMSO) 8.28 (1H, d, J=5.6 Hz), 8.17 (1H, d, J=5.5 Hz), 7.98 (1H, d, J=2.3 Hz), 7.45 (1H, d, J=8.0 Hz), 7.27 (1H, dd, J=7.8, 7.8 Hz), 7.21 (1H, d, J=7.2 Hz), 7.15 (1H, d, J=2.3 Hz), 7.05-6.98 (2H, m), 5.25-5.16 (1H, m), 3.53-3.48 (4H, m), 3.22 (4H, dd, J=5.0, 5.0 Hz), 1.47 (3H, d, J=7.0 Hz).

Example 30

(R)—N-(1-(2,2-Dimethyl-2,3-dihydrobenzofuran-4-yl)ethyl)-4-(3-fluoropyridin-4-yl)piperazine-1-carboxamide

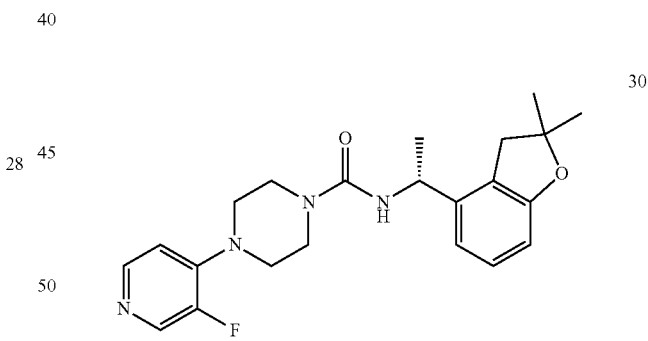

30

Following Method A from (R)-1-(2,2-dimethyl-2,3-dihydrobenzofuran-4-yl)ethan-1-amine hydrochloride (0.430 mmol) and 1-(3-fluoropyridin-4-yl)piperazine dihydrochloride (Intermediate 32, 0.430 mmol). Purification by prep HPLC gave the title compound. LCMS (ES+) 399 (M+H)$^+$, RT 2.62 min (Analytical Method 1), $^1$H NMR (400 MHz, MeOD) 8.21 (1H, d, J=5.2 Hz), 8.13 (1H, d, J=5.3 Hz), 7.11-7.00 (2H, m), 6.84 (1H, d, J=7.7 Hz), 6.55 (1H, d, J=7.8 Hz), 4.92-4.86 (1H, m), 3.62 (4H, dd, J=3.7, 6.4 Hz), 3.40 (4H, dd, J=5.1, 5.1 Hz), 3.17 (1H, d, J=15.4 Hz), 3.02 (1H, d, J=15.4 Hz), 1.48-1.44 (9H, m); SFC RT 1.4 min (SFC1, YMC AMYLOSE-C+0.1% DEAISO 25% MeOH).

Example 31

(R)-4-(3-Fluoropyridin-4-yl)-N-(1-(2-methylbenzo-furan-4-yl)ethyl)piperazine-1-carboxamide

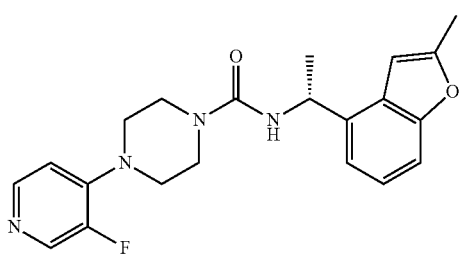

31

Following Method B from 4-nitrophenyl (R)-(1-(2-methylbenzofuran-4-yl)ethyl)carbamate (Intermediate 5, 0.138 mmol) and 1-(3-fluoropyridin-4-yl)piperazine dihydrochloride (Intermediate 32, 0.138 mmol). Purification by prep HPLC gave the title compound. LCMS (ES+) 384 (M+H)⁺, RT 2.65 min (Analytical Method 1), ¹H NMR (400 MHz, MeOD) 8.19 (1H, d, J=6.0 Hz), 8.12 (1H, d, J=5.6 Hz), 7.30-7.26 (1H, m), 7.19-7.17 (2H, m), 7.00 (1H, dd, J=5.7, 8.2 Hz), 6.63 (1H, s), 5.26 (1H, q, J=7.1 Hz), 3.65-3.59 (4H, m), 3.40-3.36 (4H, m), 2.47 (3H, s), 1.57 (3H, d, J=7.0 Hz); SFC RT 1.95 min (SFC1, LUX CELLULOSE-3+0.1% DEAISO 15% MeOH).

Examples 32 and 33 (R)-4-(3-fluoropyridin-4-yl)-N-(1-(1-methyl-1H-indol-7-yl)ethyl)piperazine-1-carboxamide and (S)-4-(3-fluoropyridin-4-yl)-N-(1-(1-methyl-1H-indol-7-yl)ethyl)piperazine-1-carboxamide

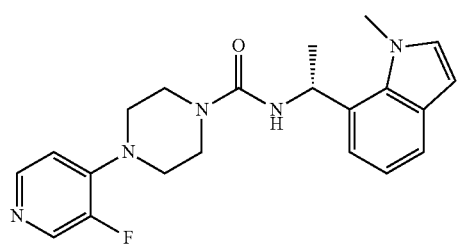

32

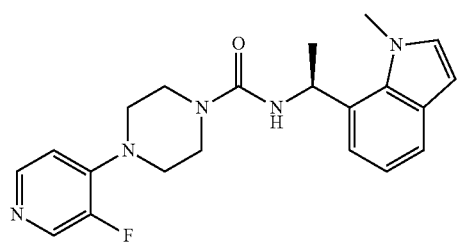

33

Following Method B from 4-nitrophenyl (R)-(1-(1-methyl-1H-indol-7-yl)ethyl)carbamate (Intermediate 14, 0.91 mmol) and (R)-1-(3-fluoropyridin-4-yl)-3-methylpiperazine dihydrochloride (Intermediate 32, 0.65 mmol). Purification by prep HPLC and chiral prep HPLC to separate the isomers gave the title compounds.

Example 32: LCMS (ES+) 382 (M+H)⁺, RT 3.15 min (Analytical Method 2), ¹H NMR (400 MHz, DMSO) 8.26 (1H, d, J=5.8 Hz), 8.14 (1H, d, J=5.5 Hz), 7.40 (1H, d, J=7.3 Hz), 7.25-7.22 (2H, m), 7.01-6.94 (3H, m), 6.39 (1H, d, J=3.0 Hz), 5.84-5.75 (1H, m), 4.40-4.35 (1H, m), 4.07 (3H, s), 3.89 (1H, d, J=13.3 Hz), 3.62-3.52 (2H, m), 3.17-3.08 (1H, m), 3.01 (1H, dd, J=3.5, 12.4 Hz), 2.88-2.79 (1H, m), 1.49 (3H, d, J=6.9 Hz), 1.16 (3H, d, J=6.7 Hz); SFC RT 1.3 min (SFC1, YMC AMYLOSE-C+0.1% DEAISO 40% MeOH).

Example 33: LCMS (ES+) 382 (M+H)⁺, RT 3.15 min (Analytical Method 2), ¹H NMR (400 MHz, DMSO) 8.28 (1H, d, J=5.6 Hz), 8.16 (1H, d, J=5.5 Hz), 7.39 (1H, dd, J=1.1, 7.8 Hz), 7.25-7.22 (2H, m), 7.06 (1H, d, J=7.5 Hz), 7.02-6.97 (2H, m), 6.39 (1H, d, J=3.1 Hz), 5.81-5.76 (1H, m), 4.08 (3H, s), 3.52-3.48 (4H, m), 3.24-3.19 (4H, m), 1.49 (3H, d, J=6.9 Hz); SFC RT 2.46 min (SFC1, YMC AMYLOSE-C+0.1% DEAISO 40% MeOH).

Examples 34 and 35 (R)-4-(3-fluoropyridin-4-yl)-N-(1-(3-methylimidazo[1,2-a]pyridin-5-yl)ethyl)piperazine-1-carboxamide and (S)-4-(3-fluoropyridin-4-yl)-N-(1-(3-methylimidazo[1,2-a]pyridin-5-yl)ethyl)piperazine-1-carboxamide

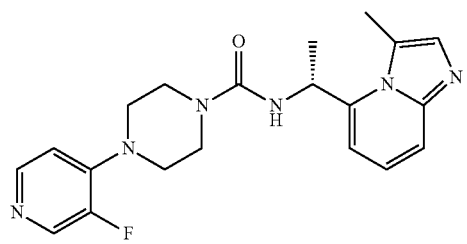

34

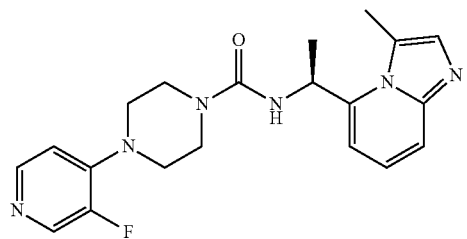

35

Following Method B from 4-nitrophenyl (R)-(1-(3-methylimidazo[1,2-a]pyridin-5-yl)ethyl)carbamate (Intermediate 10, 1.31 mmol) and 1-(3-fluoropyridin-4-yl) piperazine dihydrochloride (Intermediate 32, 0.65 mmol). Purification by prep HPLC and chiral prep HPLC to separate the isomers gave the title compounds.

Example 34: LCMS (ES+) 383 (M+H)⁺, RT 2.72 min (Analytical Method 2), ¹H NMR (400 MHz, DMSO) 8.28 (1H, d, J=5.6 Hz), 8.16 (1H, d, J=5.4 Hz), 7.39 (1H, d, J=7.5 Hz), 7.25-7.22 (2H, m), 7.06 (1H, d, J=7.7 Hz), 7.02-6.97 (2H, m), 6.39 (1H, d, J=3.1 Hz), 5.81-5.76 (1H, m), 4.08 (3H, s), 3.50 (4H, dd, J=5.0, 5.0 Hz), 3.22 (4H, dd, J=5.0, 5.0 Hz), 1.49 (3H, d, J=6.9 Hz); SFC RT 4.33 min (SFC4, LUX CELLULOSE-4+0.1% DEAISO 25% MeOH).

Example 35: LCMS (ES+) 383 (M+H)⁺, RT 2.71 min (Analytical Method 2), ¹H NMR (400 MHz, MeOD) 8.20 (1H, d, J=6.0 Hz), 8.14 (1H, d, J=5.6 Hz), 7.43 (1H, dd, J=1.1, 9.0 Hz), 7.36 (1H, s), 7.25 (1H, dd, J=7.2, 8.9 Hz), 7.05-6.98 (2H, m), 5.87 (1H, q, J=6.9 Hz), 3.68-3.64 (4H, m), 3.42-3.38 (4H, m), 2.86 (3H, s), 1.59 (3H, d, J=6.9 Hz) SFC RT 5.37 min (SFC4, LUX CELLULOSE-4+0.1% DEAISO 25% MeOH).

Example 36

(R)—N-(1-(2,2-Difluorobenzo[d][1,3]dioxol-4-yl)ethyl)-4-(3-fluoropyridin-4-yl)piperazine-1-carboxamide

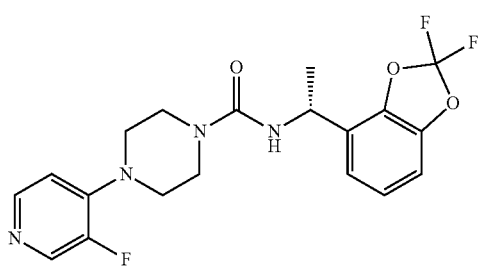

Following Method B from 1-(3-fluoropyridin-4-yl) piperazine dihydrochloride (Intermediate 32, 137 mg, 0.633 mmol) and 4-nitrophenyl (R)-(1-(2,2-difluorobenzo[d][1,3]dioxol-4-yl)ethyl)carbamate (Intermediate 15, 232 mg, 0.633 mmol). Purification via chiral SFC gave the title compound (97.2% purity, 100% ee). LCMS (ES+) 409 (M+H)$^+$, RT 3.13 min (Analytical Method 3), $^1$H NMR (400 MHz, CDCl$_3$) 8.26-8.18 (2H, m), 7.05-6.95 (3H, m), 6.73 (1H, dd, J=5.5, 7.9 Hz), 5.16-5.08 (1H, m), 4.96-4.92 (1H, m), 3.62-3.50 (4H, m), 3.32-3.28 (4H, m), 1.55 (3H, d, J=49.3 Hz); SFC RT 1.96 min (SFC4, LUX CELLULOSE-4+0.1% DEAISO 20% MeOH).

Example 37

N-(Benzo[d][1,3]dioxol-4-ylmethyl)-4-(3-fluoropyridin-4-yl)piperazine-1-carboxamide

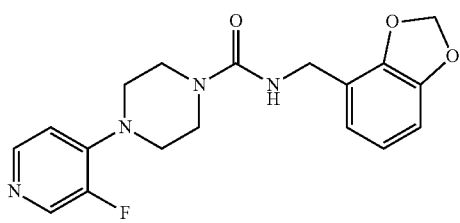

Following Method B from 4-nitrophenyl (benzo[d][1,3]dioxol-4-ylmethyl)carbamate (Intermediate 7, 0.237 mmol) and 1-(3-fluoropyridin-4-yl)piperazine dihydrochloride (Intermediate 32, 0.237 mmol). Purification by prep HPLC gave the title compound. LCMS (ES+) 359 (M+H)$^+$, RT 2.91 min (Analytical Method 2), $^1$H NMR (400 MHz, MeOD) 8.19 (1H, d, J=6.0 Hz), 8.13 (1H, d, J=5.6 Hz), 7.02 (1H, dd, J=5.7, 8.2 Hz), 6.83-6.80 (2H, m), 6.76-6.73 (1H, m), 5.97 (2H, s), 4.39 (2H, s), 3.64-3.60 (4H, m), 3.41-3.37 (4H, m).

Example 38

N-(Benzofuran-4-ylmethyl)-4-(3-fluoropyridin-4-yl)piperazine-1-carboxamide

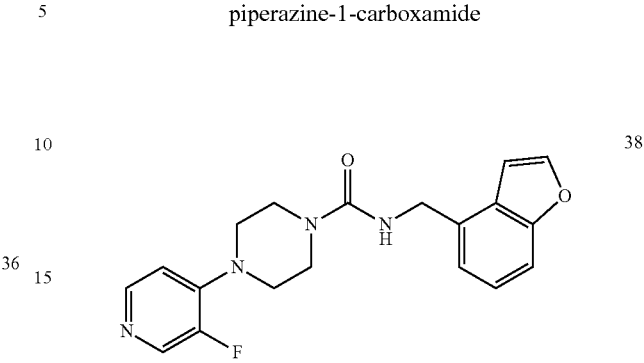

Following Method B from 1-(3-fluoropyridin-4-yl) piperazine dihydrochloride (Intermediate 32, 137 mg, 0.63 mmol) and 4-nitrophenyl (benzofuran-4-ylmethyl)carbamate (Intermediate 9, 200 mg, 0.63 mmol). Purification by SCX gave the title compound. LCMS (ES+) 355 (M+H)$^+$, RT 3.02 min (Analytical Method 2), $^1$H NMR (400 MHz, MeOD) 8.20-8.12 (2H, m), 7.78-7.77 (1H, m), 7.44-7.41 (1H, m), 7.30-7.19 (2H, m), 7.03-6.99 (2H, m), 4.67 (2H, s), 3.65-3.61 (4H, m), 3.42-3.33 (4H, m).

Example 39

N-(Benzo[d]oxazol-7-ylmethyl)-4-(3-fluoropyridin-4-yl)piperazine-1-carboxamide

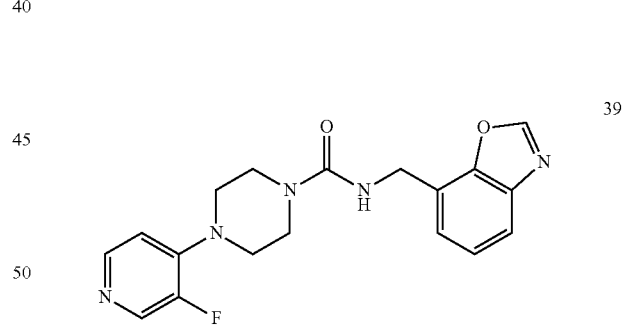

Following Method A from benzo[d]oxazol-7-ylmethanamine hydrochloride (0.542 mmol) and 1-(3-fluoropyridin-4-yl)piperazine dihydrochloride (Intermediate 32, 0.542 mmol). Purification by prep HPLC gave the title compound. LCMS (ES+) 356 (M+H)$^+$, RT 2.38 min (Analytical Method 1), $^1$H NMR (400 MHz, DMSO) 8.77 (1H, s), 8.29 (1H, d, J=5.6 Hz), 8.17 (1H, d, J=5.5 Hz), 7.70-7.66 (1H, m), 7.40-7.30 (3H, m), 7.02 (1H, dd, J=5.6, 8.3 Hz), 4.58 (2H, d, J=5.6 Hz), 3.52 (4H, dd, J=5.0, 5.0 Hz), 3.25 (4H, dd, J=5.0, 5.0 Hz).

Example 40

N-((2,3-Dihydrobenzo[b][1,4]dioxin-5-yl)methyl)-4-(3-fluoropyridin-4-yl)piperazine-1-carboxamide

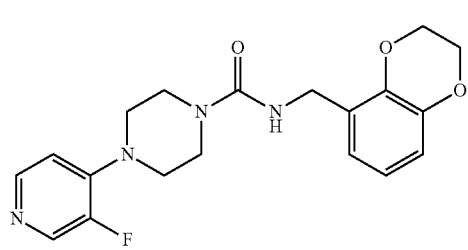

40

Following Method B from 4-nitrophenyl ((2,3-dihydrobenzo[b][1,4]dioxin-5-yl)methyl)carbamate (Intermediate 8, 0.227 mmol) and 1-(3-fluoropyridin-4-yl)piperazine dihydrochloride (Intermediate 32, 0.227 mmol). Purification by prep HPLC gave the title compound. LCMS (ES+) 373 (M+H)+, RT 2.89 min (Analytical Method 2), ¹H NMR (400 MHz, MeOD) 8.20 (1H, d, J=6.0 Hz), 8.13 (1H, d, J=5.6 Hz), 7.02 (1H, dd, J=5.6, 8.2 Hz), 6.82-6.73 (3H, m), 4.38 (2H, s), 4.33-4.24 (4H, m), 3.65-3.61 (4H, m), 3.43-3.38 (4H, m).

Example 41

N-((2,2-Difluorobenzo[d][1,3]dioxol-4-yl)methyl)-4-(3-fluoropyridin-4-yl)piperazine-1-carboxamide

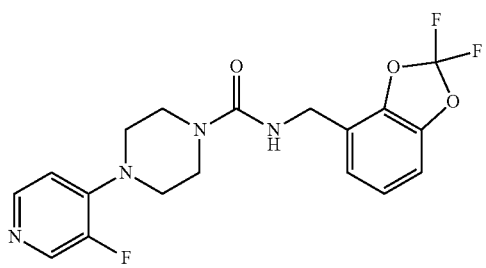

41

Following Method B from 4-nitrophenyl ((2,2-difluorobenzo[d][1,3]dioxol-4-yl)methyl)carbamate (Intermediate 6, 75 mg, 0.213 mmol) and 1-(3-fluoropyridin-4-yl)piperazine dihydrochloride (Intermediate 32, 54 mg, 0.213 mmol). Purification by prep HPLC gave the title compound. LCMS (ES+) 395 (M+H)+, RT 4.00 min (Analytical Method 4), ¹H NMR (400 MHz, MeOD) 8.48 (1H, d, J=8.7 Hz), 8.19 (1H, d, J=7.1 Hz), 7.35-7.30 (1H, m), 7.16-7.09 (3H, m), 4.49 (2H, s), 3.94-3.90 (4H, m), 3.74-3.70 (4H, m).

Example 42

(R)—N—((R)-1-(2-Chlorophenyl)ethyl)-4-(3-fluoropyridin-4-yl)-2-methylpiperazine-1-carboxamide

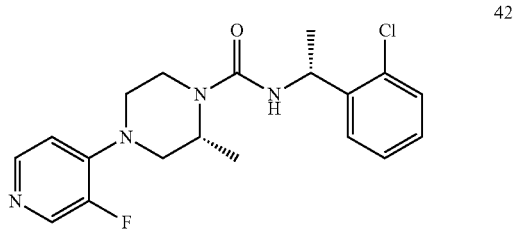

42

Following Method B from (R)-1-(3-fluoropyridin-4-yl)-3-methylpiperazine dihydrochloride (Intermediate 34, 50 mg, 0.21 mmol) and 4-nitrophenyl (R)-(1-(2-chlorophenyl)ethyl)carbamate (Intermediate 3, 69 mg). LCMS (ES+) 377 (M+H)+, RT 3.34 min (Analytical Method 2), ¹H NMR (400 MHz, DMSO) 8.31 (1H, d, J=5.6 Hz), 8.19 (1H, d, J=5.6 Hz), 7.55-7.50 (1H, m), 7.45-7.34 (2H, m), 7.31-7.24 (1H, m), 7.07-6.99 (2H, m), 5.26-5.20 (1H, m), 4.43-4.39 (1H, m), 3.93 (1H, d, J=13.1 Hz), 3.63 (2H, dd, J=12.4, 21.7 Hz), 3.25-3.15 (1H, m), 3.08 (1H, dd, J=3.2, 12.3 Hz), 2.95-2.85 (1H, m), 1.39 (3H, d, J=7.1 Hz), 1.20 (3H, d, J=6.6 Hz).

Example 43

(R)-4-(3-Fluoropyridin-4-yl)-N—((R)-1-(3-methoxyphenyl)ethyl)-2-methylpiperazine-1-carboxamide

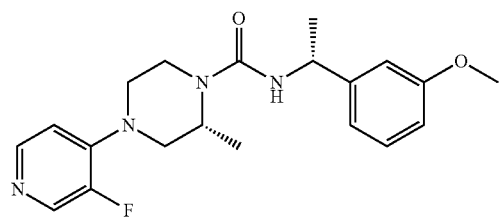

43

Following Method B from (R)-1-(3-fluoropyridin-4-yl)-3-methylpiperazine.HCl (Intermediate 34, 1.08 mmol) and 4-nitrophenyl (R)-(1-(3-methoxyphenyl)ethyl)carbamate (Intermediate 1, 1.08 mmol). Purification by preparative-HPLC gave the title compound. LCMS (ES+) 373 (M+H)+, RT 3.14 min (Analytical Method 1) ¹H NMR (400 MHz, DMSO) 8.27 (1H, d, J=5.6 Hz), 8.15 (1H, d, J=5.5 Hz), 7.22 (1H, dd, J=8.0, 8.0 Hz), 7.00 (1H, dd, J=5.5, 8.3 Hz), 6.91-6.89 (2H, m), 6.82-6.76 (2H, m), 4.90-4.81 (1H, m), 4.33 (1H, dd, J=3.0, 6.3 Hz), 3.89 (1H, d, J=13.2 Hz), 3.75 (3H, s), 3.58 (2H, dd, J=12.0, 22.1 Hz), 3.19-3.10 (1H, m), 3.02 (1H, dd, J=3.5, 12.3 Hz), 2.90-2.81 (1H, m), 1.37 (3H, d, J=7.2 Hz), 1.17 (3H, d, J=6.5 Hz); SFC RT 2.22 min (SFC1, LUX CELLULOSE-4+0.1% DEAISO 40% MeOH).

Example 44

(R)—N—((R)-1-(2-Fluoro-3-methoxyphenyl)ethyl)-4-(3-fluoropyridin-4-yl)-2-methylpiperazine-1-carboxamide

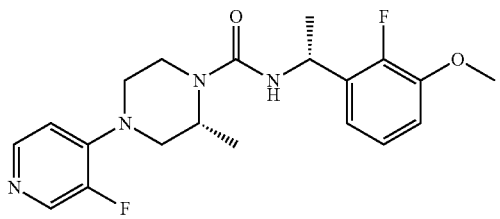

Following Method A from (R)-1-(2-fluoro-3-methoxyphenyl)ethan-1-amine hydrochloride (0.384 mmol) and (R)-1-(3-fluoropyridin-4-yl)-3-methylpiperazine dihydrochloride (Intermediate 34, 0.384 mmol). Purification by prep HPLC gave the title compound. LCMS (ES+) 391 (M+H)$^+$, RT 2.53 min (Analytical Method 1), $^1$H NMR (400 MHz, DMSO) 8.27 (1H, d, J=5.6 Hz), 8.19-8.14 (1H, m), 7.09 (1H, dd, J=8.1, 8.1 Hz), 7.03-6.93 (3H, m), 6.87 (1H, d, J=7.7 Hz), 5.16-5.09 (1H, m), 4.35-4.32 (1H, m), 3.88 (1H, d, J=13.3 Hz), 3.83 (3H, s), 3.57 (2H, dd, J=12.5, 22.4 Hz), 3.19-3.10 (1H, m), 3.02 (1H, dd, J=3.4, 12.3 Hz), 2.90-2.81 (1H, m), 1.36 (3H, d, J=7.1 Hz), 1.15 (3H, d, J=6.6 Hz).

Example 45

(R)—N—((R)-1-(2-Bromophenyl)ethyl)-4-(3-fluoropyridin-4-yl)-2-methylpiperazine-1-carboxamide

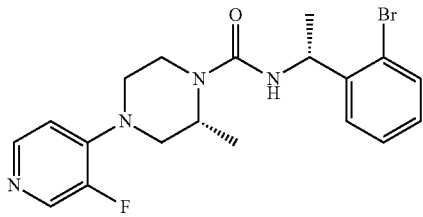

Following Method A from (R)-1-(2-bromophenyl)ethan-1-amine hydrochloride (0.384 mmol) and (R)-1-(3-fluoropyridin-4-yl)-3-methylpiperazine dihydrochloride (Intermediate 34, 0.384 mmol). Purification by prep HPLC gave the title compound. LCMS (ES+) 421 (M+H)$^+$, RT 3.21 min (Analytical Method 2), $^1$H NMR (400 MHz, MeOD) 8.19 (1H, d, J=6.1 Hz), 8.12 (1H, d, J=5.6 Hz), 7.56 (1H, d, J=7.9 Hz), 7.44 (1H, dd, J=1.6, 7.8 Hz), 7.34 (1H, dd, J=7.5, 7.5 Hz), 7.17-7.12 (1H, m), 7.01 (1H, dd, J=5.7, 8.3 Hz), 5.28 (1H, q, J=7.0 Hz), 4.43-4.36 (1H, m), 3.95 (1H, d, J=13.3 Hz), 3.73 (2H, dd, J=12.5, 12.5 Hz), 3.41-3.32 (1H, m, obsc), 3.18 (1H, dd, J=3.5, 12.5 Hz), 3.05-2.96 (1H, m), 1.47 (3H, d, J=7.1 Hz), 1.31 (3H, d, J=6.7 Hz).

Example 46

(R)-1-(3-Methoxyphenyl)ethyl (R)-4-(3-fluoropyridin-4-yl)-2-methylpiperazine-1-carboxylate

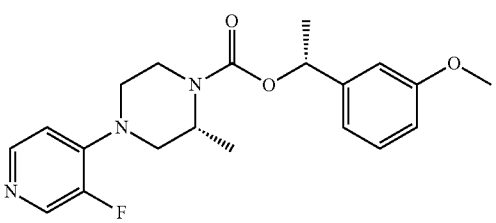

To a stirred solution of 4-nitrophenyl chloroformate (100 mg, 0.497 mmol) in DCM (2 mL) at r.t. was added a solution of (R)-1-(3-methoxyphenyl)ethan-1-ol (75 mg, 0.493 mmol) in DCM (2 mL) dropwise. The mixture was stirred at r.t. for 15 min and then treated with (R)-1-(3-fluoropyridin-4-yl)-3-methylpiperazine dihydrochloride (Intermediate 34, 134 mg, 0.493 mmol) and TEA (0.21 mL, 1.48 mmol) in DCM (5 mL). After 3 d the reaction mixture was washed with sat. NaHCO$_3$ soln. and brine, passed through a hydrophobic frit and concentrated to dryness. Purification by prep HPLC gave the title compound. LCMS (ES+) 374 (M+H)$^+$, RT 3.39 min (Analytical Method 2), $^1$H NMR (400 MHz, CDCl$_3$) 8.23 (1H, d, J=5.4 Hz), 8.17 (1H, d, J=5.5 Hz), 7.29 (1H, d, J=7.9 Hz), 6.94 (1H, d, J=7.7 Hz), 6.89 (1H, s), 6.83 (1H, dd, J=2.3, 8.2 Hz), 6.71 (1H, dd, J=5.6, 7.9 Hz), 5.83 (1H, q, J=6.5 Hz), 4.45 (1H, dd, J=2.9, 6.1 Hz), 4.06 (1H, d, J=13.2 Hz), 3.82 (3H, s), 3.59-3.51 (2H, m), 3.39-3.30 (1H, m), 3.06 (1H, dd, J=3.5, 12.3 Hz), 2.95-2.86 (1H, m), 1.56 (3H, d, J=7.1 Hz), 1.33 (3H, d, J=6.6 Hz).

Examples 47 and 48 (R)—N—((R)-1-(2-Chloro-3-fluorophenyl)ethyl)-4-(3-fluoropyridin-4-yl)-2-methylpiperazine-1-carboxamide and (R)—N—((S)-1-(2-chloro-3-fluorophenyl)ethyl)-4-(3-fluoropyridin-4-yl)-2-methylpiperazine-1-carboxamide

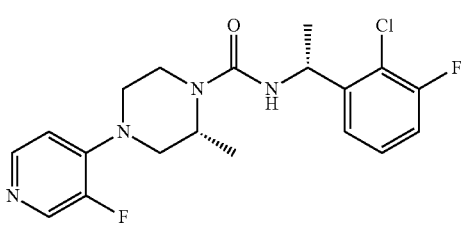

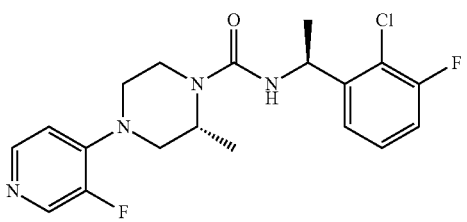

Following Method B from (R)-1-(3-fluoropyridin-4-yl)-3-methylpiperazine dihydrochloride (Intermediate 34, 79 mg, 0.29 mmol) and 4-nitrophenyl (1-(2-chloro-3-fluorophenyl)ethyl)carbamate (Intermediate 12, 100 mg, 0.29 mmol). Purification by preparative-HPLC and chiral SFC gave the title compounds:

Example 47: Percentage ee: 100%. LCMS (ES+) 395 (M+H)+, RT 3.21 min (Analytical Method 2), 1H NMR (400 MHz, MeOD) 8.03 (2H, dd, J=5.8, 27.5 Hz), 7.22-7.12 (2H, m), 7.02-6.97 (1H, m), 6.88 (1H, dd, J=5.6, 8.3 Hz), 5.20 (1H, q, J=7.0 Hz), 4.30-4.24 (1H, m), 3.83-3.78 (1H, m), 3.66-3.56 (2H, m), 3.28-3.22 (1H, obscured by MeOH) 3.08-3.02 (1H, m), 2.91-2.83 (1H, m), 1.35 (3H, d, J=7.0 Hz), 1.18 (3H, d, J=6.8 Hz); SFC RT 1.5 min (SFC4, YMC AMYLOSE-C+0.1% DEAISO 20% EtOH).

Example 48: Percentage ee: 95.7%. LCMS (ES+) 395 (M+H)+, RT 3.21 min (Analytical Method 2), 1H NMR (400 MHz, MeOD) 8.15 (2H, dd, J=5.8, 27.0 Hz), 7.36-7.26 (2H, m), 7.16-7.10 (1H, m), 7.01 (1H, dd, J=5.7, 8.2 Hz), 5.35 (1H, q, J=7.0 Hz), 4.35 (1H, s), 3.98-3.92 (1H, m), 3.80-3.68 (2H, m), 3.41-3.34 (1H, obscured by MeOH), 3.16 (1H, dd, J=3.7, 12.6 Hz), 3.05-2.97 (1H, m), 1.49-1.47 (3H, m), 1.35-1.32 (3H, m); SFC RT 2.15 min (SFC4, YMC AMYLOSE-C+0.1% DEAISO 20% EtOH).

Example 49

(R)—N—((R)-1-(2-Chloro-5-methoxyphenyl)ethyl)-4-(3-fluoropyridin-4-yl)-2-methylpiperazine-1-carboxamide

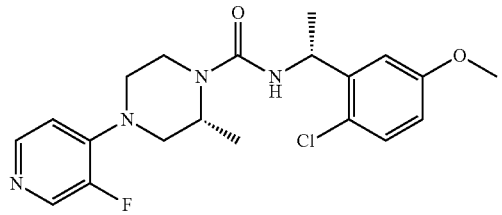

Following Method B from 4-nitrophenyl (R)-(1-(2-chloro-5-methoxyphenyl)ethyl)carbamate (Intermediate 4, 0.222 mmol) and (R)-1-(3-fluoropyridin-4-yl)-3-methylpiperazine dihydrochloride (Intermediate 34, 0.222 mmol). Purification by prep HPLC gave the title compound. LCMS (ES+) 407 (M+H)+, RT 3.21 min (Analytical Method 2), 1H NMR (400 MHz, MeOD) 8.19 (1H, d, J=6.0 Hz), 8.12 (1H, d, J=5.6 Hz), 7.27 (1H, d, J=8.8 Hz), 7.03-6.98 (2H, m), 6.81 (1H, dd, J=3.1, 8.8 Hz), 5.27 (1H, q, J=7.1 Hz), 4.43-4.38 (1H, m), 3.95 (1H, d, J=13.2 Hz), 3.81-3.70 (5H, m), 3.42-3.35 (1H, m), 3.19 (1H, dd, J=3.7, 12.5 Hz), 3.05-2.97 (1H, m), 1.46 (3H, d, J=7.0 Hz), 1.32 (3H, d, J=6.6 Hz).

Example 50

(R)—N—((R)-1-(2-Chloro-4-fluorophenyl)ethyl)-4-(3-fluoropyridin-4-yl)-2-methylpiperazine-1-carboxamide

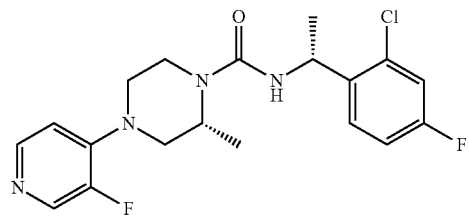

Following Method B from (R)-1-(3-fluoropyridin-4-yl)-3-methylpiperazine dihydrochloride (Intermediate 34, 63 mg, 0.19 mmol) and 4-nitrophenyl (1-(2-chloro-4-fluorophenyl)ethyl)carbamate (Intermediate 11, 50 mg, 0.19 mmol). Purification by preparative-HPLC and chiral SFC gave the title compound. Percentage ee: 100%. LCMS (ES+) 395 (M+H)+, RT 3.23 min (Analytical Method 2), 1H NMR (400 MHz, DMSO) 8.27 (1H, d, J=5.6 Hz), 8.16 (1H, d, J=5.5 Hz), 7.51 (1H, dd, J=6.3, 8.7 Hz), 7.37 (1H, dd, J=2.6, 8.8 Hz), 7.26-7.20 (1H, m), 7.03-6.97 (2H, m), 5.19-5.11 (1H, m), 4.36-4.33 (1H, m), 3.90-3.85 (1H, m), 3.63-3.53 (2H, m), 3.20-3.11 (1H, m), 3.03 (1H, dd, J=3.5, 12.3 Hz), 2.90-2.81 (1H, m), 1.34 (3H, d, J=7.2 Hz), 1.16 (3H, d, J=6.5 Hz); SFC RT 1.4 min (SFC4, YMC AMYLOSE-C+0.1% DEAISO 20% EtOH).

Example 51

(R)—N—((R)-1-(3-Fluoro-5-methoxyphenyl)ethyl)-4-(3-fluoropyridin-4-yl)-2-methylpiperazine-1-carboxamide

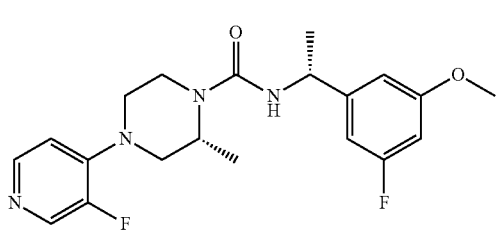

Following Method B from (R)-1-(3-fluoropyridin-4-yl)-3-methylpiperazine dihydrochloride (Intermediate 34, 179 mg, 0.67 mmol) and 4-nitrophenyl (1-(3-fluoro-5-methoxyphenyl)ethyl)carbamate (Intermediate 16, 223 mg, 0.67 mmol). Purification by preparative-HPLC and chiral SFC gave the title compound. Percentage ee: 100%. LCMS (ES+) 391 (M+H)+, RT 2.61 min (Analytical Method 1), 1H NMR (400 MHz, MeOD) 8.19 (1H, d, J=23.7 Hz), 8.12 (1H, d, J=26.1 Hz), 7.00 (1H, dd, J=42.7 Hz), 6.75 (1H, s), 6.68 (1H, d, J=19.0 Hz), 6.56-6.55 (1H, m), 4.91 (1H, q, J=37.9 Hz), 4.40 (1H, m), 3.94 (1H, d, J=52.2 Hz), 3.78-3.68 (3H, m), 3.17 (1H, dd, J=42.7 Hz), 3.01-2.96 (1H, m), 1.48 (3H, d, J=45.1 Hz), 1.31 (3H, d, J=45.1 Hz); SFC RT 2.82 min (SFC4, LUX CELLULOSE-4+0.1% DEAISO 30% IPA).

Example 52

(R)-4-(3-Fluoropyridin-4-yl)-2-methyl-N—((R)-1-(pyridin-3-yl)ethyl)piperazine-1-carboxamide

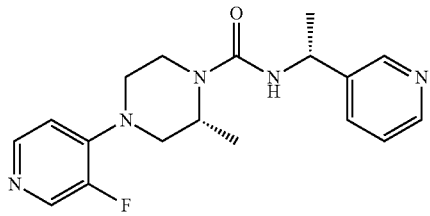

Following Method A from (R)-1-(pyridin-3-yl)ethan-1-amine (0.331 mmol) and (R)-1-(3-fluoropyridin-4-yl)-3-methylpiperazine dihydrochloride (Intermediate 34, 0.331 mmol). Purification by prep HPLC gave the title compound. LCMS (ES+) 344 (M+H)$^+$, RT 2.72 min (Analytical Method 2), $^1$H NMR (400 MHz, MeOD) 8.55 (1H, s), 8.42 (1H, d, J=4.0 Hz), 8.18 (1H, d, J=6.1 Hz), 8.11 (1H, d, J=5.6 Hz), 7.84 (1H, d, J=8.1 Hz), 7.42 (1H, dd, J=5.1, 7.6 Hz), 7.00 (1H, dd, J=5.8, 8.1 Hz), 5.01 (1H, q, J=7.0 Hz), 4.41-4.34 (1H, m), 3.93 (1H, d, J=13.1 Hz), 3.73 (2H, dd, J=13.6, 13.6 Hz), 3.43-3.28 (1H, m, obsc), 3.17 (1H, dd, J=3.3, 12.4 Hz), 3.04-2.94 (1H, m), 1.54 (3H, d, J=7.1 Hz), 1.30 (3H, d, J=6.6 Hz).

Example 53

(R)—N—((R)-1-(4-Fluoro-3-methoxyphenyl)ethyl)-4-(3-fluoropyridin-4-yl)-2-methylpiperazine-1-carboxamide

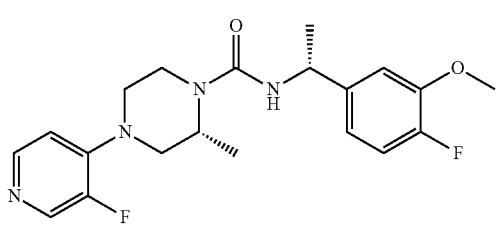

Following Method B from (R)-1-(3-fluoropyridin-4-yl)-3-methylpiperazine dihydrochloride (Intermediate 34, 189 mg, 0.70 mmol) and 4-nitrophenyl (R)-(1-(4-fluoro-3-methoxyphenyl)ethyl)carbamate (Intermediate 17, 235 mg, 0.70 mmol). Purification by preparative-HPLC and chiral SFC gave the title compound. Percentage ee: 100%. LCMS (ES+) 391 (M+H)$^+$, RT 3.10 min (Analytical Method 2), $^1$H NMR (400 MHz, CDCl$_3$) 8.24-8.16 (2H, m), 7.06-6.93 (2H, m), 6.87-6.83 (1H, m), 6.72 (1H, dd, J=5.5, 8.0 Hz), 5.03-4.98 (1H, m), 4.62 (1H, d, J=6.9 Hz), 4.18-4.14 (1H, m), 3.89-3.89 (3H, m), 3.63-3.54 (2H, m), 3.36-3.27 (1H, m), 3.10 (1H, dd, J=3.6, 12.2 Hz), 2.98-2.90 (1H, m), 1.50 (3H, d, J=6.9 Hz), 1.35-1.32 (3H, m).

Example 54

(R)—N-(2-Chlorobenzyl)-4-(3-fluoropyridin-4-yl)-2-methylpiperazine-1-carboxamide

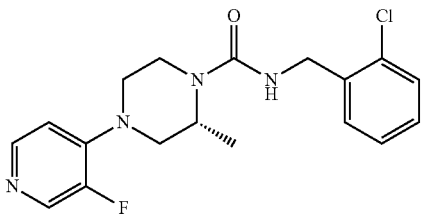

Following Method B from (R)-1-(3-fluoropyridin-4-yl)-3-methylpiperazine dihydrochloride (Intermediate 34, 90 mg, 0.39 mmol) and 4-nitrophenyl (2-chlorobenzyl)carbamate (Intermediate 2, 119 mg, 0.39 mmol). Purification by preparative-HPLC gave the title compound. LCMS (ES+) 363 (M+H)$^+$, RT 2.57 min (Analytical Method 2), $^1$H NMR (400 MHz, DMSO) 8.32 (1H, d, J=5.8 Hz), 8.20 (1H, d, J=5.6 Hz), 7.47 (1H, d, J=7.6 Hz), 7.40-7.31 (3H, m), 7.20 (1H, dd, J=5.6, 5.6 Hz), 7.05 (1H, dd, J=5.6, 8.3 Hz), 4.42-4.33 (3H, m), 3.94 (1H, d, J=13.1 Hz), 3.65 (2H, dd, J=12.5, 27.4 Hz), 3.30-3.19 (1H, m), 3.11 (1H, dd, J=3.3, 12.4 Hz), 2.99-2.90 (1H, m), 1.26 (3H, d, J=6.6 Hz).

Example 55

(R)—N-(2-Fluoro-5-methoxybenzyl)-4-(3-fluoropyridin-4-yl)-2-methylpiperazine-1-carboxamide

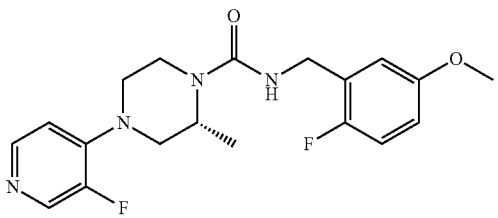

Following Method B from (R)-1-(3-fluoropyridin-4-yl)-3-methylpiperazine dihydrochloride (Intermediate 34, 258 mg, 0.80 mmol) and 4-nitrophenyl (2-fluoro-5-methoxybenzyl)carbamate (Intermediate 18, 216 mg, 0.80 mmol). Purification by preparative-HPLC gave the title compound. LCMS (ES+) 377 (M+H)$^+$, RT 3.03 min (Analytical Method 2), $^1$H NMR (400 MHz, DMSO) 8.28-8.26 (1H, m), 8.18-8.14 (1H, m), 7.14-6.98 (3H, m), 6.86-6.79 (2H, m), 4.35-4.21 (3H, m), 3.91-3.85 (1H, m), 3.72 (3H, s), 3.65-3.53 (2H, m), 3.22-3.13 (1H, m), 3.05 (1H, dd, J=3.5, 12.5 Hz), 2.92-2.83 (1H, m), 1.20 (3H, d, J=6.7 Hz).

Example 56

(R)-4-(3-Fluoropyridin-4-yl)-N-((2-methoxypyridin-3-yl)methyl)-2-methylpiperazine-1-carboxamide

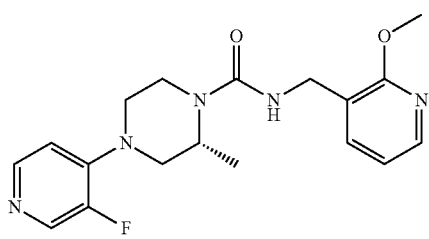

Following Method A from 4-nitrophenyl chloroformate (0.50 mmol, 1 eq), (2-methoxypyridin-3-yl)methanamine (0.50 mmol) and (R)-1-(3-fluoropyridin-4-yl)-3-methylpiperazine dihydrochloride (Intermediate 34, 0.50 mmol). Purification by prep HPLC to give the title compound. LCMS (ES+) 360 (M+H)+, RT 2.21 min (Analytical Method 3), $^1$H NMR (400 MHz, MeOD) 8.19 (1H, d, J=6.0 Hz), 8.12 (1H, d, J=5.6 Hz), 8.03 (1H, dd, J=1.9, 5.1 Hz), 7.58 (1H, dd, J=1.2, 7.1 Hz), 7.02 (1H, dd, J=5.8, 8.3 Hz), 6.95 (1H, dd, J=5.1, 7.3 Hz), 4.41-4.35 (3H, m), 3.99 (3H, s), 3.97-3.91 (1H, m), 3.79-3.70 (2H, m), 3.42-3.36 (1H, m), 3.24-3.16 (1H, m), 3.08-3.00 (1H, m), 1.34 (3H, d, J=6.7 Hz).

Example 57

(R)—N—((R)-1-(2,2-Dimethyl-2,3-dihydrobenzofuran-4-yl)ethyl)-4-(3-fluoropyridin-4-yl)-2-methylpiperazine-1-carboxamide

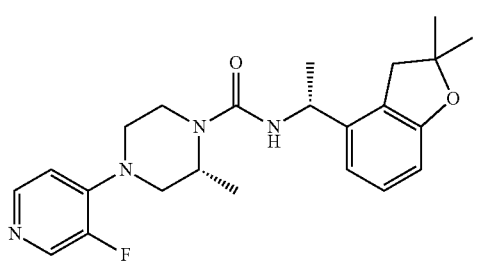

Following Method A from (R)-1-(2,2-dimethyl-2,3-dihydrobenzofuran-4-yl)ethan-1-amine hydrochloride (0.430 mmol) and (R)-1-(3-fluoropyridin-4-yl)-3-methylpiperazine dihydrochloride (Intermediate 34, 0.430 mmol). Purification by prep HPLC gave the title compound. LCMS (ES+) 414 (M+H)+, RT 2.66 min (Analytical Method 1), $^1$H NMR (400 MHz, MeOD) 8.18 (1H, d, J=6.0 Hz), 8.12 (1H, d, J=5.6 Hz), 7.08 (1H, dd, J=7.9, 7.9 Hz), 7.00 (1H, dd, J=5.7, 8.3 Hz), 6.83 (1H, d, J=7.7 Hz), 6.55 (1H, d, J=7.8 Hz), 4.95-4.89 (1H, m), 4.42-4.35 (1H, m), 3.95 (1H, d, J=13.3 Hz), 3.72 (2H, dd, J=12.9, 12.9 Hz), 3.38-3.30 (1H, m, obsc), 3.19-3.14 (2H, m), 3.04-2.98 (2H, m), 1.48-1.44 (9H, m), 1.31 (3H, d, J=6.6 Hz).

Examples 58 and 59 (R)-4-(3-fluoropyridin-4-yl)-N—((R)-1-(imidazo[1,2-a]pyridin-5-yl)ethyl)-2-methylpiperazine-1-carboxamide and (R)-4-(3-fluoropyridin-4-yl)-N—((S)-1-(imidazo[1,2-a]pyridin-5-yl)ethyl)-2-methylpiperazine-1-carboxamide

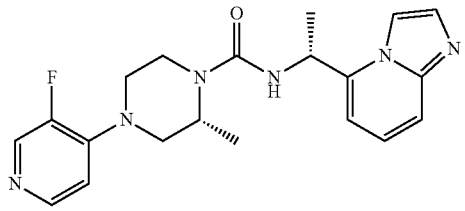

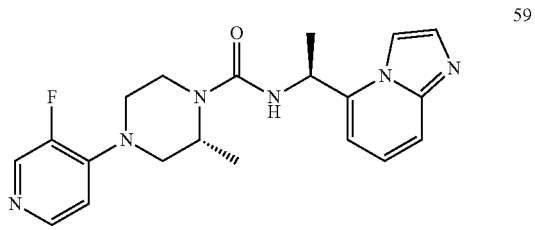 [SMILES: C[C@@H](NC(=O)N1CCN(c2ccncc2F)CC1)c1cccc2occc12]

Following Method B from 4-nitrophenyl (R)-(1-(imidazo[1,2-a]pyridin-5-yl)ethyl)carbamate (Intermediate 19, 0.50 mmol) and (R)-1-(3-fluoropyridin-4-yl)-3-methylpiperazine dihydrochloride (Intermediate 34, 0.50 mmol). Purification by prep HPLC and chiral prep HPLC to separate the isomers gave the title compounds.

Example 58: LCMS (ES+) 383 (M+H)+, RT 2.70 min (Analytical Method 2), $^1$H NMR (400 MHz, DMSO) 8.27 (1H, d, J=5.6 Hz), 8.15 (1H, d, J=5.5 Hz), 7.97 (1H, s), 7.65 (1H, s), 7.53 (1H, d, J=9.0 Hz), 7.29 (1H, dd, J=7.0, 9.0 Hz), 7.07 (1H, d, J=7.9 Hz), 7.00 (1H, dd, J=5.5, 8.3 Hz), 6.89 (1H, d, J=6.9 Hz), 5.31 (1H, dd, J=7.2, 7.2 Hz), 4.34-4.32 (1H, m), 3.87 (1H, d, J=13.3 Hz), 3.62-3.52 (2H, m), 3.17-3.10 (1H, m), 3.02 (1H, dd, J=3.5, 12.5 Hz), 2.90-2.83 (1H, m), 1.54 (3H, d, J=6.9 Hz), 1.18 (3H, d, J=6.7 Hz); SFC RT 1.83 min (SFC4, YMC AMYLOSE-C+0.1% DEAISO 20% MeOH).

Example 59: LCMS (ES+) 383 (M+H)+, RT 2.69 min (Analytical Method 2), $^1$H NMR (400 MHz, DMSO) 8.27 (1H, d, J=5.6 Hz), 8.15 (1H, d, J=5.5 Hz), 7.95 (1H, s), 7.65 (1H, d, J=1.1 Hz), 7.53 (1H, d, J=9.0 Hz), 7.30 (1H, dd, J=7.0, 9.0 Hz), 7.08 (1H, d, J=7.7 Hz), 7.00 (1H, dd, J=5.5, 8.4 Hz), 6.89 (1H, d, J=6.9 Hz), 5.32-5.27 (1H, m), 4.32-4.29 (1H, m), 3.93-3.87 (1H, m), 3.63-3.51 (2H, m), 3.21-3.12 (1H, m), 3.03 (1H, dd, J=3.5, 12.5 Hz), 2.90-2.81 (1H, m), 1.53 (3H, d, J=6.9 Hz), 1.14 (3H, d, J=6.7 Hz); SFC RT 2.6 min (SFC4, YMC AMYLOSE-C+0.1% DEAISO 20% MeOH).

Example 60

(R)-4-(3-Fluoropyridin-4-yl)-2-methyl-N—((R)-1-(2-methylbenzofuran-4-yl)ethyl)piperazine-1-carboxamide

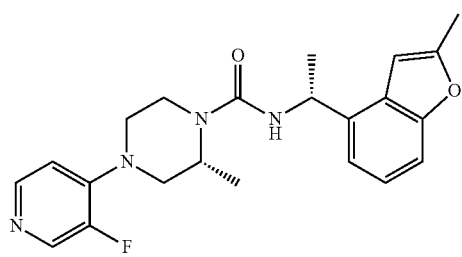

Following Method B from 4-nitrophenyl (R)-(1-(2-methylbenzofuran-4-yl)ethyl)carbamate (Intermediate 5, 0.138 mmol) and (R)-1-(3-fluoropyridin-4-yl)-3-methylpiperazine dihydrochloride (Intermediate 34, 0.138 mmol). Purification by prep HPLC gave the title compound. LCMS (ES+) 397 (M+H)$^+$, RT 3.25 min (Analytical Method 2), $^1$H NMR (400 MHz, MeOD) 8.19 (1H, d, J=6.1 Hz), 8.11 (1H, d, J=5.6 Hz), 7.28 (1H, dd, J=2.9, 6.0 Hz), 7.18-7.16 (2H, m), 7.01 (1H, dd, J=5.7, 8.3 Hz), 6.63 (1H, s), 5.28 (1H, q, J=7.1 Hz), 4.41-4.34 (1H, m), 3.95 (1H, d, J=13.2 Hz), 3.73 (2H, dd, J=12.9, 14.7 Hz), 3.38-3.29 (1H, m, obsc), 3.18 (1H, dd, J=3.7, 12.5 Hz), 3.06-2.97 (1H, m), 2.47 (3H, s), 1.57 (3H, d, J=7.0 Hz), 1.31 (3H, d, J=6.6 Hz); SFC RT 3.56 min (SFC1, LUX CELLULOSE-4+0.1% DEAISO 30% MeOH).

Examples 61 and 62 (R)-4-(3-Fluoropyridin-4-yl)-2-methyl-N—((R)-1-(pyrazolo[1,5-a]pyridin-4-yl)ethyl)piperazine-1-carboxamide and (R)-4-(3-Fluoropyridin-4-yl)-2-methyl-N—((S)-1-(pyrazolo[1,5-a]pyridin-4-yl)ethyl)piperazine-1-carboxamide

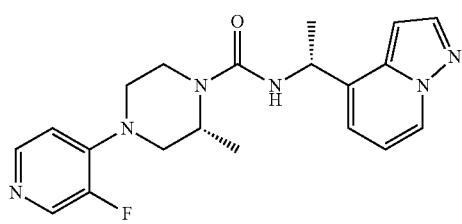

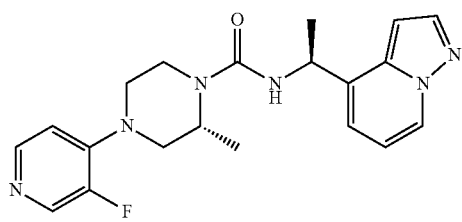

Following Method B from (R)-(1-(pyrazolo[1,5-a]pyridin-4-yl)ethyl)carbamate (Intermediate 20, 0.59 mmol) and (R)-1-(3-fluoropyridin-4-yl)-3-methylpiperazine dihydrochloride (Intermediate 34, 0.59 mmol). Purification by prep HPLC and chiral prep HPLC to separate the isomers gave the title compounds.

Example 61: LCMS (ES+) 383 (M+H)$^+$, RT 2.81 min (Analytical Method 2), $^1$H NMR (400 MHz, DMSO) 8.56 (1H, d, J=6.9 Hz), 8.27 (1H, d, J=5.6 Hz), 8.15 (1H, d, J=5.5 Hz), 7.99 (1H, d, J=2.4 Hz), 7.10 (1H, d, J=6.9 Hz), 7.02-6.95 (2H, m), 6.87 (1H, dd, J=7.0, 7.0 Hz), 6.73 (1H, d, J=2.3 Hz), 5.19-5.14 (1H, m), 4.35-4.33 (1H, m), 3.89 (1H, d, J=13.2 Hz), 3.57 (2H, dd, J=12.0, 22.4 Hz), 3.19-3.09 (1H, m), 3.02 (1H, dd, J=3.5, 12.3 Hz), 2.90-2.81 (1H, m), 1.49 (3H, d, J=7.0 Hz), 1.17 (3H, d, J=6.5 Hz); SFC RT 1.5 min (SFC4, LUX CELLULOSE-4+0.1% DEAISO 40% IPA).

Example 62: LCMS (ES+) 383 (M+H)$^+$, RT 2.80 min (Analytical Method 2), $^1$H NMR (400 MHz, DMSO) 8.56 (1H, d, J=6.9 Hz), 8.27 (1H, d, J=5.6 Hz), 8.15 (1H, d, J=5.5 Hz), 7.99 (1H, d, J=2.3 Hz), 7.11 (1H, d, J=6.9 Hz), 7.02-6.96 (2H, m), 6.90-6.85 (1H, m), 6.74 (1H, dd, J=0.9, 2.3 Hz), 5.19-5.11 (1H, m), 4.35-4.32 (1H, m), 3.94-3.87 (1H, m), 3.63-3.51 (2H, m), 3.19-3.09 (1H, m), 3.02 (1H, dd, J=3.5, 12.4 Hz), 2.90-2.80 (1H, m), 1.49 (3H, d, J=7.2 Hz), 1.15 (3H, d, J=6.5 Hz); SFC RT 2.06 min (SFC4, LUX CELLULOSE-4+0.1% DEAISO 40% IPA).

Examples 63 and 64 (R)-4-(3-Fluoropyridin-4-yl)-2-methyl-N—((R)-1-(1-methyl-1H-indol-7-yl)ethyl)piperazine-1-carboxamide (R)-4-(3-fluoropyridin-4-yl)-2-methyl-N—((S)-1-(1-methyl-1H-indol-7-yl)ethyl)piperazine-1-carboxamide

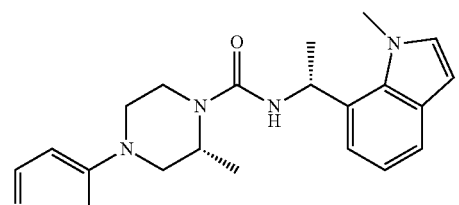

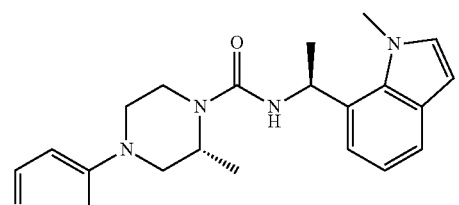

Following Method B from 4-nitrophenyl (R)-(1-(1-methyl-1H-indol-7-yl)ethyl)carbamate (Intermediate 14, 0.91 mmol) and (R)-1-(3-fluoropyridin-4-yl)-3-methylpiperazine dihydrochloride (Intermediate 34, 0.65 mmol). Purification by prep HPLC and chiral prep HPLC to separate the isomers gave the title compounds.

Example 63: LCMS (ES+) 396 (M+H)$^+$, RT 2.66 min (Analytical Method 1), $^1$H NMR (400 MHz, DMSO) 8.26 (1H, d, J=5.8 Hz), 8.14 (1H, d, J=5.5 Hz), 7.40 (1H, d, J=7.3 Hz), 7.25-7.22 (2H, m), 7.01-6.94 (3H, m), 6.39 (1H, d, J=3.0 Hz), 5.84-5.75 (1H, m), 4.40-4.35 (1H, m), 4.07 (3H, s), 3.89 (1H, d, J=13.3 Hz), 3.62-3.52 (2H, m), 3.17-3.08 (1H, m), 3.01 (1H, dd, J=3.5, 12.4 Hz), 2.88-2.79 (1H, m), 1.49 (3H, d, J=6.9 Hz), 1.16 (3H, d, J=6.7 Hz).

Example 64: LCMS (ES+) 396 (M+H)$^+$, RT 2.68 min (Analytical Method 1), $^1$H NMR (400 MHz, DMSO) 8.26

(1H, d, J=5.6 Hz), 8.15 (1H, d, J=5.5 Hz), 7.39 (1H, dd, J=1.0, 7.8 Hz), 7.26-7.22 (2H, m), 7.02-6.97 (3H, m), 6.39 (1H, d, J=3.0 Hz), 5.83-5.78 (1H, m), 4.35-4.32 (1H, m), 4.08 (3H, s), 3.93-3.88 (1H, m), 3.56 (2H, dd, J=12.9, 31.7 Hz), 3.15-3.07 (1H, m), 3.00 (1H, dd, J=3.6, 12.4 Hz), 2.88-2.80 (1H, m), 1.49 (3H, d, J=6.9 Hz), 1.15 (3H, d, J=6.7 Hz); SFC RT 2.46 min (SFC1, YMC AMYLOSE-C+0.1% DEAISO 30% MeOH).

Examples 65 and 66 (R)-4-(3-Fluoropyridin-4-yl)-2-methyl-N—((R)-1-(3-methylimidazo[1,2-a]pyridin-5-yl)ethyl)piperazine-1-carboxamide and (R)-4-(3-Fluoropyridin-4-yl)-2-methyl-N—((S)-1-(3-methylimidazo[1,2-a]pyridin-5-yl)ethyl)piperazine-1-carboxamide

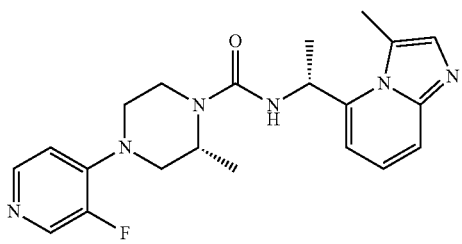

65

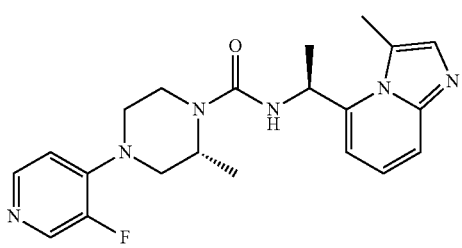

66

Following Method B from 4-nitrophenyl (R)-(1-(3-methylimidazo[1,2-a]pyridin-5-yl)ethyl)carbamate (Intermediate 10, 0.67 mmol) and (R)-1-(3-fluoropyridin-4-yl)-3-methylpiperazine dihydrochloride (Intermediate 34, 0.56 mmol). Purification by prep HPLC and chiral prep HPLC to separate the isomers gave the title compounds.

Example 65: LCMS (ES+) 397 (M+H)⁺, RT 2.75 min (Analytical Method 2), ¹H NMR (400 MHz, MeOD) 8.19 (1H, d, J=6.0 Hz), 8.12 (1H, d, J=5.6 Hz), 7.44-7.41 (1H, m), 7.36 (1H, s), 7.25 (1H, dd, J=7.1, 9.0 Hz), 7.04-6.96 (2H, m), 5.87 (1H, q, J=6.9 Hz), 4.44-4.39 (1H, m), 3.98-3.93 (1H, m), 3.78-3.71 (2H, m), 3.43-3.36 (1H, m), 3.23-3.16 (1H, m), 3.06-2.98 (1H, m), 2.86 (3H, s), 1.59 (3H, d, J=6.9 Hz), 1.33 (3H, d, J=6.7 Hz); SFC RT 1.02 min (SFC4, LUX CELLULOSE-4+0.1% DEAISO 55% IPA).

Example 66: LCMS (ES+) 397 (M+H)⁺, RT 2.74 min (Analytical Method 2), ¹H NMR (400 MHz, MeOD) 8.19 (1H, d, J=6.0 Hz), 8.12 (1H, d, J=5.6 Hz), 7.44-7.41 (1H, m), 7.36 (1H, s), 7.26 (1H, dd, J=7.0, 8.9 Hz), 7.04-6.97 (2H, m), 5.89 (1H, q, J=6.9 Hz), 4.44-4.37 (1H, m), 4.00-3.94 (1H, m), 3.79-3.69 (2H, m), 3.43-3.37 (1H, m), 3.17 (1H, dd, J=3.5, 12.7 Hz), 3.07-2.99 (1H, m), 2.87 (3H, s), 1.59 (3H, d, J=6.9 Hz), 1.35 (3H, d, J=6.7 Hz); SFC RT 1.68 min (SFC4, LUX CELLULOSE-4+0.1% DEAISO 55% IPA).

Example 67

(R)—N—((R)-1-(2,2-Difluorobenzo[d][1,3]dioxol-4-yl)ethyl)-4-(3-fluoropyridin-4-yl)-2-methylpiperazine-1-carboxamide

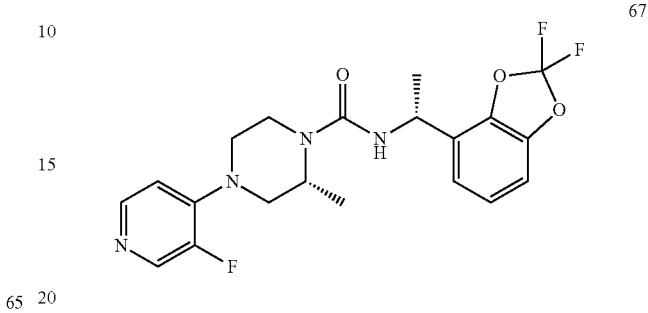

67

Following Method B from (R)-1-(3-fluoropyridin-4-yl)-3-methylpiperazine dihydrochloride (Intermediate 34, 147 mg, 0.633 mmol) and 4-nitrophenyl (R)-(1-(2,2-difluorobenzo[d][1,3]dioxol-4-yl)ethyl)carbamate (Intermediate 15, 147 mg, 0.633 mmol). Purification via chiral SFC gave the title compound (99.6% purity, 99.7% ee). LCMS (ES+) 423 (M+H)⁺, RT 3.21 min (Analytical Method 3), ¹H NMR (400 MHz, CDCl₃) 8.24 (1H, d, J=5.4 Hz), 8.18 (1H, d, J=5.4 Hz), 7.04-7.00 (2H, m), 6.96 (1H, dd, J=2.0, 7.2 Hz), 6.72 (1H, dd, J=5.5, 7.9 Hz), 5.16-5.08 (1H, m), 4.91 (1H, d, J=7.8 Hz), 4.18-4.14 (1H, m), 3.91-3.86 (1H, m), 3.62-3.55 (2H, m), 3.36-3.28 (1H, m), 3.09 (1H, dd, J=3.6, 12.4 Hz), 2.98-2.90 (1H, m), 1.55 (3H, d, J=7.7 Hz), 1.35 (3H, d, J=6.7 Hz); SFC RT 1.93 min (SFC4, LUX CELLULOSE-4+0.1% DEAISO 20% MeOH).

Example 68

(R)—N—((R)-1-(Benzo[d][1,3]dioxol-4-yl)ethyl)-4-(3-fluoropyridin-4-yl)-2-methylpiperazine-1-carboxamide

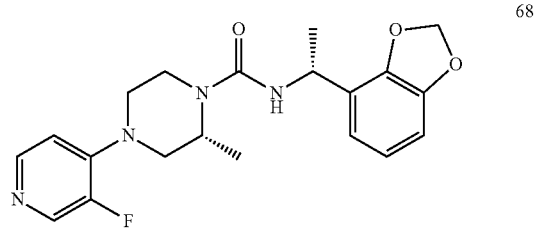 [SMILES: C[C@@H]1CN(c2ccncc2F)CCN1C(=O)N[C@H](C)c1cccc2c1OCO2]

68

Following Method A from (R)-1-(benzo[d][1,3]dioxol-4-yl)ethan-1-amine hydrochloride (45 mg, 0.224 mmol) and (R)-1-(3-fluoropyridin-4-yl)-3-methylpiperazine dihydrochloride (Intermediate 34, 60 mg, 0.224 mmol). Purification by prep HPLC gave the title compound (22 mg). LCMS (ES+) 387 (M+H)⁺, RT 3.07 min (Analytical Method 2), ¹H NMR (400 MHz, MeOD) 7.81 (1H, d, J=6.2 Hz), 6.81 (2H, d, J=4.4 Hz), 6.79-6.71 (2H, m), 6.43 (1H, dd, J=2.4, 2.4 Hz), 5.96 (2H, d, J=6.2 Hz), 5.08 (1H, q, J=7.1 Hz), 4.43-4.35 (1H, m), 3.94-3.77 (3H, m), 3.42-3.36 (2H, m), 3.19-3.10 (1H, m), 1.49 (3H, d, J=7.1 Hz), 1.22 (3H, d, J=6.7 Hz).

Examples 69 and 70 (R)-4-(3-Fluoropyridin-4-yl)-2-methyl-N—((R)-1-(2-methylbenzo[d]oxazol-4-yl)ethyl)piperazine-1-carboxamide and (R)-4-(3-Fluoropyridin-4-yl)-2-methyl-N—((S)-1-(2-methylbenzo[d]oxazol-4-yl)ethyl)piperazine-1-carboxamide Examples 71 and 72 (R)-4-(3-Fluoropyridin-4-yl)-2-methyl-N—((R)-1-(2-methyl-2H-indazol-4-yl)ethyl)piperazine-1-carboxamide and (R)-4-(3-Fluoropyridin-4-yl)-2-methyl-N—((S)-1-(2-methyl-2H-indazol-4-yl)ethyl)piperazine-1-carboxamide

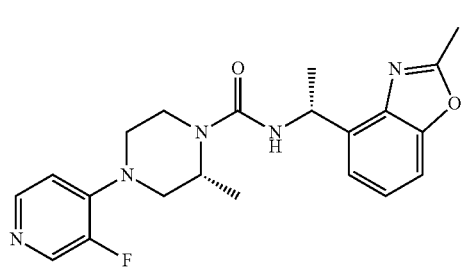

69

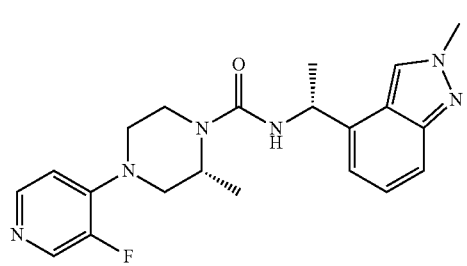

71

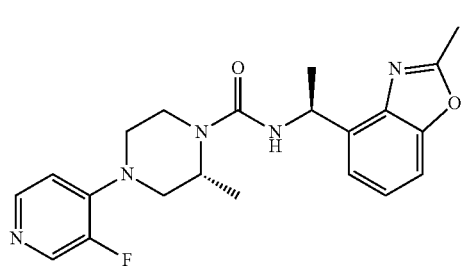

70

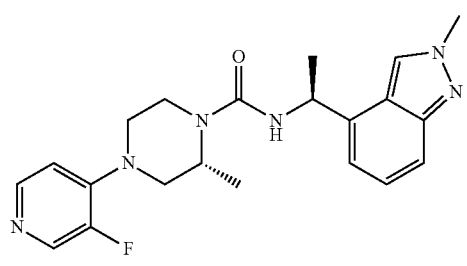

72

Following Method B from 4-nitrophenyl (R)-(1-(2-methylbenzo[d]oxazol-4-yl)ethyl)carbamate (Intermediate 21, 0.67 mmol) and (R)-1-(3-fluoropyridin-4-yl)-3-methylpiperazine dihydrochloride (Intermediate 34, 0.56 mmol). Purification by prep HPLC and chiral prep HPLC to separate the isomers gave the title compounds.

Example 69: LCMS (ES+) 398 (M+H)$^+$, RT 3.89 min (Analytical Method 4), $^1$H NMR (400 MHz, MeOD) 8.18 (1H, d, J=6.1 Hz), 8.12 (1H, d, J=5.8 Hz), 7.46-7.43 (1H, m), 7.34-7.26 (2H, m), 7.07-6.99 (2H, m), 5.44-5.38 (1H, m), 4.43-4.35 (1H, m), 3.99-3.94 (1H, m), 3.79-3.70 (2H, m), 3.41-3.37 (1H, m), 3.22-3.16 (1H, m), 3.06-2.98 (1H, m), 2.68 (3H, s), 1.59 (3H, d, J=7.0 Hz), 1.32 (3H, d, J=6.7 Hz). SFC RT 2.34 min (SFC4, LUX CELLULOSE-4+0.1% DEAISO 35% MeOH).

Example 70: LCMS (ES+) 398 (M+H)$^+$, RT 3.89 min (Analytical Method 4), $^1$H NMR (400 MHz, MeOD) 8.06 (1H, d, J=6.1 Hz), 7.99 (1H, d, J=5.6 Hz), 7.31 (1H, d, J=7.8 Hz), 7.21-7.12 (2H, m), 6.88 (2H, dd, J=5.8, 8.3 Hz), 5.28 (1H, q, J=7.0 Hz), 4.28-4.25 (1H, m), 3.87-3.82 (1H, m), 3.66-3.56 (2H, m), 3.29-3.24 (1H, m), 3.10-3.03 (1H, m), 2.94-2.85 (1H, m), 2.55 (3H, s), 1.46 (3H, d, J=7.0 Hz), 1.20 (3H, dd, J=7.1, 7.1 Hz). SFC RT 1.93 min (SFC4, LUX CELLULOSE-4+0.1% DEAISO 35% MeOH).

Following Method A from 1-(2-methyl-2H-indazol-4-yl)ethan-1-amine hydrochloride (100 mg, 0.472 mmol) and (R)-1-(3-fluoropyridin-4-yl)-3-methylpiperazine dihydrochloride (Intermediate 34, 127 mg, 0.472 mmol). Purification by prep HPLC and chiral SFC of part of the material gave the title compounds:

Example 71: LCMS (ES+) 397 (M+H)$^+$, RT 3.32 min (Analytical Method 4), $^1$H NMR (400 MHz, CD$_3$CN) 8.18 (2H, d, J=7.7 Hz), 8.12 (1H, d, J=5.5 Hz), 7.47 (1H, d, J=8.7 Hz), 7.21-7.17 (1H, m), 6.97 (1H, d, J=6.8 Hz), 6.84 (1H, dd, J=5.5, 8.2 Hz), 5.64 (1H, d, J=7.2 Hz), 5.29-5.20 (1H, m), 4.24-4.22 (1H, m), 4.15 (3H, s), 3.85-3.79 (1H, m), 3.61-3.52 (2H, m), 3.26-3.17 (1H, m), 3.03 (1H, dd, J=3.7, 12.3 Hz), 2.91-2.83 (1H, m), 1.54 (3H, d, J=7.1 Hz), 1.25-1.22 (3H, m); 98% e.e. SFC RT 1.37 min (SFC4, LUX CELLULOSE-4+0.1% DEAISO 40% MeOH).

Example 72: LCMS (ES+) 397 (M+H)$^+$, RT 3.30 min (Analytical Method 4), $^1$H NMR (400 MHz, CD$_3$CN) 8.22 (2H, dd, J=2.8, 2.8 Hz), 8.16 (1H, d, J=5.5 Hz), 7.51 (1H, d, J=8.7 Hz), 7.26-7.21 (1H, m), 7.02 (1H, d, J=6.8 Hz), 6.89 (1H, dd, J=5.5, 8.2 Hz), 5.66 (1H, d, J=7.2 Hz), 5.30-5.24 (1H, m), 4.29-4.26 (1H, m), 4.19 (3H, s), 3.85 (1H, d, J=13.2 Hz), 3.60 (2H, dd, J=12.2, 20.5 Hz), 3.31-3.23 (1H, m), 3.08 (1H, dd, J=3.5, 12.3 Hz), 2.95-2.87 (1H, m), 1.57 (3H, d, J=7.0 Hz), 1.24 (3H, d, J=6.6 Hz); 91% e.e. SFC RT 1.95 min (SFC4, LUX CELLULOSE-4+0.1% DEAISO 40% MeOH).

Example 73

Imidazo[1,2-a]pyridin-5-ylmethyl (R)-4-(3-fluoropyridin-4-yl)-2-methylpiperazine-1-carboxylate

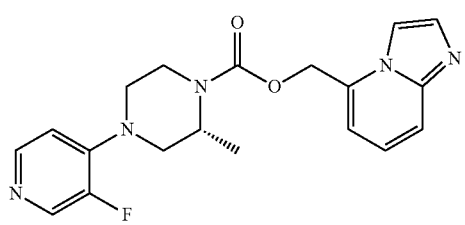

A solution of 4-nitrophenylchloroformate (68 mg, 0.337 mmol) in DCM (3 mL) was treated with a suspension of imidazo[1,2-a]pyridin-5-ylmethanol (50 mg, 0.337 mmol) and TEA (0.14 mL, 1.01 mmol) in DCM (3 mL). The suspension was stirred for 20 min, treated with (R)-1-(3-fluoropyridin-4-yl)-3-methylpiperazine dihydrochloride (Intermediate 34, 92 mg, 0.337 mmol) and stirred for a further 18 h. The reaction was washed with saturated NaHCO$_3$ solution (×3), passed through a hydrophobic frit and concentrated to dryness. Purification by prep HPLC gave the title compound (22 mg). LCMS (ES+) 370 (M+H)$^+$, RT 2.85 min (Analytical Method 2), $^1$H NMR (400 MHz, CDCl$_3$) 8.24 (1H, d, J=5.3 Hz), 8.18 (1H, d, J=5.5 Hz), 7.73 (1H, s), 7.69 (2H, d, J=8.3 Hz), 7.21 (1H, dd, J=6.8, 9.2 Hz), 6.90 (1H, d, J=6.8 Hz), 6.70 (1H, dd, J=5.5, 7.8 Hz), 5.42 (2H, d, J=2.3 Hz), 4.43-4.38 (1H, m), 4.00-4.00 (1H, m), 3.58-3.48 (2H, m), 3.41-3.32 (1H, m), 3.05 (1H, dd, J=2.9, 12.1 Hz), 2.89 (1H, dd, J=11.2, 11.2 Hz), 1.33 (3H, d, J=6.5 Hz).

Example 74

(R)—N-((2,2-Difluorobenzo[d][1,3]dioxol-4-yl)methyl)-4-(3-fluoropyridin-4-yl)-2-methylpiperazine-1-carboxamide Hemiformate

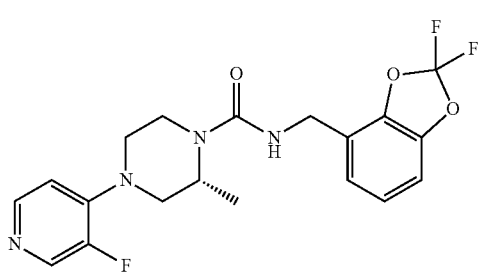

Following Method B from 4-nitrophenyl ((2,2-difluorobenzo[d][1,3]dioxol-4-yl)methyl)carbamate (Intermediate 6, 0.213 mmol) and (R)-1-(3-fluoropyridin-4-yl)-3-methylpiperazine dihydrochloride (Intermediate 34, 0.213 mmol). Purification by prep HPLC gave the title compound (89 mg). LCMS (ES+) 409 (M+H)$^+$, RT 3.17 min (Analytical Method 2), $^1$H NMR (400 MHz, MeOD) 8.22-8.19 (1.5H, m), 8.12 (1H, d, J=5.6 Hz), 7.15-7.10 (3H, m), 7.03 (1H, dd, J=5.9, 8.3 Hz), 4.49 (2H, dd, J=15.5, 19.4 Hz), 4.38-4.32 (1H, m), 3.96-3.91 (1H, m), 3.81-3.72 (2H, m), 3.42-3.36 (1H, m), 3.23 (1H, dd, J=3.6, 12.7 Hz), 3.10-3.01 (1H, m), 1.34 (3H, d, J=6.7 Hz).

Example 75

(R)—N-(Benzo[d][1,3]dioxol-4-ylmethyl)-4-(3-fluoropyridin-4-yl)-2-methylpiperazine-1-carboxamide

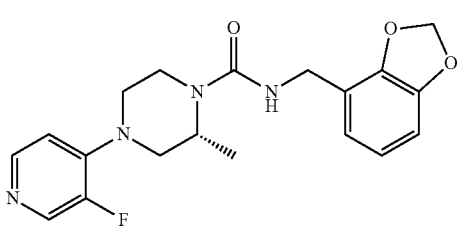

Following Method B from 4-nitrophenyl (benzo[d][1,3]dioxol-4-ylmethyl)carbamate (Intermediate 7, 0.237 mmol) and (R)-1-(3-fluoropyridin-4-yl)-3-methylpiperazine dihydrochloride (Intermediate 34, 0.237 mmol). Purification by prep HPLC gave the title compound (63 mg). LCMS (ES+) 373 (M+H)$^+$, RT 2.45 min (Analytical Method 1), $^1$H NMR (400 MHz, MeOD) 8.18 (1H, d, J=6.1 Hz), 8.12 (1H, d, J=5.6 Hz), 7.01 (1H, dd, J=5.7, 8.3 Hz), 6.81 (2H, d, J=4.9 Hz), 6.77-6.72 (1H, m), 5.97 (2H, s), 4.45-4.31 (3H, m), 3.95-3.90 (1H, m), 3.78-3.69 (2H, m), 3.40-3.36 (1H, m), 3.19 (1H, dd, J=3.7, 12.5 Hz), 3.06-2.98 (1H, m), 1.33 (3H, d, J=6.6 Hz).

Example 76

(R)—N-(Benzofuran-4-ylmethyl)-4-(3-fluoropyridin-4-yl)-2-methylpiperazine-1-carboxamide

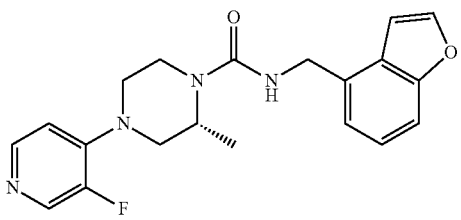

Following Method B from (R)-1-(3-fluoropyridin-4-yl)-3-methylpiperazine dihydrochloride (Intermediate 34,145 mg, 0.63 mmol) and 4-nitrophenyl (benzofuran-4-ylmethyl)carbamate (Intermediate 9, 200 mg, 0.63 mmol). Purification by SCX gave the title compound (75 mg). LCMS (ES+) 369 (M+H)$^+$, RT 3.06 min (Analytical Method 2), $^1$H NMR (400 MHz, MeOD) 8.19-8.10 (2H, m), 7.78-7.76 (1H, m), 7.44-7.40 (1H, m), 7.30-7.19 (2H, m), 7.02-6.98 (2H, m), 4.68 (2H, d, J=16.5 Hz), 4.39-4.33 (1H, m), 3.98-3.91 (1H, m), 3.79-3.68 (2H, m), 3.38 (1H, d, J=26.9 Hz), 3.22-3.16 (1H, m), 3.06-2.98 (1H, m), 1.32 (3H, d, J=6.7 Hz); SFC RT 2.84 min (SFC1, LUX CELLULOSE-3+0.1% DEA5_55% MeOH).

Example 77

(R)—N-((2,3-Dihydrobenzo[b][1,4]dioxin-5-yl)methyl)-4-(3-fluoropyridin-4-yl)-2-methylpiperazine-1-carboxamide formate

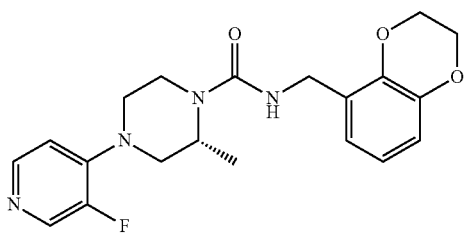

Following Method B from 4-nitrophenyl ((2,3-dihydrobenzo[b][1,4]dioxin-5-yl)methyl)carbamate (Intermediate 8, 0.227 mmol) and (R)-1-(3-fluoropyridin-4-yl)-3-methylpiperazine dihydrochloride (Intermediate 34, 0.227 mmol). Purification by prep HPLC gave the title compound (75 mg). LCMS (ES+) 387 (M+H)$^+$, RT 3.00 min (Analytical Method 2), $^1$H NMR (400 MHz, MeOD) 8.21 (1H, s), 8.20 (1H, d, J=1.7 Hz), 8.12 (1H, d, J=5.7 Hz), 7.03 (1H, dd, J=5.7, 8.3 Hz), 6.79-6.74 (3H, m), 4.39 (2H, d, J=5.7 Hz), 4.37-4.25 (5H, m), 3.96-3.91 (1H, m), 3.83-3.72 (2H, m), 3.39 (1H, dd, J=3.4, 11.9 Hz), 3.24 (1H, dd, J=3.7, 12.6 Hz), 3.11-3.02 (1H, m), 1.33 (3H, d, J=6.7 Hz).

Example 78

(R)-4-(3-Fluoropyridin-4-yl)-2-methyl-N-((2-methyl-2H-indazol-4-yl)methyl)piperazine-1-carboxamide

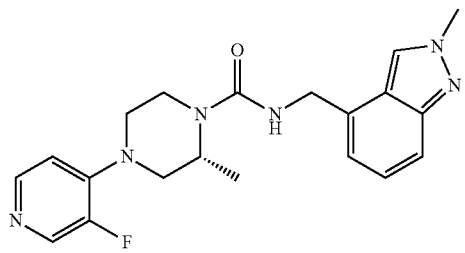

Following Method A from 4-aminomethyl-2-methyl-indazole hydrochloride (0.331 mmol) and (R)-1-(3-fluoropyridin-4-yl)-3-methylpiperazine dihydrochloride (Intermediate 34, 0.331 mmol). Purification by prep HPLC gave the title compound (45 mg). LCMS (ES+) 383 (M+H)$^+$, RT 2.28 min (Analytical Method 1), $^1$H NMR (400 MHz, MeOD) 8.30 (1H, s), 8.22-8.19 (1H, m), 8.12 (1H, d, J=5.7 Hz), 7.51 (1H, d, J=8.7 Hz), 7.27 (1H, dd, J=6.8, 8.7 Hz), 7.05-7.00 (2H, m), 4.68 (2H, dd, J=16.2, 19.8 Hz), 4.42-4.36 (1H, m), 4.24 (3H, s), 3.98-3.93 (1H, m), 3.81-3.71 (2H, m), 3.43-3.36 (1H, m), 3.23 (1H, dd, J=3.7, 12.6 Hz), 3.10-3.01 (1H, m), 1.33 (3H, d, J=6.7 Hz).

Example 79

(R)-4-(3-Fluoropyridin-4-yl)-2-methyl-N-((1-methyl-1H-indazol-4-yl)methyl)piperazine-1-carboxamide

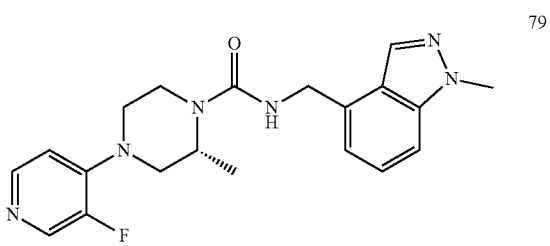 [SMILES: C[C@@H]1CN(c2ccncc2F)CCN1C(=O)NCc1cccc2c1cnn2C]

Following Method A from (1-methyl-1H-indazol-4-yl)methaneamine hydrochloride (100 mg, 0.506 mmol) and (R)-1-(3-fluoropyridin-4-yl)-3-methylpiperazine dihydrochloride (Intermediate 34, 136 mg, 0.506 mmol). Purification by prep HPLC gave the title compound (15 mg). LCMS (ES+) 383 (M+H)$^+$, RT 2.45 min (Analytical Method 3), $^1$H NMR (400 MHz, MeOD) 8.19 (1H, d, J=6.1 Hz), 8.12 (1H, d, J=5.6 Hz), 7.99 (1H, s), 7.69 (1H, d, J=8.1 Hz), 7.35 (1H, d, J=7.1 Hz), 7.13 (1H, dd, J=7.6, 7.6 Hz), 7.01 (1H, dd, J=5.7, 8.1 Hz), 4.94-4.89 (2H, m), 4.43-4.37 (1H, m), 4.32 (3H, s), 3.96 (1H, d, J=13.3 Hz), 3.78-3.69 (2H, m), 3.43-3.36 (1H, m), 3.20 (1H, dd, J=3.6, 12.5 Hz), 3.08-2.99 (1H, m), 1.35 (3H, d, J=6.6 Hz).

Example 80

(R)-4-(3-Fluoropyridin-4-yl)-2-methyl-N-(quinolin-5-ylmethyl)piperazine-1-carboxamide

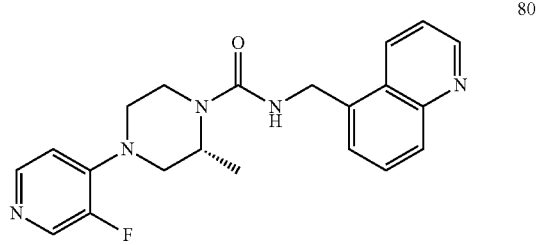 [SMILES: C[C@@H]1CN(c2ccncc2F)CCN1C(=O)NCc1cccc2ncccc12]

Following Method A from quinolin-5-ylmethanamine (44 mg, 0.280 mmol) and (R)-1-(3-fluoropyridin-4-yl)-3-methylpiperazine dihydrochloride (Intermediate 34, 75 mg, 0.280 mmol). Purification by prep HPLC gave the title compound (12 mg). LCMS (ES+) 380 (M+H)$^+$, RT 2.81 min (Analytical Method 2), $^1$H NMR (400 MHz, MeOD) 8.89-8.88 (1H, m), 8.72 (1H, d, J=8.6 Hz), 8.18 (1H, d, J=6.0 Hz), 8.11 (1H, d, J=5.6 Hz), 7.99 (1H, d, J=8.4 Hz), 7.79-7.74 (1H, m), 7.65-7.59 (2H, m), 7.00 (1H, dd, J=5.7, 8.2 Hz), 4.92 (2H, d, J=6.1 Hz), 4.38-4.37 (1H, m), 3.95 (1H, d, J=13.3 Hz), 3.77-3.68 (2H, m), 3.42-3.30 (1H, m), 3.19 (1H, dd, J=3.7, 12.6 Hz), 3.06-2.98 (1H, m), 1.32 (3H, d, J=6.7 Hz).

Example 81

(R)-4-(3-Fluoropyridin-4-yl)-N—((R)-1-(3-(methoxy-d₃)phenyl)ethyl-2,2,2-d₃)-2-methylpiperazine-1-carboxamide

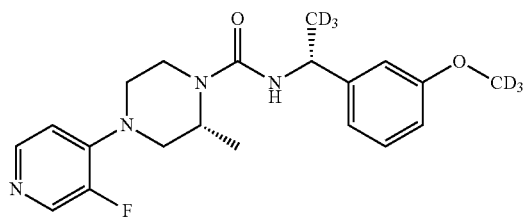

Following Method B from (R)-1-(3-fluoropyridin-4-yl)-3-methylpiperazine dihydrochloride (Intermediate 34, 50 mg, 0.21 mmol) and 4-nitrophenyl (R)-(1-(3-(methoxy-d₃)phenyl)ethyl-2,2,2-d₃)carbamate (Intermediate 29, 68 mg, 0.21 mmol). Purification by preparative-HPLC gave the title compound (49 mg). LCMS (ES+) 379 (M+H)⁺, RT 2.55 min (Analytical Method 1), ¹H NMR (400 MHz, DMSO) 8.31 (1H, d, J=5.6 Hz), 8.19 (1H, d, J=5.6 Hz), 7.29-7.23 (1H, m), 7.04 (1H, dd, J=5.6, 8.1 Hz), 6.94 (2H, dd, J=2.0, 4.0 Hz), 6.86-6.78 (2H, m), 4.87 (1H, d, J=8.1 Hz), 4.41-4.34 (1H, m), 3.92 (1H, d, J=13.1 Hz), 3.62 (2H, dd, J=12.0, 22.1 Hz), 3.23-3.13 (1H, m), 3.06 (1H, dd, J=3.3, 12.4 Hz), 2.94-2.85 (1H, m), 1.20 (3H, d, J=6.6 Hz).

Example 82

(R)-4-(3-Fluoropyridin-4-yl)-N—((R)-1-(3-(methoxy-d₃)phenyl)ethyl)-2-methylpiperazine-1-carboxamide

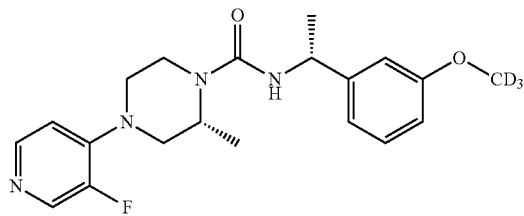

Following Method B from (R)-1-(3-fluoropyridin-4-yl)-3-methylpiperazine dihydrochloride (Intermediate 34, 90 mg, 0.39 mmol) and 4-nitrophenyl (R)-(1-(3-(methoxy-d₃)phenyl)ethyl)carbamate (Intermediate 30, 124 mg, 0.39 mmol). Purification by preparative-HPLC gave the title compound (80 mg). LCMS (ES+) 376 (M+H)⁺, RT 3.15 min (Analytical Method 2), ¹H NMR (400 MHz, DMSO) 8.31 (1H, d, J=5.8 Hz), 8.19 (1H, d, J=5.6 Hz), 7.29-7.23 (1H, m), 7.04 (1H, dd, J=5.6, 8.3 Hz), 6.96-6.92 (2H, m), 6.86-6.80 (2H, m), 4.94-4.84 (1H, m), 4.42-4.34 (1H, m), 3.92 (1H, d, J=13.1 Hz), 3.62 (2H, dd, J=12.0, 22.1 Hz), 3.23-3.13 (1H, m), 3.06 (1H, dd, J=3.2, 12.3 Hz), 2.94-2.85 (1H, m), 1.41 (3H, d, J=7.1 Hz), 1.20 (3H, d, J=6.6 Hz).

Example 83

(R)-2-Ethyl-4-(3-fluoropyridin-4-yl)-N—((R)-1-(3-methoxyphenyl)ethyl)piperazine-1-carboxamide

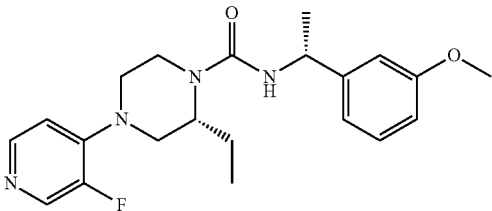

Following Method B from 4-nitrophenyl (R)-(1-(3-methoxyphenyl)ethyl)carbamate (Intermediate 1, 0.190 mmol) and (R)-3-ethyl-1-(3-fluoropyridin-4-yl)piperazine dihydrochloride (Intermediate 42, 0.190 mmol). Purification by prep HPLC gave the title compound (54 mg). LCMS (ES+) 387 (M+H)⁺, RT 2.62 min (Analytical Method 1), ¹H NMR (400 MHz, MeOD) 8.19 (1H, d, J=6.1 Hz), 8.12 (1H, d, J=5.6 Hz), 7.23 (1H, dd, J=8.0, 8.0 Hz), 7.01 (1H, dd, J=5.7, 8.2 Hz), 6.94 (2H, d, J=7.1 Hz), 6.81-6.77 (1H, m), 4.94 (1H, q, J=7.1 Hz), 4.19 (1H, dd, J=7.5, 7.5 Hz), 3.99 (1H, d, J=13.6 Hz), 3.85-3.81 (4H, m), 3.71 (1H, dd, J=1.4, 11.1 Hz), 3.28 (1H, dd, J=3.2, 13.3 Hz), 3.08 (1H, dd, J=3.5, 12.6 Hz), 3.01-2.92 (1H, m), 1.88-1.73 (2H, m), 1.48 (3H, d, J=7.1 Hz), 0.95 (3H, t, J=7.5 Hz).

Examples 84 and 85 (S)-2-(3-Fluoro-5-methoxybenzyl)-7-(3-fluoropyridin-4-yl)hexahydroimidazo[1,5-a]pyrazin-3(2H)-one and (R)-2-(3-Fluoro-5-methoxybenzyl)-7-(3-fluoropyridin-4-yl)hexahydroimidazo[1,5-a]pyrazin-3(2H)-one

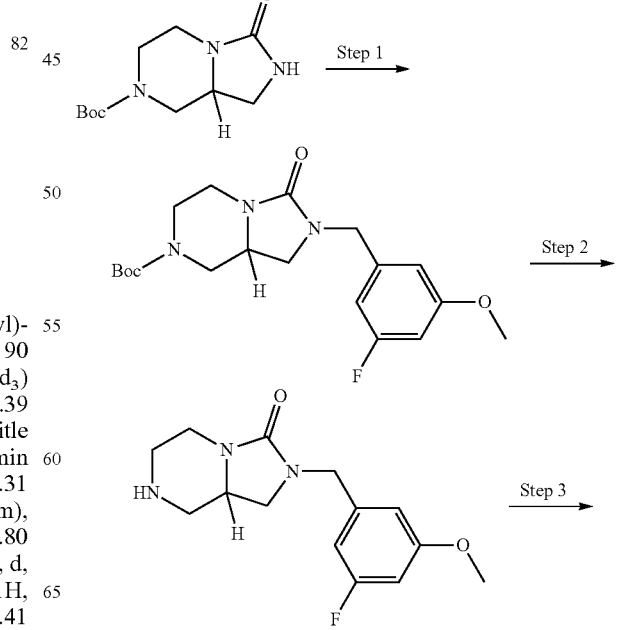

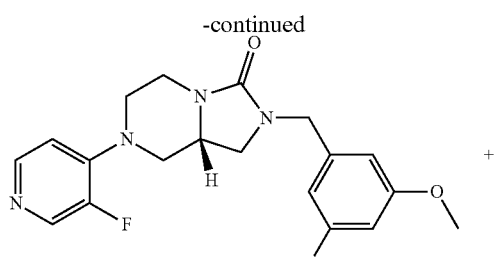

84

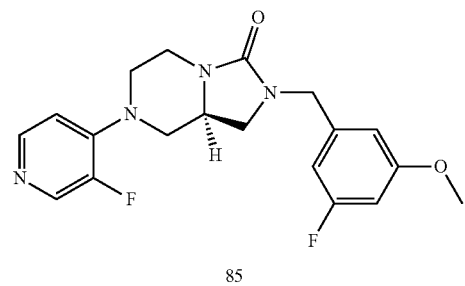

85

Step 1: Tert-butyl 2-(3-fluoro-5-methoxybenzyl)-3-oxohexahydroimidazo[1,5-a]pyrazine-7(1H)-carboxylate A stirred r.t. solution of tert-butyl 3-oxohexahydroimidazo[1,5-a]pyrazine-7(1H)-carboxylate (200 mg, 0.829 mmol) in DMF (2.0 mL) was treated with NaH (60%, 50 mg, 1.24 mmol). After 10 mins, 1-(bromomethyl)-3-fluoro-5-methoxybenzene (182 mg, 0.829 mmol) was added and the reaction stirred for 24 h. The reaction was diluted with DCM (10 mL), washed with saturated sodium bicarbonate solution (10 mL×1), water (10 mL×1) and brine (10 mL×1), the organics were dried ($Na_2SO_4$), filtered and concentrated in vacuo to give the title compound. The compound was taken onto the next step without further purification.

Step 2: 2-(3-Fluoro-5-methoxybenzyl)hexahydroimidazo[1,5-a]pyrazin-3(2H)-one

4 M HCl in dioxane (2.1 mL, 8.30 mmol) was added to a solution of tert-butyl 2-(3-fluoro-5-methoxybenzyl)-3-oxohexahydroimidazo[1,5-a]pyrazine-7(1H)-carboxylate (315 mg, 0.830 mmol) in MeOH (3.0 mL). The reaction was irradiated in the microwave at 100° C. for 10 minutes. The reaction was concentrated in vacuo and the residue applied to an SCX-2 column. Elution with methanol followed by 3 M $NH_3$ in MeOH gave the title compound.

Step 3: (S)-2-(3-Fluoro-5-methoxybenzyl)-7-(3-fluoropyridin-4-yl)hexahydroimidazo[1,5-a]pyrazin-3(2H)-one and (R)-2-(3-Fluoro-5-methoxybenzyl)-7-(3-fluoropyridin-4-yl)hexahydroimidazo[1,5-a]pyrazin-3(2H)-one To 2-(3-fluoro-5-methoxybenzyl)hexahydroimidazo[1,5-a]pyrazin-3(2H)-one (244 mg, 0.874 mmol) in DMF (1.0 mL) was added 3,4-difluoropyridine (101 mg, 0.874 mmol) and $Cs_2CO_3$ (285 mg, 0.874 mmol). The reaction was stirred at 100° C. for 24 hours. The reaction was diluted with DCM (10 mL), washed with saturated sodium bicarbonate solution (10 mL×1), water (10 mL×1) and brine (10 mL×1), the organics were dried ($MgSO_4$), filtered and concentrated in vacuo. The residue was applied to an SCX-2 column and eluted with methanol followed by 3 M $NH_3$ in MeOH, the resulting crude was further purified by silica gel column chromatography (gradient elution, 0-100% ethyl acetate/cyclohexane). The two enantiomers were separated via chiral SFC to give the tittle compounds.

Examples 84 & 85: 99.5% e.e, LCMS (ES+) 375 (M+H)$^+$, RT 2.79 min (Analytical Method 3), $^1$H NMR (400 MHz, CDCl$_3$) 8.23 (2H, dd, J=5.3, 24.0 Hz), 6.74 (1H, dd, J=5.5, 7.9 Hz), 6.60-6.51 (3H, m), 4.35 (2H, s), 4.04-3.98 (1H, m), 3.79-3.79 (4H, m), 3.64-3.53 (2H, m), 3.39 (1H, t, J=8.7 Hz), 3.19 (1H, ddd, J=2.4, 10.9, 14.5 Hz), 2.96-2.87 (2H, m), 2.74 (1H, t, J=11.4 Hz), SFC RT 3.66 min (SFC1, LUX CELLULOSE-4+0.1% DEAISO 35% IPA); 97.2% e.e., LCMS (ES+) 375 (M+H)$^+$, RT 2.78 min (Analytical Method 3), $^1$H NMR (400 MHz, CDCl$_3$) 8.23 (2H, dd, J=5.3, 23.9 Hz), 6.74 (1H, dd, J=5.5, 7.8 Hz), 6.60-6.51 (3H, m), 4.35 (2H, s), 4.03-3.99 (1H, m), 3.79-3.79 (4H, m), 3.65-3.53 (2H, m), 3.39 (1H, t, J=8.7 Hz), 3.23-3.15 (1H, m), 2.96-2.87 (2H, m), 2.74 (1H, t, J=11.4 Hz). SFC RT 4.5 min (SFC1, LUX CELLULOSE-4+0.1% DEAISO 35% IPA).

Examples 86 and 87 (S)-7-(3-Fluoropyridin-4-yl)-2-(3-methoxybenzyl)hexahydroimidazo[1,5-a]pyrazin-3(2H)-one and (R)-7-(3-Fluoropyridin-4-yl)-2-(3-methoxybenzyl)hexahydroimidazo[1,5-a]pyrazin-3(2H)-one

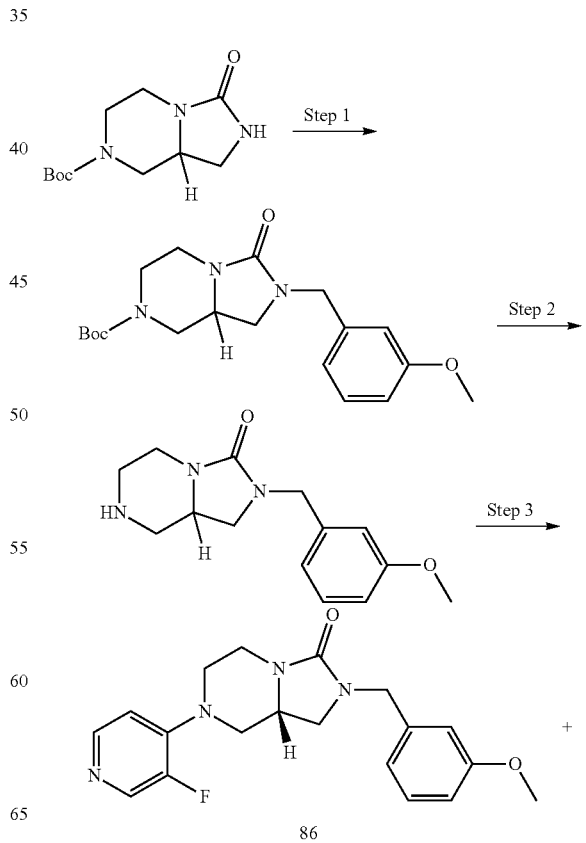

86

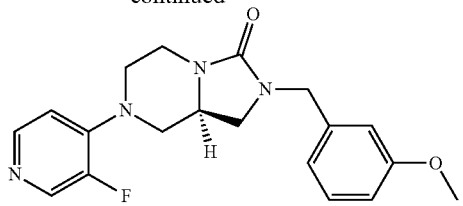

87

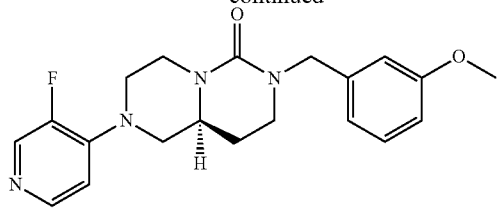

88

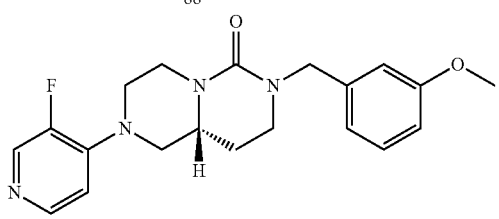

89

Examples 86 and 87 were synthesized according to the method for Examples 84 and 85 from 3-methoxybenzyl bromide and tert-butyl 3-oxohexahydroimidazo[1,5-a]pyrazine-7(1H)-carboxylate. 2-(3-Methoxybenzyl)hexahydroimidazo[1,5-a]pyrazin-3(2H)-one (45 mg, 0.172 mmol) and 3,4-difluoropyridine (20 mg, 0.172 mmol) were used in step 3. Purification via chiral SFC gave the tittle compounds. Examples 86 & 87: 100% e.e., LCMS (ES+) 358 (M+H)+, RT 2.64 min (Analytical Method 3), $^1$H NMR (400 MHz, CDCl$_3$) 8.25 (1H, d, J=5.3 Hz), 8.19 (1H, d, J=5.4 Hz), 7.28-7.24 (1H, m), 6.86-6.80 (3H, m), 6.73 (1H, dd, J=5.5, 7.8 Hz), 4.38 (2H, d, J=1.3 Hz), 4.01 (1H, dd, J=2.1, 13.4 Hz), 3.86-3.81 (1H, m), 3.80 (3H, s), 3.61-3.52 (2H, m), 3.37 (1H, dd, J=8.7, 8.7 Hz), 3.22-3.14 (1H, m), 2.95-2.85 (2H, m), 2.73 (1H, dd, J=11.4, 11.4 Hz); SFC RT 4.21 min (SFC4, LUX CELLULOSE-4+0.1% DEAISO 15% IPA); 97.7% e.e., LCMS (ES+) 358 (M+H)+, RT 2.63 min (Analytical Method 3), $^1$H NMR (400 MHz, CDCl$_3$) 8.25 (1H, d, J=5.1 Hz), 8.19 (1H, d, J=5.5 Hz), 7.26 (1H, s), 7.28-7.23 (1H, m), 6.87-6.79 (3H, m), 6.73 (1H, dd, J=5.5, 7.8 Hz), 4.38 (2H, d, J=1.3 Hz), 4.01 (1H, dd, J=2.2, 13.4 Hz), 3.86-3.81 (1H, m), 3.80 (3H, s), 3.61-3.52 (2H, m), 3.37 (1H, dd, J=8.7, 8.7 Hz), 3.22-3.14 (1H, m), 2.95-2.85 (2H, m), 2.73 (1H, dd, J=11.4, 11.4 Hz); SFC RT 5.11 min (SFC4, LUX CELLULOSE-4+0.1% DEAISO 15% IPA).

Examples 88 and 89 (S)-2-(3-Fluoropyridin-4-yl)-7-(3-methoxybenzyl)octahydro-6H-pyrazino[1,2-c]pyrimidin-6-one and (R)-2-(3-Fluoropyridin-4-yl)-7-(3-methoxybenzyl)octahydro-6H-pyrazino[1,2-c]pyrimidin-6-one

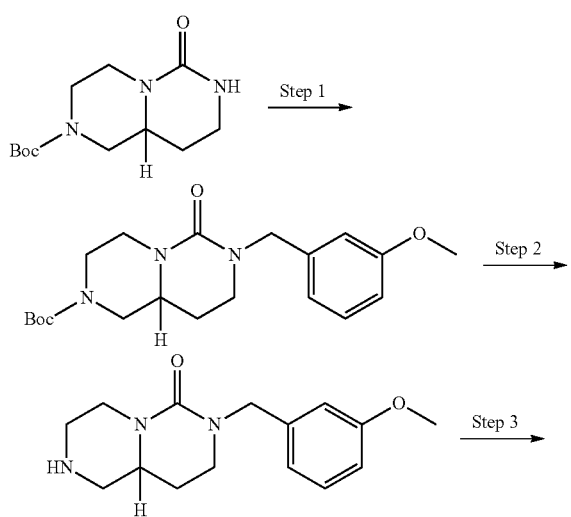

Step 1: Tert-butyl 7-(3-methoxybenzyl)-6-oxooctahydro-2H-pyrazino[1,2-c]pyrimidine-2-carboxylate A stirred solution of tert-butyl 6-oxooctahydro-2H-pyrazino[1,2-c]pyrimidine-2-carboxylate (150 mg, 0.59 mmol) in DMF (5 mL), under nitrogen, was treated portionwise with NaH (60%, 35 mg, 0.88 mmol). After 15 min, 3-methoxybenzyl bromide (0.09 mL, 0.646 mmol) was added dropwise and the reaction stirred for 18 h. The mixture was diluted with EtOAc and water, the organics separated, washed with brine and passed through a hydrophobic frit. The organics were evaporated to dryness and the residue purified by gradient column chromatography 0-80% EtOAc in in iso-hexanes to give the title compound.

Step 2: 7-(3-Methoxybenzyl)octahydro-6H-pyrazino[1,2-c]pyrimidin-6-one hydrochloride A stirred solution of tert-butyl 7-(3-methoxybenzyl)-6-oxooctahydro-2H-pyrazino[1,2-c]pyrimidine-2-carboxylate (146 mg, 0.389 mmol) in methanol (5 mL) was treated with 4 M HCl in dioxane (0.97 mL, 3.89 mmol) for 18 h. The reaction was co-evaporated with toluene (2×) to give the title compound. Used directly in the next step.

Step 3: (S)-2-(3-Fluoropyridin-4-yl)-7-(3-methoxybenzyl)octahydro-6H-pyrazino[1,2-c]pyrimidin-6-one and (R)-2-(3-Fluoropyridin-4-yl)-7-(3-methoxybenzyl)octahydro-6H-pyrazino[1,2-c]pyrimidin-6-one A stirred solution of 7-(3-methoxybenzyl)octahydro-6H-pyrazino[1,2-c]pyrimidin-6-one hydrochloride (110 mg, 0.35 mmol) in DMF (10 mL) was treated with cesium carbonate (115 mg, 0.35 mmol) and 3,4 difluoropyridine (41 mg, 0.35 mmol). The resulting suspension was heated at 90° C., under a nitrogen atmosphere, in a sealed tube for 18 h. The mixture was evaporated to dryness and the residue purified by gradient column chromatography 20-80% (10% MeOH in EtOAc) in iso-hexanes to give a colorless gum. Purification by chiral prep HPLC to separate the isomers gave the title compounds.
Examples 88 & 89: LCMS (ES+) 371 (M+H)+, RT 3.84 min (Analytical Method 4), $^1$H NMR (400 MHz, MeOD) 8.20 (1H, d, J=6.0 Hz), 8.13 (1H, d, J=5.6 Hz), 7.29-7.24 (1H, m), 7.04 (1H, dd, J=5.7, 8.2 Hz), 6.89-6.84 (3H, m), 4.63 (1H, d, J=15.3 Hz), 4.50-4.40 (2H, m), 3.81 (5H, s), 3.69-3.61 (1H, m), 3.40-3.35 (1H, m), 3.28-3.22 (1H, m), 3.12-2.97 (2H, m), 2.79 (1H, dd, J=10.8, 12.3 Hz), 2.15-2.07 (1H, m), 1.88-1.77 (1H, m); SFC RT 1.96 min (SFC4, LUX CELLULOSE-4+0.1% DEAISO 50% IPA); LCMS (ES+) 371 (M+H)+, RT 3.84 min (Analytical Method 4), ¹H NMR (400 MHz, MeOD) 8.20 (1H, d, J=6.0 Hz), 8.13 (1H, d, J=5.6 Hz), 7.29-7.24 (1H, m), 7.04 (1H, dd, J=5.7, 8.2 Hz), 6.90-6.84 (3H, m), 4.65-4.60 (1H, m), 4.50-4.40 (2H, m), 3.87-3.82 (2H, m), 3.81 (3H, s), 3.69-3.60 (1H, m), 3.40-3.35 (1H, m), 3.29-3.23 (1H, m), 3.12-2.97 (2H, m), 2.82-2.75 (1H, m), 2.15-2.07 (1H, m), 1.89-1.77 (1H, m); SFC RT 2.69 min (SFC4, LUX CELLULOSE-4+0.1% DEAISO 50% IPA).

Example 90

(S)-4-(3-Fluoropyridin-4-yl)-N—((R)-1-(3-methoxyphenyl)ethyl)-3-methylpiperazine-1-carboxamide

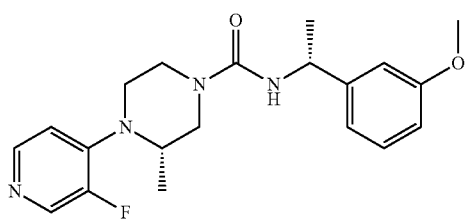

Using Method B from (R)-(1-(3-methoxyphenyl)ethyl) carbamate (Intermediate 1, 183 mg, 0.580 mmol) and (S)-1-(3-fluoropyridin-4-yl)-2-methylpiperazine dihydrochloride (Intermediate 39, 156 mg, 0.58 mmol 1.0 eq). Purification by preparative-HPLC to give title compound. LCMS (ES+) 373 (M+H)+, RT 2.54 min (Analytical Method 1), ¹H NMR (400 MHz, DMSO) 8.27 (1H, d, J=6.0 Hz), 8.14 (1H, d, J=5.5 Hz), 7.22 (1H, dd, J=8.1, 8.1 Hz), 6.98 (1H, dd, J=5.6, 8.3 Hz), 6.92-6.89 (2H, m), 6.85 (1H, d, J=8.0 Hz), 6.78 (1H, dd, J=2.3, 7.9 Hz), 4.89-4.80 (1H, m), 4.05-3.99 (2H, m), 3.83 (1H, d, J=13.3 Hz), 3.75 (3H, s), 3.33-3.29 (1H, m), 3.25-3.18 (2H, m), 3.09-3.00 (1H, m), 1.37 (3H, d, J=7.0 Hz), 1.01 (3H, d, J=6.5 Hz).

Example 91

(R)-4-(3-Fluoropyridin-4-yl)-N—((R)-1-(3-methoxyphenyl)ethyl)-3-methylpiperazine-1-carboxamide

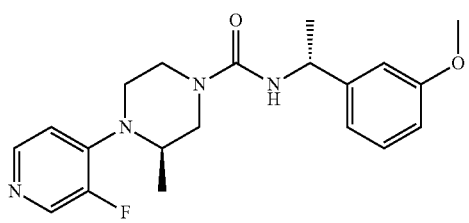

Using Method B from 4-nitrophenyl (R)-(1-(3-methoxyphenyl)ethyl)carbamate (Intermediate 1, 173 mg, 0.548 mmol) and (R)-1-(3-fluoropyridin-4-yl)-2-methylpiperazine dihydrochloride (Intermediate 38, 147 mg, 0.548 mmol, 1.0 eq). Purification by preparative-HPLC gave the title compound. LCMS (ES+) 373 (M+H)+, RT 2.54 min (Analytical Method 1), ¹H NMR (400 MHz, DMSO) 8.26 (1H, d, J=6.0 Hz), 8.14 (1H, d, J=5.5 Hz), 7.21 (1H, dd, J=8.1, 8.1 Hz), 6.97 (1H, dd, J=5.6, 8.4 Hz), 6.91-6.88 (2H, m), 6.84 (1H, d, J=7.9 Hz), 6.78-6.75 (1H, m), 4.89-4.80 (1H, m), 4.06-3.98 (2H, m), 3.83 (1H, d, J=13.3 Hz), 3.74 (3H, s), 3.31-3.16 (3H, m), 3.01 (1H, ddd, J=3.6, 11.0, 12.9 Hz), 1.37 (3H, d, J=7.2 Hz), 1.03 (3H, d, J=6.5 Hz).

Example 92

(2R,6R)—N-(2-Chlorobenzyl)-4-(3-fluoropyridin-4-yl)-2,6-dimethylpiperazine-1-carboxamide

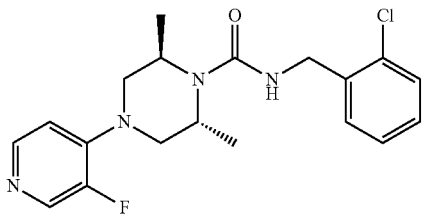

Following Method A from 2-chlorobenzylamine (0.266 mmol) and (3R,5R)-1-(3-fluoropyridin-4-yl)-3,5-dimethylpiperazine dihydrochloride (Intermediate 40, 0.266 mmol). Purification by prep HPLC gave the title compound. LCMS (ES+) 377 (M+H)+, RT 2.58 min (Analytical Method 1), ¹H NMR (400 MHz, MeOD) 8.13 (1H, d, J=6.5 Hz), 8.05 (1H, d, J=5.7 Hz), 7.41-7.37 (2H, m), 7.33-7.24 (2H, m), 6.85 (1H, dd, J=5.7, 8.4 Hz), 4.53 (2H, dd, J=14.5, 43.6 Hz), 4.32-4.26 (2H, m), 4.06 (2H, dd, J=3.5, 12.7 Hz), 3.57 (2H, d, J=12.7 Hz), 1.37 (6H, d, J=6.6 Hz).

Example 93

(2R,6R)—N—((S)-1-(2-Chlorophenyl)ethyl)-4-(3-fluoropyridin-4-yl)-2,6-dimethylpiperazine-1-carboxamide

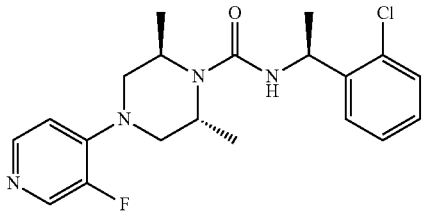

Following Method B from 4-nitrophenyl (1-(2-chlorophenyl)ethyl)carbamate (Intermediate 22, 0.298 mmol) and (3R,5R)-1-(3-fluoropyridin-4-yl)-3,5-dimethylpiperazine dihydrochloride (Intermediate 40, 0.298 mmol). Purification by prep HPLC and chiral SFC gave the title compound after freeze drying. LCMS (ES+) 391 (M+H)+, RT 2.67 min (Analytical Method 1), ¹H NMR (400 MHz, MeOD) 8.12 (1H, d, J=6.6 Hz), 8.05 (1H, d, J=5.7 Hz), 7.48 (1H, d, J=6.8 Hz), 7.38 (1H, d, J=7.7 Hz), 7.32 (1H, dd, J=7.4, 7.4 Hz), 7.26-7.22 (1H, m), 6.84 (1H, dd, J=5.9, 8.3 Hz), 5.44-5.39 (1H, m), 4.31-4.26 (2H, m), 4.02 (2H, dd, J=3.2, 12.5 Hz), 3.54 (2H, d, J=12.6 Hz), 1.50 (3H, d, J=7.1 Hz), 1.35 (6H, d, J=6.6 Hz); SFC RT 3.13 min (SFC1, LUX CELLULOSE-4+0.1% DEAISO 40% MeOH).

Example 94

(2R,6R)—N—((R)-1-(2-Chlorophenyl)ethyl)-4-(3-fluoropyridin-4-yl)-2,6-dimethylpiperazine-1-carboxamide

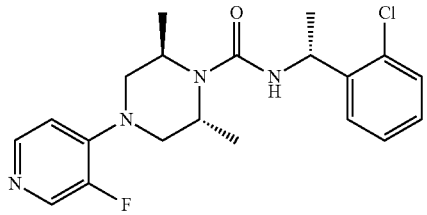

Following Method B from 4-nitrophenyl (1-(2-chlorophenyl)ethyl)carbamate (Intermediate 22, 0.298 mmol) and (3R,5R)-1-(3-fluoropyridin-4-yl)-3,5-dimethylpiperazine dihydrochloride (Intermediate 40, 0.298). Purification by prep HPLC and chiral SFC gave the title compound (31 mg). LCMS (ES+) 391 (M+H)⁺, RT 3.24 min (Analytical Method 2), ¹H NMR (400 MHz, MeOD) 8.13 (1H, d, J=6.5 Hz), 8.05 (1H, d, J=5.7 Hz), 7.46 (1H, dd, J=1.2, 7.7 Hz), 7.38 (1H, d, J=7.9 Hz), 7.32 (1H, dd, J=7.2, 7.2 Hz), 7.26-7.21 (1H, m), 6.85 (1H, dd, J=5.8, 8.4 Hz), 5.39-5.31 (1H, m), 4.36-4.28 (2H, m), 4.04 (2H, dd, J=3.4, 12.6 Hz), 3.56 (2H, d, J=12.7 Hz), 1.50 (3H, d, J=7.1 Hz), 1.31 (6H, d, J=6.6 Hz); SFC RT 1.68 min (SFC4, LUX CELLULOSE-4+0.1% DEAISO 35% MeOH).

Example 95

(2R,6R)-4-(3-Fluoropyridin-4-yl)-N-(3-methoxybenzyl)-2,6-dimethylpiperazine-1-carboxamide

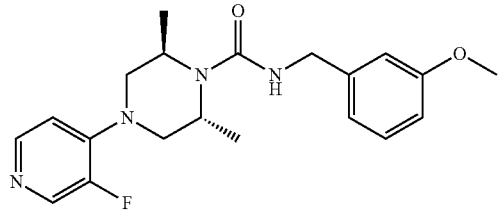

Following Method A from 3-methoxybenzylamine (0.266 mmol) and (3R,5R)-1-(3-fluoropyridin-4-yl)-3,5-dimethylpiperazine dihydrochloride (Intermediate 40, 0.266 mmol). Purification by prep HPLC gave the title compound (40 mg). LCMS (ES+) 373 (M+H)⁺, RT 3.01 min (Analytical Method 2), ¹H NMR (400 MHz, MeOD) 8.14 (1H, d, J=6.6 Hz), 8.05 (1H, d, J=5.7 Hz), 7.24 (1H, dd, J=8.1, 8.1 Hz), 6.93-6.89 (2H, m), 6.88-6.79 (2H, m), 4.50-4.25 (4H, m), 4.06 (2H, dd, J=3.4, 12.7 Hz), 3.81 (3H, s), 3.57 (2H, d, J=12.6 Hz), 1.35 (6H, d, J=6.6 Hz); SFC RT 2.94 min (SFC1, LUX CELLULOSE-4+0.1% DEAISO 40% MeOH).

Example 96

(2R,6R)—N—((R)-1-(2,3-Dihydrobenzofuran-4-yl)ethyl)-4-(3-fluoropyridin-4-yl)-2,6-dimethylpiperazine-1-carboxamide

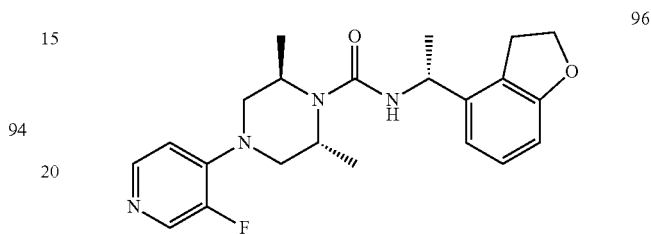

Following Method A from (R)-1-(2,3-dihydrobenzofuran-4-yl)ethan-1-amine hydrochloride (0.27 mmol) and (3R,5R)-1-(3-fluoropyridin-4-yl)-3,5-dimethylpiperazine dihydrochloride (Intermediate 40, 0.266 mmol). Purification by prep HPLC gave the title compound (7 mg). LCMS (ES+) 399 (M+H)⁺, RT 2.59 min (Analytical Method 1), ¹H NMR (400 MHz, DMSO) 8.20 (1H, d, J=6.1 Hz), 8.07 (1H, d, J=5.5 Hz), 7.06 (1H, dd, J=7.8, 7.8 Hz), 6.87 (1H, d, J=7.7 Hz), 6.82 (1H, dd, J=5.6, 8.4 Hz), 6.60 (2H, dd, J=7.8, 10.8 Hz), 4.90-4.82 (1H, m), 4.53 (2H, dd, J=8.8, 8.8 Hz), 4.23-4.18 (2H, m), 3.84 (2H, dd, J=3.3, 12.5 Hz), 3.43-3.11 (4H, m, obsc), 1.37 (3H, d, J=7.1 Hz), 1.16 (6H, d, J=6.5 Hz).

Example 97

(2R,6R)-4-(3-Fluoropyridin-4-yl)-N—((R)-1-(3-methoxyphenyl)ethyl)-2,6-dimethylpiperazine-1-carboxamide Formate

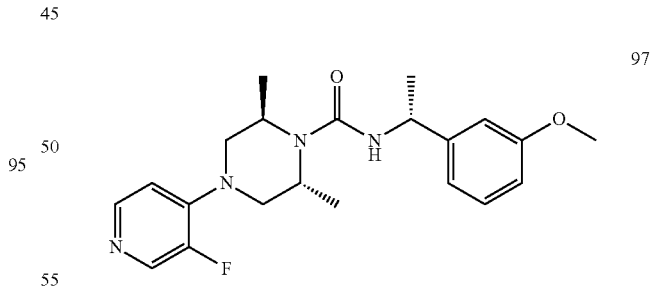

Following Method A from (3R,5R)-1-(3-fluoropyridin-4-yl)-3,5-dimethylpiperazine dihydrochloride (Intermediate 40, 0.617 mmol) and (R)-1-(3-methoxyphenyl)ethylamine. Purification by prep HPLC gave the title compound. LCMS (ES+) 387 (M+H)⁺, RT 2.60 min (Analytical Method 1), ¹H NMR (400 MHz, MeOD) 8.26 (1H, s), 8.16 (1H, d, J=6.7 Hz), 8.06 (1H, d, J=5.9 Hz), 7.25 (1H, dd, J=7.9, 7.9 Hz), 6.95 (2H, d, J=7.3 Hz), 6.88 (1H, dd, J=5.9, 8.4 Hz), 6.81 (1H, dd, J=1.8, 7.3 Hz), 4.99 (1H, q, J=7.1 Hz), 4.04 (2H, dd, J=3.5, 12.7 Hz), 3.82 (3H, s), 3.58 (2H, d, J=12.7 Hz), 1.51 (3H, d, J=7.1 Hz), 1.32 (6H, d, J=6.6 Hz).

Example 98

(2R,5R)-4-(3-Fluoropyridin-4-yl)-N—((R)-1-(3-methoxyphenyl)ethyl)-2,5-dimethylpiperazine-1-carboxamide

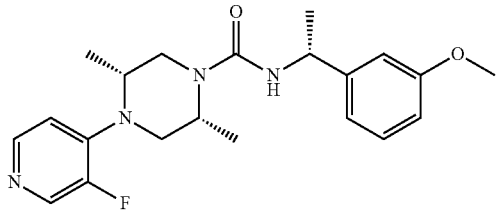

98

Following Method B from 4-nitrophenyl (R)-(1-(3-methoxyphenyl)ethyl)carbamate (Intermediate 1, 0.119 mmol) and (2R,5R)-1-(3-fluoropyridin-4-yl)-2,5-dimethylpiperazine dihydrochloride (Intermediate 43, 0.119 mmol). Purification by prep HPLC gave the title compound. LCMS (ES+) 387 (M+H)$^+$, RT 3.07 min (Analytical Method 2), $^1$H NMR (400 MHz, CDCl$_3$) 8.19 (1H, d, J=6.1 Hz), 8.08 (1H, d, J=5.6 Hz), 7.18 (1H, dd, J=7.8, 7.8 Hz), 6.83-6.79 (2H, m), 6.76 (1H, dd, J=2.4, 8.1 Hz), 6.67 (1H, dd, J=5.7, 8.1 Hz), 5.02-4.93 (1H, m), 4.51 (1H, d, J=7.1 Hz), 4.20 (1H, dd, J=6.1, 14.1 Hz), 4.02-3.82 (2H, m), 3.75 (3H, s), 3.71 (1H, dd, J=5.7, 14.1 Hz), 3.10 (1H, dd, J=8.7, 14.1 Hz), 2.81 (1H, dd, J=10.4, 14.1 Hz), 2.62 (1H, s), 1.47 (3H, d, J=6.9 Hz), 1.26 (3H, d, J=6.4 Hz), 1.15 (3H, d, J=6.1 Hz); SFC RT 1.6 min (SFC1, LUX CELLULOSE-4+0.1% DEAISO 40% MeOH).

Example 99

(1S,4S)-5-(3-Fluoropyridin-4-yl)-N-(3-methoxybenzyl)-2,5-diazabicyclo[2.2.1]heptane-2-carboxamide

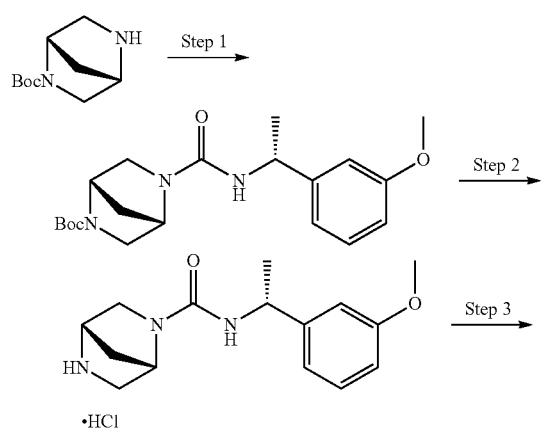

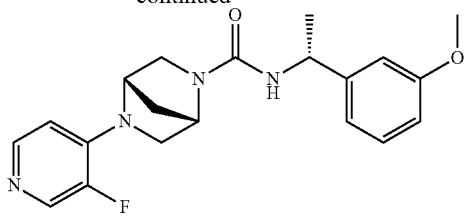

99

Step 1: Tert-butyl (1S,4S)-5-(((R)-1-(3-methoxyphenyl)ethyl)carbamoyl)-2,5-diazabicyclo[2.2.1]heptane-2-carboxylate Following Method A from tert-butyl (1S,4S)-2,5-diazabicyclo[2.2.1]heptane-2-carboxylate (1.02 g, 5.2 mmol) and (R)-1-(3-methoxyphenyl)ethan-1-amine (0.76 g, 5.02 mmol). Purification by flash silica chromatography (gradient elution i-hex to EtOAc) gave the title compound.

Step 2: (1S,4S)—N—((R)-1-(3-Methoxyphenyl)ethyl)-2,5-diazabicyclo[2.2.1]heptane-2-carboxamide.HCl Following Method C from tert-butyl (1S,4S)-5-(((R)-1-(3-methoxyphenyl)ethyl)carbamoyl)-2,5-diazabicyclo[2.2.1]heptane-2-carboxylate (1.15 g, 3.06 mmol) gave the title compound.

Step 3: (1S,4S)-5-(3-Fluoropyridin-4-yl)-N-(3-methoxybenzyl)-2,5-diazabicyclo[2.2.1]heptane-2-carboxamide Following Method E from (1S,4S)—N—((R)-1-(3-methoxyphenyl)ethyl)-2,5-diazabicyclo[2.2.1]heptane-2-carboxamide.HCl (200 mg, 0.64 mmol) and 4-bromo-3-fluoropyridine (103 mg, 0.58 mmol). Purification by preparative-HPLC gave the title compound. LCMS (ES+) 371 (M+H)$^+$, RT 2.50 min (Analytical Method 1). $^1$H NMR (400 MHz, DMSO) 8.17 (1H, d, J=5.9 Hz), 8.00 (1H, d, J=5.5 Hz), 7.13 (1H, dd, J=7.8, 7.8 Hz), 6.80 (2H, d, J=7.6 Hz), 6.75-6.70 (2H, m), 6.61 (1H, d, J=8.2 Hz), 4.82-4.73 (1H, m), 4.70 (1H, s), 4.62 (1H, s), 3.71-3.61 (4H, m), 3.39 (2H, s), 3.27-3.20 (1H, m), 1.93 (2H, dd, J=12.2, 12.2 Hz), 1.33 (3H, d, J=7.1 Hz).

Example 100

(R)-4-(3-Fluoropyridin-4-yl)-N-(1-(3-methoxyphenyl)ethyl)-3-oxopiperazine-1-carboxamide

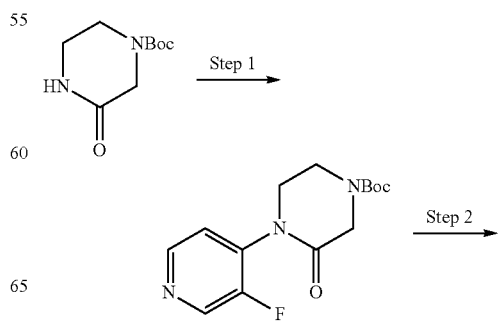

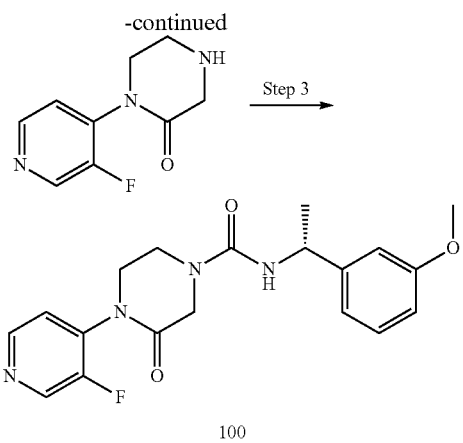

Step 1: Tert-butyl 4-(3-fluoropyridin-4-yl)-3-oxopiperazine-1-carboxylate

A mixture of 3-fluoro-4-iodopyridine (500 mg, 2.24 mmol), tert-butyl 3-oxopiperazine-1-carboxylate (539 mg, 2.69 mmol), copper(I) iodide (21 mg, 0.11 mmol), potassium phosphate tribasic (952 mg, 4.48 mmol), N,N-dimethylethylenediamine (20 mg, 0.22 mmol) in toluene (5 mL) was degassed with $N_2$ for 10 min before heating to 150° C. for 20 min in a microwave. The reaction mixture was diluted with water, extracted with EtOAc (2×) and washed with brine, passed through a phase separator and evaporated to dryness. This was purified by column chromatography using gradient elution 5-100% EtOAc in i-hex to give title compound.

Step 2: 1-(3-Fluoropyridin-4-yl)piperazin-2-one

To a solution of tert-butyl 4-(3-fluoropyridin-4-yl)-3-oxopiperazine-1-carboxylate (200 mg, 0.677 mmol) in acetonitrile (10 ml) and 4N HCl in dioxane (1 ml) were combined and stirred at room temperature for 18 hours. The reaction mixture was then evaporated to dryness and azeotroped with toluene to give crude 2 HCl salt of title compound which was used crude in the next step.

Step 3: (R)-4-(3-Fluoropyridin-4-yl)-N-(1-(3-methoxyphenyl)ethyl)-3-oxopiperazine-1-carboxamide Using Method A from 4-nitrophenyl (S)-(1-(3-methoxyphenyl)ethyl)carbamate (Intermediate 1, 212 mg, 0.67 mmol, 1 eq) and (1-(3-fluoropyridin-4-yl)piperazin-2-one.2HCl salt (198 mg, 0.737 mmol, 1.1 eq). Purification by preparative-HPLC gave the title compound. LCMS (ES+) 373 (M+H)+, RT 2.82 min (Analytical Method 1). 1H NMR (400 MHz, DMSO) 8.67 (1H, d, J=2.4 Hz), 8.50 (1H, d, J=5.1 Hz), 7.59 (1H, dd, J=5.3, 6.4 Hz), 7.23 (1H, dd, J=8.1, 8.1 Hz), 7.01 (1H, d, J=7.9 Hz), 6.94-6.91 (2H, m), 6.79 (1H, dd, J=2.2, 8.0 Hz), 4.89-4.80 (1H, m), 4.23 (2H, d, J=1.9 Hz), 3.76 (7H, d, J=1.8 Hz), 1.39 (3H, d, J=7.2 Hz).

The following compounds were synthesized using the methodologies described above:

| Example | Structure and Name | Analytical data |
|---|---|---|
| Example 101 | | LCMS (ES+) 359 (M + H)+, RT 3.13 min (Analytical Method 2), 1H NMR (400 MHz, DMSO) 7.87 (1H, d, J = 6.1 Hz), 7.29-7.23 (1H, m), 6.96-6.91 (3H, m), 6.86 (1H, d, J = 6.1 Hz), 6.84-6.79 (1H, m), 6.55 (1H, s), 4.92-4.84 (1H, m), 3.79 (3H, s), 3.54-3.47 (4H, m), 3.46-3.40 (4H, m), 1.41 (3H, d, J = 7.1 Hz). |
| Example 102 | | LCMS (ES+) 371 (M + H)+, RT 3.03 min (Analytical Method 2), 1H NMR (400 MHz, DMSO) 7.87 (1H, d, J = 6.1 Hz), 7.09 (1H, dd, J = 7.8, 7.8 Hz), 6.94 (1H, d, J = 7.6 Hz), 6.91-6.82 (2H, m), 6.64 (1H, d, J = 7.6 Hz), 6.54 (1H, s), 4.91-4.80 (1H, m), 4.59-4.51 (2H, m), 3.52-3.45 (4H, m), 3.45-3.41 (4H, m), 3.33-3.14 (2H, m), 1.39 (3H, d, J = 7.1 Hz). |
| Example 103 | | LCMS (ES+) 381 (M + H)+, RT 3.05 min (Analytical Method 2), 1H NMR (400 MHz, DMSO) 7.83 (1H, d, J = 6.1 Hz), 7.37 (1H, t, J = 7.9 Hz), 7.26 (1H, dd, J = 5.8, 5.8 Hz), 7.21 (1H, t, J = 74.2 Hz), 7.16 (1H, d, J = 7.9 Hz), 7.08-7.02 (2H, m), 6.84-6.81 (1H, m), 6.51-6.51 (1H, m), 4.28 (2H, d, J = 5.6 Hz), 3.50-3.38 (8H, m). |

-continued

| Example | Structure and Name | Analytical data |
|---|---|---|
| Example 104 | | LCMS (ES+) 369 (M + H)+, 3.08 RT min (Analytical Method 1), ¹H NMR (400 MHz, DMSO) 8.01 (1H, d, J = 2.0 Hz), 7.87 (1H, d, J = 6.1 Hz), 7.49 (1H, d, J = 7.8 Hz), 7.31 (1H, dd, J = 7.8, 7.8 Hz), 7.25 (1H, d, J = 7.3 Hz), 7.21-7.17 (1H, m), 7.08 (1H, d, J = 7.3 Hz), 6.85 (1H, d, J = 6.1 Hz), 6.54 (1H, s), 5.27-5.19 (1H, m), 3.54-3.47 (4H, m), 3.46-3.39 (4H, m), 1.51 (3H, d, J = 6.8 Hz). |
| Example 105 | | (Analytical Method 1), ¹H NMR (400 MHz, DMSO) 7.83 (1H, d, J = 6.1 Hz), 7.37 (1H, t, J = 7.8 Hz), 7.22 (1H, t, J = 74.2 Hz), 7.23-7.20 (1H, m), 7.14 (1H, s), 7.03-7.00 (1H, m), 6.97 (1H, d, J = 7.8 Hz), 6.84-6.80 (1H, m), 6.51-6.50 (1H, m), 4.91-4.82 (1H, m), 3.50-3.45 (4H, m), 3.41-3.36 (4H, m), 1.38 (3H, d, J = 7.0 Hz). |
| Example 106 | | LCMS (ES+) 363 (M + H)+, RT 3.11 min (Analytical Method 1), ¹H NMR (400 MHz, DMSO) 7.81 (1H, d, J = 6.1 Hz), 7.43 (1H, dd, J = 0.9, 7.7 Hz), 7.34-7.26 (3H, m), 7.15 (1H, dd, J = 5.6, 5.6 Hz), 6.83-6.80 (1H, m), 6.51-6.49 (1H, m), 4.41-4.25 (3H, m), 3.90-3.79 (3H, m), 3.26-3.16 (2H, m), 3.05-2.96 (1H, m), 1.12 (3H, d, J = 6.5 Hz). |
| Example 107 | | LCMS (ES+) 359 (M + H)+, RT 2.97 min (Analytical Method 1), ¹H NMR (400 MHz, DMSO) 7.80 (1H, d, J = 6.1 Hz), 7.22 (1H, t, J = 8.0 Hz), 7.11 (1H, t, J = 5.8 Hz), 6.86-6.77 (4H, m), 6.50-6.48 (1H, m), 4.31-4.19 (3H, m), 3.89-3.77 (3H, m), 3.74 (3H, s), 3.23-3.12 (2H, m), 3.02-2.93 (1H, m), 1.09 (3H, d, J = 6.5 Hz). |
| Example 108 | | LCMS (ES+) 409 (M + H)+, RT 3.16 min (Analytical Method 1), ¹H NMR (400 MHz, DMSO) 7.80 (1H, d, J = 6.1 Hz), 7.36 (1H, t, J = 7.7 Hz), 7.21 (1H, t, J = 74.1 Hz), 7.22-7.19 (1H, m), 7.13 (1H, s), 7.03-7.00 (1H, m), 6.86 (1H, d, J = 7.9 Hz), 6.82-6.79 (1H, m), 6.50-6.49 (1H, m), 4.93-4.84 (1H, m), 4.34-4.27 (1H, m), 3.89-3.78 (3H, m), 3.20-3.10 (2H, m), 2.99-2.90 (1H, m), 1.38 (3H, d, J = 7.2 Hz), 1.06 (3H, d, J = 6.7 Hz). |
| Example 109 | | LCMS (ES+) 377 (M + H)+, RT 3.22 min (Analytical Method 2), ¹H NMR (400 MHz, DMSO) 7.81 (1H, d, J = 6.1 Hz), 7.48 (1H, dd, J = 1.3, 7.6 Hz), 7.38 (1H, d, J = 7.8 Hz), 7.32 (1H, dd, J = 7.2, 7.2 Hz), 7.26-7.21 (1H, m), 6.98 (1H, d, J = 7.6 Hz), 6.81 (1H, d, J = 6.1 Hz), 6.50 (1H, s), 5.23-5.14 (1H, m), 4.37-4.29 (1H, m), 3.89-3.78 (3H, m), 3.21-3.11 (2H, m), 3.00-2.91 (1H, m), 1.35 (3H, d, J = 7.1 Hz), 1.06 (3H, d, J = 6.5 Hz); SFC RT 4.03 min (SFC4, LUX CELLULOSE-3 + 0.1% DEAISO 10% MeOH). |

| Example | Structure and Name | Analytical data |
|---|---|---|
| Example 110 | 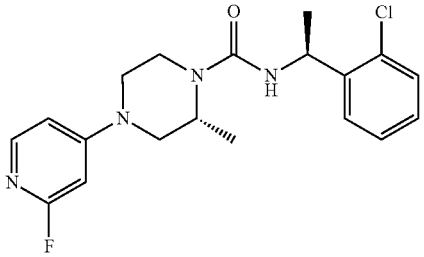 [SMILES: C[C@H](NC(=O)N1CCN(c2ccnc(F)c2)C[C@H]1C)c1ccccc1Cl] | LCMS (ES+) 377 (M + H)+, RT 3.22 min (Analytical Method 2), 1H NMR (400 MHz, DMSO) 7.80 (1H, d, J = 6.1 Hz), 7.49 (1H, dd, J = 1.4, 7.6 Hz), 7.39-7.31 (2H, m), 7.26-7.21 (1H, m), 6.99 (1H, d, J = 7.2 Hz), 6.81 (1H, d, J = 6.1 Hz), 6.50 (1H, s), 5.22-5.16 (1H, m), 4.32-4.28 (1H, m), 3.90-3.77 (3H, m), 3.19-3.09 (2H, m), 2.98-2.92 (1H, m), 1.35 (3H, d, J = 7.1 Hz), 1.09 (3H, d, J = 6.6 Hz); SFC RT 3.54 min (SFC4, LUX CELLULOSE-3 + 0.1% DEAISO 10% MeOH). |
| Example 111 | 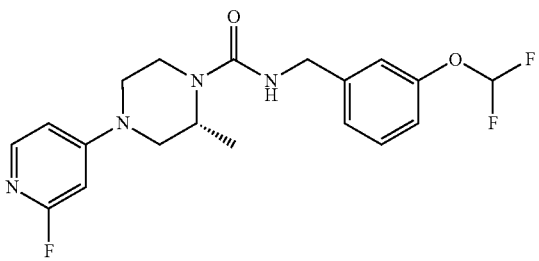 [SMILES: C[C@@H]1CN(c2ccnc(F)c2)CCN1C(=O)NCc1cccc(OC(F)F)c1] | LCMS (ES+) 395 (M + H)+, RT 3.09 min (Analytical Method 1), 1H NMR (400 MHz, DMSO) 7.80 (1H, d, J = 6.1 Hz), 7.37 (1H, t, J = 7.8 Hz), 7.21 (1H, t, J = 74.1 Hz), 7.20-7.14 (2H, m), 7.08-7.03 (2H, m), 6.81-6.79 (1H, m), 6.49 (1H, s), 4.31-4.23 (3H, m), 3.89-3.78 (3H, m), 3.23-3.13 (2H, m), 3.02-2.93 (1H, m), 1.09 (3H, d, J = 6.7 Hz). |
| Example 112 | 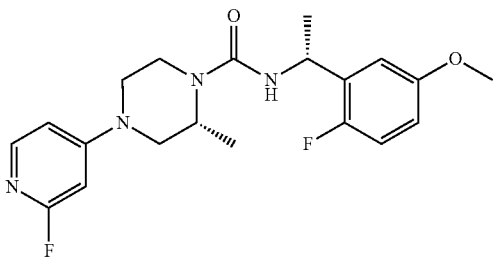 [SMILES: COc1ccc(F)c([C@@H](C)NC(=O)N2CCN(c3ccnc(F)c3)C[C@H]2C)c1] | LCMS (ES+) 391 (M + H)+, RT 3.12 min (Analytical Method 1), 1H NMR (400 MHz, DMSO) 7.81 (1H, d, J = 6.1 Hz), 7.05 (1H, t, J = 9.4 Hz), 6.96 (1H, dd, J = 3.2, 6.2 Hz), 6.86 (1H, d, J = 7.8 Hz), 6.81-6.76 (2H, m), 6.50 (1H, s), 5.12-5.07 (1H, m), 4.34-4.30 (1H, m), 3.87-3.78 (3H, m), 3.72 (3H, s), 3.21-3.11 (2H, m), 3.00-2.91 (1H, m), 1.35 (3H, d, J = 7.0 Hz), 1.06 (3H, d, J = 6.6 Hz). |
| Example 113 | 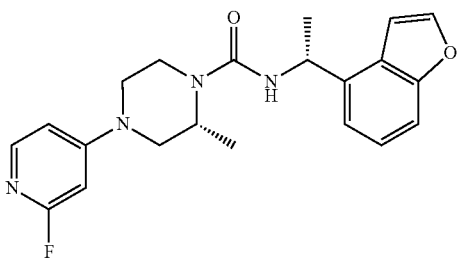 | LCMS (ES+) 383 (M + H)+, RT 3.15 min (Analytical Method 2), 1H NMR (400 MHz, DMSO) 7.97 (1H, d, J = 2.3 Hz), 7.81 (1H, d, J = 6.1 Hz), 7.46 (1H, d, J = 8.1 Hz), 7.27 (1H, dd, J = 7.7, 7.7 Hz), 7.21 (1H, d, J = 7.3 Hz), 7.14 (1H, d, J = 1.3 Hz), 6.95 (1H, d, J = 7.6 Hz), 6.81 (1H, d, J = 6.1 Hz), 6.50 (1H, s), 5.27-5.19 (1H, m), 4.36-4.31 (1H, m), 3.90-3.79 (3H, m), 3.20-3.10 (2H, m), 2.99-2.92 (1H, m), 1.48 (3H, d, J = 7.1 Hz), 1.06 (3H, d, J = 6.6 Hz). |
| Example 114 | 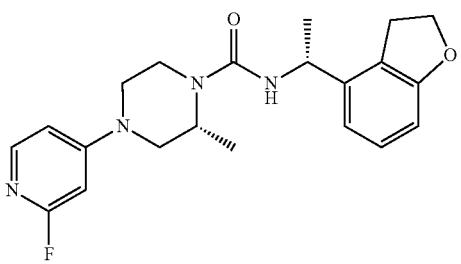 | (Analytical Method 1), 1H NMR (400 MHz, DMSO) 7.84 (1H, d, J = 6.1 Hz), 7.09 (1H, dd, J = 7.7, 7.7 Hz), 6.88 (1H, d, J = 7.6 Hz), 6.86-6.80 (2H, m), 6.64 (1H, d, J = 7.8 Hz), 6.53 (1H, s), 4.92-4.82 (1H, m), 4.58-4.51 (2H, m), 4.38-4.30 (1H, m), 3.91-3.80 (3H, m), 3.30-3.10 (4H, m), 3.01-2.92 (1H, m), 1.39 (3H, d, J = 7.1 Hz), 1.09 (3H, d, J = 6.3 Hz). |

-continued

| Example | Structure and Name | Analytical data |
|---|---|---|
| Example 115 | 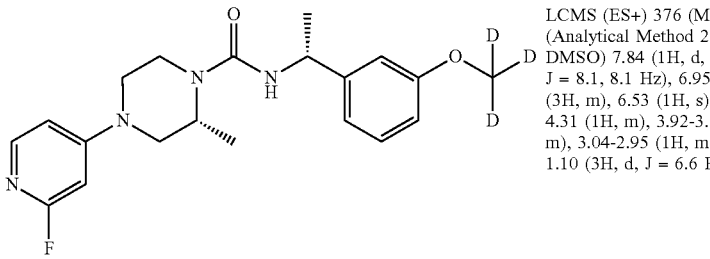 | LCMS (ES+) 376 (M + H)+, RT 3.04 min (Analytical Method 2), ¹H NMR (400 MHz, DMSO) 7.84 (1H, d, J = 6.3 Hz), 7.25 (1H, dd, J = 8.1, 8.1 Hz), 6.95-6.91 (2H, m), 6.86-6.78 (3H, m), 6.53 (1H, s), 4.94-4.84 (1H, m), 4.39-4.31 (1H, m), 3.92-3.80 (3H, m), 3.24-3.12 (2H, m), 3.04-2.95 (1H, m), 1.41 (3H, d, J = 7.1 Hz), 1.10 (3H, d, J = 6.6 Hz). |
| Example 116 | 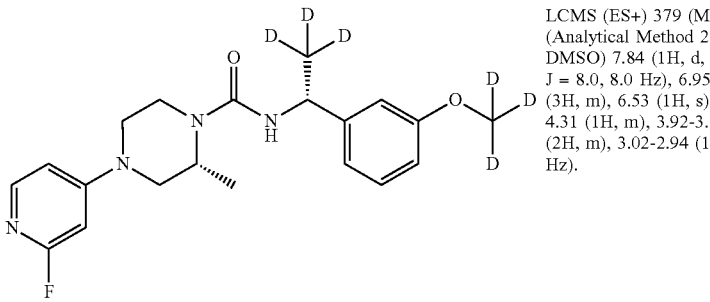 | LCMS (ES+) 379 (M + H)+, RT 3.04 min (Analytical Method 2), ¹H NMR (400 MHz, DMSO) 7.84 (1H, d, J = 6.1 Hz), 7.25 (1H, dd, J = 8.0, 8.0 Hz), 6.95-6.91 (2H, m), 6.86-6.79 (3H, m), 6.53 (1H, s), 4.87 (1H, d, J = 7.8 Hz), 4.39-4.31 (1H, m), 3.92-3.81 (3H, m), 3.24-3.12 (2H, m), 3.02-2.94 (1H, m), 1.10 (3H, d, J = 6.3 Hz). |
| Example 117 | 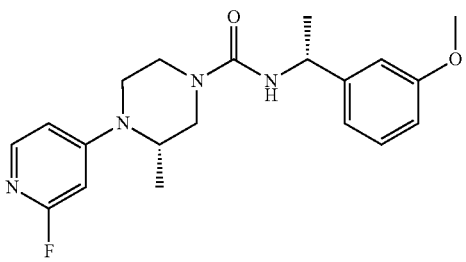 [SMILES: COc1cccc([C@@H](C)NC(=O)N2CCN(c3ccnc(F)c3)[C@@H](C)C2)c1] | (Analytical Method 2), ¹H NMR (400 MHz, DMSO) 7.86 (1H, d, J = 6.1 Hz), 7.30-7.23 (1H, m), 6.97-6.92 (2H, m), 6.89 (1H, d, J = 8.1 Hz), 6.81 (2H, d, J = 5.8 Hz), 6.49 (1H, s), 4.93-4.84 (1H, m), 4.24-4.16 (1H, m), 4.06 (1H, d, J = 12.4 Hz), 3.97 (1H, d, J = 13.1 Hz), 3.79 (3H, s), 3.71 (1H, d, J = 12.4 Hz), 3.21-2.96 (3H, m), 1.41 (3H, d, J = 7.1 Hz), 1.07 (3H, d, J = 6.6 Hz). |
| Example 118 | 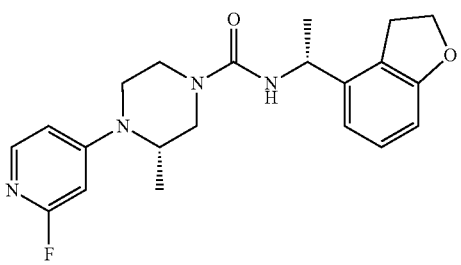 | LCMS (ES+) 385 (M + H)+, RT 3.06 min (Analytical Method 1), ¹H NMR (400 MHz, DMSO) 7.86 (1H, d, J = 6.1 Hz), 7.10 (1H, t, J = 7.7 Hz), 6.89 (2H, d, J = 7.8 Hz), 6.81 (1H, d, J = 6.1 Hz), 6.64 (1H, d, J = 7.8 Hz), 6.48 (1H, s), 4.91-4.82 (1H, m), 4.55 (2H, dd, J = 8.8, 8.8 Hz), 4.20-4.15 (1H, m), 4.05 (1H, d, J = 12.6 Hz), 3.96 (1H, d, J = 12.9 Hz), 3.70 (1H, d, J = 12.6 Hz), 3.32-2.95 (5H, m), 1.39 (3H, d, J = 7.1 Hz), 1.06 (3H, d, J = 6.6 Hz). |
| Example 119 | 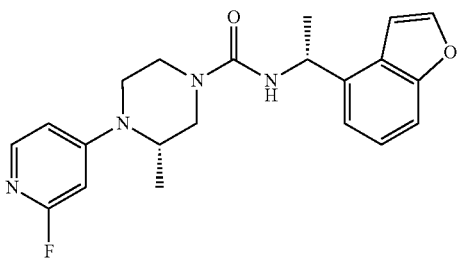 | LCMS (ES+) 383 (M + H)+, RT 3.14 min (Analytical Method 2), ¹H NMR (400 MHz, DMSO) 7.97 (1H, d, J = 2.3 Hz), 7.82 (1H, d, J = 6.1 Hz), 7.45 (1H, d, J = 8.0 Hz), 7.27 (1H, t, J = 7.7 Hz), 7.23-7.20 (1H, m), 7.14 (1H, d, J = 2.3 Hz), 6.99 (1H, d, J = 7.7 Hz), 6.78-6.76 (1H, m), 6.45 (1H, s), 5.24-5.18 (1H, m), 4.18-4.13 (1H, m), 4.05-3.92 (2H, m), 3.70-3.63 (1H, m), 3.15-2.93 (3H, m), 1.47 (3H, d, J = 7.0 Hz), 1.02 (3H, d, J = 6.5 Hz). |

-continued

| Example | Structure and Name | Analytical data |
|---|---|---|
| Example 120 | 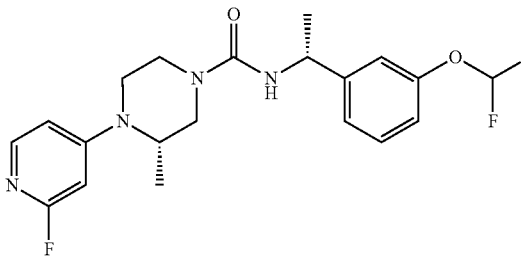 | LCMS (ES+) 409 (M + H)+, RT 3.17 min (Analytical Method 1), ¹H NMR (400 MHz, DMSO) 7.82 (1H, d, J = 6.1 Hz), 7.37 (1H, t, J = 8.0 Hz), 7.22 (1H, d, J = 7.2 Hz), 7.21 (1H, t, J = 74.2 Hz), 7.15-7.13 (1H, m), 7.04-7.00 (1H, m), 6.93 (1H, d, J = 7.8 Hz), 6.79-6.76 (1H, m), 6.46-6.44 (1H, m), 4.93-4.84 (1H, m), 4.20-4.14 (1H, m), 4.02 (1H, d, J = 12.7 Hz), 3.92 (1H, d, J = 13.3 Hz), 3.71-3.65 (1H, m), 3.17-2.93 (3H, m), 1.38 (3H, d, J = 7.2 Hz), 1.03 (3H, d, J = 6.5 Hz). |
| Example 121 | 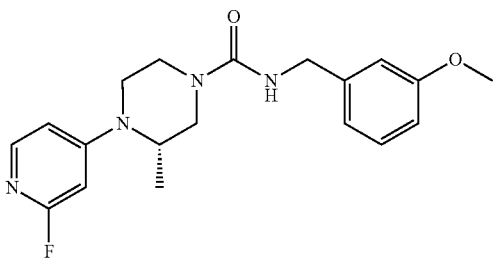 [SMILES: COc1cccc(CNC(=O)N2CCN(c3ccnc(F)c3)[C@@H](C)C2)c1] | LCMS (ES+) 359 (M + H)+, RT 2.96 min (Analytical Method 1), ¹H NMR (400 MHz, DMSO) 7.82 (1H, d, J = 6.0 Hz), 7.25-7.15 (2H, m), 6.86-6.83 (2H, m), 6.80-6.76 (2H, m), 6.45 (1H, s), 4.28-4.15 (3H, m), 4.04-3.98 (1H, m), 3.93-3.87 (1H, m), 3.74 (3H, s), 3.71-3.66 (1H, m), 3.19-2.95 (3H, m), 1.06 (3H, d, J = 6.5 Hz). |
| Example 122 | 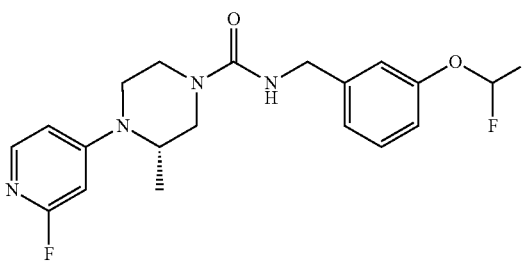 | LCMS (ES+) 395 (M + H)+, RT 3.09 min (Analytical Method 2), ¹H NMR (400 MHz, DMSO) 7.82 (1H, d, J = 6.0 Hz), 7.37 (1H, t, J = 7.5 Hz), 7.24 (1H, t, J = 5.8 Hz), 7.21 (1H, t, J = 74.0 Hz), 7.15 (1H, d, J = 8.0 Hz), 7.08-7.01 (2H, m), 6.79-6.76 (1H, m), 6.45-6.44 (1H, m), 4.31-4.17 (3H, m), 4.04-3.97 (1H, m), 3.92-3.86 (1H, m), 3.72-3.65 (1H, m), 3.20-2.96 (3H, m), 1.06 (3H, d, J = 6.5 Hz). |
| Example 123 | 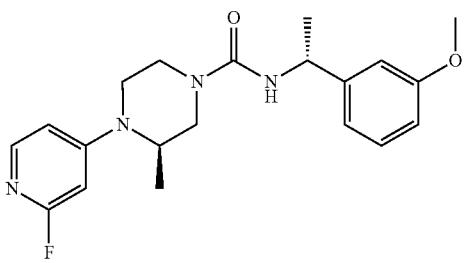 | LCMS (ES+) 373 (M + H)+, RT 3.06 min (Analytical Method 1), ¹H NMR (400 MHz, DMSO) 7.82 (1H, d, J = 6.1 Hz), 7.21 (1H, t, J = 8.1 Hz), 6.91-6.84 (3H, m), 6.78-6.75 (2H, m), 6.45 (1H, s), 4.88-4.80 (1H, m), 4.18-4.16 (1H, m), 4.04 (1H, d, J = 13.6 Hz), 3.93 (1H, d, J = 13.3 Hz), 3.74 (3H, s), 3.68-3.63 (1H, m), 3.15-2.91 (3H, m), 1.37 (3H, d, J = 7.1 Hz), 1.05 (3H, d, J = 6.5 Hz). |
| Example 124 | 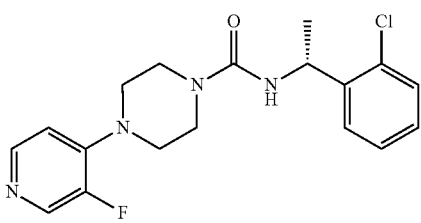 [SMILES: C[C@@H](NC(=O)N1CCN(c2ccncc2F)CC1)c1ccccc1Cl] | LCMS (ES+) 363 (M + H)+, RT 2.59 min (Analytical Method 1), ¹H NMR (400 MHz, DMSO) 8.29 (1H, d, J = 5.6 Hz), 8.17 (1H, d, J = 5.5 Hz), 7.50 (1H, dd, J = 1.6, 7.8 Hz), 7.39-7.32 (2H, m), 7.26-7.21 (1H, m), 7.07 (1H, d, J = 7.4 Hz), 7.01 (1H, dd, J = 5.5, 8.3 Hz), 5.21-5.15 (1H, m), 3.54-3.49 (4H, m), 3.24 (4H, t, J = 4.8 Hz), 1.36-1.33 (3H, m). |
| Example 125 | 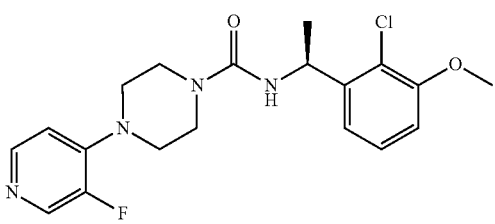 [SMILES: COc1cccc([C@H](C)NC(=O)N2CCN(c3ccncc3F)CC2)c1Cl] | LCMS (ES+) 393 (M + H)+, RT 3.05 min (Analytical Method 2), ¹H NMR (400 MHz, DMSO) 8.29 (1H, d, J = 5.6 Hz), 8.17 (1H, d, J = 5.5 Hz), 7.29 (1H, t, J = 8.0 Hz), 7.09-6.98 (4H, m), 5.24-5.15 (1H, m), 3.85 (3H, s), 3.53-3.49 (4H, m), 3.26-3.21 (4H, m), 1.33 (3H, d, J = 7.0 Hz); SFC RT 3.18 min (SFC1, YMC AMYLOSE-C + 0.1% DEAISO 25% IPA). |

-continued

| Example | Structure and Name | Analytical data |
|---|---|---|
| Example 126 | | LCMS (ES+) 377 (M + H)+, RT 3.19 min (Analytical Method 2), $^1$H NMR (400 MHz, DMSO) 8.29 (1H, d, J = 5.6 Hz), 8.17 (1H, d, J = 5.5 Hz), 7.08-6.94 (4H, m), 6.82-6.77 (1H, m), 5.13-5.04 (1H, m), 3.73 (3H, s), 3.54-3.49 (4H, m), 3.27-3.22 (4H, m), 1.35 (3H, d, J = 7.0 Hz). |
| Example 127 | | LCMS (ES+) 395 (M + H)+, RT 3.06 min (Analytical Method 2), $^1$H NMR (400 MHz, DMSO) 8.33 (1H, d, J = 5.6 Hz), 8.21 (1H, d, J = 5.3 Hz), 7.41 (1H, t, J = 7.8 Hz), 7.26 (1H, t, J = 74.7 Hz), 7.26-7.23 (1H, m), 7.18 (1H, s), 7.08-7.02 (2H, m), 6.99 (1H, d, J = 7.8 Hz), 4.96-4.86 (1H, m), 3.57-3.51 (4H, m), 3.30-3.24 (4H, m), 1.42 (3H, d, J = 7.1 Hz). |
| Example 128 | | LCMS (ES+) 377 (M + H)+, RT 3.87 min (Analytical Method 4), $^1$H NMR (400 MHz, DMSO) 8.29 (1H, d, J = 5.6 Hz), 8.17 (1H, d, J = 5.5 Hz), 7.01 (1H, dd, J = 5.5, 8.3 Hz), 6.92 (1H, d, J = 7.9 Hz), 6.76-6.72 (2H, m), 6.68-6.63 (1H, m), 4.86-4.77 (1H, m), 3.76 (3H, s), 3.52-3.48 (4H, m), 3.26-3.21 (4H, m), 1.36 (3H, d, J = 7.0 Hz); SFC RT 2.54 min (SFC1, LUX CELLULOSE-4 + 0.1% DEAISO 40% IPA). |
| Example 129 | | LCMS (ES+) 381 (M + H)+, RT 2.51 min (Analytical Method 1), $^1$H NMR (400 MHz, DMSO) 8.29 (1H, d, J = 5.6 Hz), 8.17 (1H, d, J = 5.5 Hz), 7.38 (1H, t, J = 7.9 Hz), 7.26 (1H, t, J = 5.8 Hz), 7.21 (1H, t, J = 74.3 Hz), 7.16 (1H, d, J = 7.7 Hz), 7.09-6.99 (3H, m), 4.29 (2H, d, J = 5.8 Hz), 3.53-3.49 (4H, m), 3.27-3.23 (4H, m). |
| Example 130 | | LCMS (ES+) 349 (M + H)+, RT 2.52 min (Analytical Method 1), $^1$H NMR (400 MHz, DMSO) 8.33 (1H, d, J = 5.8 Hz), 8.21 (1H, d, J = 5.6 Hz), 7.47 (1H, d, J = 7.6 Hz), 7.40-7.36 (2H, m), 7.35-7.24 (2H, m), 7.06 (1H, dd, J = 5.6, 8.3 Hz), 4.39 (2H, d, J = 5.6 Hz), 3.61-3.55 (4H, m), 3.35-3.28 (4H, m). |
| Example 131 | | LCMS (ES+) 365 (M + H)+, RT 3.10 min (Analytical Method 2), $^1$H NMR (400 MHz, DMSO) 8.32 (1H, d, J = 5.6 Hz), 8.21 (1H, d, J = 5.3 Hz), 7.26 (1H, t, J = 8.1 Hz), 7.05 (1H, dd, J = 5.6, 8.1 Hz), 6.96-6.90 (3H, m), 6.84-6.79 (1H, m), 4.85 (1H, d, J = 7.8 Hz), 3.57-3.51 (4H, m), 3.31-3.24 (4H, m). |
| Example 132 | | LCMS (ES+) 362 (M + H)+, RT 3.11 min (Analytical Method 2), $^1$H NMR (400 MHz, DMSO) 8.32 (1H, d, J = 5.6 Hz), 8.21 (1H, d, J = 5.3 Hz), 7.26 (1H, t, J = 8.1 Hz), 7.05 (1H, dd, J = 5.6, 8.1 Hz), 6.97-6.90 (3H, m), 6.81 (1H, dd, J = 1.8, 8.1 Hz), 4.92-4.83 (1H, m), 3.57-3.50 (4H, m), 3.30-3.23 (4H, m), 1.41 (3H, d, J = 7.1 Hz). |

| Example | Structure and Name | Analytical data |
|---|---|---|
| Example 133 | 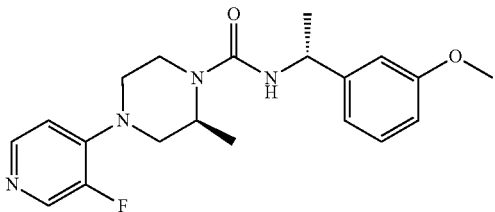 [SMILES: COc1cccc([C@@H](C)NC(=O)N2CCN(c3ccncc3F)C[C@@H]2C)c1] | LCMS (ES+) 373 (M + H)⁺, RT 3.21 min (Analytical Method 2), ¹H NMR (400 MHz, DMSO) 8.27 (1H, d, J = 5.6 Hz), 8.15 (1H, d, J = 5.5 Hz), 7.22 (1H, t, J = 8.1 Hz), 7.00 (1H, dd, J = 5.5, 8.3 Hz), 6.92-6.89 (2H, m), 6.82 (1H, d, J = 7.8 Hz), 6.79-6.76 (1H, m), 4.89-4.80 (1H, m), 4.34-4.31 (1H, m), 3.91-3.86 (1H, m), 3.75 (3H, s), 3.63-3.52 (2H, m), 3.17-2.99 (2H, m), 2.89-2.81 (1H, m), 1.37 (3H, d, J = 7.0 Hz), 1.17 (3H, d, J = 6.7 Hz); SFC RT 5.64 min (SFC1, LUX CELLULOSE-4 + 0.1% DEAISO 25% MeOH). |
| Example 134 | 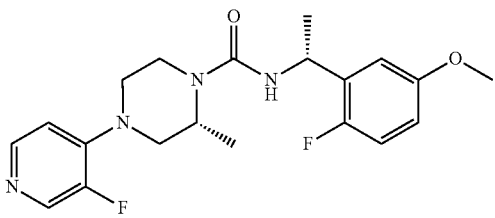 [SMILES: COc1ccc(F)c([C@@H](C)NC(=O)N2CCN(c3ccncc3F)C[C@H]2C)c1] | (Analytical Method 2), ¹H NMR (400 MHz, DMSO) 8.27 (1H, d, J = 5.6 Hz), 8.15 (1H, d, J = 5.5 Hz), 7.08-6.94 (3H, m), 6.87 (1H, d, J = 7.9 Hz), 6.82-6.77 (1H, m), 5.14-5.05 (1H, m), 4.36-4.32 (1H, m), 3.91-3.86 (1H, m), 3.73 (3H, s), 3.68-3.53 (2H, m), 3.21-3.12 (1H, m), 3.03 (1H, dd, J = 3.5, 12.4 Hz), 2.90-2.82 (1H, m), 1.36 (3H, d, J = 7.0 Hz), 1.17 (3H, d, J = 6.7 Hz). |
| Example 135 | 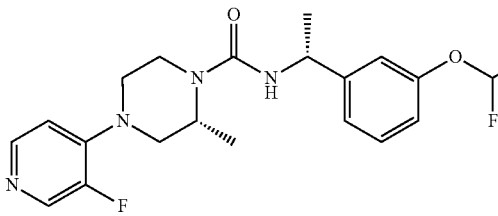 | LCMS (ES+) 407 (M + H)⁺, RT 3.11 min (Analytical Method 2), ¹H NMR (400 MHz, DMSO) 8.27 (1H, d, J = 5.6 Hz), 8.15 (1H, d, J = 5.4 Hz), 7.28 (1H, t, J = 8.0 Hz), 7.08-7.05 (1H, m), 7.03-6.93 (3H, m), 5.22-5.17 (1H, m), 4.36-4.34 (1H, m), 3.91-3.85 (4H, m), 3.63-3.53 (2H, m), 3.20-3.11 (1H, m), 3.03 (1H, dd, J = 3.6, 12.4 Hz), 2.90-2.81 (1H, m), 1.33 (3H, d, J = 7.0 Hz), 1.15 (3H, d, J = 6.7 Hz); SFC RT 3.02 min (SFC1, YMC AMYLOSE-C + 0.1% DEAISO 25% IPA). |
| Example 136 | 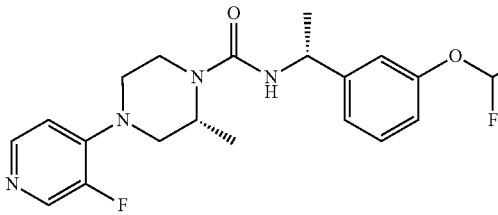 | LCMS (ES+) 309 (M + H)⁺, RT 2.64 min (Analytical Method 1), ¹H NMR (400 MHz, DMSO) 8.31 (1H, d, J = 5.6 Hz), 8.19 (1H, d, J = 5.6 Hz), 7.40 (1H, t, J = 7.8 Hz), 7.26 (1H, t, J = 74.3 Hz), 7.24 (1H, d, J = 5.8 Hz), 7.17 (1H, s), 7.08-7.01 (2H, m), 6.91 (1H, d, J = 7.8 Hz), 4.98-4.89 (1H, m), 4.41-4.34 (1H, m), 3.92 (1H, d, J = 12.9 Hz), 3.69-3.55 (2H, m), 3.24-3.14 (1H, m), 3.07 (1H, dd, J = 3.2, 12.5 Hz), 2.95-2.85 (1H, m), 1.42 (3H, d, J = 7.1 Hz), 1.20 (3H, d, J = 6.6 Hz). |
| Example 137 | 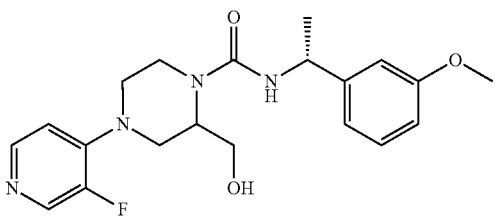 [SMILES: COc1cccc([C@@H](C)NC(=O)N2CCN(c3ccncc3F)CC2CO)c1] | LCMS (ES+) 389 (M + H)⁺, RT 2.83 min (Analytical Method 2), ¹H NMR (400 MHz, DMSO) 8.26 (1H, d, J = 5.6 Hz), 8.14 (1H, d, J = 5.5 Hz), 7.24-7.19 (1H, m), 7.00 (1H, dd, J = 5.5, 8.4 Hz), 6.92-6.88 (2H, m), 6.79-6.73 (2H, m), 4.92-4.79 (2H, m), 3.92-3.88 (1H, m), 3.84-3.74 (4H, m), 3.63-3.57 (2H, m), 3.46-3.41 (1H, m), 3.18-3.10 (1H, m), 3.02 (1H, dd, J = 3.7, 12.6 Hz), 2.94-2.87 (1H, m), 1.36 (3H, d, J = 7.0 Hz). |
| Example 138 | 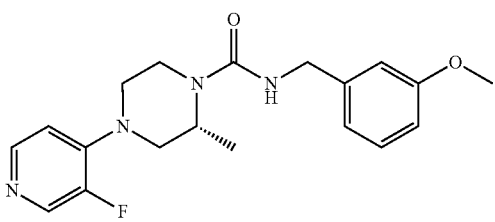 [SMILES: COc1cccc(CNC(=O)N2CCN(c3ccncc3F)C[C@H]2C)c1] | LCMS (ES+) 359 (M + H)⁺, RT 2.45 min (Analytical Method 1), ¹H NMR (400 MHz, DMSO) 8.27 (1H, d, J = 5.8 Hz), 8.15 (1H, d, J = 5.5 Hz), 7.25-7.20 (1H, m), 7.13 (1H, t, J = 5.8 Hz), 7.00 (1H, dd, J = 5.5, 8.3 Hz), 6.86-6.83 (2H, m), 6.81-6.77 (1H, m), 4.32-4.19 (3H, m), 3.90-3.84 (1H, m), 3.74 (3H, s), 3.64-3.53 (2H, m), 3.21-3.12 (1H, m), 3.04 (1H, dd, J = 3.6, 12.5 Hz), 2.92-2.83 (1H, m), 1.19 (3H, d, J = 6.7 Hz). |
| Example 139 | 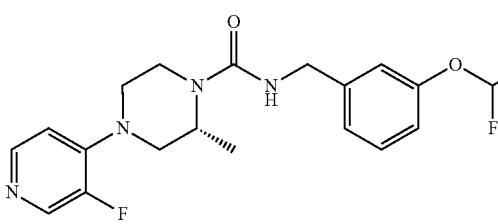 | LCMS (ES+) 395 (M + H)⁺, RT 2.55 min (Analytical Method 1), ¹H NMR (400 MHz, DMSO) 8.10 (1H, d, J = 5.6 Hz), 7.98 (1H, d, J = 5.6 Hz), 7.24-7.17 (1H, m), 7.05 (1H, t, J = 73.7 Hz), 7.05-6.95 (2H, m), 6.92-6.80 (3H, m), 4.16-4.09 (3H, m), 3.73-3.66 (3H, m), 3.43 (2H, dd, J = 12.6, 26.3 Hz), 3.06-2.96 (1H, m), 2.88 (1H, dd, J = 3.3, 12.4 Hz), 2.76-2.67 (1H, m), 1.02 (3H, d, J = 6.6 Hz). |

-continued

| Example | Structure and Name | Analytical data |
|---|---|---|
| Example 140 | 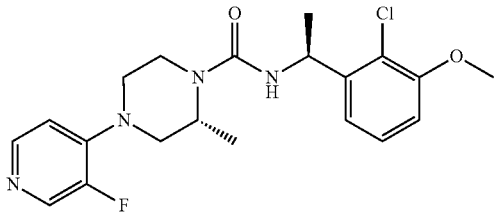 [SMILES: COc1cccc([C@H](C)NC(=O)N2CCN(c3ccncc3F)C[C@H]2C)c1Cl] | LCMS (ES+) 407 (M + H)+, RT 3.10 min (Analytical Method 2), ¹H NMR (400 MHz, DMSO) 8.27 (1H, d, J = 5.6 Hz), 8.16 (1H, d, J = 5.5 Hz), 7.29 (1H, t, J = 8.0 Hz), 7.08 (1H, dd, J = 1.3, 7.8 Hz), 7.03-6.95 (3H, m), 5.24-5.18 (1H, m), 4.34-4.32 (1H, m), 3.94-3.88 (1H, m), 3.85 (3H, s), 3.64-3.52 (2H, m), 3.17-3.08 (1H, m), 3.01 (1H, dd, J = 3.5, 12.5 Hz), 2.90-2.82 (1H, m), 1.33 (3H, d, J = 7.0 Hz), 1.18 (3H, d, J = 6.7 Hz); SFC RT 4.07 min (SFC1, YMC AMYLOSE-C + 0.1% DEAISO 25% IPA). |
| Example 141 | 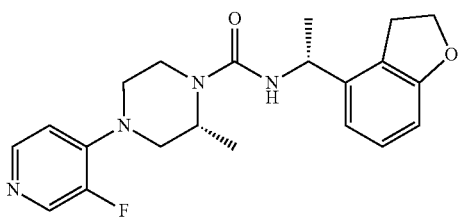 | LCMS (ES+) 385 (M + H)+, RT 2.51 min (Analytical Method 1), ¹H NMR (400 MHz, DMSO) 8.30 (1H, d, J = 5.8 Hz), 8.23-8.16 (1H, m), 7.13-6.99 (2H, m), 6.88 (1H, d, J = 7.6 Hz), 6.83 (1H, d, J = 7.3 Hz), 6.64 (1H, d, J = 7.8 Hz), 4.93-4.82 (1H, m), 4.55 (2H, t, J = 8.8 Hz), 4.41-4.32 (1H, m), 3.91 (1H, d, J = 13.1 Hz), 3.68-3.53 (2H, m), 3.33-3.13 (3H, m), 3.05 (1H, dd, J = 3.0, 12.4 Hz), 2.94-2.82 (1H, m), 1.39 (3H, d, J = 6.8 Hz), 1.19 (3H, d, J = 6.6 Hz). |
| Example 142 | 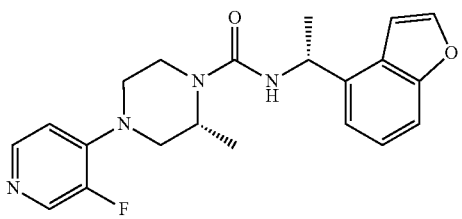 | LCMS (ES+) 383 (M + H)+, RT 2.59 min (Analytical Method 1), ¹H NMR (400 MHz, DMSO) 8.27 (1H, d, J = 5.6 Hz), 8.15 (1H, d, J = 5.5 Hz), 7.97 (1H, d, J = 2.2 Hz), 7.45 (1H, d, J = 8.1 Hz), 7.27 (1H, t, J = 7.8 Hz), 7.22-7.19 (1H, m), 7.14 (1H, d, J = 1.6 Hz), 6.99 (1H, dd, J = 5.5, 8.3 Hz), 6.94 (1H, d, J = 7.6 Hz), 5.25-5.20 (1H, m), 4.36-4.33 (1H, m), 3.93-3.86 (1H, m), 3.62-3.52 (2H, m), 3.18-3.09 (1H, m), 3.01 (1H, dd, J = 3.4, 12.4 Hz), 2.89-2.80 (1H, m), 1.48 (3H, d, J = 7.1 Hz), 1.16 (3H, d, J = 6.6 Hz). |
| Example 143 | 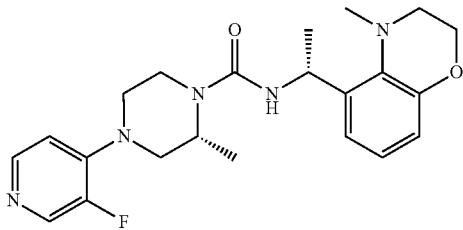 [SMILES: C[C@@H]1CN(c2ccncc2F)CCN1C(=O)N[C@H](C)c1cccc2c1N(C)CCO2] | LCMS (ES+) 414 (M + H)+, RT 3.12 min (Analytical Method 2), ¹H NMR (400 MHz, DMSO) 8.27 (1H, d, J = 5.6 Hz), 8.15 (1H, d, J = 5.5 Hz), 7.02-6.95 (2H, m), 6.90 (1H, t, J = 7.8 Hz), 6.74 (1H, d, J = 7.5 Hz), 6.64 (1H, dd, J = 1.3, 7.8 Hz), 5.25 (1H, t, J = 7.1 Hz), 4.36-4.34 (1H, m), 4.22-4.10 (2H, m), 3.92-3.89 (1H, m), 3.63-3.51 (2H, m), 3.17-2.82 (8H, m), 1.28 (3H, d, J = 6.8 Hz), 1.16 (3H, d, J = 6.6 Hz); SFC RT 1.44 min (SFC4, LUX CELLULOSE-4 + 0.1% DEAISO 45% IPA). |
| Example 144 | 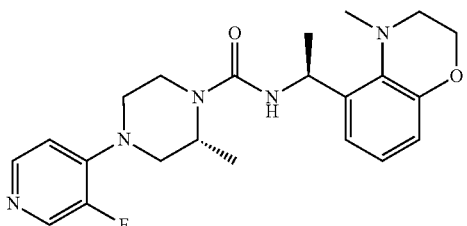 | LCMS (ES+) 414 (M + H)+, RT 3.13 min (Analytical Method 2), ¹H NMR (400 MHz, DMSO) 8.27 (1H, d, J = 5.7 Hz), 8.15 (1H, d, J = 5.5 Hz), 7.02-6.94 (2H, m), 6.90 (1H, t, J = 7.8 Hz), 6.70 (1H, d, J = 7.6 Hz), 6.64 (1H, dd, J = 1.3, 7.8 Hz), 5.28-5.23 (1H, m), 4.37-4.35 (1H, m), 4.22-4.09 (2H, m), 3.89 (1H, d, J = 13.3 Hz), 3.62-3.53 (2H, m), 3.16-2.84 (5H, m), 2.82 (3H, s), 1.28 (3H, d, J = 6.8 Hz), 1.16 (3H, d, J = 6.6 Hz); SFC RT 2.23 min (SFC4, LUX CELLULOSE-4 + 0.1% DEAISO 45% IPA). |
| Example 145 | 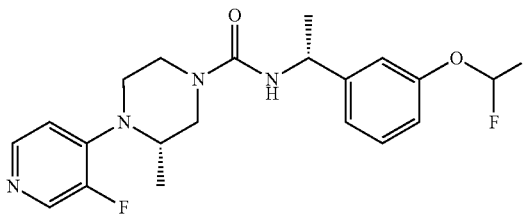 | LCMS (ES+) 409 (M + H)+, RT 3.13 min (Analytical Method 2), ¹H NMR (400 MHz, DMSO) 8.30 (1H, d, J = 5.8 Hz), 8.18 (1H, d, J = 5.6 Hz), 7.41 (1H, t, J = 7.6 Hz), 7.26 (1H, t, J = 74.3 Hz), 7.29-7.21 (1H, m), 7.18 (1H, d, J = 7.6 Hz), 7.08-6.98 (2H, m), 6.95 (1H, d, J = 7.8 Hz), 4.98-4.86 (1H, m), 4.09-3.99 (2H, m), 3.86 (1H, d, J = 12.9 Hz), 3.40-3.20 (3H, m), 3.15-3.03 (1H, m), 1.42 (3H, d, J = 7.1 Hz), 1.05 (3H, d, J = 6.6 Hz). |

| Example | Structure and Name | Analytical data |
|---|---|---|
| Example 146 | 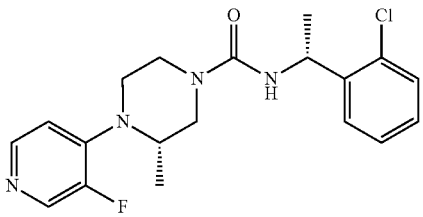 [SMILES: C[C@@H](NC(=O)N1CCN(c2ccncc2F)[C@@H](C)C1)c1ccccc1Cl] | LCMS (ES+) 377 (M + H)+, RT 2.61 min (Analytical Method 1), $^1$H NMR (400 MHz, DMSO) 8.31 (1H, d, J = 5.8 Hz), 8.19 (1H, d, J = 5.3 Hz), 7.55-7.49 (1H, m), 7.45-7.33 (2H, m), 7.31-7.24 (1H, m), 7.08-6.98 (2H, m), 5.26-5.18 (1H, m), 4.07-4.02 (2H, m), 3.88 (1H, d, J = 13.1 Hz), 3.30-3.25 (3H, m), 3.15-3.03 (1H, m), 1.38 (3H, d, J = 6.1 Hz), 1.06 (3H, dd, J = 6.4, 17.3 Hz). |
| Example 147 | 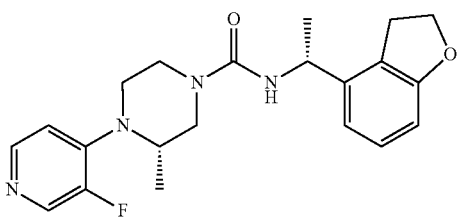 | LCMS (ES+) 385 (M + H)+, RT 2.51 min (Analytical Method 1), $^1$H NMR (400 MHz, DMSO) 8.30 (1H, d, J = 6.1 Hz), 8.18 (1H, d, J = 5.3 Hz), 7.10 (1H, t, J = 7.8 Hz), 7.01 (1H, dd, J = 5.7, 8.2 Hz), 6.92-6.84 (2H, m), 6.65 (1H, d, J = 7.8 Hz), 4.90-4.83 (1H, m), 4.59-4.52 (2H, m), 4.08-3.99 (2H, m), 3.86 (1H, d, J = 12.9 Hz), 3.36-3.05 (6H, m), 1.39 (3H, d, J = 7.1 Hz), 1.05 (3H, d, J = 6.6 Hz). |
| Example 148 | 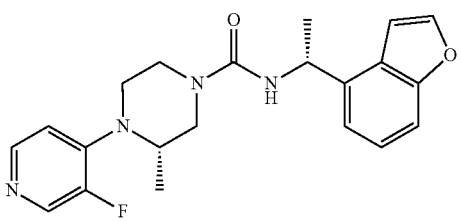 | LCMS (ES+) 383 (M + H)+, RT 2.58 min (Analytical Method 1), $^1$H NMR (400 MHz, DMSO) 8.30 (1H, d, J = 6.1 Hz), 8.18 (1H, d, J = 5.6 Hz), 8.01 (1H, d, J = 2.0 Hz), 7.49 (1H, d, J = 8.1 Hz), 7.31 (1H, t, J = 7.8 Hz), 7.28-7.23 (1H, m), 7.20-7.17 (1H, m), 7.04-6.97 (2H, m), 5.28-5.21 (1H, m), 4.09-4.01 (2H, m), 3.88 (1H, d, J = 13.4 Hz), 3.33-3.20 (3H, m), 3.13-3.03 (1H, m), 1.51 (3H, d, J = 7.1 Hz), 1.04 (3H, d, J = 6.6 Hz). |
| Example 149 | 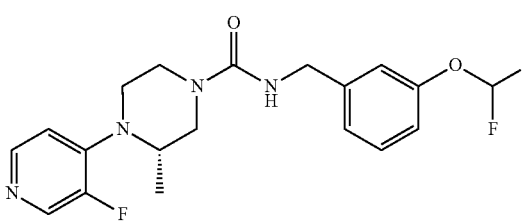 | LCMS (ES+) 395 (M + H)+, RT 2.55 min (Analytical Method 1), $^1$H NMR (400 MHz, DMSO) 8.31 (1H, d, J = 6.1 Hz), 8.18 (1H, d, J = 5.6 Hz), 7.41 (1H, dd, J = 7.5, 7.5 Hz), 7.30-7.23 (1H, m), 7.24 (1H, t, J = 74.0 Hz), 7.19 (1H, d, J = 7.6 Hz), 7.13-7.04 (2H, m), 7.01 (1H, dd, J = 5.7, 8.2 Hz), 4.36-4.32 (1H, m), 4.30-4.22 (1H, m), 4.10-4.00 (2H, m), 3.84 (1H, d, J = 12.9 Hz), 3.61 (1H, s), 3.33-3.24 (2H, m), 3.15-3.06 (1H, m), 1.08 (3H, d, J = 6.6 Hz). |
| Example 150 | 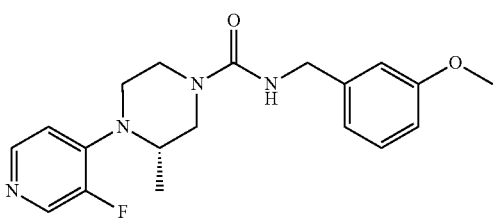 [SMILES: COc1cccc(CNC(=O)N2CCN(c3ccncc3F)[C@@H](C)C2)c1] | LCMS (ES+) 359 (M + H)+, RT 2.45 min (Analytical Method 1), $^1$H NMR (400 MHz, DMSO) 8.30 (1H, d, J = 6.1 Hz), 8.18 (1H, d, J = 5.6 Hz), 7.27 (1H, t, J = 8.0 Hz), 7.19 (1H, t, J = 5.7 Hz), 7.01 (1H, dd, J = 5.8, 8.3 Hz), 6.91-6.86 (2H, m), 6.86-6.80 (1H, m), 4.33-4.29 (2H, m), 4.10-4.02 (2H, m), 3.89-3.82 (1H, m), 3.78 (3H, s), 3.32-3.22 (3H, m), 3.14-3.05 (1H, m), 1.08 (3H, d, J = 6.3 Hz). |
| Example 151 | 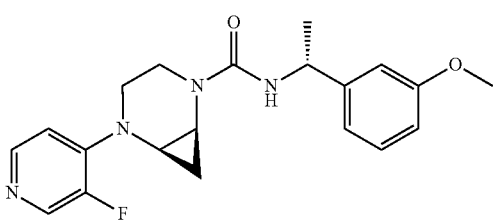 [SMILES: COc1cccc([C@@H](C)NC(=O)N2CCN(c3ccncc3F)[C@@H]3C[C@@H]32)c1] | LCMS (ES+) 371 (M + H)+, RT 2.97 min (Analytical Method 2), $^1$H NMR (400 MHz, DMSO) 8.25 (1H, d, J = 6.3 Hz), 8.12 (1H, d, J = 5.6 Hz), 7.24 (1H, t, J = 7.7 Hz), 7.04 (1H, dd, J = 5.7, 8.5 Hz), 6.97-6.93 (2H, m), 6.82-6.77 (1H, m), 6.73 (1H, d, J = 8.1 Hz), 4.99-4.90 (1H, m), 3.77 (3H, s), 3.69-3.44 (3H, m), 3.27-3.10 (3H, m), 1.45 (3H, d, J = 7.1 Hz), 1.29-1.22 (1H, m), 0.45-0.39 (1H, m); SFC RT 4.86 min (SFC1, YMC AMYLOSE-C + 0.1% DEAISO 20% MeOH). |
| Example 152 | 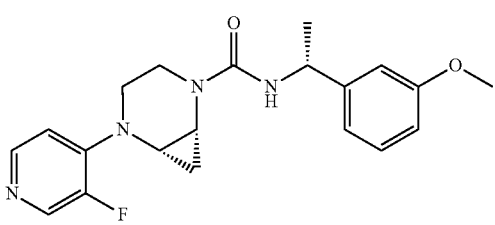 [SMILES: COc1cccc([C@@H](C)NC(=O)N2CCN(c3ccncc3F)[C@H]3C[C@H]32)c1] | LCMS (ES+) 371 (M + H)+, RT 3.01 min (Analytical Method 2), $^1$H NMR (400 MHz, DMSO) 8.26 (1H, d, J = 6.3 Hz), 8.13 (1H, d, J = 5.6 Hz), 7.27 (1H, t, J = 8.1 Hz), 7.06 (1H, dd, J = 5.7, 8.5 Hz), 7.01-6.96 (2H, m), 6.85-6.81 (1H, m), 6.70 (1H, d, J = 8.1 Hz), 4.93-4.85 (1H, m), 3.80 (3H, s), 3.67-3.43 (3H, m), 3.25-3.11 (3H, m), 1.44 (3H, d, J = 7.1 Hz), 1.22 (1H, q, J = 6.2 Hz), 0.50 (1H, q, J = 4.8 Hz). |

| Example | Structure and Name | Analytical data |
|---|---|---|
| Example 153 | 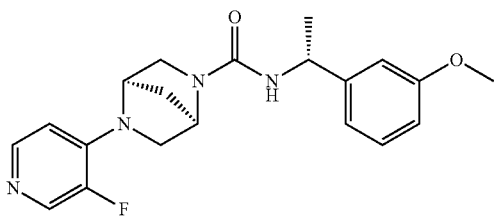 [SMILES: COc1cccc([C@@H](C)NC(=O)N2C[C@H]3C[C@@H]2CN3c2ccncc2F)c1] | LCMS (ES+) 371 (M + H)+, RT 2.45 min (Analytical Method 1), $^1$H NMR (400 MHz, DMSO) 8.16 (1H, d, J = 5.9 Hz), 7.99 (1H, d, J = 5.5 Hz), 7.20 (1H, t, J = 8.1 Hz), 6.88-6.85 (2H, m), 6.78-6.69 (2H, m), 6.63 (1H, d, J = 8.1 Hz), 4.79-4.68 (2H, m), 4.62 (1H, s), 3.74 (3H, s), 3.69 (1H, d, J = 9.4 Hz), 3.42-3.34 (2H, m), 3.25 (1H, dd, J = 3.1, 9.4 Hz), 1.97-1.89 (2H, m), 1.32 (3H, d, J = 7.1 Hz). |
| Example 154 | 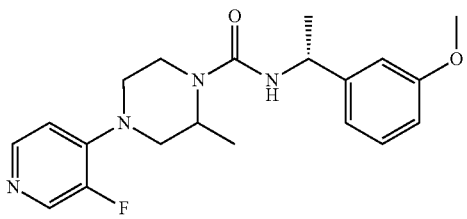 | LCMS (ES+) 373 (M + H)+, RT 2.55 min (Analytical Method 1), $^1$H NMR (400 MHz, DMSO) 8.50 (1H, s), 8.27 (1H, d, J = 5.6 Hz), 8.15 (1H, d, J = 5.4 Hz), 7.25-7.20 (1H, m), 7.00 (1H, dd, J = 5.7, 8.3 Hz), 6.92-6.88 (2H, m), 6.84-6.76 (1H, m), 4.88-4.82 (1H, m), 4.33 (1H, s), 3.91-3.87 (1H, m), 3.75 (3H, s), 3.63-3.53 (2H, m), 3.16-3.01 (2H, m), 2.90-2.82 (1H, m), 1.36 (3H, d, J = 7.1 Hz), 1.19-1.15 (3H, m). |
| Example 155 | 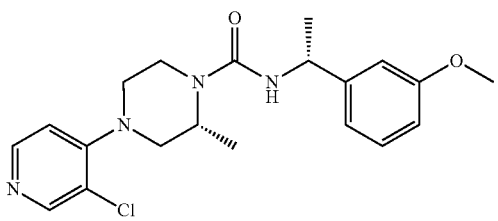 [SMILES: COc1cccc([C@@H](C)NC(=O)N2CCN(c3ccncc3Cl)C[C@H]2C)c1] | LCMS (ES+) 389, 391 (M + H)+, RT 3.31 min (Analytical Method 4) $^1$H NMR (400 MHz, DMSO) 8.47 (1H, s), 8.39 (1H, d, J = 5.3 Hz), 7.26 (1H, dd, J = 8.0, 8.0 Hz), 7.13 (1H, d, J = 5.3 Hz), 6.94 (2H, dd, J = 2.0, 2.5 Hz), 6.84 (2H, dd, J = 9.0, 9.0 Hz), 4.95-4.85 (1H, m), 4.44-4.37 (1H, m), 3.96 (1H, d, J = 13.1 Hz), 3.79 (3H, s), 3.51 (2H, dd, J = 11.7, 22.6 Hz), 3.24-3.13 (1H, m), 2.93-2.77 (2H, m), 1.42 (3H, d, J = 7.1 Hz), 1.29 (3H, d, J = 6.6 Hz). |
| Example 156 | 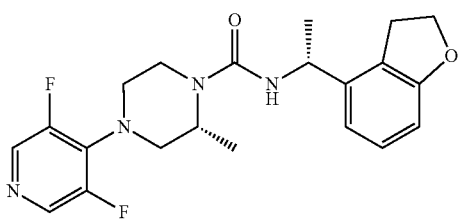 [SMILES: C[C@@H]1CN(c2c(F)cncc2F)CCN1C(=O)N[C@H](C)c1cccc2c1CCO2] | LCMS (ES+) 403 (M + H)+, RT 3.14 min (Analytical Method 4) $^1$H NMR (400 MHz, MeOD) 8.18 (2H, s), 7.09 (1H, dd, J = 7.8, 7.8 Hz), 6.85 (1H, d, J = 7.7 Hz), 6.62 (1H, d, J = 7.8 Hz), 4.96 (1H, q, J = 7.1 Hz), 4.57 (2H, t, J = 8.8 Hz), 4.37-4.31 (1H, m), 3.92-3.87 (1H, m), 3.62 (1H, d, J = 8.9 Hz), 3.51-3.15 (6H, m, obsc), 1.47 (3H, d, J = 7.0 Hz), 1.32 (3H, d, J = 6.7 Hz); |

In some embodiments, provided is a compound selected from those in Table 1:
TABLE 1
| Ex. No. | Structure |
|---|---|
| 1 | 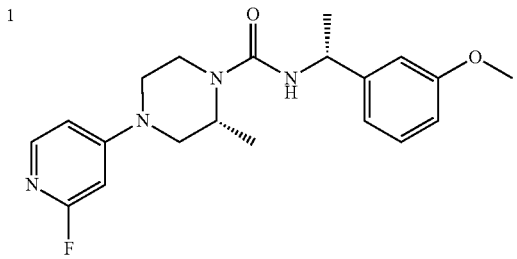 |
| 2 | 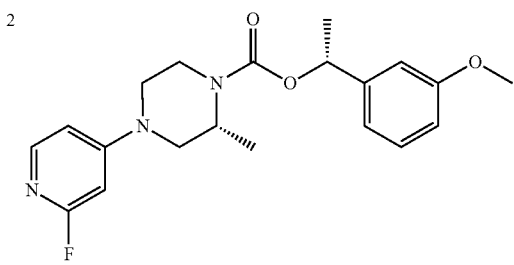 |
| 3 | 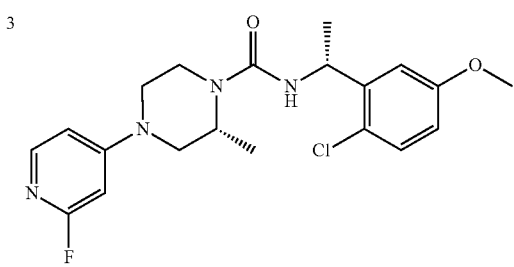 |
| 4 | 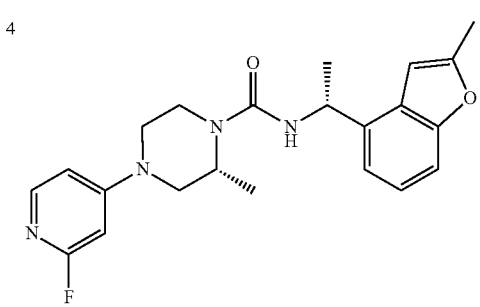 |
| 5 | 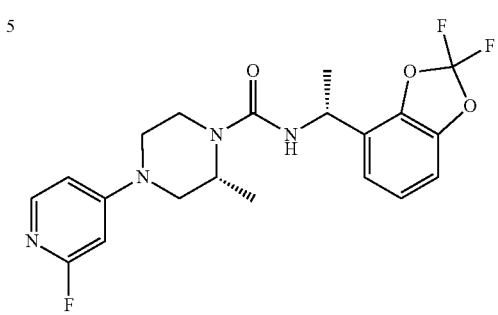 |
TABLE 1-continued
| Ex. No. | Structure |
|---|---|
| 6 | 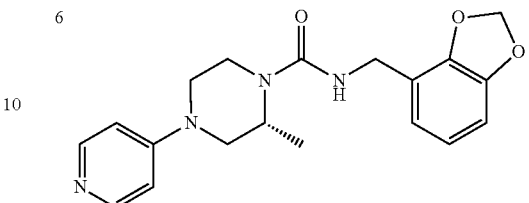 |
| 7 | 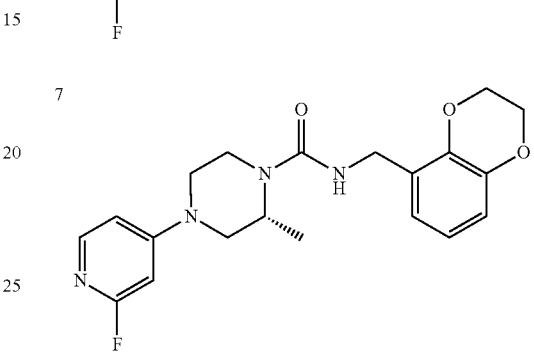 |
| 8 | 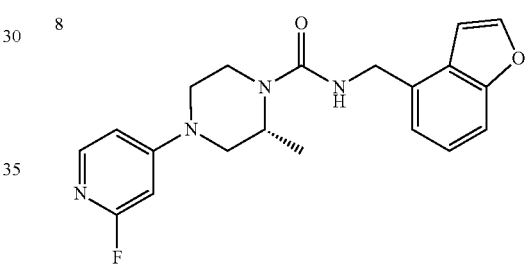 |
| 9 | 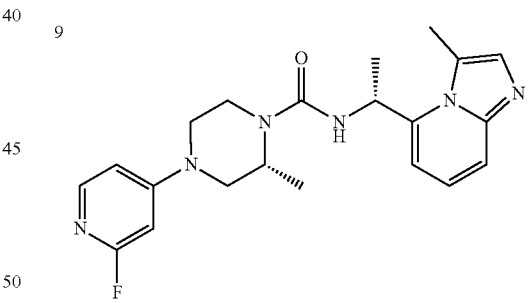 |
| 10 | 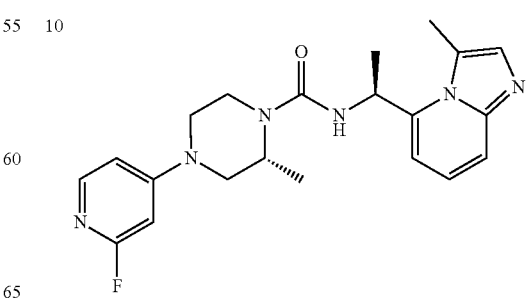 |

TABLE 1-continued
| Ex. No. | Structure |
|---|---|
| 11 | 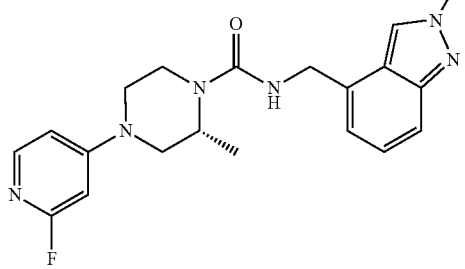 |
| 12 | 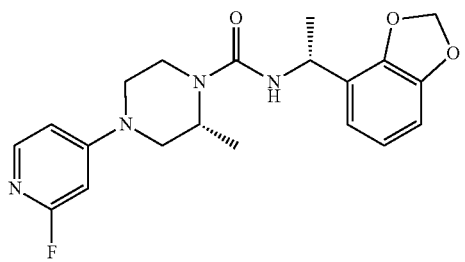 |
| 13 | 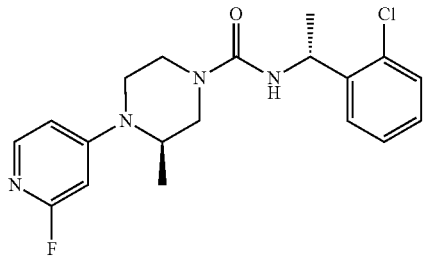 [SMILES: C[C@@H]1CN(C(=O)N[C@H](C)c2ccccc2Cl)CCN1c1ccnc(F)c1] |
| 14 | 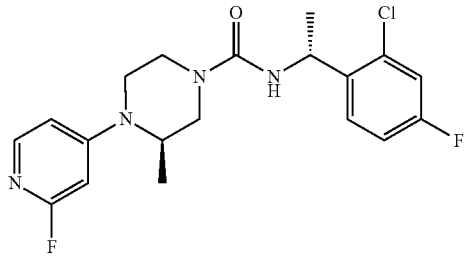 [SMILES: C[C@@H]1CN(C(=O)N[C@H](C)c2ccc(F)cc2Cl)CCN1c1ccnc(F)c1] |
| 15 | 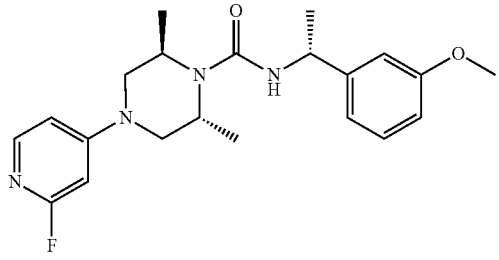 [SMILES: COc1cccc([C@@H](C)NC(=O)N2[C@H](C)CN(c3ccnc(F)c3)C[C@H]2C)c1] |
| 16 | 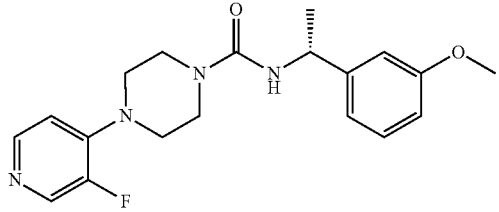 [SMILES: COc1cccc([C@@H](C)NC(=O)N2CCN(c3ccncc3F)CC2)c1] |
TABLE 1-continued
| Ex. No. | Structure |
|---|---|
| 17 | 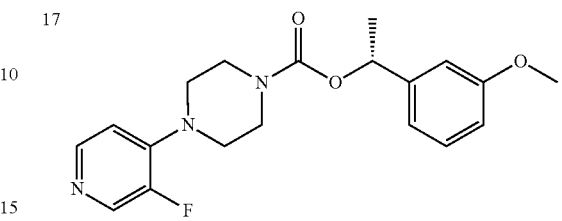 |
| 18 | 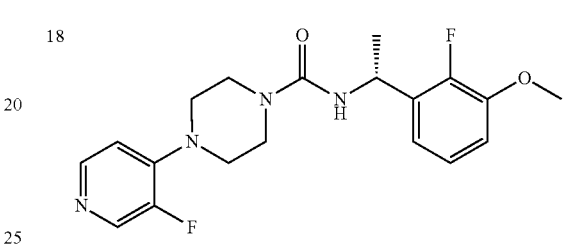 |
| 19 | 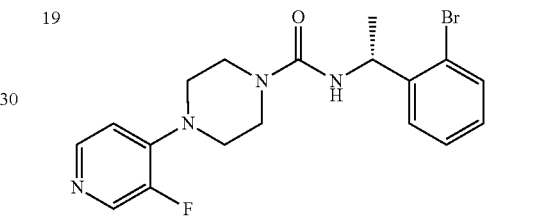 |
| 20 | 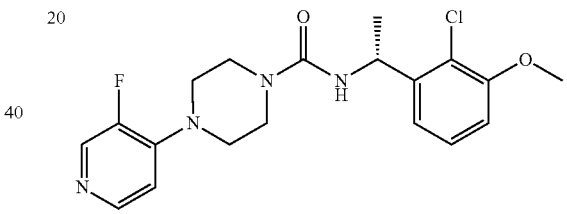 |
| 21 | 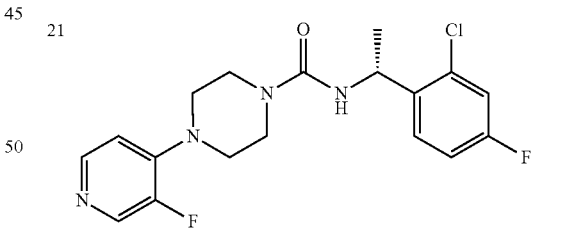 |
| 22 | 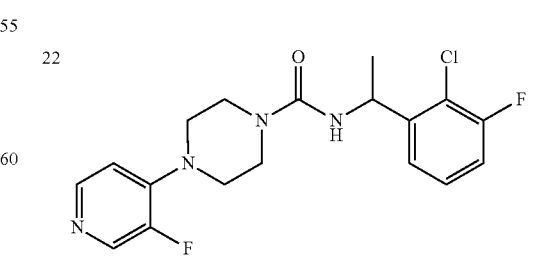<br>Enantiomer 1 |

TABLE 1-continued
| Ex. No. | Structure |
|---|---|
| 23 | 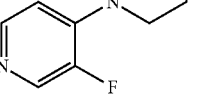 Enantiomer 2 |
| 24 | 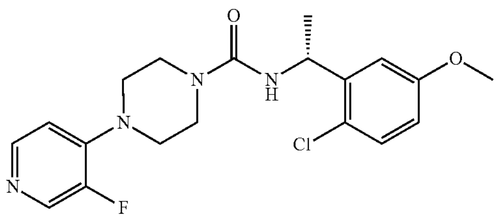 [SMILES: COc1ccc(Cl)c([C@@H](C)NC(=O)N2CCN(c3ccncc3F)CC2)c1] |
| 25 | 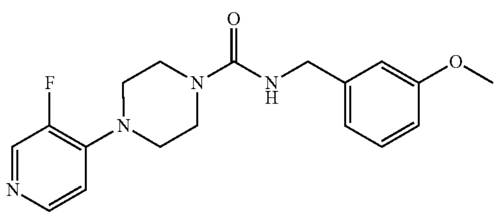 [SMILES: COc1cccc(CNC(=O)N2CCN(c3ccncc3F)CC2)c1] |
| 26 | 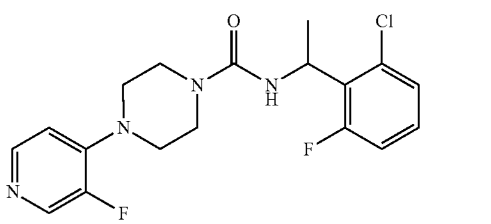 [SMILES: CC(NC(=O)N1CCN(c2ccncc2F)CC1)c1c(F)cccc1Cl] |
| 27 | 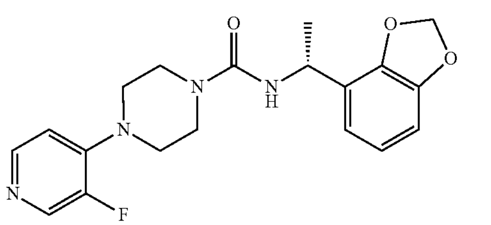 [SMILES: C[C@@H](NC(=O)N1CCN(c2ccncc2F)CC1)c1cccc2c1OCO2] |
| 28 | 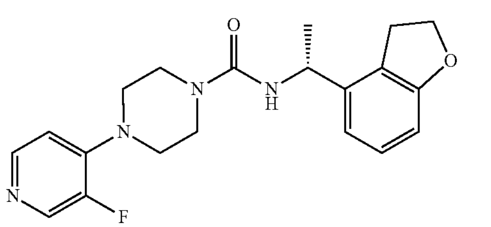 [SMILES: C[C@@H](NC(=O)N1CCN(c2ccncc2F)CC1)c1cccc2c1CCO2] |
| 29 | 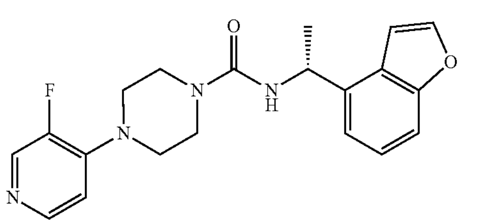 [SMILES: C[C@@H](NC(=O)N1CCN(c2ccncc2F)CC1)c1cccc2occc12] |
TABLE 1-continued
| Ex. No. | Structure |
|---|---|
| 30 | 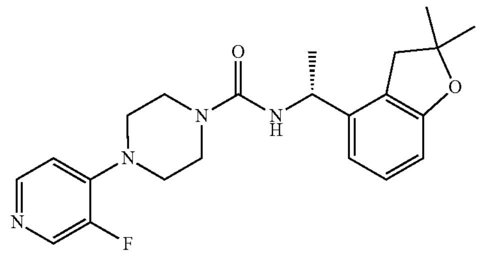 [SMILES: C[C@@H](NC(=O)N1CCN(c2ccncc2F)CC1)c1cccc2c1CC(C)(C)O2] |
| 31 | 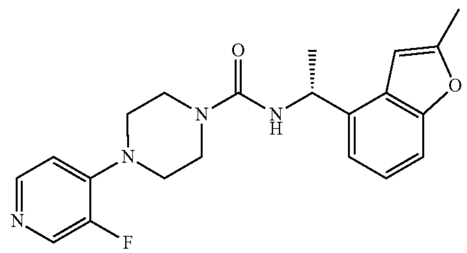 [SMILES: Cc1cc2c([C@@H](C)NC(=O)N3CCN(c4ccncc4F)CC3)cccc2o1] |
| 32 | 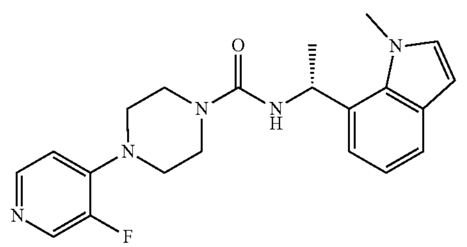 [SMILES: C[C@@H](NC(=O)N1CCN(c2ccncc2F)CC1)c1cccc2ccn(C)c12] |
| 33 | 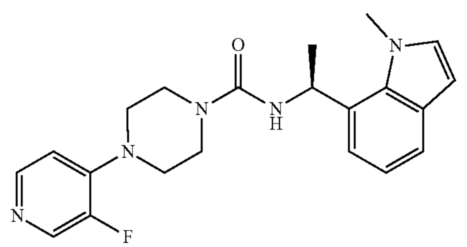 [SMILES: C[C@H](NC(=O)N1CCN(c2ccncc2F)CC1)c1cccc2ccn(C)c12] |
| 34 | 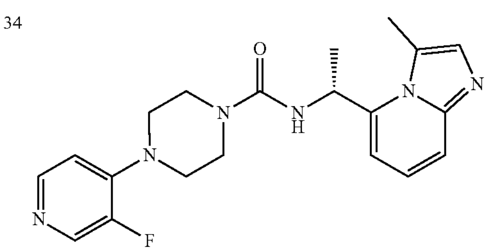 |
| 35 | 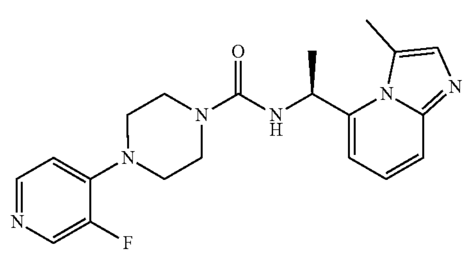 [SMILES: Cc1cnc2cccc([C@H](C)NC(=O)N3CCN(c4ccncc4F)CC3)n12] |

TABLE 1-continued

| Ex. No. | Structure |
|---|---|
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |

TABLE 1-continued
| Ex. No. | Structure |
|---|---|
| 49 | 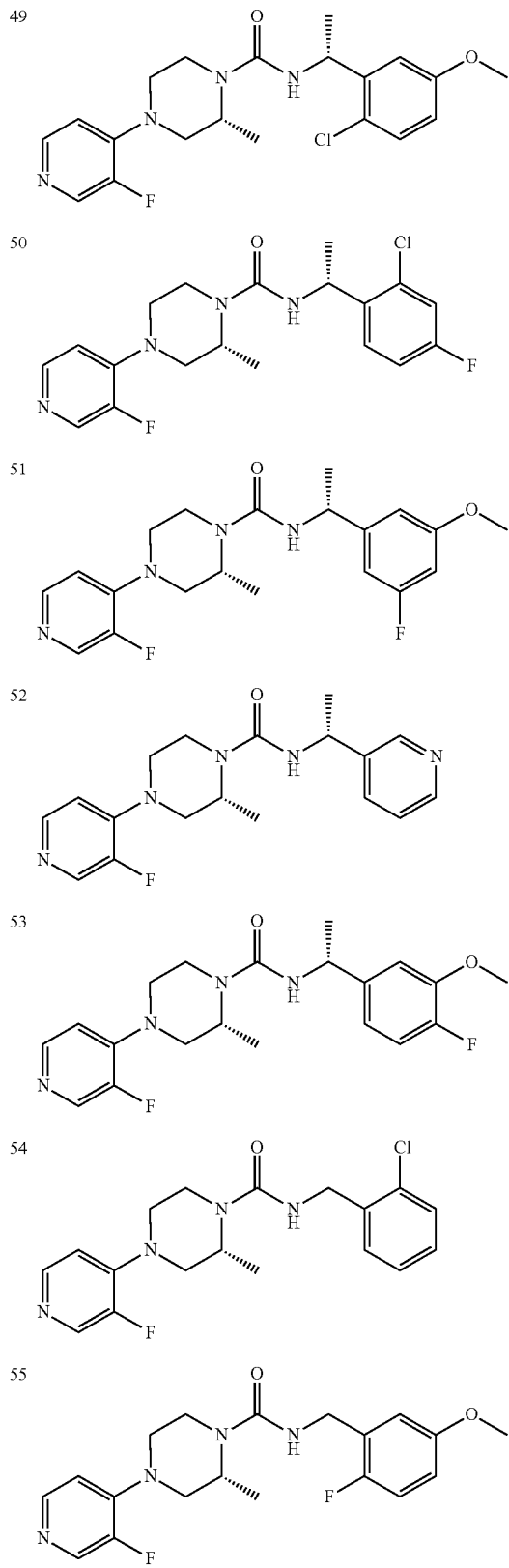 |
| 50 | 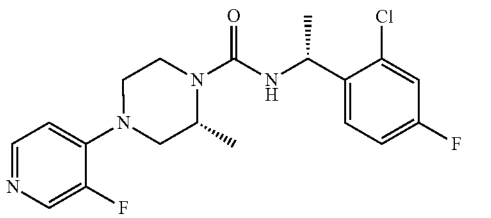 [SMILES: C[C@@H]1CN(c2ccncc2F)CCN1C(=O)N[C@H](C)c1ccc(F)cc1Cl] |
| 51 | 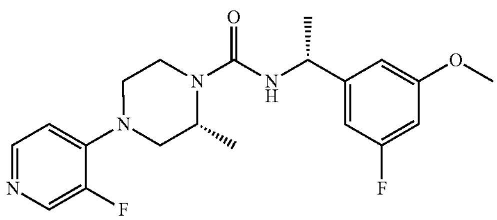 [SMILES: COc1cc(F)cc([C@@H](C)NC(=O)N2CCN(c3ccncc3F)C[C@H]2C)c1] |
| 52 | 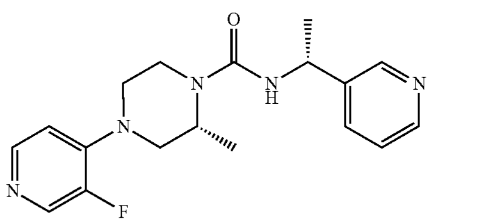 [SMILES: C[C@@H]1CN(c2ccncc2F)CCN1C(=O)N[C@H](C)c1cccnc1] |
| 53 | 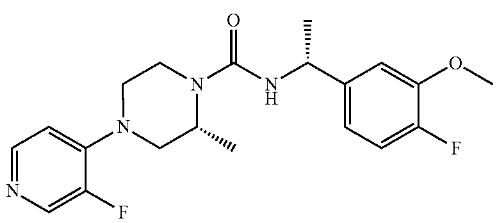 [SMILES: COc1cc([C@@H](C)NC(=O)N2CCN(c3ccncc3F)C[C@H]2C)ccc1F] |
| 54 | 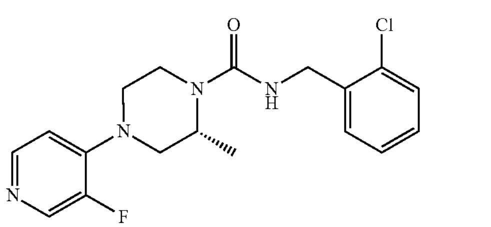 [SMILES: C[C@@H]1CN(c2ccncc2F)CCN1C(=O)NCc1ccccc1Cl] |
| 55 | 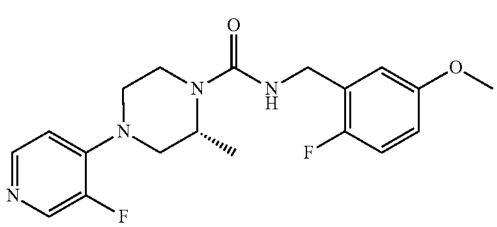 [SMILES: COc1ccc(F)c(CNC(=O)N2CCN(c3ccncc3F)C[C@H]2C)c1] |
TABLE 1-continued
| Ex. No. | Structure |
|---|---|
| 56 | 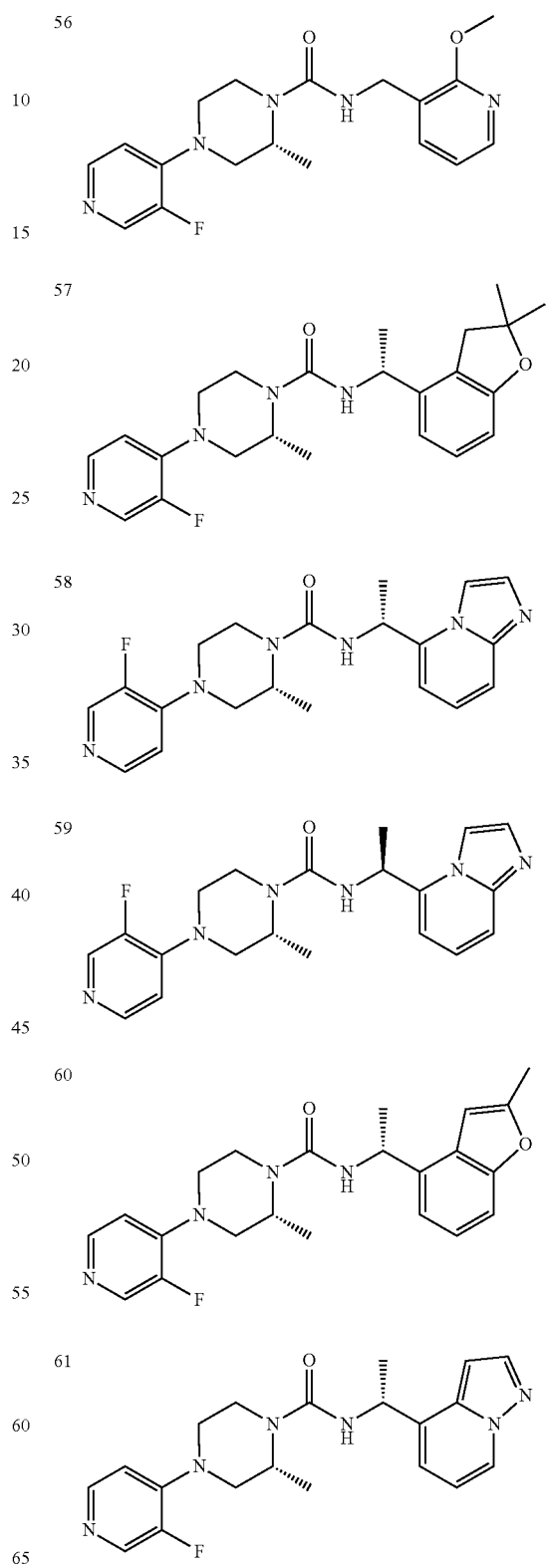 |
| 57 | 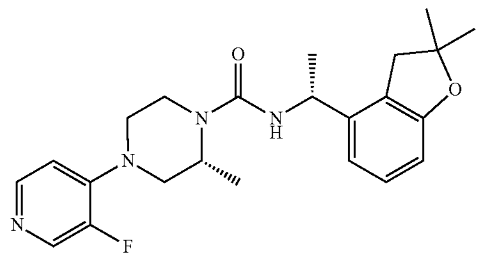 [SMILES: C[C@@H]1CN(c2ccncc2F)CCN1C(=O)N[C@H](C)c1cccc2c1CC(C)(C)O2] |
| 58 | 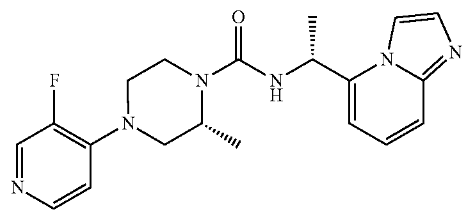 [SMILES: C[C@@H]1CN(c2ccncc2F)CCN1C(=O)N[C@H](C)c1cccc2nccn12] |
| 59 | 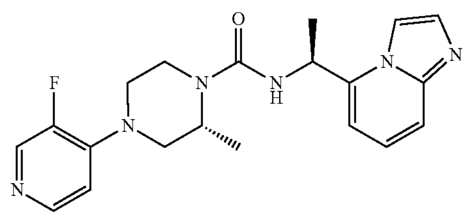 [SMILES: C[C@H](NC(=O)N1CCN(c2ccncc2F)C[C@H]1C)c1cccc2nccn12] |
| 60 | 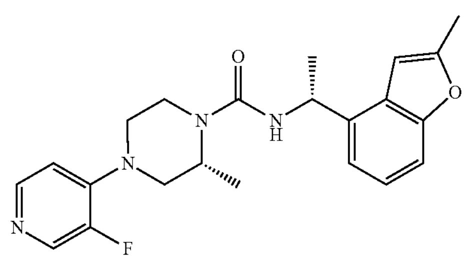 [SMILES: Cc1cc2c([C@@H](C)NC(=O)N3CCN(c4ccncc4F)C[C@H]3C)cccc2o1] |
| 61 | 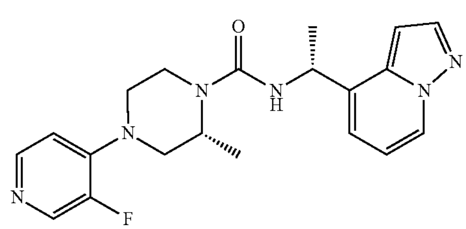 [SMILES: C[C@@H]1CN(c2ccncc2F)CCN1C(=O)N[C@H](C)c1cccn2nccc12] |

TABLE 1-continued
| Ex. No. | Structure |
|---|---|
| 62 | 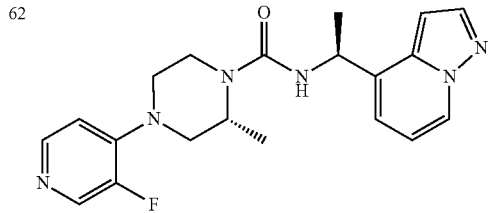 |
| 63 | 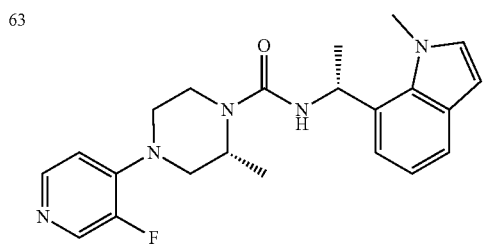 |
| 64 | 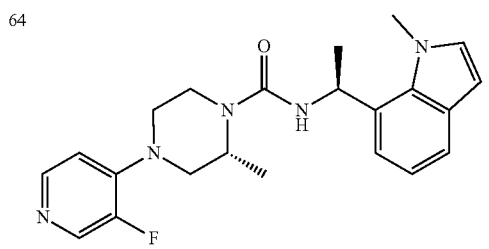 |
| 65 | 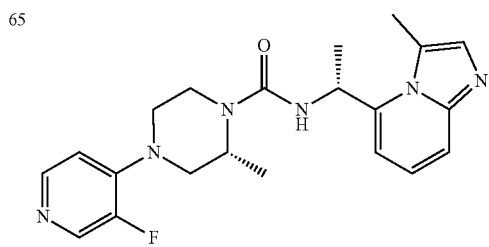 |
| 66 | 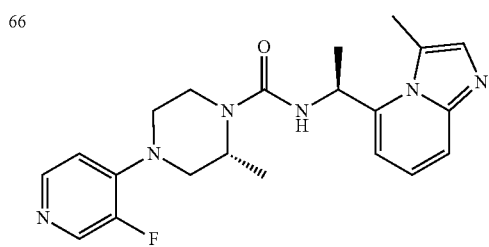 |
| 67 | 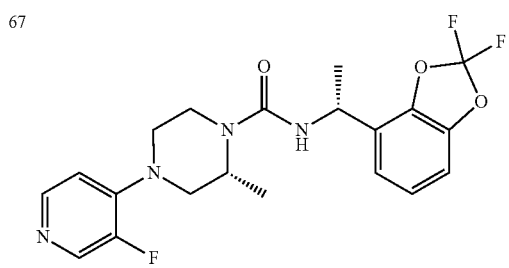 |
| 68 | 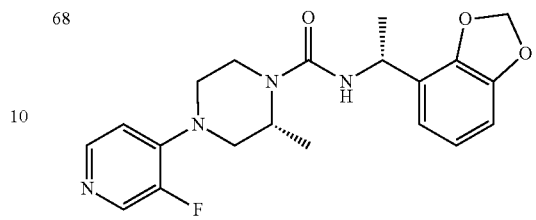 |
| 69 | 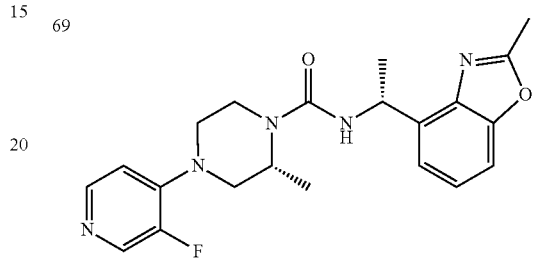 |
| 70 | 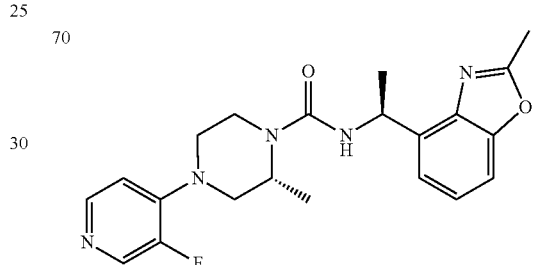 |
| 71 | 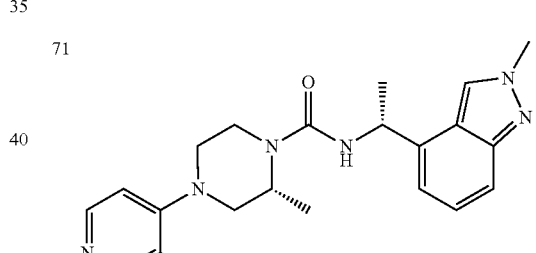 |
| 72 | 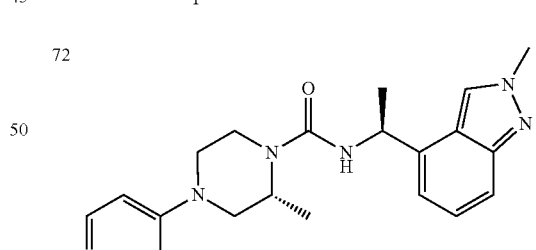 |
| 73 | 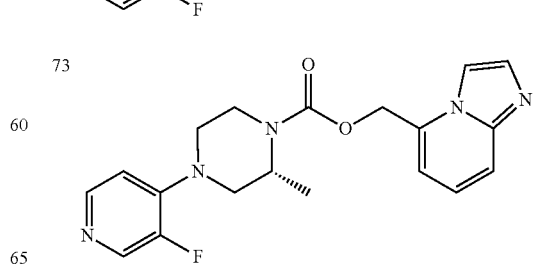 |

TABLE 1-continued
| Ex. No. | Structure |
|---|---|
| 74 | 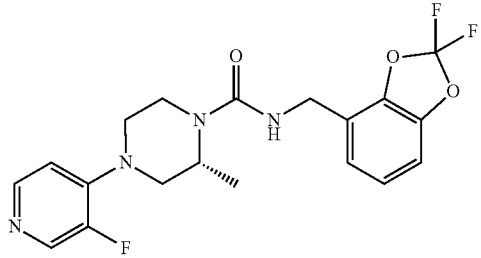 [SMILES: C[C@@H]1CN(c2ccncc2F)CCN1C(=O)NCc1cccc2c1OC(F)(F)O2] |
| 75 | 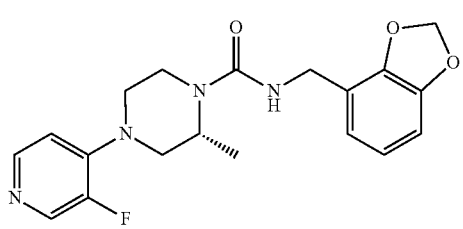 |
| 76 | 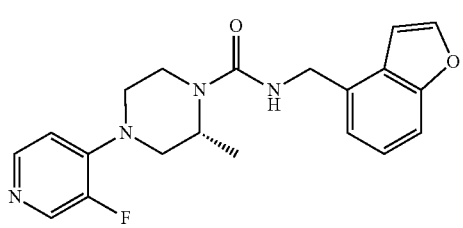 [SMILES: C[C@@H]1CN(c2ccncc2F)CCN1C(=O)NCc1cccc2occc12] |
| 77 | 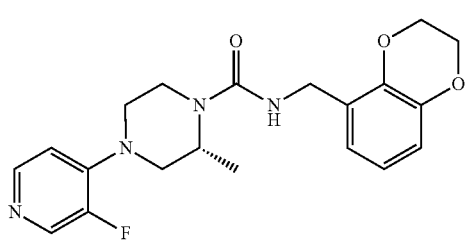 [SMILES: C[C@@H]1CN(c2ccncc2F)CCN1C(=O)NCc1cccc2c1OCCO2] |
| 78 | 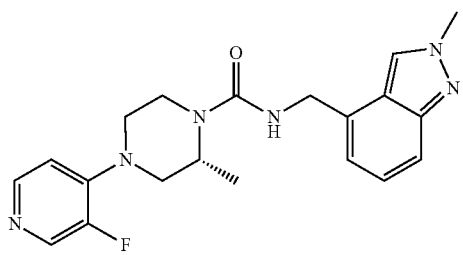 [SMILES: C[C@@H]1CN(c2ccncc2F)CCN1C(=O)NCc1cccc2nn(C)cc12] |
| 79 | 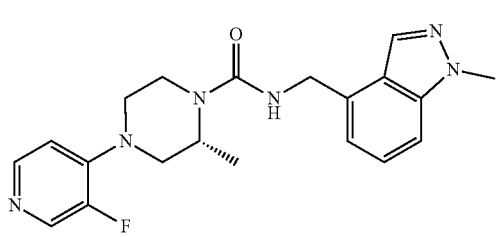 [SMILES: C[C@@H]1CN(c2ccncc2F)CCN1C(=O)NCc1cccc2c1cnn2C] |
| 80 | 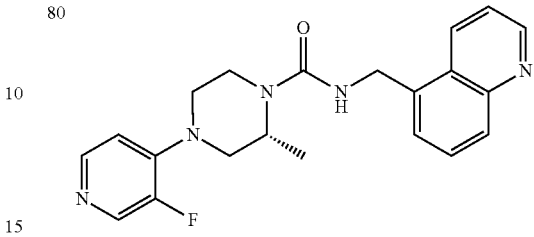 |
| 81 | 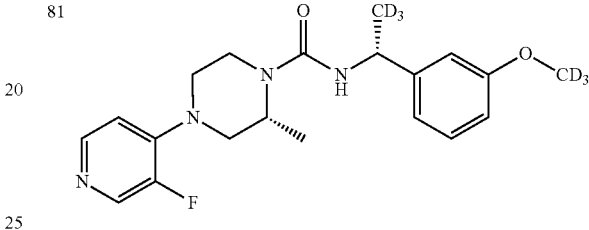 |
| 82 | 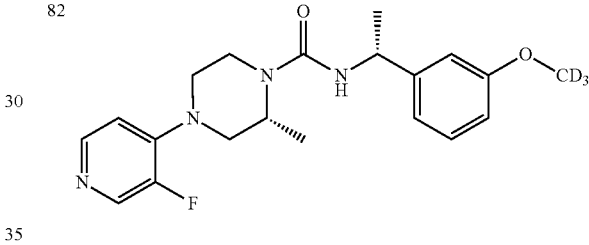 |
| 83 | 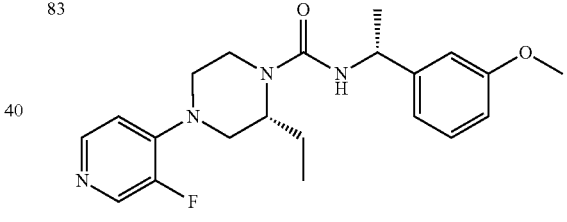 |
| 84 | 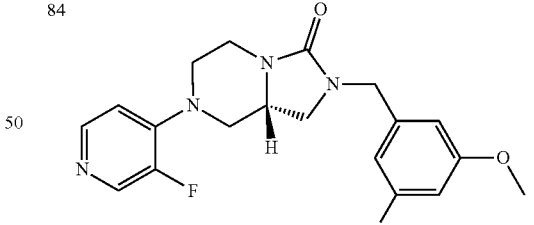 |
| 85 | 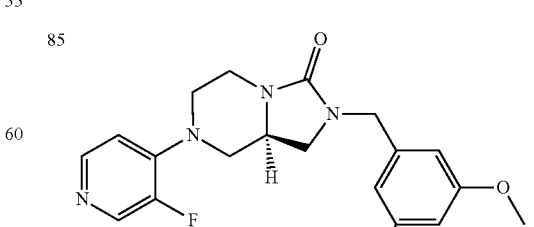 |

TABLE 1-continued
| Ex. No. | Structure |
|---|---|
| 86 | 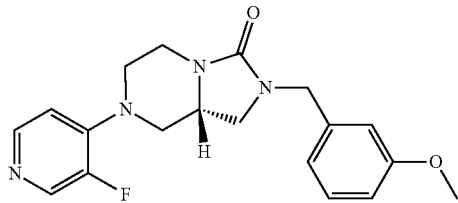 [SMILES: COc1cccc(CN2C[C@@H]3CN(c4ccncc4F)CCN3C2=O)c1] |
| 87 | 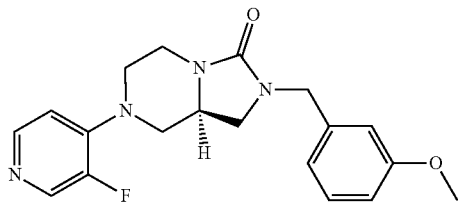 [SMILES: COc1cccc(CN2C[C@H]3CN(c4ccncc4F)CCN3C2=O)c1] |
| 88 | 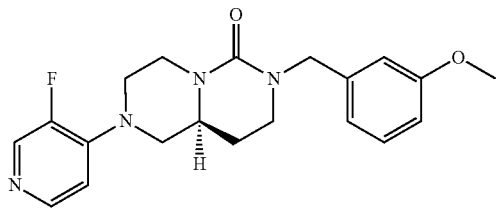 [SMILES: COc1cccc(CN2CC[C@H]3CN(c4ccncc4F)CCN3C2=O)c1] |
| 89 | 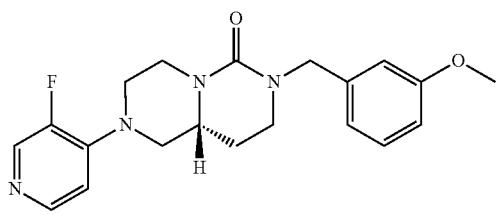 [SMILES: COc1cccc(CN2CC[C@@H]3CN(c4ccncc4F)CCN3C2=O)c1] |
| 90 | 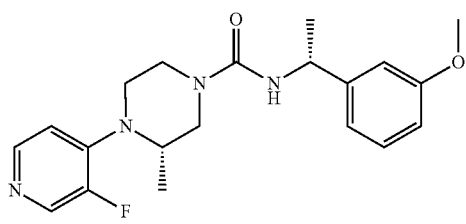 [SMILES: COc1cccc([C@@H](C)NC(=O)N2CCN(c3ccncc3F)[C@@H](C)C2)c1] |
| 91 | 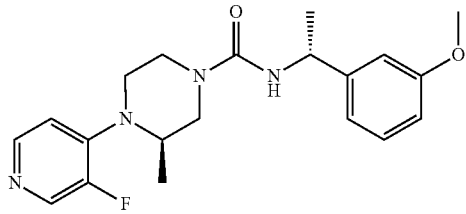 [SMILES: COc1cccc([C@@H](C)NC(=O)N2CCN(c3ccncc3F)[C@H](C)C2)c1] |
| 92 | 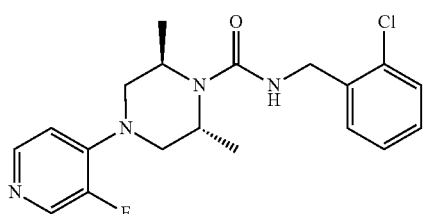 |
| 93 | 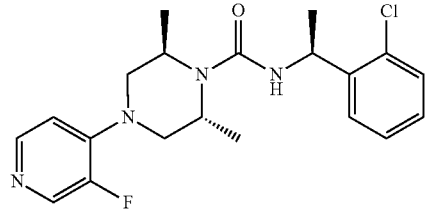 [SMILES: C[C@H](NC(=O)N1[C@H](C)CN(c2ccncc2F)C[C@H]1C)c1ccccc1Cl] |
| 94 | 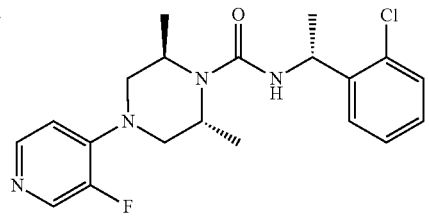 [SMILES: C[C@@H]1CN(c2ccncc2F)C[C@@H](C)N1C(=O)N[C@H](C)c1ccccc1Cl] |
| 95 | 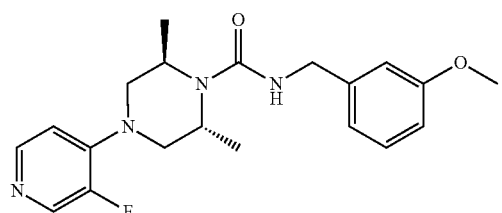 |
| 96 | 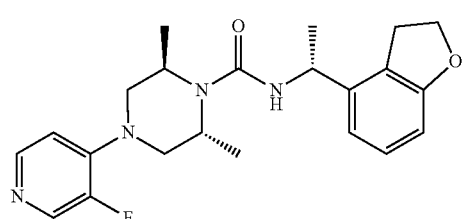 |
| 97 | 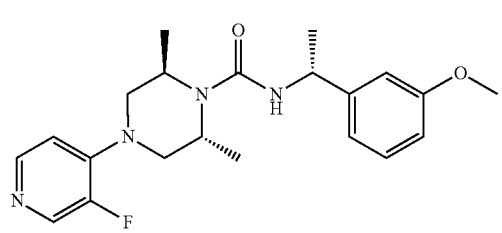 [SMILES: COc1cccc([C@@H](C)NC(=O)N2[C@H](C)CN(c3ccncc3F)C[C@H]2C)c1] |
| 98 | 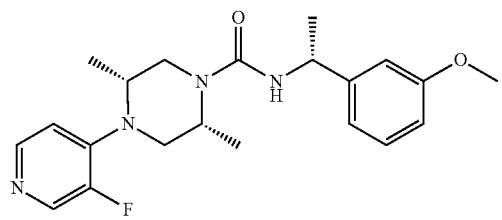 [SMILES: COc1cccc([C@@H](C)NC(=O)N2C[C@@H](C)N(c3ccncc3F)C[C@H]2C)c1] |
| 99 | 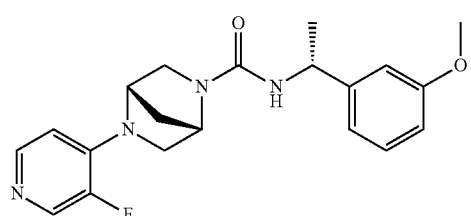 |

TABLE 1-continued
| Ex. No. | Structure |
|---|---|
| 100 | 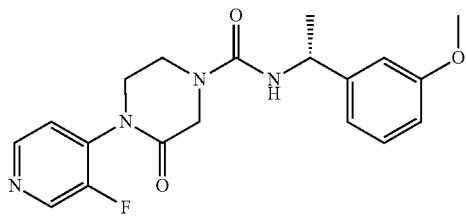 [SMILES: COc1cccc([C@@H](C)NC(=O)N2CCN(c3ccncc3F)C(=O)C2)c1] |
| 101 | 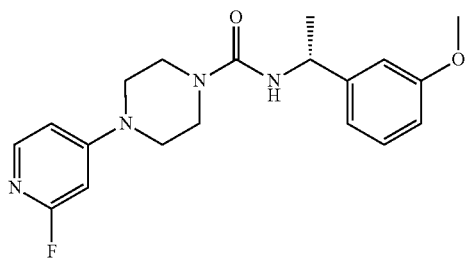 [SMILES: COc1cccc([C@@H](C)NC(=O)N2CCN(c3ccnc(F)c3)CC2)c1] |
| 102 | 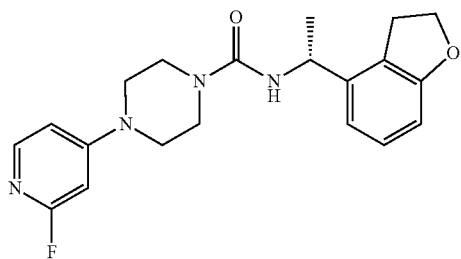 |
| 103 | 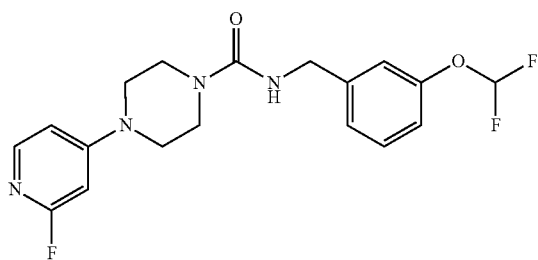 |
| 104 | 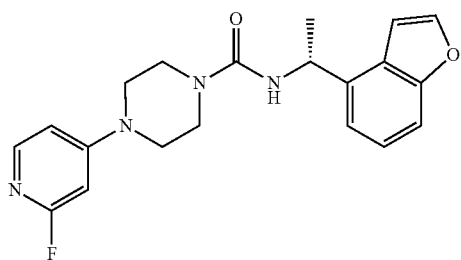 [SMILES: C[C@@H](NC(=O)N1CCN(c2ccnc(F)c2)CC1)c1cccc2occc12] |
| 105 | 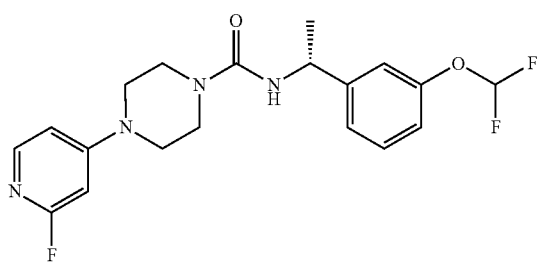 |
| 106 | 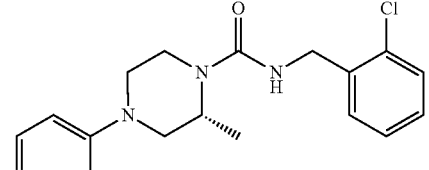 |
| 107 | 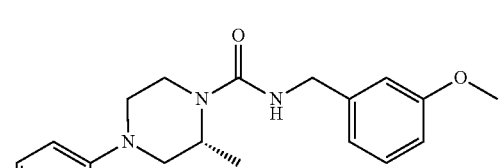 |
| 108 | 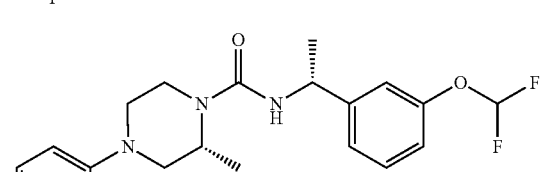 |
| 109 |  |
| 110 |  |
| 111 | 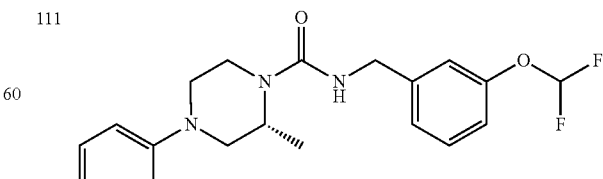 |

TABLE 1-continued

| Ex. No. | Structure |
|---|---|
| 112 | |
| 113 | |
| 114 | |
| 115 | |
| 116 | |
| 117 | 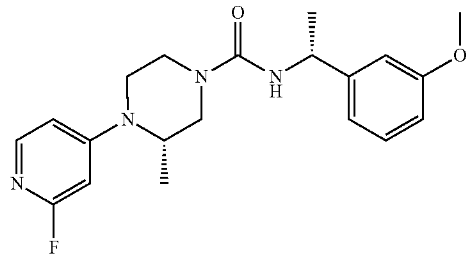 [SMILES: COc1cccc([C@@H](C)NC(=O)N2CCN(c3ccnc(F)c3)[C@@H](C)C2)c1] |
| 118 | 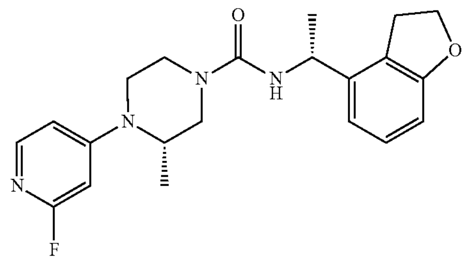 [SMILES: C[C@@H](NC(=O)N1CCN(c2ccnc(F)c2)[C@@H](C)C1)c1cccc2c1CCO2] |
| 119 | 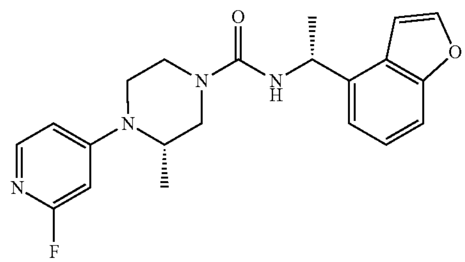 [SMILES: C[C@@H](NC(=O)N1CCN(c2ccnc(F)c2)[C@@H](C)C1)c1cccc2occc12] |
| 120 | 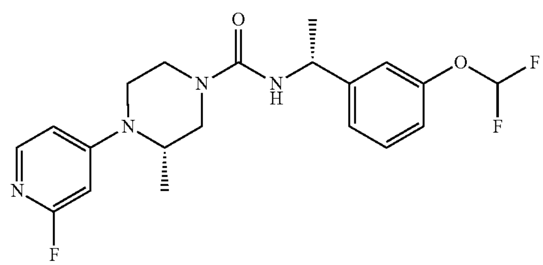 [SMILES: C[C@@H](NC(=O)N1CCN(c2ccnc(F)c2)[C@@H](C)C1)c1cccc(OC(F)F)c1] |
| 121 | 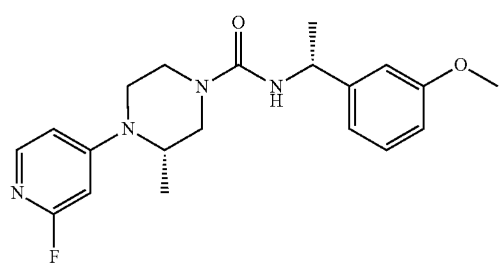 [SMILES: COc1cccc([C@@H](C)NC(=O)N2CCN(c3ccnc(F)c3)[C@@H](C)C2)c1] |
| 122 | 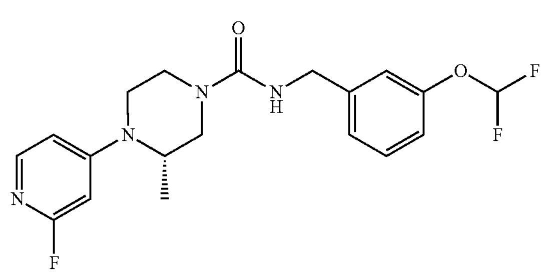 [SMILES: C[C@H]1CN(C(=O)NCc2cccc(OC(F)F)c2)CCN1c1ccnc(F)c1] |

TABLE 1-continued
| Ex. No. | Structure |
|---|---|
| 123 | 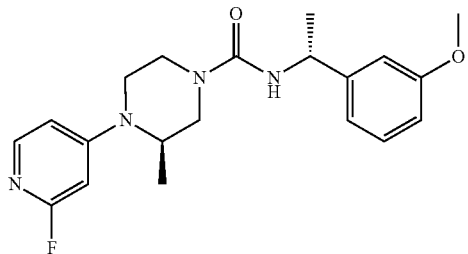 [SMILES: COc1cccc([C@@H](C)NC(=O)N2CCN(c3ccnc(F)c3)[C@H](C)C2)c1] |
| 124 | 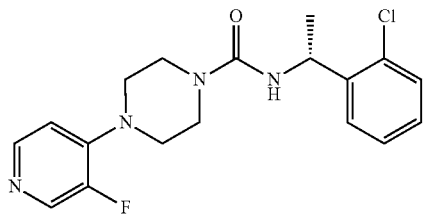 |
| 125 | 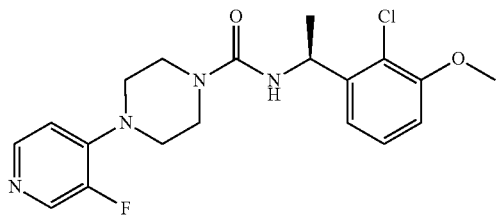 |
| 126 | 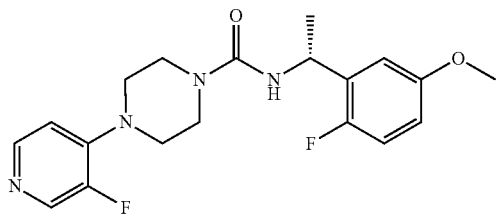 [SMILES: COc1ccc(F)c([C@@H](C)NC(=O)N2CCN(c3ccncc3F)CC2)c1] |
| 127 | 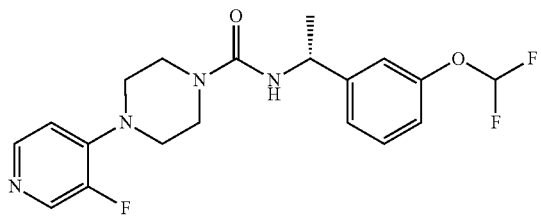 |
| 128 | 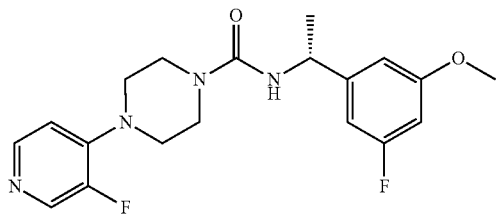 [SMILES: COc1cc(F)cc([C@@H](C)NC(=O)N2CCN(c3ccncc3F)CC2)c1] |
TABLE 1-continued
| Ex. No. | Structure |
|---|---|
| 129 | 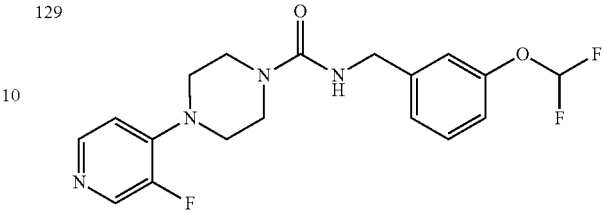 |
| 130 | 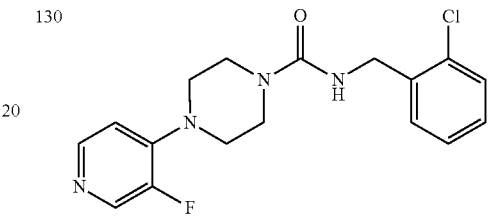 |
| 131 | 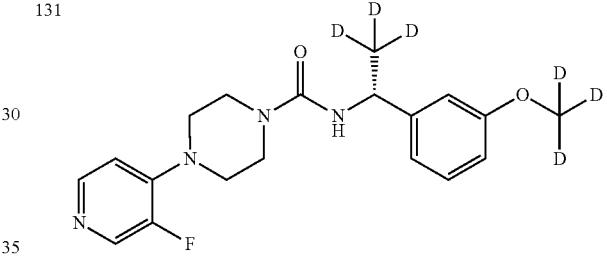 |
| 132 | 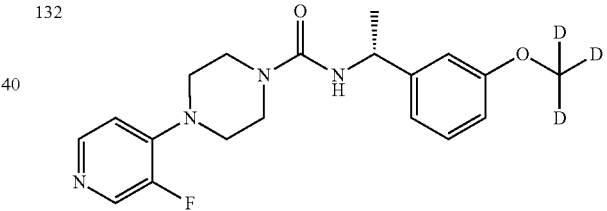 |
| 133 | 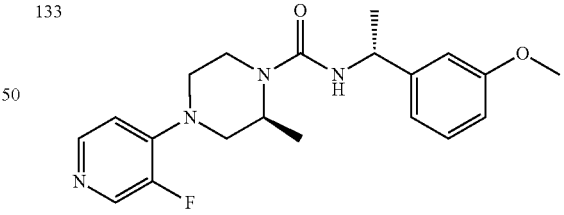 |
| 134 | 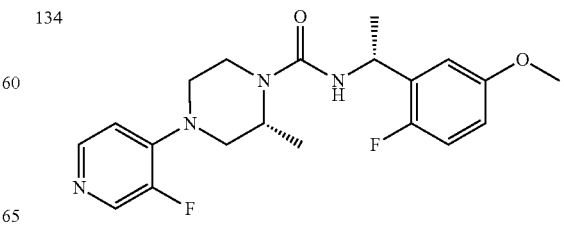 |

TABLE 1-continued

| Ex. No. | Structure |
|---|---|
| 135 | *(structure)* |
| 136 | *(structure)* |
| 137 | *(structure)* |
| 138 | *(structure)* |
| 139 | *(structure)* |
| 140 | *(structure)* |
| 141 | *(structure)* |
| 142 | *(structure)* |
| 143 | *(structure)* |
| 144 | *(structure)* |
| 145 | *(structure)* |
| 146 | *(structure)* |
| 147 | *(structure)* |

TABLE 1-continued

| Ex. No. | Structure |
|---|---|
| 148 | 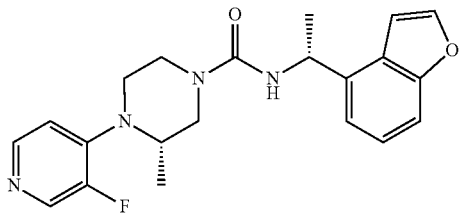 |
| 149 | 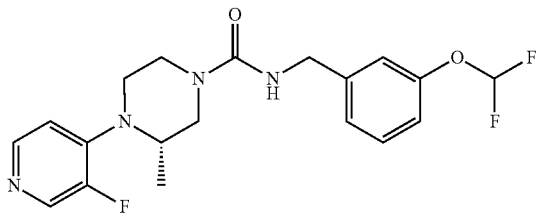 [SMILES: C[C@H]1CN(C(=O)NCc2cccc(OC(F)F)c2)CCN1c1ccncc1F] |
| 150 | 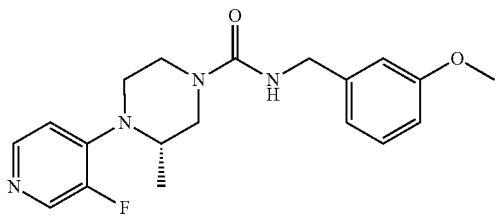 [SMILES: COc1cccc(CNC(=O)N2CCN(c3ccncc3F)[C@@H](C)C2)c1] |
| 151 | 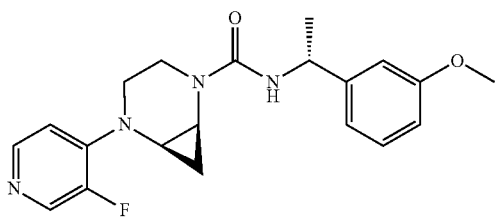 [SMILES: COc1cccc([C@@H](C)NC(=O)N2CCN(c3ccncc3F)[C@@H]3C[C@@H]32)c1] |
| 152 | 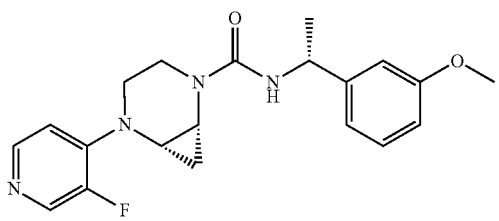 [SMILES: COc1cccc([C@@H](C)NC(=O)N2CCN(c3ccncc3F)[C@H]3C[C@H]32)c1] |
| 153 | 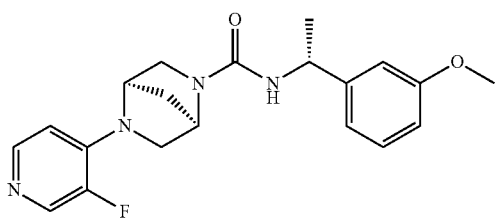 [SMILES: COc1cccc([C@@H](C)NC(=O)N2C[C@H]3C[C@@H]2CN3c2ccncc2F)c1] |
| 154 | 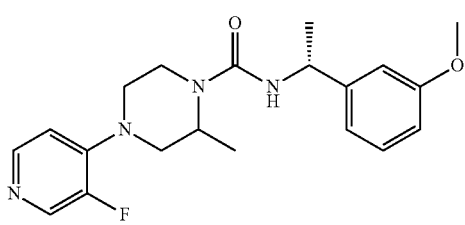 [SMILES: COc1cccc([C@@H](C)NC(=O)N2CCN(c3ccncc3F)CC2C)c1] |

TABLE 1-continued

| Ex. No. | Structure |
|---|---|
| 155 | 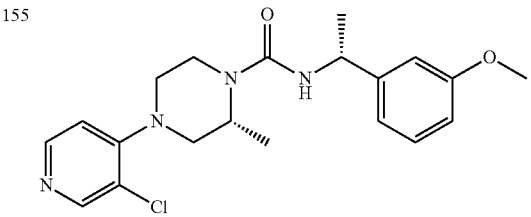 |
| 156 | 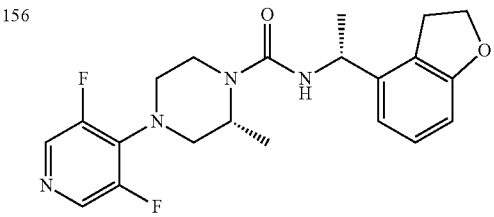 | or a deuterated analog, pharmaceutically acceptable salt, solvate, prodrug, stereoisomer, or mixture of stereoisomers thereof.

Biological Assays

Example 1: Analysis of Inhibition of ROCKII Enzyme with Rho-Associated Protein Kinase (ROCK) Inhibitors The potency of Rho-associated protein kinase (ROCK) II inhibitors was quantified by measuring ROCKII kinase domain enzymatic activity using ADP-Glo™ Kinase Assay format. The S6K peptide substrate was phosphorylated by active ROCKII by transferring phosphate group from ATP molecule and generating ADP molecule. ADP-Glo™ Reagent was added that terminates ROCKII reaction and depletes remaining ATP. Kinase Detection Reagent was added to convert ADP to ATP and allow newly synthesized ATP to be measured using luciferase/luciferin reaction. The light generated correlates to the amount of ADP generated in the ROCKII biochemical reaction, which is indicative of ROCKII activity.

ROCK inhibitor compound plate preparation. Lyophilized ROCK inhibitors were re-suspended to a final concentration of 10 mM in 100% dimethyl sulfoxide (DMSO) and control reference compound, Fasudil HCl, to a final concentration of 100 mM in 100% DMSO using Janus automated liquid handler workstation (Perkin Elmer) and were stored at room temperature under nitrogen. Stock compounds and controls were added directly to ECHO plate (Labcyte) by Janus. The Echo 555 liquid handler (Labcyte) dispensed duplicate 10-point concentration-response curves for each compound directly into 384-well, black, U-bottom assay plate (Matrix Technologies Ltd) at 100× final assay concentration. Final compound or control volume per well is 100 nl (0.1 µl). Assay standards were prepared by Echo dispensing 5 nl of 100 mM Fasudil HCl and 95 nl DMSO for full inhibition control (50 µM final assay concentration and 1% DMSO) and 100 nl of DMSO for full activity control (1% DMSO).

Preparation of ROCKII catalytic domain active enzyme (2.5 nM). The ROCKII catalytic domain enzyme was human catalytic domain ROCK II protein (amino acids 5-554) with a N-terminal GST tag (SignalChem). A 2× working solution of enzyme was prepared from 100 ng/µl stock aliquot of ROCKII catalytic domain diluted to 2.2 ng/10 µl (2.5 nM) with assay buffer (25 mM MOPS, 12.5 mM 2-glycerophosphate, 5 mM EGTA pH 8.0, 25 mM MgCl2, 2 mM EDTA, 0.25 mM DTT (added on the day of assay) and 0.01% BSA (added on the day of assay)) just prior to the addition of the enzyme to the assay.

Preparation of S6K peptide substrate (20 µM) and ATP (10 µM). The S6K peptide sequence (amino acid sequence KRRRLASLR) was based on human 40 S ribosomal protein S6 (amino acids 230-238) (SignalChem). A 2× working solution of substrate and ATP was prepared from 5 mg/ml stock aliquot (dissolved in 20 mM Tris-HCl, pH 7.5) of S6K peptide diluted to 0.25 µg/10 µl (20 µM) with assay buffer (25 mM MOPS, 12.5 mM 2-glycerophosphate, 5 mM EGTA pH 8.0, 25 mM MgCl2, 2 mM EDTA, 0.25 mM DTT (added on the day of assay) and 0.01% BSA (added on the day of assay)). 10 mM ultrapure ATP stock aliquot (ADP-Glo™ kit) was added to assay buffer, containing S6K substrate, to final assay concentration of 10 µM (ATP Km), just prior to the addition of the peptide substrate/ATP mix to the assay.

Assay procedure. 5 µl/well substrate/ATP mix was added to each well of the assay plate containing compounds using 125 µl 16-channel Matrix electronic pipette (Matrix Technologies Ltd.). The plate was sealed, mixed on orbital shaker at 1000 rpm (rotations per minute) for 10 seconds and centrifuged at 1000 rpm for 1 min. The assay was started by addition of 5 µl/well of the ROCKII enzyme mix to each well using 125 µl 16-channel Matrix electronic pipette. The assay plate was sealed, mixed on orbital shaker at 1000 rpm for 10 seconds and centrifuged at 1000 rpm for 1 min. The assay plate was incubated for 30 min at room temperature on an orbital shaker at 400 rpm. The enzyme reaction was stopped by addition of 10 µl/well of ADP-Glo™ solution to assay plate using 125 µl 16-channel Matrix electronic pipette. The assay plate was sealed, mixed on orbital shaker at 1000 rpm for 10 seconds and centrifuged at 1000 rpm for 1 min. The assay plate was placed in a polystyrene box for 40 minutes at room temperature. Next, 20 µl/well of Kinase Detection Reagent was added to assay plate using 125 µl 16-channel Matrix electronic pipette. The assay plate was further incubated in a polystyrene box for 30 min at room temperature without the seal and luminescence signal was measured using EnVision (Perkin Elmer) in top read mode.

Example 2: Analysis of Inhibition of Cellular ROCK Enzyme with Rho-Associated Protein Kinase (ROCK) Inhibitors The potency of Rho-associated protein kinase (ROCK) inhibitors was quantified by measuring cofilin phosphorylation levels at Serine 3 (Ser3) as a measure of cellular ROCK activity by In-Cell Western assay. After A7r5 rat smooth muscle cell cells are fixed and permeabilized, cofilin phosphorylation levels were measured by immunocytochemical staining using specific monoclonal phospho-cofilin (Ser3) antibodies (Cell Signaling Technology) in combination with anti-rabbit IRDye 800CW (LICOR Biosciences) and Alexa Fluor™ 647 Conjugated Wheat Germ Agglutinin (WGA) as a measure of cell number. The assay plate was imaged and quantified on the Odyssey imager (LICOR Biosciences).

ROCK inhibitor compound plate preparation. Lyophilized ROCK inhibitors were re-suspended to a final concentration of 10 mM in 100% dimethyl sulfoxide (DMSO) and control reference compound, Fasudil HCl, to a final concentration of 100 mM in 100% DMSO using Janus automated liquid handler workstation (Perkin Elmer) and were stored at room temperature under nitrogen. Stock compounds and control are added directly to ECHO plate (Labcyte) by Janus. The Echo 555 liquid handler (Labcyte) dispenses duplicate 10-point concentration-response curves for each compound directly into the 384-well plate (384-well V-bottom polypropylene, Greiner) at 2000× final assay concentration. Final compound or control volume per well is 100 nl (0.1 µl). Assay standards were prepared by Echo dispensing 100 nl of 100 mM Fasudil HCl for full inhibition control (50 µM final assay concentration and 0.5% DMSO) and 100 nl of DMSO for full activity control (0.5% DMSO).

A7r5 cell culture and plating. A7r5 cells were cultured according to standard cell culture protocols in A7r5 growth media (DMEM with Glutamax and 10% FBS). A7r5 cells were counted using a Coulter Counter and re-suspended to $6.67 \times 10^4$ cells/ml in growth media. 45 µl of re-suspended A7r5 cells were plated at 3000 cells/well in a sterile, µclear, black, F-bottom, 384-well microplate (Greiner bio-one). Seeded cells allowed to settle in wells on the bench for 1 hour before incubation at 37° C., 5% CO2 overnight.

Assay reagent and antibody preparations. Wash buffer was prepared by addition of Tween-20 to Dulbecco's Phosphate Buffered Saline (DPBS) (1×) without calcium and magnesium to make 1% Tween-20 as final concentration. Blocking buffer was prepared by addition of TritonX-100 to SeaBlock buffer (ThermoFisher) to make 0.3% TritonX-100 as final concentration. Primary antibody mix was prepared by diluting phospho-cofilin (Ser3) antibody (Cell Signaling Technology, 3313) 1:200 and Alexa® Fluor 647 WGA (Molecular Probes) 1:10000 in SeaBlock buffer. Secondary antibody mix was prepared by diluting donkey anti-rabbit 800CW antibody (LICOR Biosciences) 1:1000 in SeaBlock buffer.

Assay procedure. Compound plate was diluted by addition of 19 µl/well compound dilution buffer (DMEM with Glutamax) using 125 µl 16-channel Matrix electronic pipette. 5 µl diluted compound was stamped from compound plate to assay plate containing A7r5 cells using Bravo (384-well head from Agilent) liquid handler and incubated at 37° C., 5% CO2 for 1 hour. Cells were fixed by addition of 5 µl 37% formaldehyde using 125 µl 16-channel Matrix electronic pipette and incubation for 20 min at room temperature. The assay plate was washed 5× with 60 µl/well wash buffer. Next 25 µl/well blocking buffer containing 0.3% TritonX-100 was added to each well using 125 µl 16-channel Matrix electronic pipette, plate sealed, centrifuged for 5 seconds at 1000 rpm and put on an orbital shaker at 300 rpm for 60 min at room temperature. The solution from assay plate was emptied by flicking and gently tapping the plate onto tissue and 25 µl/well primary antibody mix was added to each well using 125 µl 16-channel Matrix electronic pipette. Next, the assay plate was sealed, centrifuged at 1000 rpm for 5 seconds and incubated at 4° C. overnight on an orbital shaker at 300 rpm. The assay plate was washed 4× with wash buffer and 25 µl/well secondary antibody mix was added to each well using 125 µl 16-channel Matrix electronic pipette. The assay plate was centrifuged at 1000 rpm for 5 seconds and incubated on an orbital shaker at 300 rpm for 60 min at room temperature. Finally, assay plate was washed and wells left empty before measurement of 700 nm and 800 nm fluorescence intensities on Odyssey imager set at 4.0 mm focus offset.

Example compounds of the disclosure provided assay results as indicated in the table below:

| Example No. | CELL_IC50 (µM) | ROCK_IC50 (µM) |
| --- | --- | --- |
| 1 | 0.1219 | 0.0065 |
| 2 | 1.6949 | 0.0307 |
| 3 | 2.411 | 0.0599 |
| 4 | 0.3564 | 0.0045 |
| 5 |  | 0.8636 |
| 6 |  | 0.1171 |
| 7 |  | 0.1045 |
| 8 | 0.6758 | 0.022 |
| 9 | 0.2402 | 0.0123 |
| 10 | 5 |  |
| 11 | 0.4112 | 0.0327 |
| 12 | 0.1997 | 0.0115 |
| 13 | 5 | 4.7903 |
| 14 |  | 3.4067 |
| 15 | 1.391 | 0.0759 |
| 16 | 0.1216 | 0.0076 |
| 17 | 1.0903 | 0.0323 |
| 18 | 2.5476 | 0.1979 |
| 19 | 1.4681 | 0.1012 |
| 20 | 5 | 0.5811 |
| 21 | 1.7837 | 0.1025 |
| 22 | 1.0241 | 0.0467 |
| 23 | 1.4449 | 0.0888 |
| 24 | 0.9016 | 0.0375 |
| 25 | 0.7489 | 0.0523 |
| 26 | 1.1616 | 0.0655 |
| 27 | 0.0877 | 0.0058 |
| 28 | 0.0272 | 0.0028 |
| 29 | 0.0541 | 0.0045 |
| 30 | 0.3009 | 0.0224 |
| 31 | 0.1887 | 0.0037 |
| 32 | 0.4101 | 0.0072 |
| 33 |  | 0.1964 |
| 34 | 0.1043 | 0.0075 |
| 35 |  | 0.1418 |
| 36 | 1.4358 | 0.0881 |
| 37 |  | 0.133 |
| 38 | 0.7613 | 0.0364 |
| 39 | 0.5594 | 0.0546 |
| 40 |  | 0.0647 |
| 41 |  | 0.7063 |
| 42 | 0.073 | 0.0079 |
| 43 | 0.0075 | 0.0029 |
| 44 | 0.3231 | 0.0263 |
| 45 | 0.1254 | 0.0076 |
| 46 | 0.2949 | 0.0039 |
| 47 | 0.1306 | 0.0057 |
| 48 | 0.2794 | 0.0145 |
| 49 | 0.1638 | 0.0034 |
| 50 | 0.1841 | 0.0078 |
| 51 | 0.0152 | 0.0026 |
| 52 | 0.2339 | 0.0201 |
| 53 | 0.0333 | 0.0035 |
| 54 | 0.1439 | 0.013 |
| 55 | 0.602 | 0.0233 |
| 56 | 3.0522 | 0.3603 |
| 57 | 0.0391 | 0.005 |
| 58 | 0.0176 | 0.0047 |
| 59 |  | 0.7246 |
| 60 | 0.0331 | 0.0023 |
| 61 | 0.0138 | 0.0024 |
| 62 | 0.4896 | 0.1082 |
| 63 | 0.0442 | 0.0045 |
| 64 |  | 0.1334 |
| 65 | 0.0132 | 0.0034 |
| 66 | 1.2707 | 0.2974 |
| 67 | 0.2433 | 0.0101 |
| 68 | 0.017 | 0.0042 |
| 69 | 0.1035 | 0.0078 |
| 70 | 2.9979 | 1.5018 |
| 71 | 0.0016 | 0.0031 |
| 72 |  | 0.0866 |
| 73 | 1.4188 | 0.2266 |
| 74 | 0.9777 | 0.0568 |
| 75 | 0.1497 | 0.0082 |
| 76 | 0.0861 | 0.0033 |
| 77 | 0.1907 | 0.0076 |
| 78 | 0.0343 | 0.0042 |
| 79 | 2.0083 | 0.1398 |
| 80 | 0.0755 | 0.0053 |
| 81 | 0.0081 | 0.0037 |
| 82 | 0.0091 | 0.0028 |
| 83 | 0.0314 | 0.005 |
| 84 |  | 5 |
| 85 |  | 4.6804 |
| 86 | 5 | 3.2098 |
| 87 | 5 | 1.4903 |
| 88 | 3.798 | 0.3617 |
| 89 | 1.153 | 0.0551 |
| 90 | 0.062 | 0.0048 |
| 91 | 0.7833 | 0.1497 |
| 92 |  | 0.5635 |
| 93 |  | 4.4218 |
| 94 |  | 0.1145 |
| 95 | 1.1574 | 0.0383 |
| 96 | 0.0347 | 0.0065 |
| 97 | 0.1143 | 0.012 |
| 98 |  | 3.212 |
| 99 | 5 | 3.1216 |
| 100 | 5 | 2.1202 |
| 101 | 0.8707 | 0.0459 |
| 102 | 0.1979 | 0.0057 |
| 103 |  | 1.058 |
| 104 | 0.83 | 0.0146 |
| 105 |  | 0.1703 |
| 106 | 1.6245 | 0.1841 |
| 107 | 1.071 | 0.0422 |
| 108 | 0.6384 | 0.0234 |
| 109 | 1.0857 | 0.0385 |
| 110 |  | 0.7806 |
| 111 |  | 0.1139 |
| 112 | 1.3176 | 0.0383 |
| 113 | 0.1218 | 0.0039 |
| 114 | 0.0303 | 0.0035 |
| 115 | 0.1375 | 0.0081 |
| 116 | 0.1266 | 0.0069 |
| 117 | 0.1066 | 0.0049 |
| 118 | 0.7106 | 0.0162 |
| 119 | 0.4109 | 0.01 |
| 120 | 3.9651 | 0.0595 |
| 121 |  | 0.1016 |
| 122 |  | 0.8016 |
| 123 |  | 1.8284 |
| 124 | 1.1642 | 0.0611 |
| 125 | 4.3083 | 1.1574 |
| 126 | 0.9245 | 0.0609 |
| 127 | 0.4275 | 0.0242 |
| 128 | 0.1633 | 0.009 |
| 129 | 3.5404 | 0.0845 |
| 130 | 1.657 | 0.1222 |
| 131 | 0.1519 | 0.008 |
| 132 | 0.1849 | 0.0067 |
| 133 | 2.4357 | 0.167 |
| 134 | 0.1077 | 0.0066 |
| 135 | 1.0436 | 0.0737 |
| 136 | 0.0531 | 0.0038 |
| 137 | 0.0798 | 0.0048 |
| 138 | 0.0975 | 0.0042 |
| 139 | 0.4858 | 0.01 |
| 140 | 2.6185 | 0.178 |
| 141 | 0.0017 | 0.0018 |
| 142 | 0.0091 | 0.0026 |
| 143 |  | 3.0654 |
| 144 | 0.6736 | 0.0128 |
| 145 | 0.413 | 0.0124 |
| 146 | 2.0877 | 0.1105 |
| 147 | 0.023 | 0.0032 |
| 148 | 0.0716 | 0.0037 |
| 149 | 2.743 | 0.0995 |
| 150 | 0.7073 | 0.0201 |
| 151 | 0.7031 | 0.0519 |
| 152 | 0.2477 | 0.0163 |

| Example No. | CELL_IC50 (μM) | ROCK_IC50 (μM) |
| --- | --- | --- |
| 153 | 2.4288 | 0.238 |
| 154 | 0.0602 | 0.0196 |
| 155 | 0.0422 | 0.0027 |
| 156 | 0.0049 | 0.0025 |

Unless otherwise defined, all technical and scientific terms used herein have the same meaning as commonly understood by one of ordinary skill in the art to which this invention belongs.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the subject matter claimed.

Thus, it should be understood that although the present subject matter has been specifically disclosed by preferred embodiments and optional features, modification, improvement and variation of the embodiments embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the subject matter.

The subject matter has been described broadly and generically herein. Each of the narrower species and subgeneric groupings falling within the generic disclosure also form part of the subject matter. This includes the generic description of the subject matter with a proviso or negative limitation removing any subject matter from the genus, regardless of whether or not the excised material is specifically recited herein.

In addition, where features or aspects of the disclosure are described in terms of Markush groups, those skilled in the art will recognize that the subject matter is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of formula I:

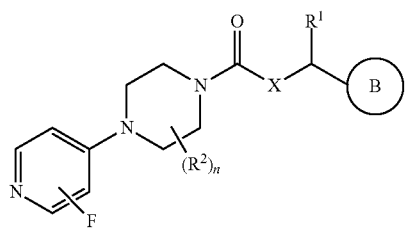

or a deuterated analog, pharmaceutically acceptable salt, solvate, stereoisomer, or mixture of stereoisomers thereof, wherein:

ring B is a 6-10 membered aryl or 6-10 membered heteroaryl ring, wherein ring B is optionally substituted with 1-5 $R^4$;

X is —O— or —N($R^3$)—;

$R^1$ is H or optionally substituted $C_{1-3}$alkyl;

each $R^2$ is independently oxo, halo, $C_{1-3}$alkyl, $C_{1-3}$haloalkyl, $C_{1-3}$hydroxyalkyl, or $C_{1-3}$alkoxy;

$R^3$ is H or $C_{1-3}$ alkyl;

each $R^4$ is independently halo, $C_{1-3}$ alkyl, $C_{1-3}$ alkoxy, or $C_{1-3}$ haloalkoxy;

and n is 0, 1, or 2.

2. The compound of claim 1, wherein the compound is a compound of formula II:

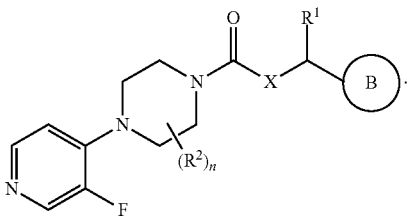

3. The compound of claim 1, wherein n is 0.

4. The compound of claim 1, wherein n is 2, and each $R^2$ is methyl.

5. The compound of claim 1, wherein the compound is a compound of formula III:

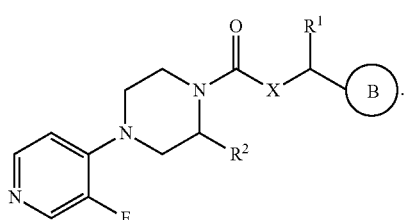

6. The compound of claim 5, wherein the compound is a compound of formula III(a):

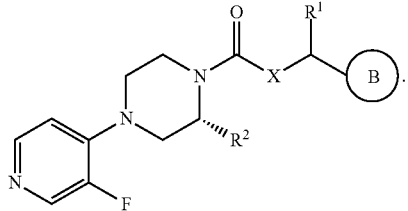

7. The compound of claim 5, wherein the compound is a compound of formula III(b):

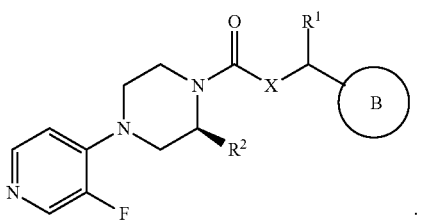

8. The compound of claim 6, wherein the compound is a compound of formula IV(a):

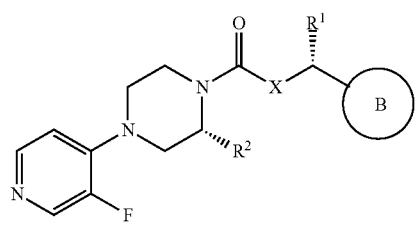

and $R^1$ is optionally substituted $C_{1-3}$alkyl, or the compound is a compound of formula IV(b):

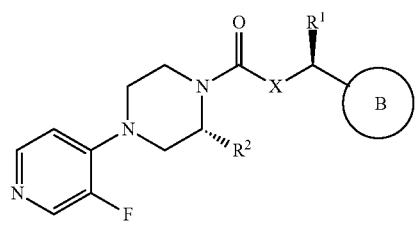

and $R^1$ is optionally substituted $C_{1-3}$alkyl.

9. The compound of claim 7, wherein the compound is a compound of formula IV(c):

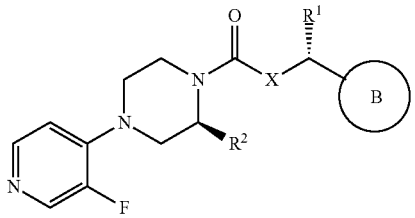

and $R^1$ is optionally substituted $C_{1-3}$alkyl, or the compound is a compound of formula IV(d):

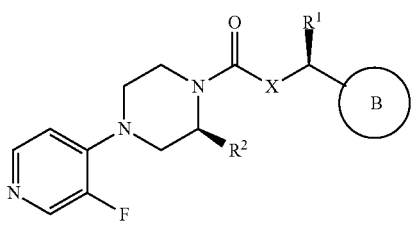

and $R^1$ is optionally substituted $C_{1-3}$alkyl.

10. The compound of claim 1, wherein X is $—N(R^3)—$.

11. The compound of claim 10, wherein $R^3$ is H.

12. The compound of claim 1, wherein $R^1$ is methyl.

13. The compound of claim 1, wherein $R^2$ is methyl.

14. The compound of claim 1, wherein ring B is a 6-10 membered aryl optionally substituted with 1 to 3 substituents selected from halo, $C_{1-3}$ alkyl, $C_{1-3}$ alkoxy, and $C_{1-3}$ haloalkoxy.

15. The compound of claim 1, wherein ring B is a 6-10 membered heteroaryl optionally substituted with 1 to 3 substituents selected from halo, $C_{1-3}$ alkyl, $C_{1-3}$ alkoxy, and $C_{1-3}$ haloalkoxy.

16. A compound selected from:

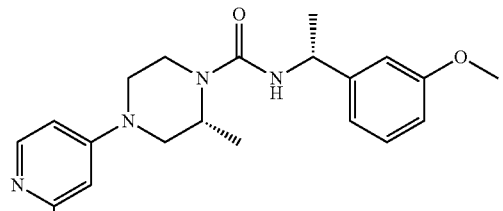

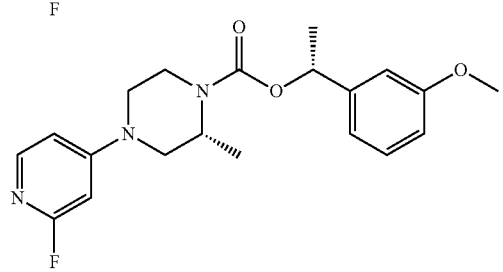

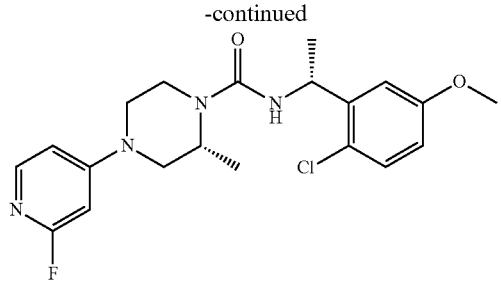
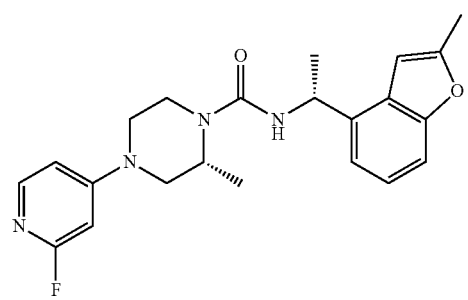
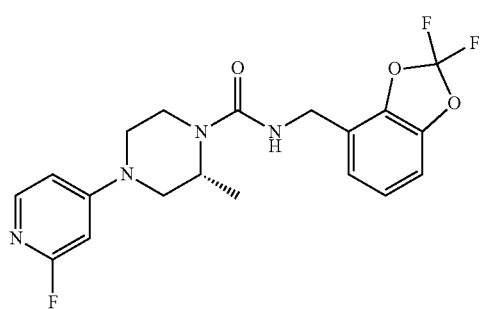
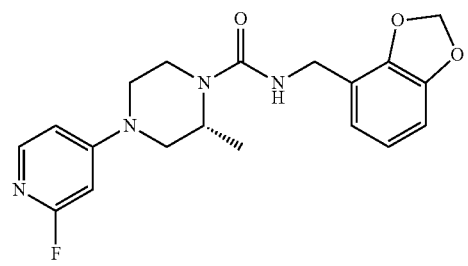
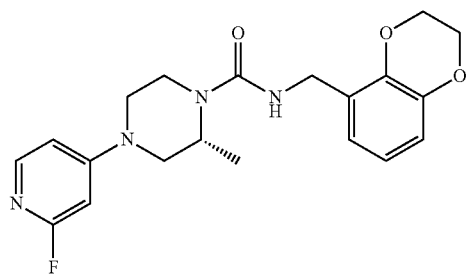
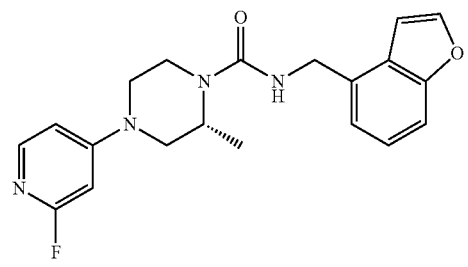
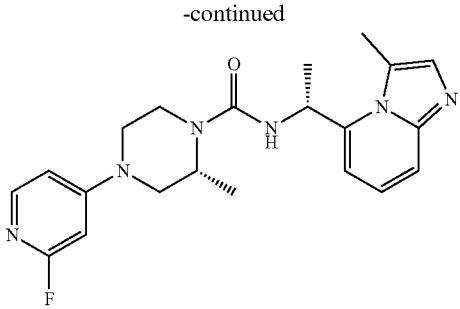
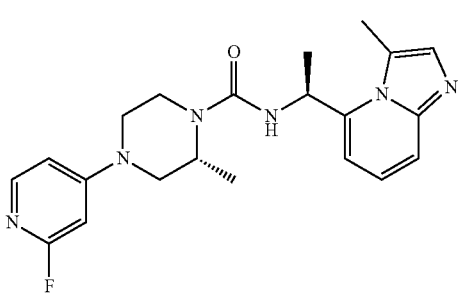
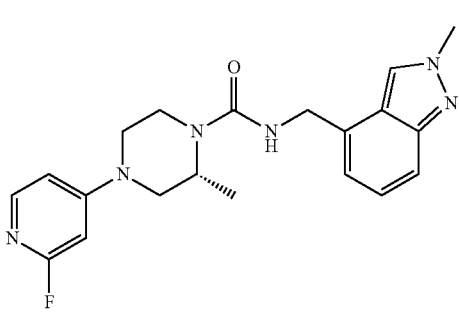
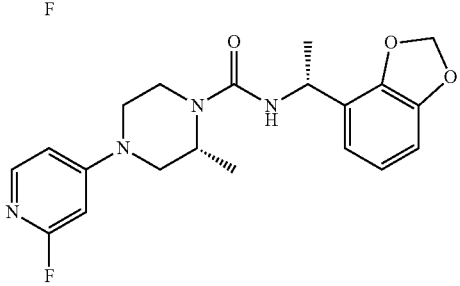
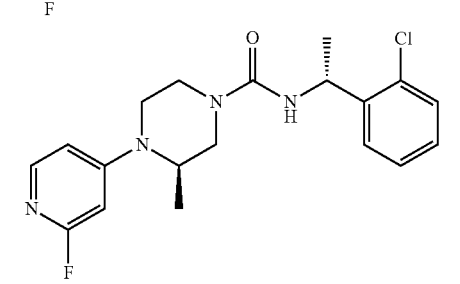
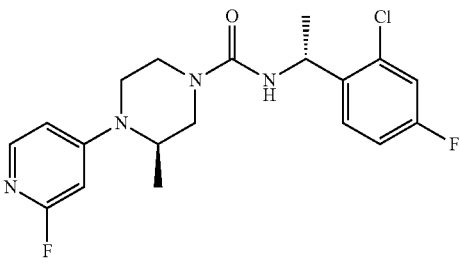

165
-continued
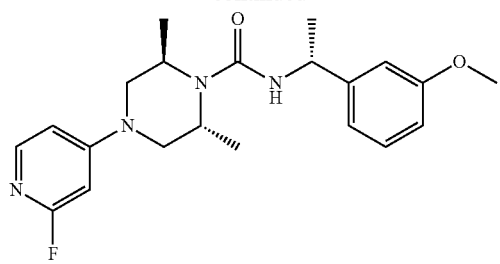
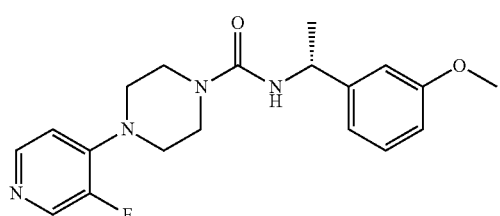
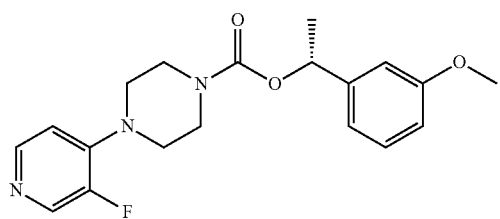
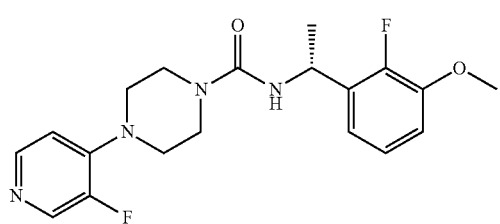
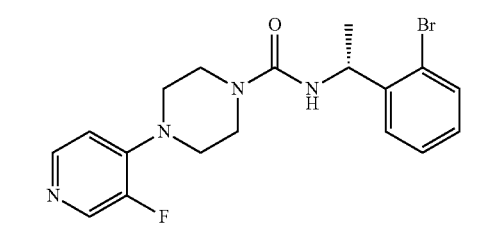
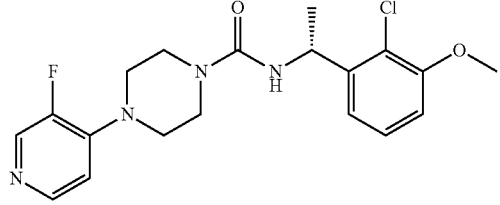
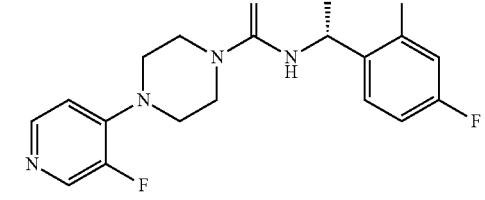
166
-continued
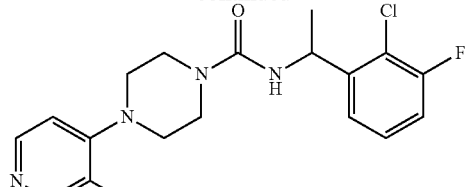
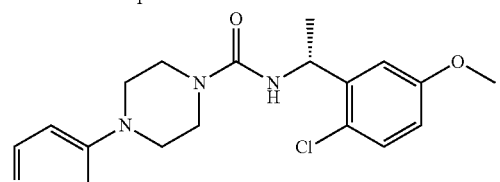
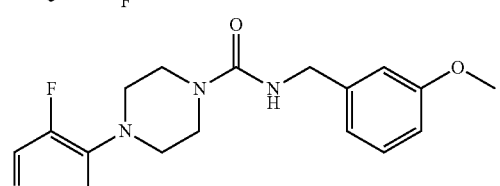
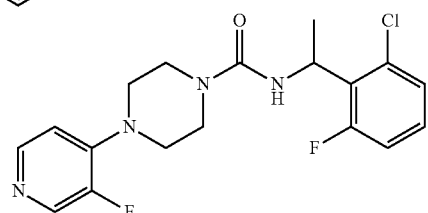
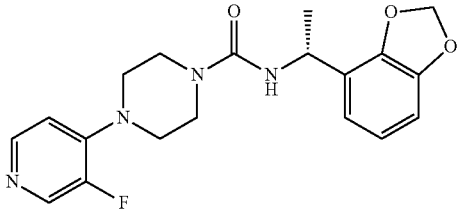
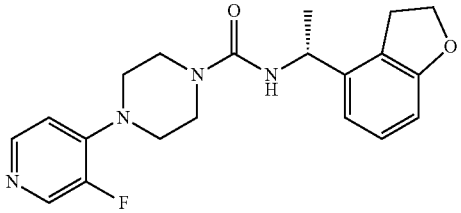
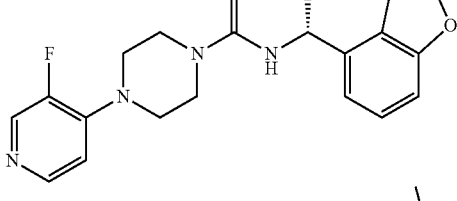
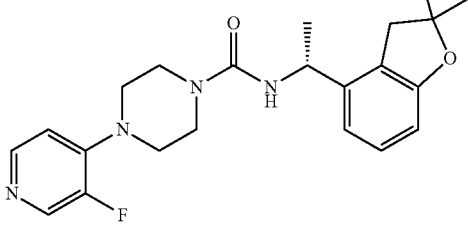

167
-continued
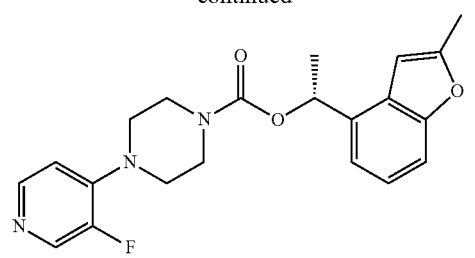
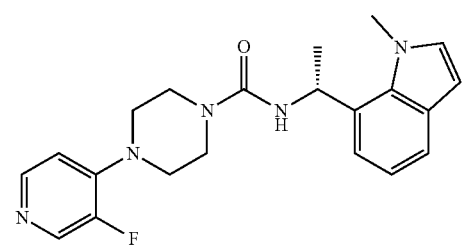
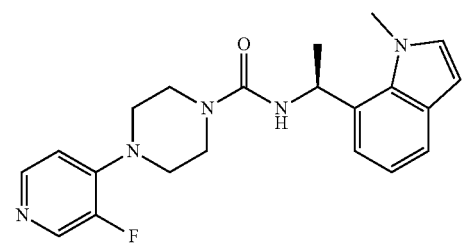
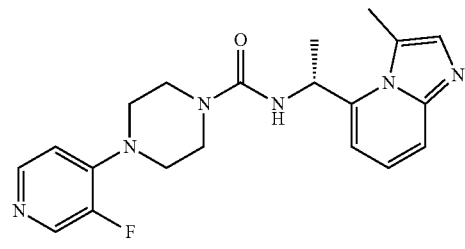
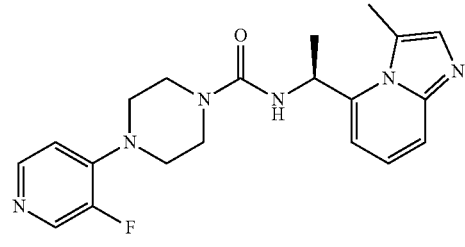
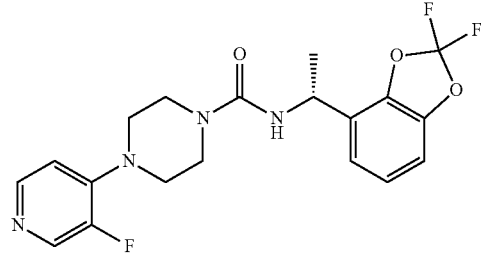
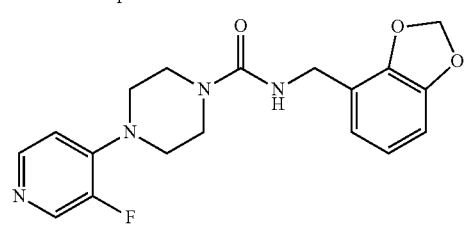
168
-continued
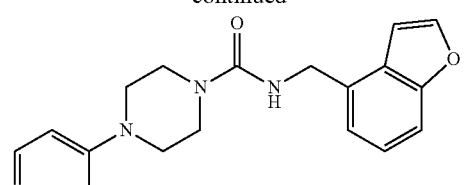
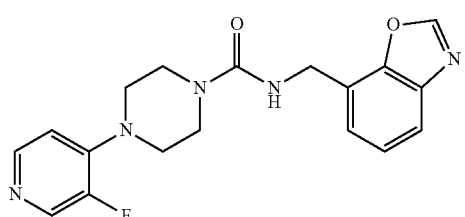
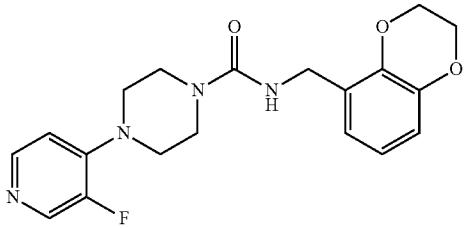
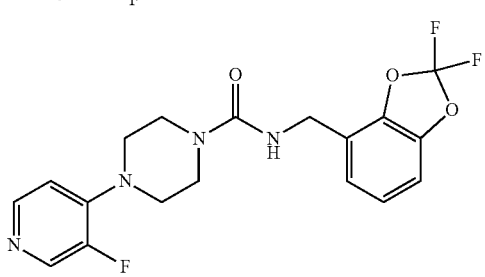
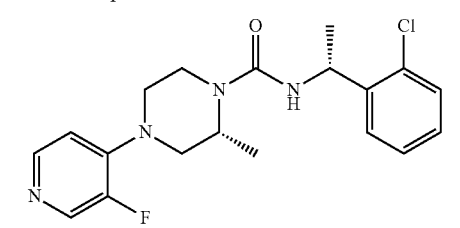
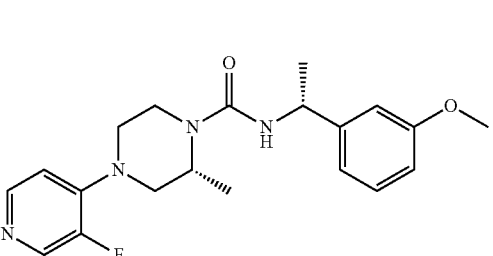
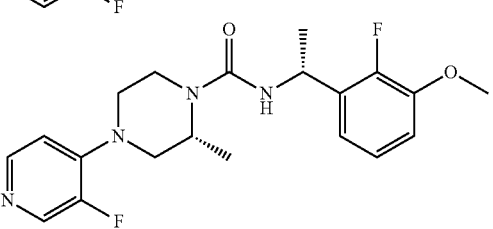

-continued
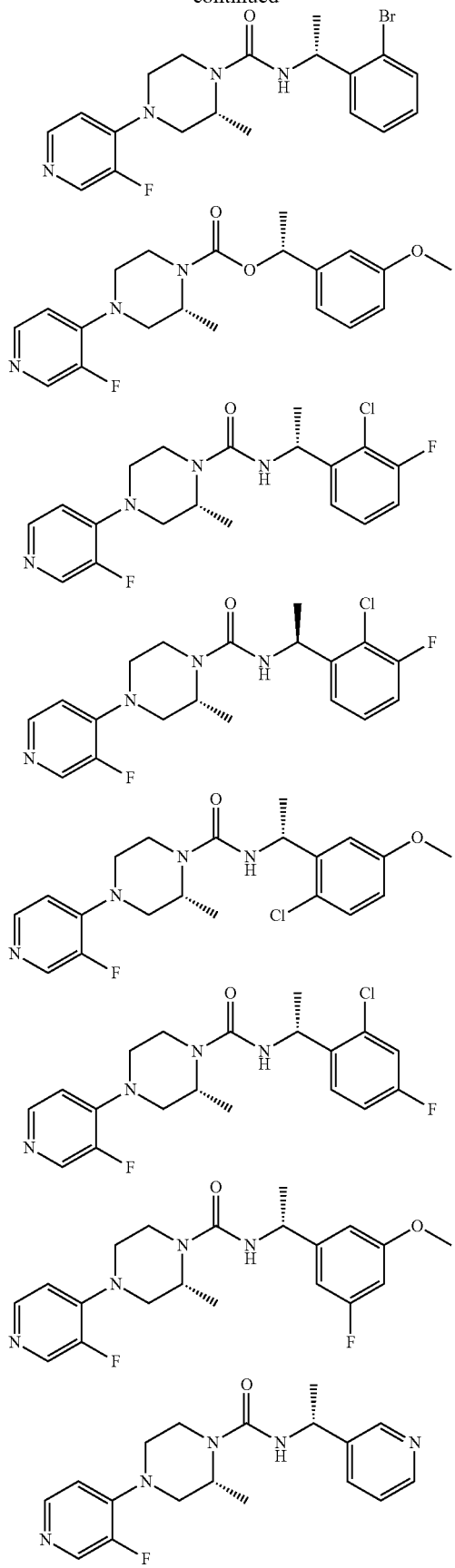
-continued
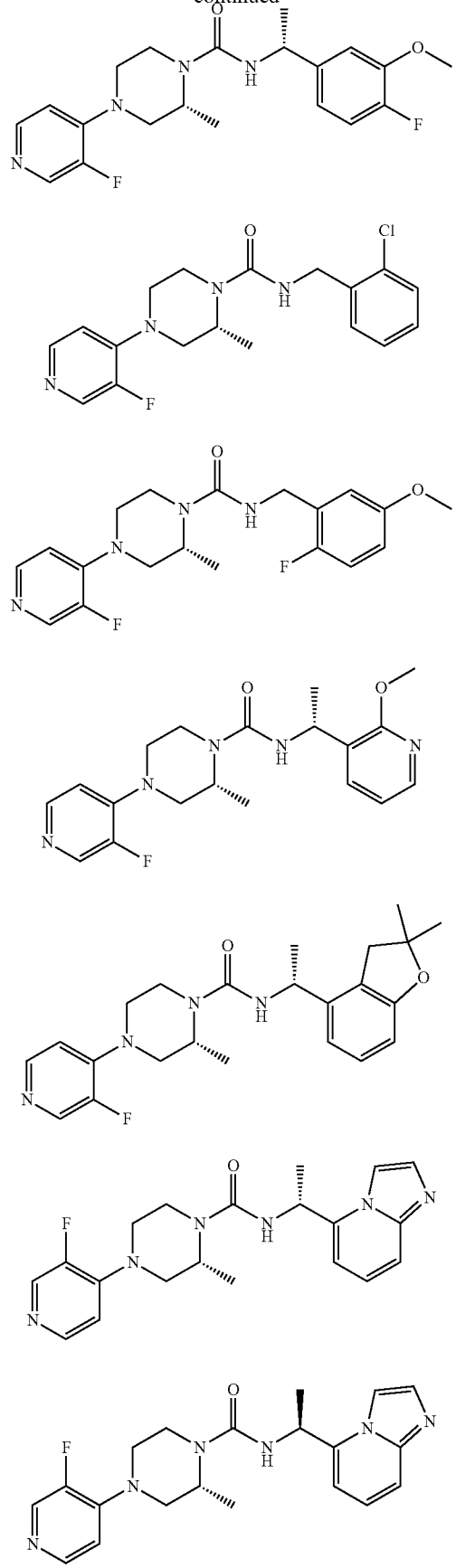

171
-continued
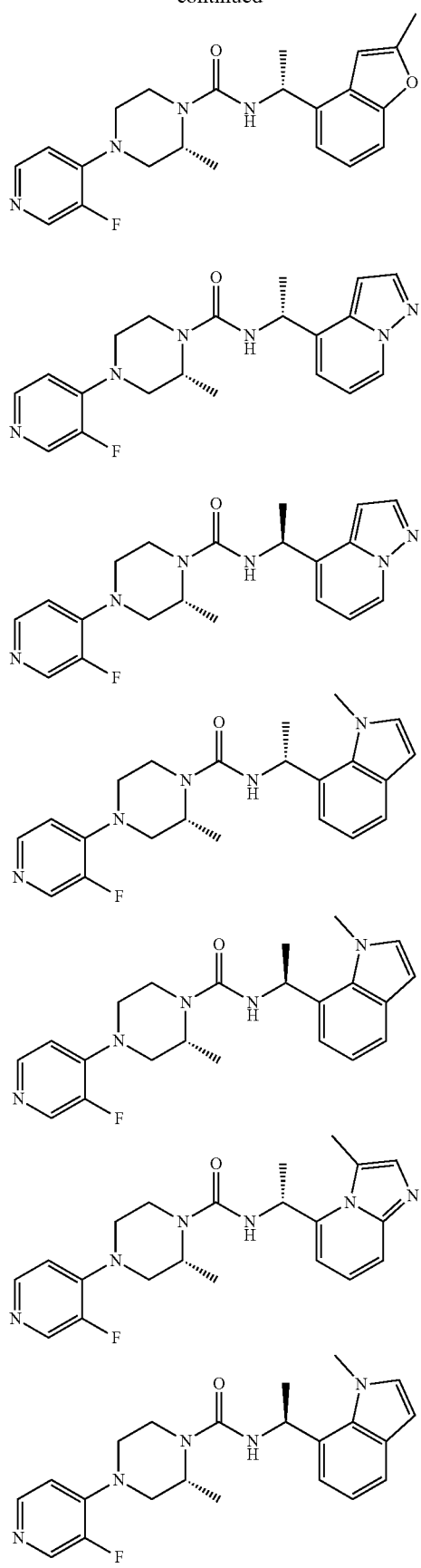
172
-continued
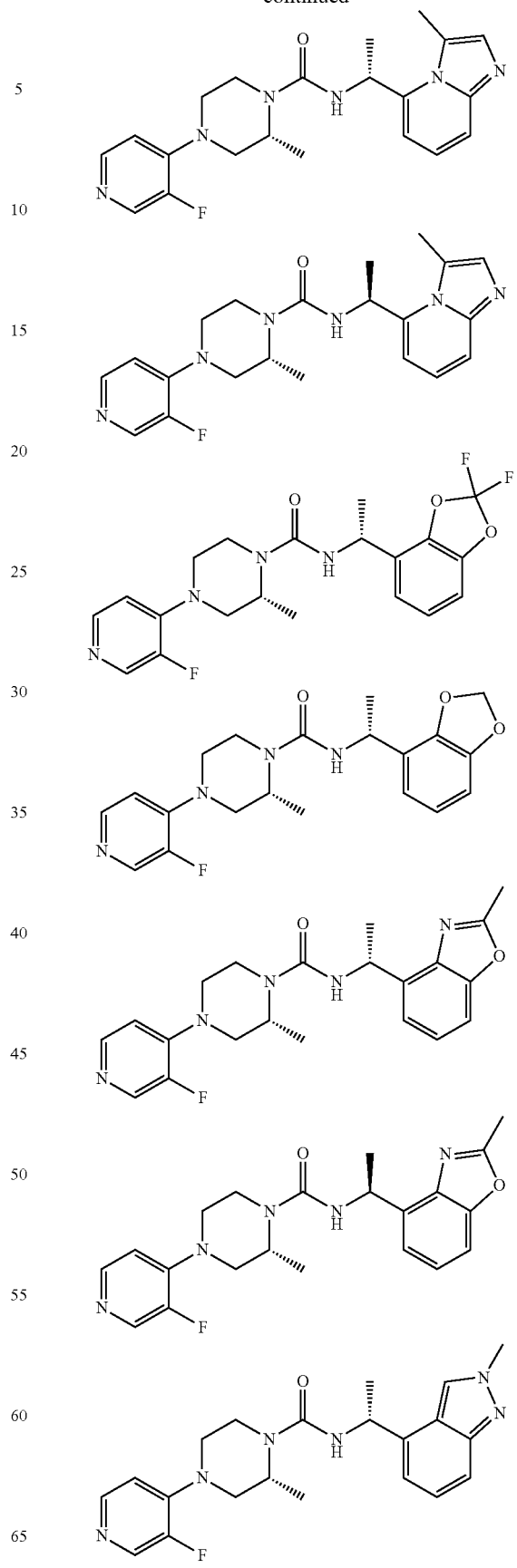

| 173 -continued | 174 -continued |
|---|---|
| 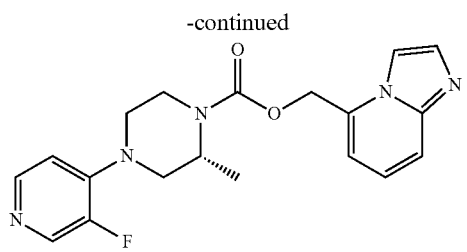 | 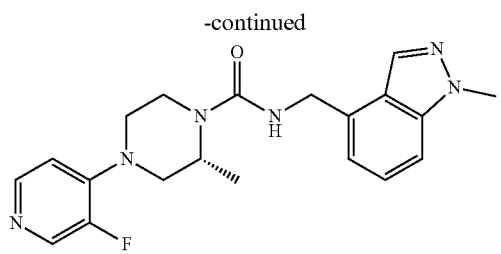 |
| 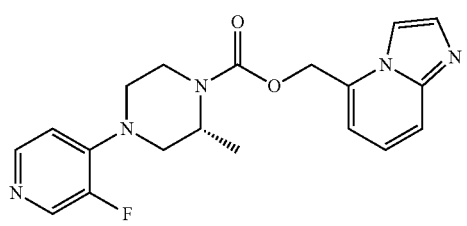 | 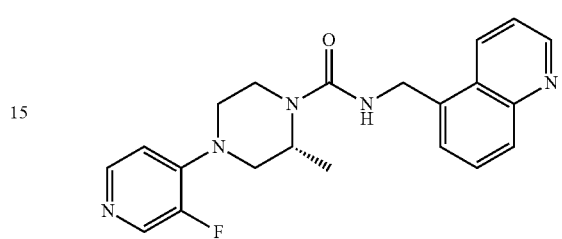 |
| 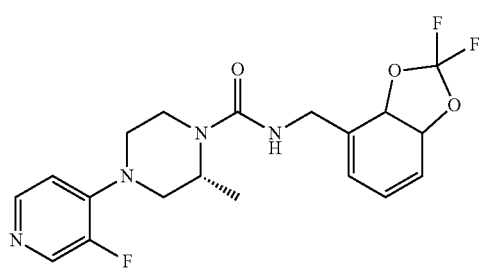 | 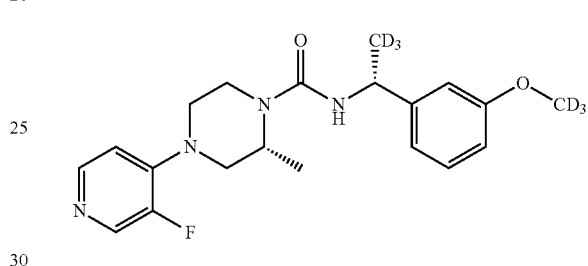 |
| 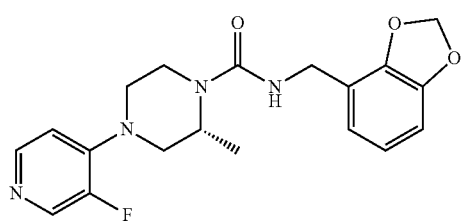 | 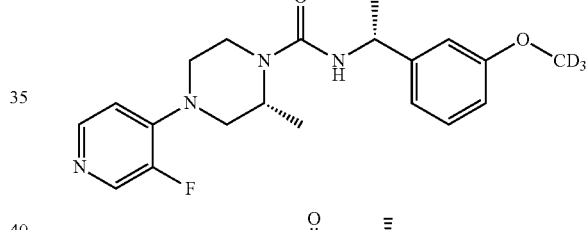 |
| 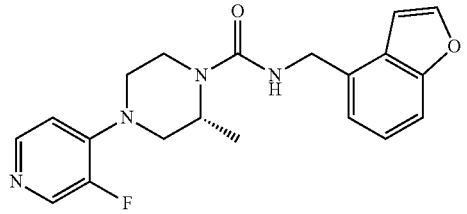 | 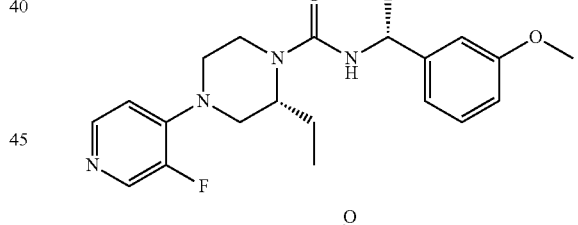 |
| 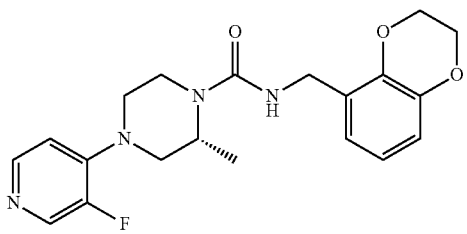 | 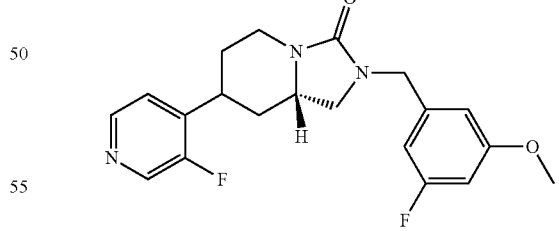 |
| 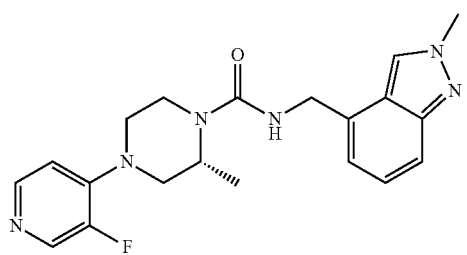 | 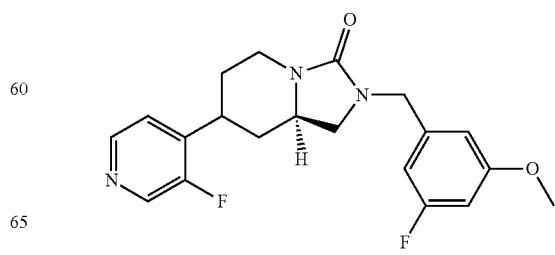 |

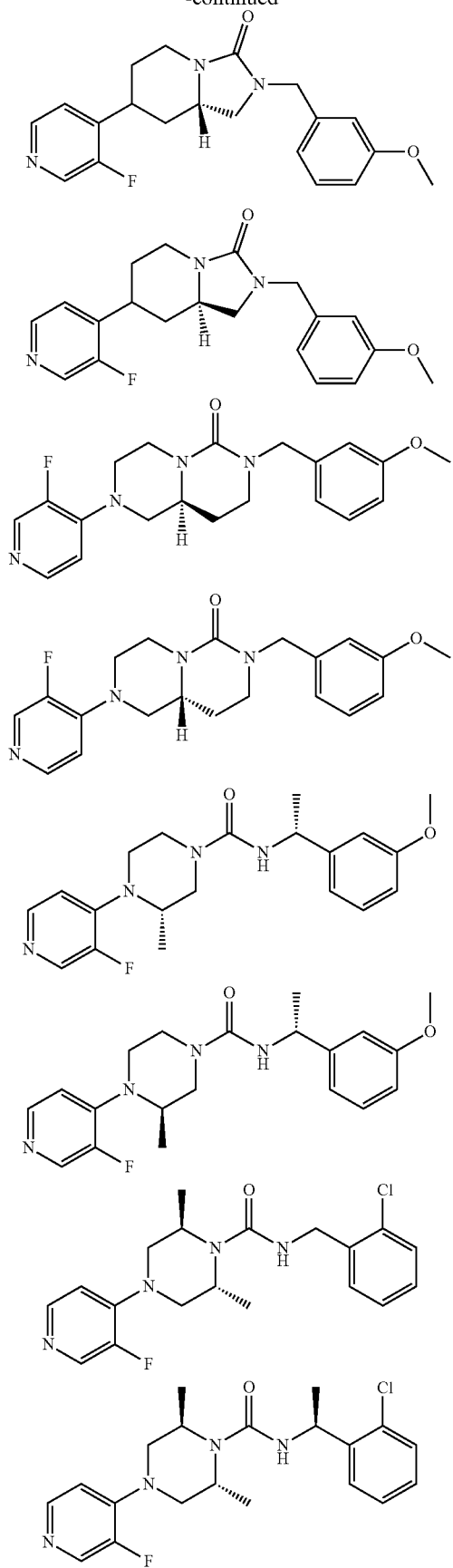

-continued
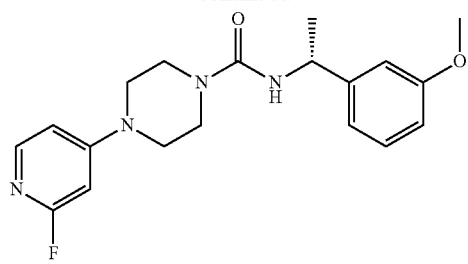
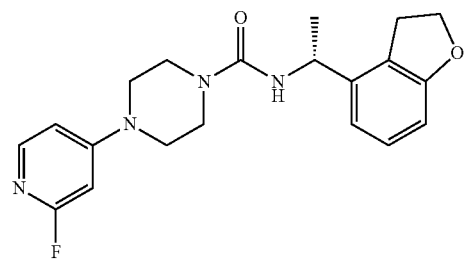
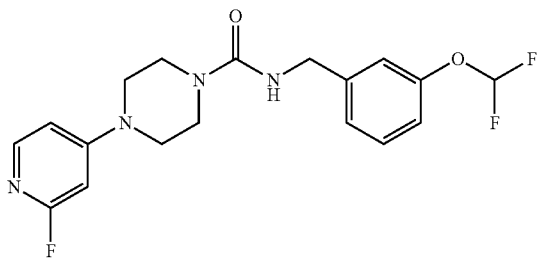
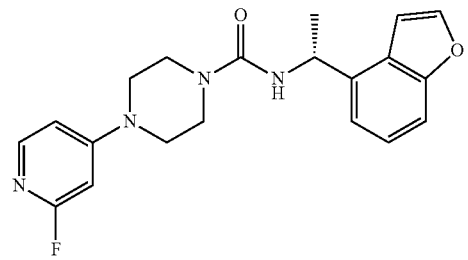
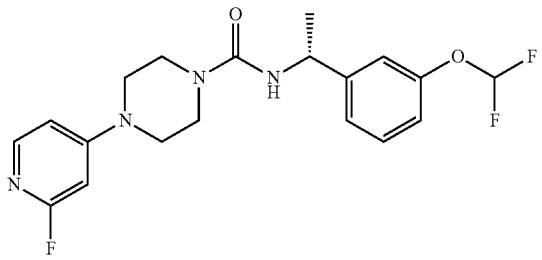
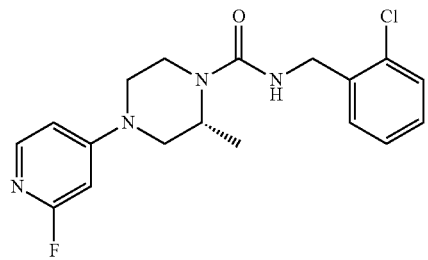
-continued
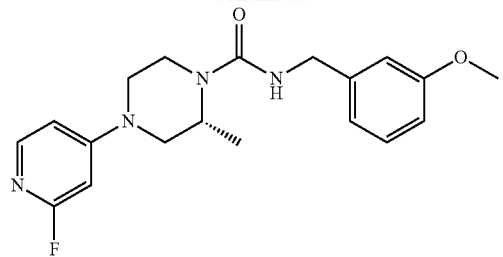
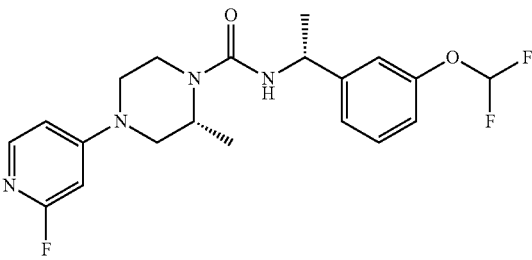
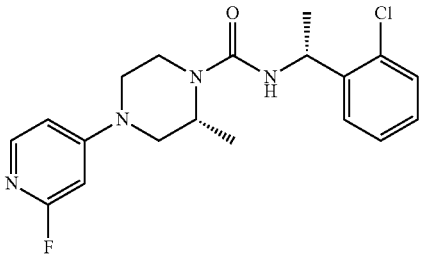
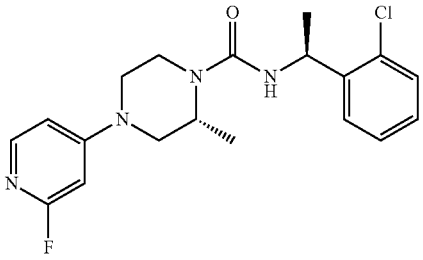
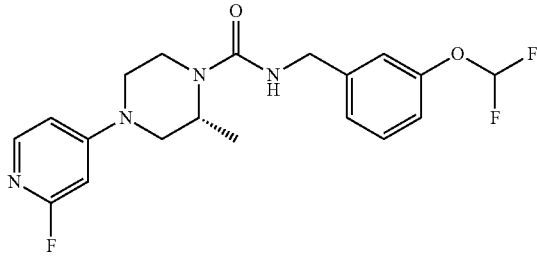
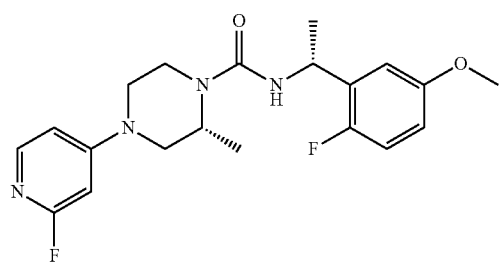

179
-continued
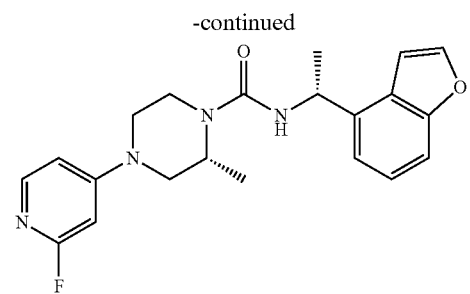
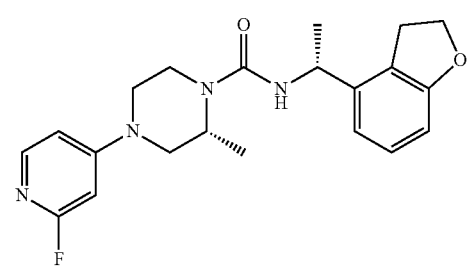
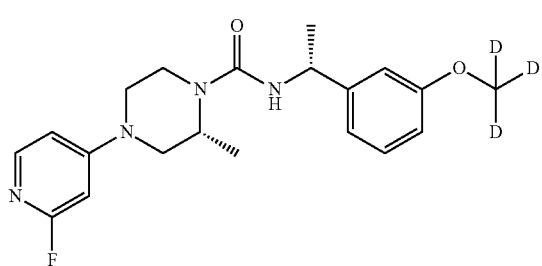
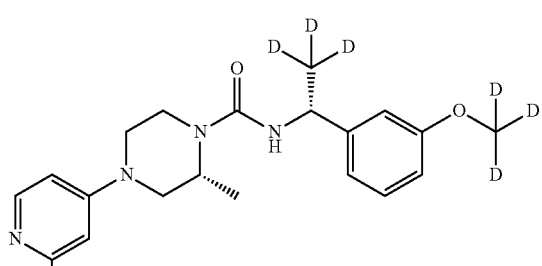
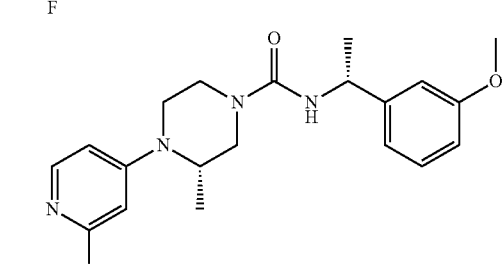
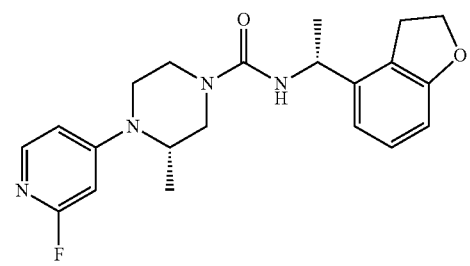
180
-continued
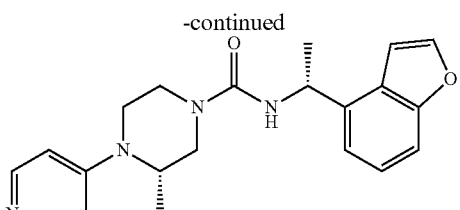
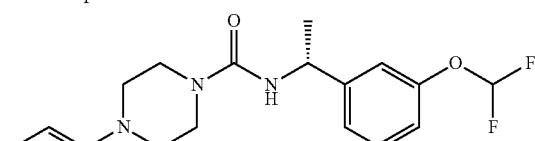
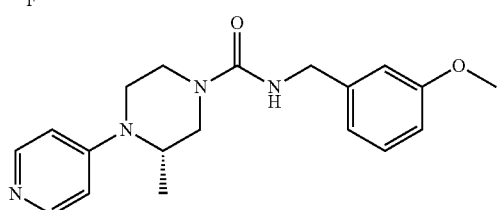
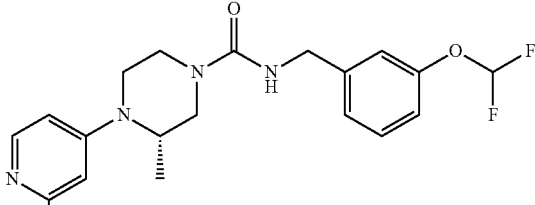
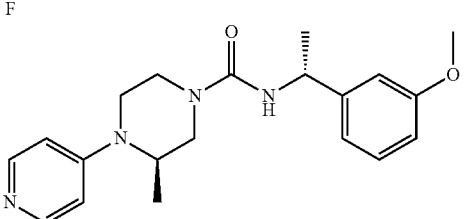
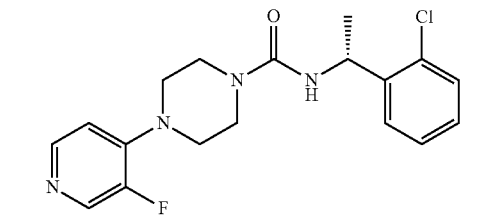

181
-continued
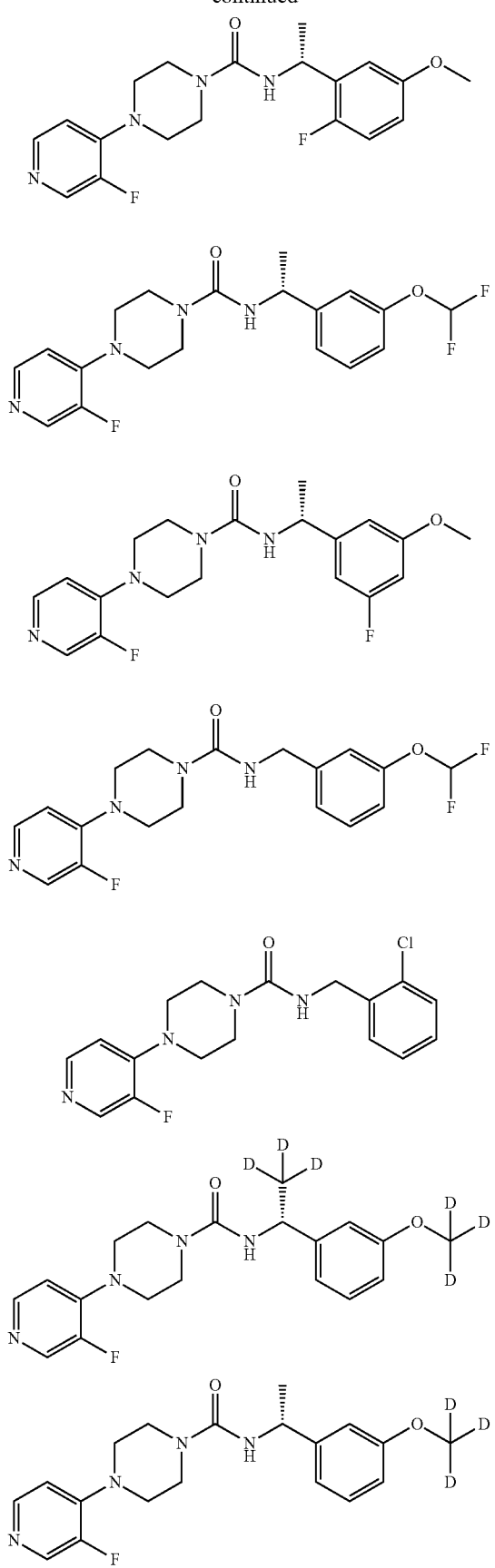
182
-continued
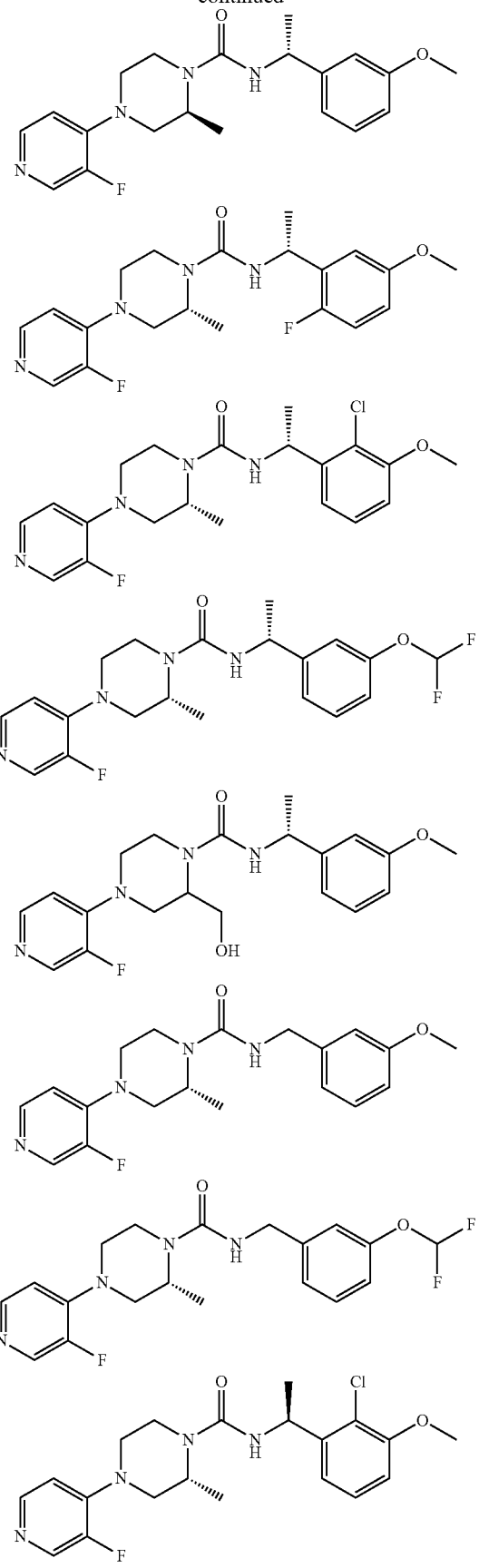

-continued
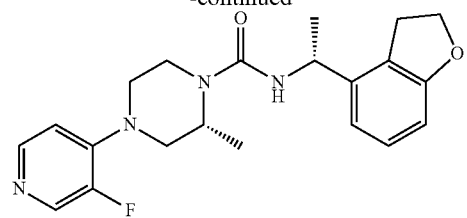
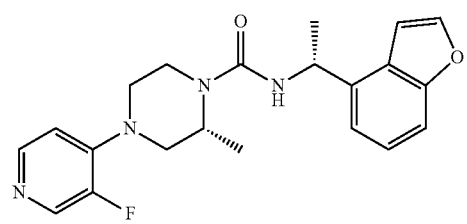
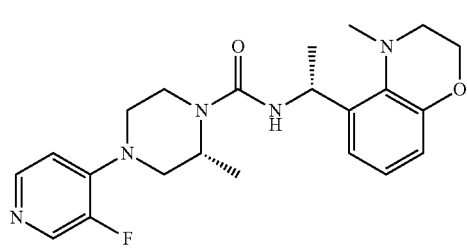
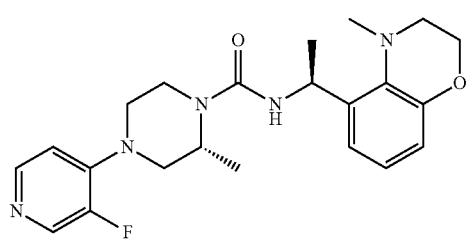
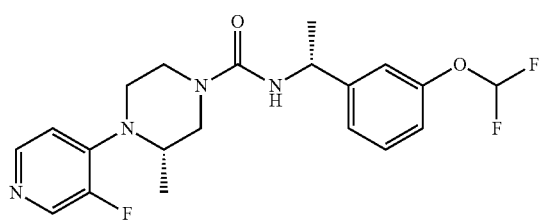
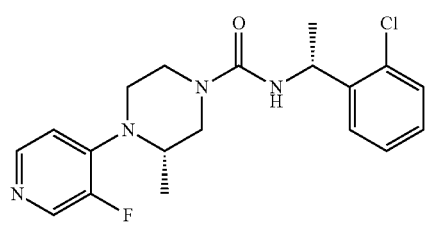
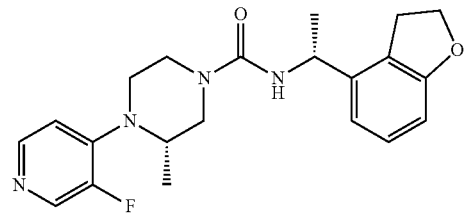
-continued
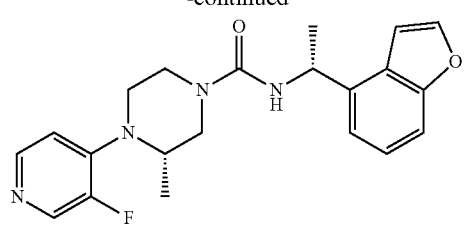
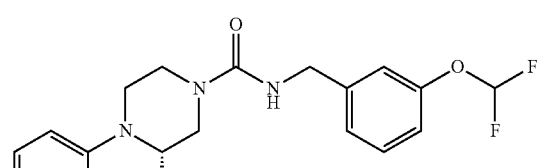
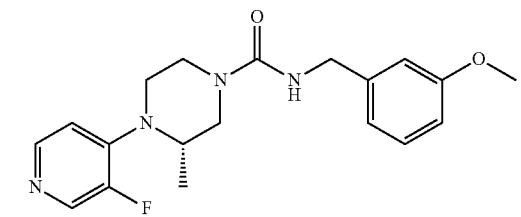
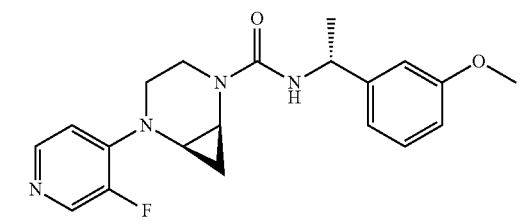
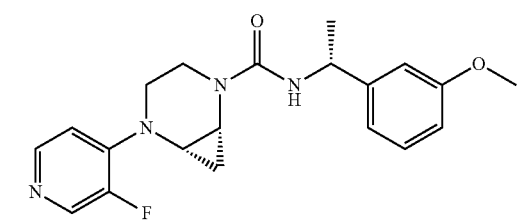
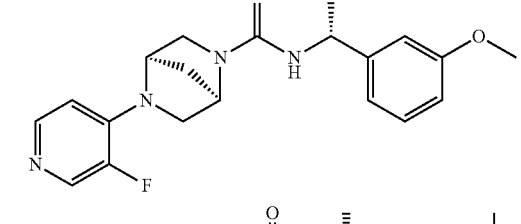
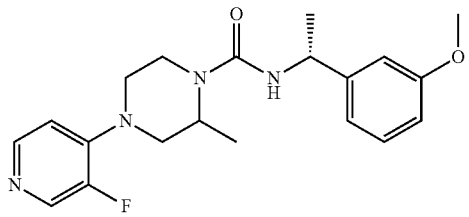

-continued

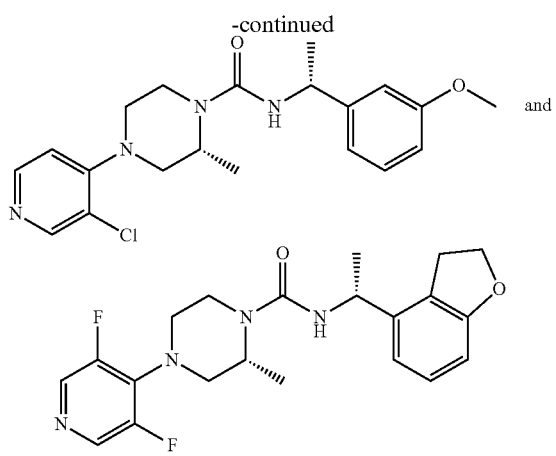

or a deuterated analog, pharmaceutically acceptable salt, solvate, stereoisomer, or mixture of stereoisomers thereof.

17. A pharmaceutical composition comprising a compound of claim 1 and a pharmaceutically acceptable carrier.

18. A method of inhibiting rho-kinase in a patient having a condition or disorder, comprising administering to the patient a therapeutically effective amount of a compound of claim 1, wherein the condition or disorder is selected from Huntington's disease (HD), spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, non-hypertensive nephropathy, hypertensive nephropathy, hypertension, optic nerve lesion, hepatic fibrosis, lupus, liver failure after transplant, encephalomyelitis, epilepsy, and glioblastoma.

19. The method of claim 18, wherein the condition or disorder is Huntington's disease.

* * * * *

UNITED STATES PATENT AND TRADEMARK OFFICE
CERTIFICATE OF CORRECTION

| | | Page 1 of 4 |
|---|---|---|
| PATENT NO. | : 12,428,413 B2 | |
| APPLICATION NO. | : 17/621567 | |
| DATED | : September 30, 2025 | |
| INVENTOR(S) | : Michel C. Maillard et al. | |

It is certified that error appears in the above-identified patent and that said Letters Patent is hereby corrected as shown below:

In the Claims

In Claim 16, Column 167, Lines 1-11, please replace

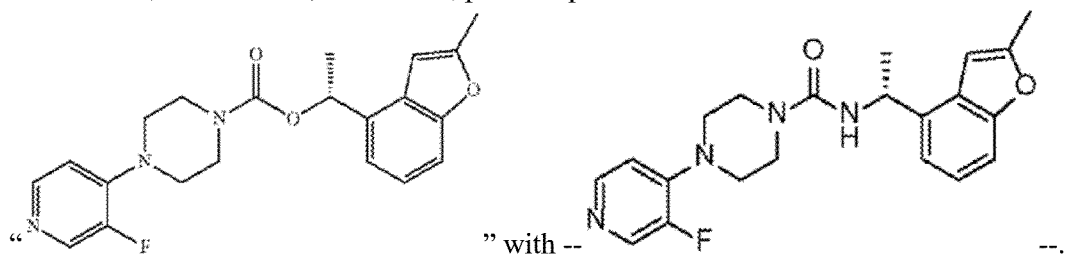

In Claim 16, Column 171, Lines 48-65, please replace

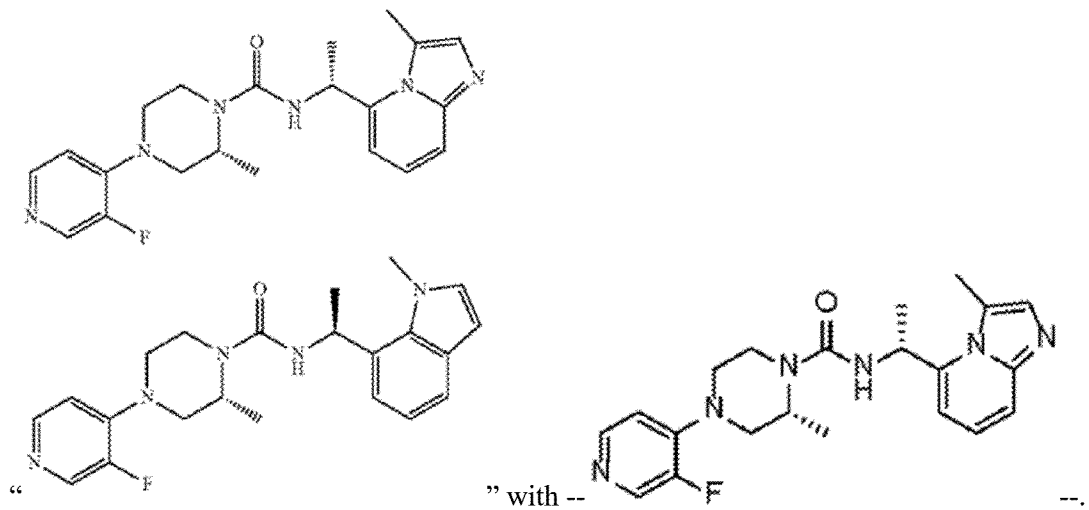

Signed and Sealed this
Third Day of February, 2026

John A. Squires
*Director of the United States Patent and Trademark Office*

CERTIFICATE OF CORRECTION (continued)
U.S. Pat. No. 12,428,413 B2

Page 2 of 4

In Claim 16, Column 172, Lines 1-20, please replace

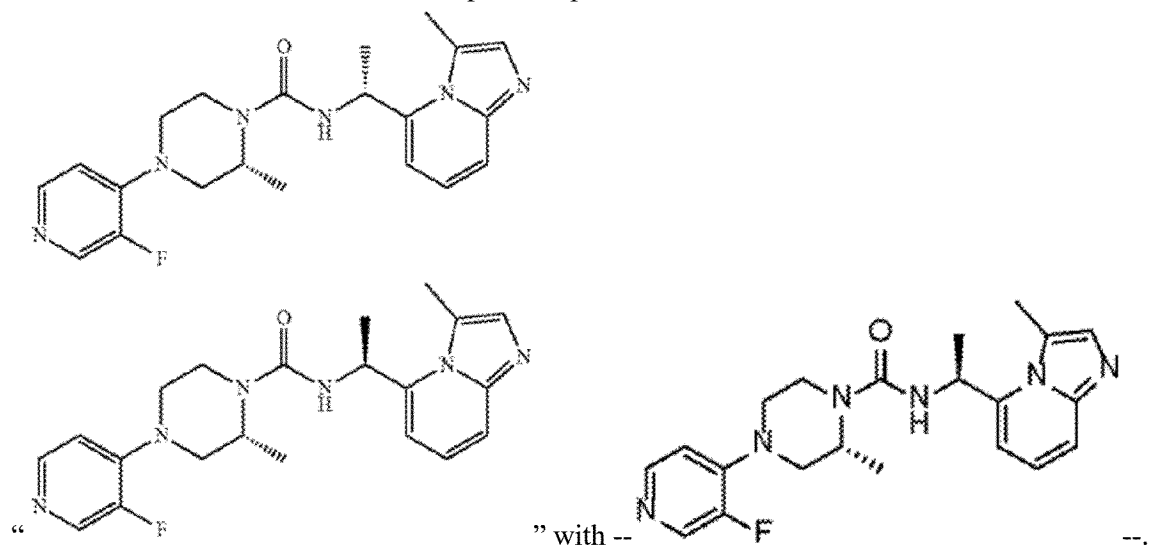

" with --  --.

In Claim 16, Column 172, Lines 57-66, please replace

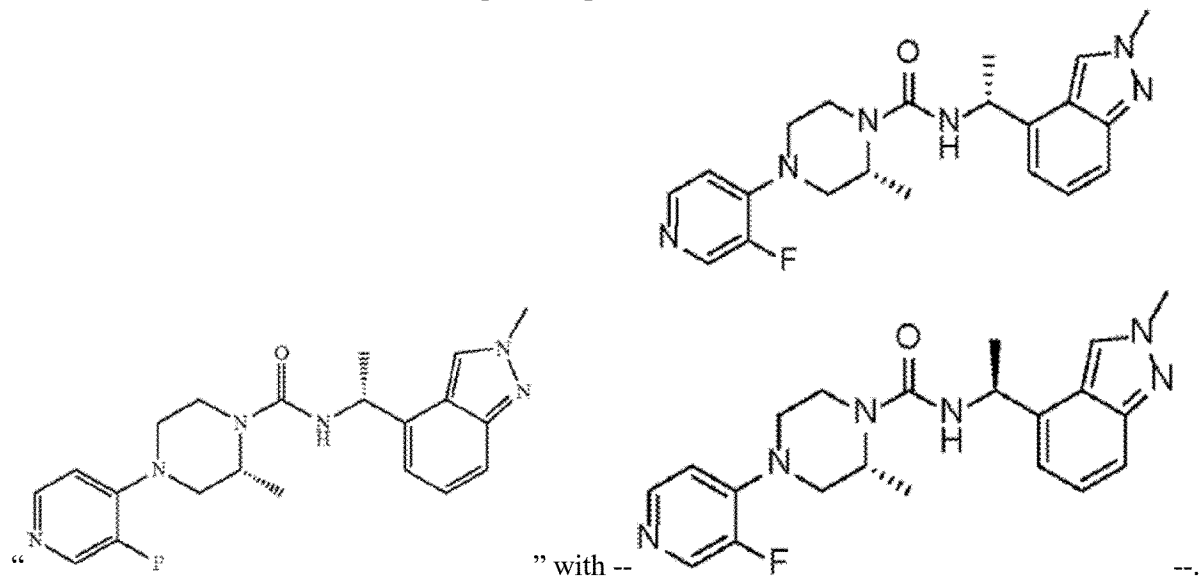

" with --  --.

CERTIFICATE OF CORRECTION (continued)
U.S. Pat. No. 12,428,413 B2

In Claim 16, Column 173, Lines 1-19, please replace

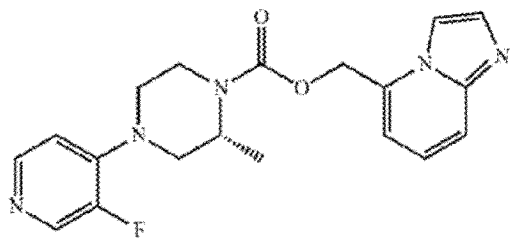

"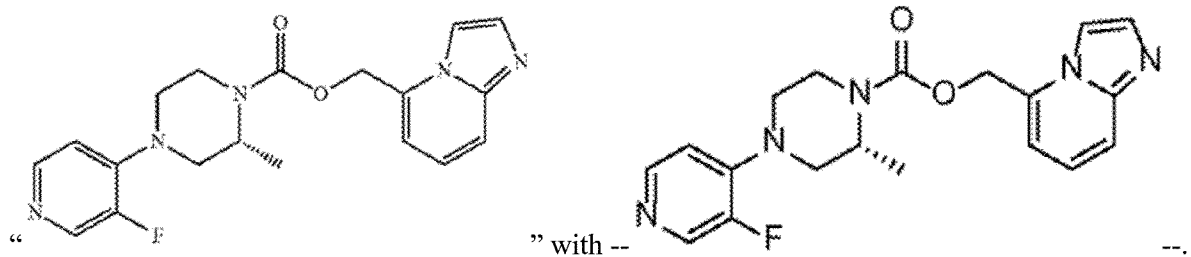" with --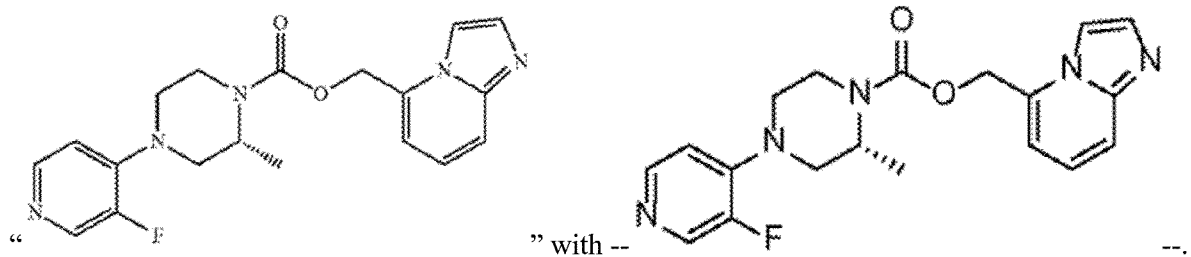--.

In Claim 16, Column 174, Lines 47-56, please replace

"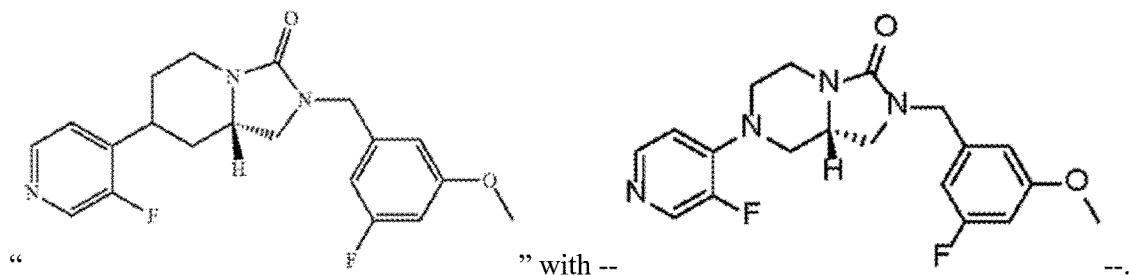" with --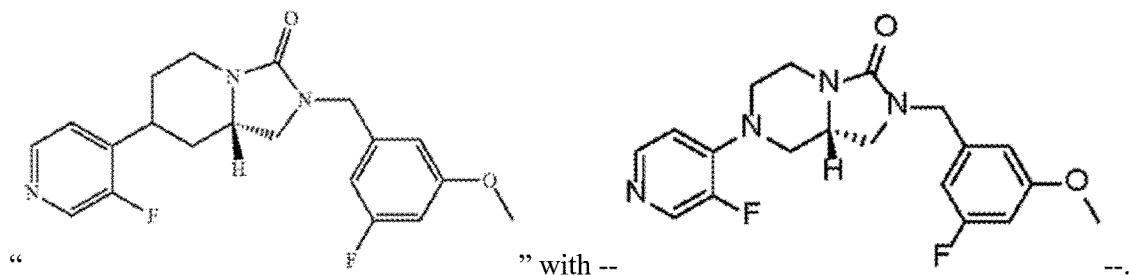--.

In Claim 16, Column 174, Lines 57-66, please replace

"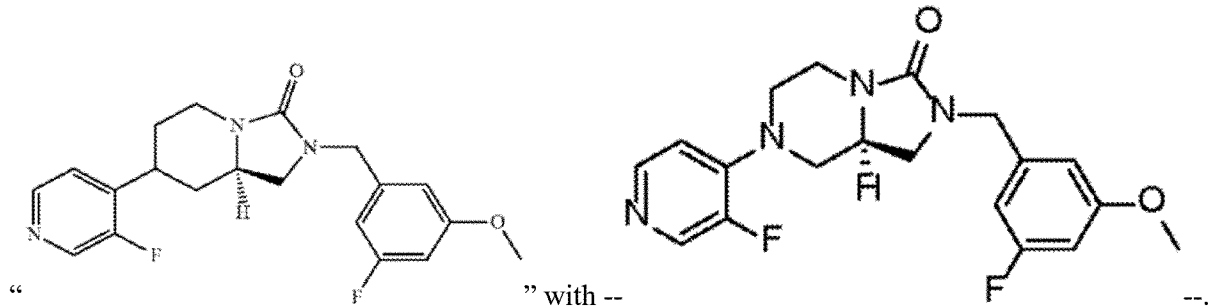" with --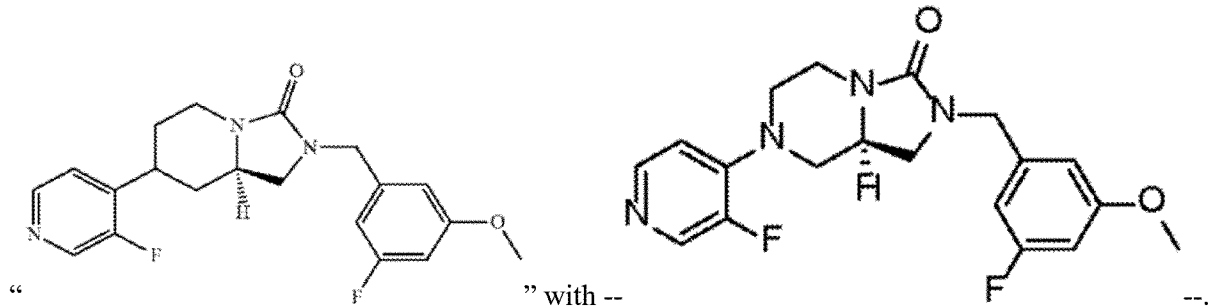--.

CERTIFICATE OF CORRECTION (continued)
U.S. Pat. No. 12,428,413 B2

Page 4 of 4

In Claim 16, Column 175, Lines 1-9, please replace

" 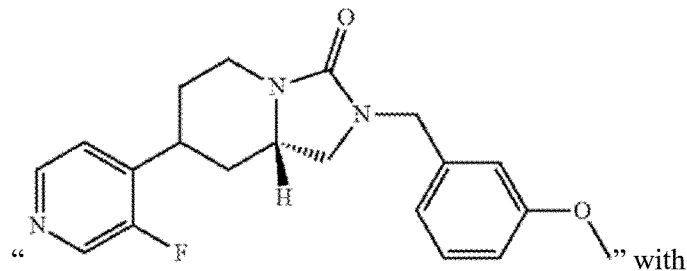 " with

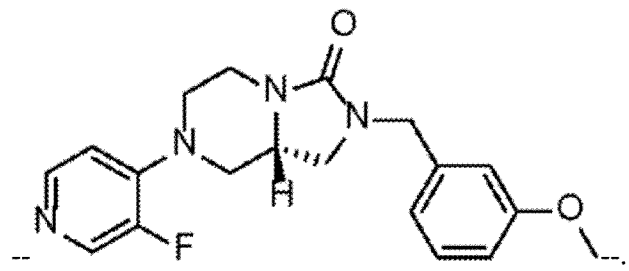 .

In Claim 16, Column 175, Lines 10-17, please replace

" 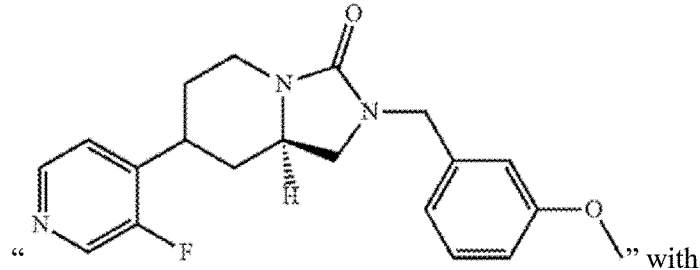 " with

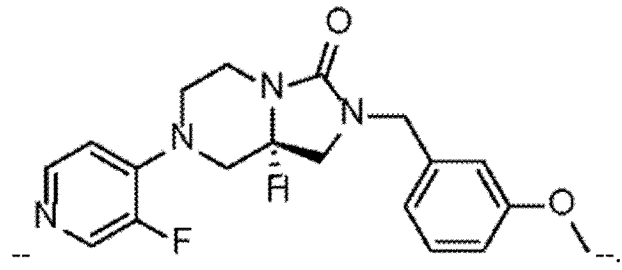 .